US007741493B2

(12) United States Patent
Shum et al.

(10) Patent No.: US 7,741,493 B2
(45) Date of Patent: Jun. 22, 2010

(54) HETEROCYCLIC COMPOUNDS AS P2X7 ION CHANNEL BLOCKERS

(75) Inventors: Patrick Shum, Flemington, NJ (US); Alexandre Gross, Jersey City, NJ (US); Liang Ma, Hillsborough, NJ (US); Daniel G. McGarry, Branchburg, NJ (US); Gregory H. Merriman, Phillipsburg, NJ (US); David Rampe, Bernardsville, NJ (US); Garth Ringheim, Belle Mead, NJ (US); Jeffrey Stephen Sabol, Bridgewater, NJ (US); Francis A. Volz, Neshanic Station, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 11/947,442

(22) Filed: Nov. 29, 2007

(65) Prior Publication Data

US 2008/0132550 A1    Jun. 5, 2008

Related U.S. Application Data

(62) Division of application No. 10/896,166, filed on Jul. 21, 2004, now Pat. No. 7,326,792.

(60) Provisional application No. 60/489,246, filed on Jul. 21, 2003.

(51) Int. Cl.
    *A61K 31/4184* (2006.01)
    *C07D 235/02* (2006.01)
(52) U.S. Cl. .................................... 548/302.7; 514/388
(58) Field of Classification Search ............... 548/302.7
    See application file for complete search history.

(56) References Cited

U.S. PATENT DOCUMENTS

| 4,308,277 | A |   | 12/1981 | Ferrini et al. |        |
|-----------|---|---|---------|----------------|--------|
| 5,106,845 | A | * | 4/1992  | Carr et al. ...| 514/218|

FOREIGN PATENT DOCUMENTS

| JP | 54-112864   | 9/1979  |
| JP | 2-83372     | 3/1990  |
| WO | WO 99/29660 | 6/1999  |
| WO | WO 99/29661 | 6/1999  |
| WO | WO 99/29686 | 6/1999  |
| WO | WO 00/61569 | 10/2000 |
| WO | WO 01/44213 | 6/2001  |
| WO | WO 01/46200 | 6/2001  |

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*

Vippagunta et al., Advanced Drug Delivery Reviews, 48 (2001), pp. 3-26.*

Isobe et al., Journal of Organic Chemistry, 2000, 65(23), pp. 7774-7778.*

A. D. Michel, et. al., Antagonist Effects on Human P2X7 Receptor-Mediated Cellular Accumulation of YO-PRO-1, British Journal of Pharmacology (2000, pp. 513-520, vol. 130).

B. J. Gu, et. al., Expression of P2X7 Purinoceptors on Human Lymphocytes and Monocytes: Evidence for Nonfunctional P2X7 Receptors, Am J. Physiol Cell Physiol (2000, pp. C1189-1197, vol. 279).

David G. Perregaux, et. al., ATP Acts As an Agonist to Promote Stimulus-Induced Secretion of IL-1 Beta and IL-18 in Human Blood, The Journal of Immunology (2000, pp. 4615-4623, vol. 165).

Davide Ferrari, et. al., Extracellular ATP Triggers IL-1Beta Release by Activating the Purinergic P2Z Receptor of Human Macrophages, The Journal of Immunology (1997, pp. 1451-1458, vol. 159).

Davide Ferrari, et. al., Purinergic Modulation of Interleukin-1Beta Release From Microglial Cells Stimulated With Bacterial Endotoxin, Journal Exp. Med (1997, pp. 579-582, vol. 185, No. 3).

Francesco Di Virgilio, et. al., The P2Z Purinoceptor: an Intriguing Role in Immunity, Inflammation and Cell Death, Immunology Today (1995, pp. 524-528, vol. 16, No. 11).

Geoffrey Burnstock, et. al., P2 Purinergic Receptors: Modulation of Cell Function and Therapeutic Potential, The Journal of Pharmacology and Experimental Therapeutics (2000, pp. 862-869, vol. 295).

M. Schon, et. al., Pathogenic Function of IL-1 Beta in Psoriasiform Skin Lesions of Flaky Skin (fsn/fsn) Mice, Clin Exp. Immunol (2001, pp. 505-510, vol. 123).

Martin G. Schwacha, et. al., Macrophages and Post-Burn Immune Dysfunction, Elsevier Science Ltd (2003, pp. 1-14, vol. 29).

(Continued)

*Primary Examiner*—Laura L. Stockton
(74) *Attorney, Agent, or Firm*—Balaram Gupta

(57) ABSTRACT

The present invention relates to a novel series of 4,5-diphenyl-2-amino-4,5-dihydro-imidazole derivatives of the formula II:

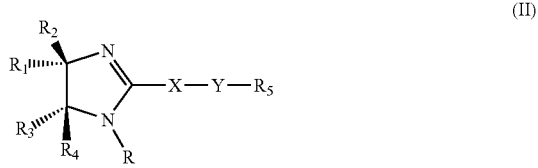

wherein R, $R_1$, $R_2$, $R_3$, $R_4$, $R_5$, X and Y are as defined herein. This invention also relates to methods of making these compounds. The compounds of this invention are P2X7 ion channel blockers and are therefore useful as pharmaceutical agents, especially in the treatment and/or prevention of a variety of diseases having an inflammatory component, including inflammatory bowel disease, rheumatoid arthritis and disease conditions associated with the central nervous system, such as stroke, Alzheimer's disease, etc.

10 Claims, No Drawings

OTHER PUBLICATIONS

Michael Williams, et. al., P2- Purinoceptors: Advances and Therapeutic Opportunities, Exp. Opin. Invest. Drugs (1995, pp. 925-934, vol. 4, No. 10).

Mike Solle, et. al., Altered Cytokine Production in Mice Lacking P2X7 Receptors, The Journal of Biological Chemistry (2001, pp. 125-132, vol. 276, No. 1).

Moriz Von Rauch, et. al., Effects of C2-Alkylation, N-Alkylation, and N,N'-Dialkylation on the Stability and Estrogen Receptor Interaction of (4R,5S)/(4S,5R)-4.5-Bis (4-Hydroxyphenyl)-2-Imidazolines, J. Med. Chem (2004, pp. 915-927, vol. 47).

Muller, W., et. al., Darstellung Neuer -Imidazolin-Derivate, Chemische Berichte (1951), vol. 84, pp. 71-76.

N. Kanda, et. al., The Skin Fungus-Induced Th1-and Th2-Related Cytokine, Chemokine and Prostraglandin E2 Production in Peripheral Blood Mononuclear Cells From Patients With Atopic Dermatitis and Psoriasis Vulgaris, Clin Exp Allergy (2002, pp. 1243-1250, vol. 32).

Richard J. Griffiths, et. al., ATP Induces the Release of IL-1 From LPS-Primed Cells In Vivo, The Journal of Immunology (1995, pp. 2821-2828, vol. 154).

S. Jeffrey Dixon, et. al., P2 Purinergic Receptors on Osteoblasts and Osteoclasts: Potential Targets for Drug Development, Drug Development Research (2000, pp. 187-200, vol. 49).

* cited by examiner

HETEROCYCLIC COMPOUNDS AS P2X7 ION CHANNEL BLOCKERS

This application is a division of U.S. application Ser. No. 10/896,166, filed Jul. 21, 2004, now allowed, which claims the benefit of U.S. Provisional Application No. 60/489,246, filed Jul. 21, 2003.

BACKGROUND OF THE INVENTION

1. Field of the Invention

The present invention relates to a series of dihydro-imidazole (also referred to herein as imidazoline) compounds. More specifically, the present invention relates to a novel series of 4,5-diphenyl-2-amino-4,5-dihydro-imidazole derivatives having certain geometric configuration. This invention also relates to methods of making these compounds. The compounds of this invention are P2X7 ion channel blockers and are therefore useful as pharmaceutical agents, especially in the treatment and/or prevention of a variety of diseases having an inflammatory component, including inflammatory bowel disease, rheumatoid arthritis and disease conditions associated with the central nervous system, such as stroke, Alzheimer's disease, etc.

2. Description of the Art

The P2X7 receptor, a ligand-gated ion channel, is present on a variety of cell types, mostly the ones believed to be involved in the inflammatory/immune process. In particular, macrophages, mast cells and lymphocytes (T and B) are known to have P2X7 receptor sites. Activation of the P2X7 receptor by extracellular nucleotides, particularly, adenosine triphosphate, leads to the release of interleukin-1β (IL-1β) and giant cell formation (macrophages/microglial cells), degranulation (mast cells) and L-selectin shedding (lymphocytes). P2X7 receptors are also located on antigen presenting cells (APC), keratinocytes, salivary acinar cells (parotid cells) and hepatocytes.

Thus, compounds exhibiting antagonistic activity at the P2X7 receptor site are expected to show anti-inflammatory activity and thereby exhibit therapeutic efficacy in diseases due to P2X7 receptor activation. The diseases that are implicated include rheumatoid arthritis, Alzheimer's disease, stroke and inflammatory bowel disease, psoriasis and various other diseases where an inflammatory component is present. It has also been reported that macrophages are also involved in the thermal injuries such as burns (see, e.g., Schwacha, Burns Vol. 29 pages 1-14 (2003)).

As noted above, the P2X7 protein is mainly localized to immune system cells such as macrophages and microglia, see for example, Collo et al., Neuropharmacology Vol. 36 pages 1277-1283 (1997). Also as noted above, activation of P2X7 results in the release of proinflammatory substances such as IL-1β and IL-18, see for example, Hlide et al., Journal of Neurochemistry Vol. 75 pages 965-972 (2000); Perregaux et al., Journal of Immunology Vol. 165 pages 4615-4623 (2000). This is further demonstrated by the fact that the mice lacking the P2X7 receptor are unable to release IL-1β via ATP stimulation. See Solle et al., Journal of Biological Chemistry Vol. 276 pages 125-132 (2001).

It has been reported that certain compounds act as P2X7 antagonists. For example, WO99/29660 and WO99/29661 disclose that certain adamantane derivatives exhibit P2X7 antagonistic activity having therapeutic efficacy in the treatment of rheumatoid arthritis and psoriasis. Similarly, WO99/29686 discloses that certain heterocyclic derivatives are P2X7 receptor antagonists and are useful as immunosuppressive agents and treating rheumatoid arthritis, asthma, septic shock and atherosclerosis. Finally, WO00/71529 discloses certain substituted phenyl compounds exhibiting immunosuppressing activity. All of the references described herein are incorporated herein by reference in their entirety.

It is an object of this invention to provide a novel series of compounds, which can modify the activity of P2X7 receptor and thus the release of the mediators of inflammation. It is further an object of this invention to provide a series of compounds that can treat or alleviate symptoms of inflammation caused due to the activation of P2X7 receptor. A still further object of this invention is to provide pharmaceutical compositions that are effective in the treatment or prevention of a variety of disease states, including the diseases associated with the central nervous system, such as stroke and Alzheimer's disease, inflammatory bowel disease, rheumatoid arthritis, and other diseases where an inflammatory component is present.

Other objects and further scope of the applicability of the present invention will become apparent from the detailed description to follow.

SUMMARY OF THE INVENTION

Thus in accordance with the practice of this invention there is provided a compound including enantiomers, stereoisomers, rotomers and tautomers of said compound and pharmaceutically acceptable salts, solvates or derivatives thereof. The compound of this invention has the general structure shown in formula II:

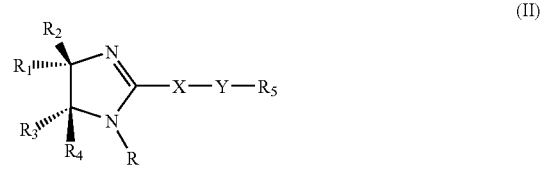

(II)

wherein:
R is hydrogen, $C_{1-6}$ alkyl, $C_{2-6}$ acyl, $C_{1-6}$ alkoxycarbonyl, or
$C_{6-12}$ aryloxycarbonyl;
$R_1$ and $R_3$ are the same or different and are each independently selected from:
  $C_{5-8}$ cycloalkyl,
  heterocyclyl, selected from morpholinyl, piperidinyl, piperazinyl, pyrrolidinyl, tetrahydrofuranyl, tetrahydropyranyl, tetrahydrothiophenyl or thiazolinyl,
  aryl, selected from phenyl, biphenyl or naphthyl,
  heteroaryl, selected from benzimidazolyl, benzofuranyl, benzoxazolyl, furanyl, imidazolyl, indolyl, isoxazolyl, isoquinolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl or triazolyl,
  aryl $C_{1-4}$ alkyl, $C_{5-8}$ cycloalkyl $C_{1-4}$ alkyl, heteroaryl $C_{1-4}$ alkyl, wherein aryl and heteroaryl are as defined above, and
  wherein $C_{5-8}$ cycloalkyl, aryl or heteroaryl is optionally substituted with one or more substituents selected from the group consisting of halogen, $C_{1-4}$ alkyl, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, $C_{1-4}$ alkoxy, $C_{1-4}$ thioalkyl, hydroxy, $C_{1-4}$ acyloxy, nitro, amino, $C_{1-4}$ alkylamino, $C_{1-4}$ dialkylamino, amino $C_{1-4}$ alkyl, $C_{1-4}$ alkylamino $C_{1-4}$ alkyl, $C_{1-4}$ dialkylamino $C_{1-4}$ alkyl, —CN, —CO$_2$H, —CO$_2$C$_{1-4}$ alkyl, phenyl, phenoxy and benzyloxy; or $R_1$ and $R_3$ taken together with the carbon atoms to which they are attached form a cyclopentane, cyclohexane, cycloheptane or cyclooctane;

$R_2$ and $R_4$ are the same or different and are each independently selected from:

hydrogen, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1;

$R_5$ is hydrogen, $C_{3-8}$ cycloalkyl, $C_{2-4}$ alkynyl, heterocyclyl, selected from morpholinyl, piperidinyl, piperazinyl, pyrrolidinyl, pyridinonyl, tetrahydrofuranyl, tetrahydropyranyl, dioxanyl, benzopyranyl, dihydrobenzodioxanyl, tetrahydrothiophenyl or thiazolinyl, aryl, selected from phenyl, biphenyl, naphthyl or anthracenyl, heteroaryl, selected from benzimidazolyl, benzofuranyl, benzoxazolyl, furanyl, imidazolyl, indolyl, isoxazolyl, isoquinolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl or triazolyl, wherein $C_{5-8}$ cycloalkyl, heterocyclyl, aryl or heteroaryl is optionally substituted with one or more substituents selected from the group consisting of halogen, $C_{1-4}$ alkyl, fluoroalkyl fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, $C_{1-4}$ alkoxy, $C_{1-4}$ thioalkyl, hydroxy, $C_{1-4}$ acyloxy, nitro, amino, $C_{1-4}$ alkylamino, $C_{1-4}$ dialkylamino, amino $C_{1-4}$ alkyl, $C_{1-4}$ alkylamino $C_{1-4}$ alkyl, $C_{1-4}$ dialkylamino $C_{1-4}$ alkyl, —CN, —CO$_2$H, —CO$_2$C$_{1-4}$ alkyl, phenyl, phenoxy and benzyloxy;

X—Y is —(CH$_2$)$_a$—Z—(CH$_2$)$_b$—, —(CH$_2$)$_a$—Z—(CH$_2$)$_b$—Z$^1$— or —NHCO—, wherein (CH$_2$) is optionally substituted with one or more groups selected independently from:

hydroxy, $C_{1-6}$ alkoxy, arylaminocarbonyloxy, $C_{3-8}$ cycloalkyl, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1, wherein said alkoxy or alkyl or fluoroalkyl is optionally substituted with at least one substituent selected from the group consisting of: hydroxy, —SH, $C_{1-4}$ alkoxy, $C_{1-4}$ thioalkyl, $C_{1-4}$ acyloxy, nitro, amino, $C_{1-4}$ alkylamino, $C_{1-4}$ dialkylamino, —CN, —CO$_2$H, and —CO$_2$C$_{1-4}$ alkyl, aryl;

Z and Z$^1$ are the same or different and are each independently selected from:

O, S, NR$_6$, NR$_6$—NR$_6$, —OCONH—, —NH—CO—NH—, —SO$_2$—NH—, —(NR$_6$)SO$_2$— or a bond, wherein R$_6$ is selected from:

hydrogen, $C_{1-6}$ alkoxy, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1, wherein said alkoxy or alkyl or fluoroalkyl is optionally substituted with at least one substituent selected from the group consisting of: hydroxy, —SH, $C_{1-4}$ alkoxy, $C_{1-4}$ thioalkyl, $C_{1-4}$ acyloxy, nitro, amino, $C_{1-4}$ alkylamino, $C_{1-4}$ dialkylamino, —CN, —CO$_2$H, and —CO$_2$C$_{1-4}$ alkyl, aryl;

a is an integer from 0 to 2 and b is an integer from 0 to 4 provided that sum of a and b is at least 1, and with the proviso that:

when X—Y is —(CH$_2$)$_a$—Z—(CH$_2$)$_b$—, where Z is S, R, R$_2$, and R$_4$ are hydrogen, R$_1$ and R$_3$ are phenyl or p-Cl-phenyl, a is 0 and b is 1, R$_5$ is not hydrogen or phenyl; and when X—Y is —(CH$_2$)$_a$—Z—(CH$_2$)$_b$—, where Z is a bond, R, R$_2$, and R$_4$ are hydrogen, R$_1$ and R$_3$ are phenyl, a is 0 and b is 1, R$_5$ is not hydrogen.

In another aspect of this invention there is also provided a method for the treatment of diseases selected from the group consisting of inflammatory bowel disease, rheumatoid arthritis, and diseases associated with central nervous system, which comprises administering to a patient in need of such treatment a therapeutically effective amount of a compound of the formula (II), as described herein, including the pharmaceutically acceptable salt thereof, optionally in combination with a pharmaceutically acceptable carrier. However, in this aspect of the invention all of the compounds encompassing the generic scope of the formula (II) are useful in the method of this invention.

In yet another aspect of this invention there is also provided a pharmaceutical composition comprising a compound or a pharmaceutically acceptable salt thereof in combination with at least one pharmaceutically acceptable carrier for treating diseases selected from the group consisting of inflammatory bowel disease, rheumatoid arthritis, and diseases associated with central nervous system, wherein said compound is of the formula (II) as described herein, including the pharmaceutically acceptable salt thereof, optionally in combination with a pharmaceutically acceptable carrier. Again, in this aspect of the invention all of the compounds encompassing the generic scope of the formula (II) are used in the composition of this invention.

DETAILED DESCRIPTION OF THE INVENTION

The terms as used herein have the following meanings:

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-4}$alkoxy", "$C_{1-4}$alkoxy $C_{1-4}$alkyl", "hydroxy$C_{1-4}$alkyl", "$C_{1-4}$alkylcarbonyl", "$C_{1-4}$ alkoxycarbonyl$C_{1-4}$alkyl", "$C_{1-4}$alkoxycarbonyl", "amino$C_{1-4}$alkyl", "$C_{1-4}$alkylamino", "$C_{1-4}$alkylcarbamoyl$C_{1-6}$ alkyl", "$C_{1-4}$dialkylcarbamoyl$C_{1-4}$alkyl" "mono- or di-$C_{1-4}$alkylamino$C_{1-4}$alkyl", "amino$C_{1-4}$alkylcarbonyl" "diphenyl$C_{1-4}$alkyl", "phenyl$C_{1-4}$alkyl", "phenylcarboyl $C_{1-4}$alkyl" and "phenoxy$C_{1-4}$alkyl" are to be construed accordingly.

As used herein, the expression "$C_{2-6}$alkenyl" includes ethenyl and straight-chained or branched propenyl, butenyl, pentenyl and hexenyl groups. Similarly, the expression "$C_{2-6}$ alkynyl" includes ethynyl and propynyl, and straight-chained or branched butynyl, pentynyl and hexynyl groups.

As used herein, the expression "$C_{1-6}$ perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$C_{1-6}$ perfluoroalkoxy", is to be construed accordingly.

As used herein, the expression "$C_{3-8}$cycloalkyl" means cyclopropyl, cyclobutyl, cyclopentyl, cyclohexyl, cycloheptyl and cyclooctyl.

As used herein, the expression "$C_{3-8}$cycloalkyl$C_{1-6}$alkyl" means that the $C_{3-8}$cycloalkyl as defined herein is further attached to $C_{1-6}$alkyl as defined herein. Representative examples include cyclopropylmethyl, 1-cyclobutylethyl, 2-cyclopentylpropyl, cyclohexylmethyl, 2-cycloheptylethyl and 2-cyclooctylbutyl and the like.

"Halogen" or "halo" means chloro, fluoro, bromo, and iodo.

As used herein, "patient" means a warm blooded animal, such as for example rat, mice, dogs, cats, guinea pigs, and primates such as humans.

As used herein, the expression "pharmaceutically acceptable carrier" means a non-toxic solvent, dispersant, excipient, adjuvant, or other material which is mixed with the compound of the present invention in order to permit the formation of a pharmaceutical composition, i.e., a dosage form capable of administration to the patient. One example of such a carrier is pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, hydrobromic acid, sulfuric acid, methanesulfonic acid, 2-hydroxyethanesulfonic acid, p-toluenesulfonic acid, fumaric acid, maleic acid, hydroxymaleic acid, malic acid, ascorbic acid, succinic acid, glutaric acid, acetic acid, salicylic acid, cinnamic acid, 2-phenoxybenzoic acid, hydroxybenzoic acid, phenylacetic acid, benzoic acid, oxalic acid, citric acid, tartaric acid, glycolic acid, lactic acid, pyruvic acid, malonic acid, carbonic acid or phosphoric acid. The acid metal salts such as sodium monohydrogen orthophosphate and potassium hydrogen sulfate can also be formed. Also, the salts so formed may present either as mono- or di-acid salts and can exist either as hydrated or can be substantially anhydrous. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The expression "stereoisomers" is a general term used for all isomers of the individual molecules that differ only in the orientation of their atoms in space. Typically it includes mirror image isomers that are usually formed due to at least one asymmetric center, (enantiomers). Where the compounds according to the invention possess two or more asymmetric centers, they may additionally exist as diastereoisomers, also certain individual molecules may exist as geometric isomers (cis/trans). It is to be understood that all such isomers and mixtures thereof in any proportion are encompassed within the scope of the present invention.

In a broad sense, the term "substituted" is contemplated to include all permissible substituents of organic compounds. In a few of the specific embodiments as disclosed herein, the term "substituted" means substituted with one or more substituents independently selected from the group consisting of $C_{1-6}$ alkyl, $C_{1-6}$ perfluoroalkyl, hydroxy, —$CO_2H$, an ester, an amide, $C_1$-$C_6$ alkoxy, $C_1$-$C_6$ perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

"Therapeutically effective amount" means an amount of the compound which is effective in treating the named disorder or condition.

In one aspect of this invention, there is disclosed a series of imidazoline compounds (also referred to herein as dihydro imidazole compounds) having certain therapeutic properties. In this aspect of the invention, the imidazoline compound includes all of the possible enantiomers, stereoisomers, rotomers and tautomers. The pharmaceutically acceptable salts, solvates or derivatives thereof are also included in this aspect of the invention. The imidazoline compound of this invention is having the general structure shown in formula I:

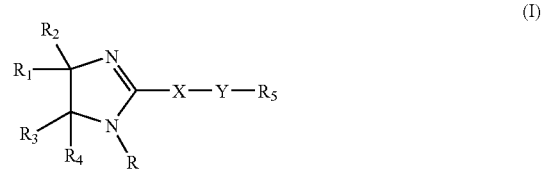

wherein:

R is hydrogen, $C_{1-6}$ alkyl, $C_{2-6}$ acyl, $C_{1-6}$ alkoxycarbonyl, or $C_{6-12}$ aryloxycarbonyl;

$R_1$ and $R_3$ are the same or different and are each independently selected from:

$C_{5-8}$ cycloalkyl, heterocyclyl, selected from morpholinyl, piperidinyl, piperazinyl, pyrrolidinyl, tetrahydrofuranyl, tetrahydropyranyl, tetrahydrothiophenyl or thiazolinyl, aryl, selected from phenyl, biphenyl or naphthyl, heteroaryl, selected from benzimidazolyl, benzofuranyl, benzoxazolyl, furanyl, imidazolyl, indolyl, isoxazolyl, isoquinolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl or triazolyl, aryl $C_{1-4}$ alkyl, $C_{5-8}$ cycloalkyl $C_{1-4}$ alkyl, heteroaryl $C_{1-4}$ alkyl, wherein aryl and heteroaryl are as defined above, and wherein $C_{5-8}$ cycloalkyl, aryl or heteroaryl is optionally substituted with one or more substituents selected from the group consisting of halogen, $C_{1-4}$ alkyl, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, $C_{1-4}$ alkoxy, $C_{1-4}$ thioalkyl, hydroxy, $C_{1-4}$ acyloxy, nitro, amino, $C_{1-4}$ alkylamino, $C_{1-4}$ dialkylamino, amino $C_{1-4}$ alkyl, $C_{1-4}$ alkylamino $C_{1-4}$ alkyl, $C_{1-4}$ dialkylamino $C_{1-4}$ alkyl, —CN, —$CO_2H$, —$CO_2C_{1-4}$ alkyl, phenyl, phenoxy and benzyloxy; or $R_1$ and $R_3$ taken together with the carbon atoms to which they are attached form a cyclopentane, cyclohexane, cycloheptane or cyclooctane;

$R_2$ and $R_4$ are the same or different and are each independently selected from:

hydrogen, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1;

$R_5$ is hydrogen, $C_{3-8}$ cycloalkyl, $C_{2-4}$ alkynyl, heterocyclyl, selected from morpholinyl, piperidinyl, piperazinyl, pyrrolidinyl, pyridinonyl, tetrahydrofuranyl, tetrahydropyranyl, dioxanyl, benzopyranyl, dihydrobenzodioxanyl, tetrahydrothiophenyl or thiazolinyl, aryl, selected from phenyl, biphenyl, naphthyl or anthracenyl, heteroaryl, selected from benzimidazolyl, benzofuranyl, benzoxazolyl, furanyl, imidazolyl, indolyl, isoxazolyl, isoquinolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl or triazolyl, wherein $C_{5-8}$ cycloalkyl, heterocyclyl, aryl or heteroaryl is optionally substituted with one or more substituents selected from the group consisting of halogen, $C_{1-4}$ alkyl, fluoroalkyl fluoroalkoxy of the formula $C_nH_xF_y$, or $OC_nH_xF_y$ wherein n is an integer from 1 to 4, x is an integer from 0 to 8, y is an integer from 1 to 9 and sum of x and y is 2n+1, $C_{1-4}$ alkoxy, $C_{1-4}$ thioalkyl, hydroxy, $C_{1-4}$ acyloxy, nitro, amino, $C_{1-4}$ alkylamino, $C_{1-4}$ dialkylamino, amino $C_{1-4}$ alkyl, $C_{1-4}$ alkylamino $C_{1-4}$ alkyl, $C_{1-4}$ dialkylamino $C_{1-4}$ alkyl, —CN, —$CO_2H$, —$CO_2C_{1-4}$ alkyl, phenyl, phenoxy and benzyloxy;

X—Y is —$(CH_2)_a$—Z—$(CH_2)_b$—, —$(CH_2)_a$—Z—$(CH_2)_b$—$Z^1$— or —NHCO—, wherein ($CH_2$) is optionally substituted with one or more groups selected independently from:

hydroxy, $C_{1-6}$ alkoxy, arylaminocarbonyloxy, $C_{3-8}$ cycloalkyl, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1, wherein said alkoxy or alkyl or fluoroalkyl is optionally substituted with at least one substituent selected from the group consisting of: hydroxy, —SH, $C_{1-4}$ alkoxy, $C_{1-4}$ thioalkyl, $C_{1-4}$ acyloxy, nitro, amino, $C_{1-4}$ alkylamino, $C_{1-4}$ dialkylamino, —CN, —$CO_2H$, and —$CO_2C_{1-4}$ alkyl, aryl;

Z and $Z^1$ are the same or different and are each independently selected from:

O, S, $NR_6$, $NR_6$—$NR_6$, —OCONH—, —NH—CO—NH—, —$SO_2$—NH—, —$(NR_6)SO_2$— or a bond, wherein $R_6$ is selected from:

hydrogen, $C_{1-6}$ alkoxy, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1, wherein said alkoxy or alkyl or fluoroalkyl is optionally substituted with at least one substituent selected from the group consisting of: hydroxy, —SH, $C_{1-4}$ alkoxy, $C_{1-4}$ thioalkyl, $C_{1-4}$ acyloxy, nitro, amino, $C_{1-4}$ alkylamino, $C_{1-4}$ dialkylamino, —CN, —$CO_2H$, and —$CO_2C_{1-4}$ alkyl, aryl;

a is an integer from 0 to 2 and b is an integer from 0 to 4 provided that sum of a and b is at least 1, and with the proviso that:

when X—Y is —$(CH_2)_a$—Z—$(CH_2)_b$—, where Z is S, R, $R_2$, and $R_4$ are hydrogen, $R_1$ and $R_3$ are phenyl or p-Cl-phenyl, a is 0 and b is 1, $R_5$ is not hydrogen or phenyl; and when X—Y is —$(CH_2)_a$—Z—$(CH_2)_b$—, where Z is a bond, R, $R_2$, and $R_4$ are hydrogen, $R_1$ and $R_3$ are phenyl, a is 0 and b is 1, $R_5$ is not hydrogen.

In a preferred embodiment of this invention, there is disclosed a compound including enantiomers, stereoisomers, rotomers and tautomers of said compound and pharmaceutically acceptable salts, solvates or derivatives thereof. The compound of this embodiment is having the general structure shown in formula II:

(II)

$$R_1\text{''''} \overset{R_2}{\underset{R_3\text{''''}}{\diagdown}} \overset{N}{\underset{R_4}{\diagup}} \text{—X—Y—}R_5$$

wherein:

R is hydrogen, $C_{1-6}$ alkyl, $C_{2-6}$ acyl, $C_{1-6}$ alkoxycarbonyl, or $C_{6-12}$ aryloxycarbonyl;

$R_1$ and $R_3$ are the same or different and are each independently selected from:

$C_{5-8}$ cycloalkyl, heterocyclyl, selected from morpholinyl, piperidinyl, piperazinyl, pyrrolidinyl, tetrahydrofuranyl, tetrahydropyranyl, tetrahydrothiophenyl or thiazolinyl, aryl, selected from phenyl, biphenyl or naphthyl, heteroaryl, selected from benzimidazolyl, benzofuranyl, benzoxazolyl, furanyl, imidazolyl, indolyl, isoxazolyl, isoquinolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl or triazolyl, aryl $C_{1-4}$ alkyl, $C_{5-8}$ cycloalkyl $C_{1-4}$ alkyl, heteroaryl $C_{1-4}$ alkyl, wherein aryl and heteroaryl are as defined above, and wherein $C_{5-8}$ cycloalkyl, aryl or heteroaryl is optionally substituted with one or more substituents selected from the group consisting of halogen, $C_{1-4}$ alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, $C_{1-4}$ alkoxy, $C_{1-4}$ thioalkyl, hydroxy, $C_{1-4}$ acyloxy, nitro, amino, $C_{1-4}$ alkylamino, $C_{1-4}$ dialkylamino, amino $C_{1-4}$ alkyl, $C_{1-4}$ alkylamino $C_{1-4}$ alkyl, $C_{1-4}$ dialkylamino $C_{1-4}$ alkyl, —CN, —$CO_2H$, —$CO_2C_{1-4}$ alkyl, phenyl, phenoxy and benzyloxy; or $R_1$ and $R_3$ taken together with the carbon atoms to which they are attached form a cyclopentane, cyclohexane, cycloheptane or cyclooctane;

$R_2$ and $R_4$ are the same or different and are each independently selected from:

hydrogen, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1;

$R_5$ is hydrogen, $C_{3-8}$ cycloalkyl, $C_{2-4}$ alkynyl, heterocyclyl, selected from morpholinyl, piperidinyl, piperazinyl, pyrrolidinyl, pyridinonyl, tetrahydrofuranyl, tetrahydropyranyl, dioxanyl, benzopyranyl, dihydrobenzodioxanyl, tetrahydrothiophenyl or thiazolinyl, aryl, selected from phenyl, biphenyl, naphthyl or anthracenyl, heteroaryl, selected from benzimidazolyl, benzofuranyl, benzoxazolyl, furanyl, imidazolyl, indolyl, isoxazolyl, isoquinolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl or triazolyl, wherein $C_{5-8}$ cycloalkyl, heterocyclyl, aryl or heteroaryl is optionally substituted with one or more substituents selected from the group consisting of halogen, $C_{1-4}$ alkyl, fluoroalkyl fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, $C_{1-4}$ alkoxy, $C_{1-4}$ thioalkyl, hydroxy, $C_{1-4}$ acyloxy, nitro, amino, $C_{1-4}$ alkylamino, $C_{1-4}$ dialkylamino, amino $C_{1-4}$ alkyl, $C_{1-4}$ alkylamino $C_{1-4}$ alkyl, $C_{1-4}$ dialkylamino $C_{1-4}$ alkyl, —CN, —$CO_2H$, —$CO_2C_{1-4}$ alkyl, phenyl, phenoxy and benzyloxy;

X—Y is —$(CH_2)_a$—Z—$(CH_2)_b$—, —$(CH_2)_a$—Z—$(CH_2)_b$—$Z^1$— or —NHCO—, wherein ($CH_2$) is optionally substituted with one or more groups selected independently from:

hydroxy, $C_{1-6}$ alkoxy, arylaminocarbonyloxy, $C_{3-8}$ cycloalkyl, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1, wherein said alkoxy or alkyl or fluoroalkyl is optionally substituted with at least one substituent selected from the group consisting of: hydroxy, —SH, $C_{1-4}$ alkoxy, $C_{1-4}$ thioalkyl, $C_{1-4}$ acyloxy, nitro, amino, $C_{1-4}$ alkylamino, $C_{1-4}$ dialkylamino, —CN, —$CO_2H$, and —$CO_2C_{1-4}$ alkyl, aryl;

Z and $Z^1$ are the same or different and are each independently selected from:

O, S, $NR_6$, $NR_6$—$NR_6$, —OCONH—, —NH—CO—NH—, —$SO_2$—NH—, —($NR_6$)$SO_2$— or a bond, wherein $R_6$ is selected from:

hydrogen, $C_{1-6}$ alkoxy, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1, wherein said alkoxy or alkyl or fluoroalkyl is optionally substituted with at least one substituent selected from the group consisting of: hydroxy, —SH, $C_{1-4}$ alkoxy, $C_{1-4}$ thioalkyl, $C_{1-4}$ acyloxy, nitro, amino, $C_{1-4}$ alkylamino, $C_{1-4}$ dialkylamino, —CN, —$CO_2H$, and —$CO_2C_{1-4}$ alkyl, aryl;

a is an integer from 0 to 2 and b is an integer from 0 to 4 provided that sum of a and b is at least 1, and with the proviso that:

when X—Y is —$(CH_2)_a$—Z—$(CH_2)_b$—, where Z is S, R, $R_2$ and $R_4$ are hydrogen, $R_1$ and $R_3$ are phenyl or p-Cl-phenyl, a is 0 and b is 1, $R_5$ is not hydrogen or phenyl; and when X—Y is —$(CH_2)_a$—Z—$(CH_2)_b$—, where Z is a bond, R, $R_2$, and $R_4$ are hydrogen, $R_1$ and $R_3$ are phenyl, a is 0 and b is 1, $R_5$ is not hydrogen.

In one embodiment of this invention the compound of formula (II) having X—Y as —$(CH_2)_a$—Z—$(CH_2)_b$— in which Z is $NR_6$, wherein $R_6$ is hydrogen or methyl, and a is 0 or 1 and b is 1 is preferred. In this embodiment of the invention the compound of formula (II) further having $R_1$ and $R_3$ as phenyl, $R_4$ as hydrogen and $R_2$ as hydrogen or methyl is particularly preferred. Thus, the compound in accordance with this preferred embodiment may generically be represented by the formula (III):

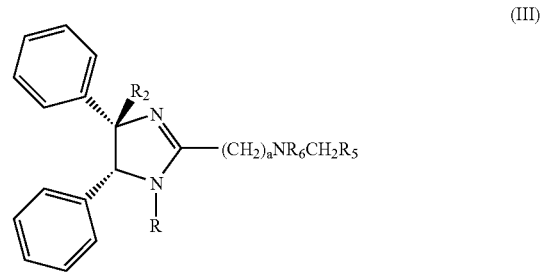

In formula (III), as noted herein $R_2$ and $R_6$ are hydrogen or methyl, a is 0 or 1, R and $R_5$ are as defined above. Specific compounds in accordance with this embodiment of the invention are listed below:

[(cis-4,5-diphenyl-4,5-dihydro-1H-imidazol-2-yl)methyl] benzylamine, cis-4,5-diphenyl-2-benzylamino-4,5-dihydro-1H-imidazole, cis-4,5-diphenyl-2-(3,4,5-trifluorobenzyl)amino-4,5-dihydro-1H-imidazole, cis-4,5-diphenyl-2-(2,4-difluorobenzyl)amino-4,5-dihydro-1H-imidazole, cis-4,5-diphenyl-2-(2,6-difluorobenzyl)amino-4,5-dihydro-1H-imidazole, cis-4,5-diphenyl-2-[(3,4-difluorobenzyl)amino]-4,5-dihydro-1H-imidazole, cis-4,5-diphenyl-2-(3,5-difluorobenzyl)amino-4,5-dihydro-1H-imidazole, cis-4,5-diphenyl-2-(2-fluorobenzyl)amino-4,5-dihydro-1H-imidazole, cis-4,5-diphenyl-2-(3-fluorobenzyl)amino-4,5-dihydro-1H-imidazole, cis-4,5-diphenyl-2-(4-fluorobenzyl)amino-4,5-dihydro-1H-imidazole, cis-4,5-diphenyl-4-methyl-2-(4-fluorobenzyl)amino-4,5-dihydro-1H-imidazole, cis-4,5-diphenyl-2-(2-chloro-3-fluorobenzyl)amino-4,5-dihydro-1H-imidazole, cis-4,5-diphenyl-2-(2-chloro-4-fluorobenzyl)amino-4,5-dihydro-1H-imidazole, cis-4,5-diphenyl-2-(4-chloro-2-fluorobenzyl)amino-4,5-dihydro-1H-imidazole, cis-4,5-diphenyl-2-(2-chlorobenzyl)amino-4,5-dihydro-1H-imidazole, cis-4,5-diphenyl-2-(3-chlorobenzyl)amino-4,5-dihydro-1H-imidazole, cis-4,5-diphenyl-2-(4-chlorobenzyl)amino-4,5-dihydro-1H-imidazole, cis-4,5-diphenyl-2-(2,4-dichlorobenzyl)amino-4,5-dihydro-1H-imidazole, cis-4,5-diphenyl-2-(3,4-dichlorobenzyl)amino-4,5-dihydro-1H-imidazole,
cis-4,5-diphenyl-2-(2-bromobenzyl)amino-4,5-dihydro-1H-imidazole,
cis-4,5-diphenyl-2-(3-bromobenzyl)amino-4,5-dihydro-1H-imidazole,
cis-4,5-diphenyl-2-(2-trifluoromethylbenzyl)amino-4,5-dihydro-1H-imidazole,
cis-4,5-diphenyl-2-(4-trifluoromethylbenzyl)amino-4,5-dihydro-1H-imidazole,
cis-4,5-diphenyl-2-(2-methoxybenzyl)amino-4,5-dihydro-1H-imidazole,
cis-4,5-diphenyl-2-(3-methoxybenzyl)amino-4,5-dihydro-1H-imidazole,
cis-4,5-diphenyl-2-(4-methoxybenzyl)amino-4,5-dihydro-1H-imidazole,
cis-4,5-diphenyl-2-(3,4,5-trimethoxybenzyl)amino-4,5-dihydro-1H-imidazole,
cis-4,5-diphenyl-2-(2-methylbenzyl)amino-4,5-dihydro-1H-imidazole,
cis-4,5-diphenyl-2-(3-methylbenzyl)amino-4,5-dihydro-1H-imidazole,
cis-4,5-diphenyl-2-(4-methylbenzyl)amino-4,5-dihydro-1H-imidazole,
cis-4,5-diphenyl-2-(cyclohexylmethyl)amino-4,5-dihydro-1H-imidazole,
cis-4,5-diphenyl-2-(N-benzyl, N-methyl)amino-4,5-dihydro-1H-imidazole, and
2-(4-fluorobenzylamino)-cis-4,5-diphenyl-4,5-dihydro-imidazole-1-carboxylic acid phenyl ester In an additional feature of the above mentioned embodiment, the phenyl moieties on the cis-4,5-diphenyl-imidazoline compounds of formula (III) are substituted each with 1 to 3 halogens and R group is hydrogen. In this embodiment the suitable halogens are fluorine, chlorine or bromine. Thus, in accordance with this aspect of the embodiment of this invention the compound is generically represented by formula (IV):

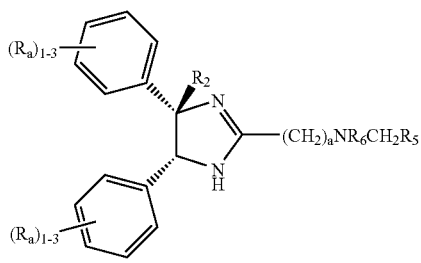

(IV)

As noted above, in formula (IV), $R_a$ is halogen, $R_2$ and $R_6$ are hydrogen or methyl and a is 0 or 1, and $R_5$ is as defined above. Specific compounds encompassing this embodiment of this invention are enumerated below:
cis-4,5-bis(2-fluorophenyl)-2-benzylamino-4,5-dihydro-1H-imidazole,
cis-4,5-bis(2-fluorophenyl)-2-(3-methylbenzyl)amino-4,5-dihydro-1H-imidazole,
cis-4,5-bis(2-fluorophenyl)-2-(4-fluorobenzyl)amino-4,5-dihydro-1H-imidazole,
cis-4,5-bis(2-fluorophenyl)-2-(3,4-difluorobenzyl)amino-4,5-dihydro-1H-imidazole,
cis-4,5-bis(3-fluorophenyl)-2-benzylamino-4,5-dihydro-1H-imidazole,
cis-4,5-bis(3-fluorophenyl)-2-(3-fluorobenzyl)amino-4,5-dihydro-1H-imidazole,
cis-4,5-bis(3-fluorophenyl)-2-(4-fluorobenzyl)amino-4,5-dihydro-1H-imidazole,
cis-4,5-bis(3-fluorophenyl)-2-(3,4-difluorobenzyl)amino-4,5-dihydro-1H-imidazole,
cis-4,5-bis(3-fluorophenyl)-4-methyl-2-(3-fluorobenzyl)amino-4,5-dihydro-1H-imidazole,
cis-4,5-bis(3-fluorophenyl)-4-methyl-2-(4-fluorobenzyl)amino-4,5-dihydro-1H-imidazole,
cis-4,5-bis(4-fluorophenyl)-2-benzylamino-4,5-dihydro-1H-imidazole,
cis-4,5-bis(4-fluorophenyl)-2-(4-fluorobenzyl)amino-4,5-dihydro-1H-imidazole,
cis-4,5-bis(4-fluorophenyl)-2-(3,4-difluorobenzyl)amino-4,5-dihydro-1H-imidazole,
cis-4,5-bis(4-fluorophenyl)-4-methyl-2-(3-fluorobenzyl)amino-4,5-dihydro-1H-imidazole,
cis-4,5-bis(4-fluorophenyl)-4-methyl-2-(4-fluorobenzyl)amino-4,5-dihydro-1H-imidazole,
cis-4,5-bis(2-chlorophenyl)-2-benzylamino-4,5-dihydro-1H-imidazole,
cis-4,5-bis(2-chlorophenyl)-2-(3-fluorobenzyl)amino-4,5-dihydro-1H-imidazole,
cis-4,5-bis(2-chlorophenyl)-2-(4-fluorobenzyl)amino-4,5-dihydro-1H-imidazole,
cis-4,5-bis(2-chlorophenyl)-2-(3,4-difluorobenzyl)amino-4,5-dihydro-1H-imidazole,
cis-4,5-bis(3-chlorophenyl)-2-benzylamino-4,5-dihydro-1H-imidazole,
cis-4,5-bis(3-chlorophenyl)-2-(4-fluorobenzyl)amino-4,5-dihydro-1H-imidazole,
cis-4,5-bis(3-chlorophenyl)-2-(3,4-difluorobenzyl)amino-4,5-dihydro-1H-imidazole,
cis-4,5-bis(4-chlorophenyl)-2-benzylamino-4,5-dihydro-1H-imidazole,
cis-4,5-bis(4-chlorophenyl)-2-(3-fluorobenzyl)amino-4,5-dihydro-1H-imidazole,
cis-4,5-bis(4-chlorophenyl)-2-(3,4-difluorobenzyl)amino-4,5-dihydro-1H-imidazole,
cis-4,5-bis(2-bromophenyl)-2-(3-fluorobenzyl)amino-4,5-dihydro-1H-imidazole,
cis-4,5-bis(2-bromophenyl)-2-(4-fluorobenzyl)amino-4,5-dihydro-1H-imidazole, and
cis-4,5-bis(2-bromophenyl)-2-(3,4-difluorobenzyl)amino-4,5-dihydro-1H-imidazole.

In yet an additional feature of the above mentioned embodiment of this invention the phenyl moieties on the cis-4,5-diphenyl-imidazoline compounds of formula (III) are substituted each with 1 to 3 $C_{1-4}$ alkyl, and R is hydrogen. In this embodiment, the preferred $C_{1-4}$ alkyl is methyl. Thus, in accordance with this embodiment of this invention the specific compounds are as listed below:
cis-4,5-bis(2-methylphenyl)-2-benzylamino-4,5-dihydro-1H-imidazole,
cis-4,5-bis(2-methylphenyl)-2-(3-fluorobenzyl)amino-4,5-dihydro-1H-imidazole,
cis-4,5-bis(2-methylphenyl)-2-(4-fluorobenzyl)amino-4,5-dihydro-1H-imidazole,
cis-4,5-bis(2-methylphenyl)-2-(3,4-difluorobenzyl)amino-4,5-dihydro-1H-imidazole,
cis-4,5-bis(3-methylphenyl)-2-benzylamino-4,5-dihydro-1H-imidazole,
cis-4,5-bis(3-methylphenyl)-2-(3-fluorobenzyl)amino-4,5-dihydro-1H-imidazole,
cis-4,5-bis(3-methylphenyl)-2-(4-fluorobenzyl)amino-4,5-dihydro-1H-imidazole, cis-4,5-bis(3-methylphenyl)-2-(3,4-difluorobenzyl)amino-4,5-dihydro-1H-imidazole,
cis-4,5-bis(4-methylphenyl)-2-benzylamino-4,5-dihydro-1H-imidazole,
cis-4,5-bis(4-methylphenyl)-2-(3-fluorobenzyl)amino-4,5-dihydro-1H-imidazole,
cis-4,5-bis(4-methylphenyl)-2-(4-fluorobenzyl)amino-4,5-dihydro-1H-imidazole, and
cis-4,5-bis(4-methylphenyl)-2-(3,4-difluorobenzyl)amino-4,5-dihydro-1H-imidazole.

In another embodiment of this invention, the compound in which $R_1$ and $R_3$ taken together with the carbon atoms to which they are attached form a cyclohexane ring. In this embodiment R, $R_2$ and $R_4$ are hydrogen. Thus, in accordance with this aspect of the embodiment of this invention the compound is generically represented by formula (V):

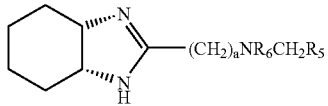

(V)

As noted above, in formula (V), $R_6$ is hydrogen or methyl and a is 0 or 1, and $R_5$ is as defined above. Specific compounds encompassing this embodiment of this invention are enumerated below:
(cis-3a,4,5,6,7,7a-hexahydro-1H-benzimidazol-2-yl)-benzylamine,
(cis-3a,4,5,6,7,7a-hexahydro-1H-benzimidazol-2-yl)-(3-fluorobenzyl)amine,
(cis-3a,4,5,6,7,7a-hexahydro-1H-benzimidazol-2-yl)-(4-fluorobenzyl)amine, and
(cis-3a,4,5,6,7,7a-hexahydro-1H-benzimidazol-2-yl)-(3,4-difluorobenzyl)amine.

In another embodiment of this invention the compound of formula (II) having X—Y as —$(CH_2)_a$—Z—$(CH_2)_b$— in which Z is $NR_6$, wherein $R_6$ is hydrogen, and a is 0 and b is 2 is preferred. In this embodiment of the invention the compound of formula (II) further having $R_1$ and $R_3$ as phenyl, R, $R_2$ and $R_4$ as hydrogen is particularly preferred. Thus, the compound in accordance with this embodiment may generically be represented by the formula (VI):

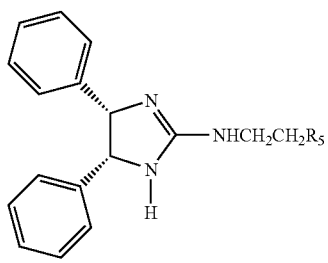

(VI)

In formula (VI), $R_5$ is as defined above. Specific compounds in accordance with this embodiment of this invention are listed below:
cis-4,5-diphenyl-2-[(2-phenyl)ethyl]amino-4,5-dihydro-1H-imidazole,
cis-4,5-diphenyl-2-[2-(2-fluorophenyl)ethyl]amino-4,5-dihydro-1H-imidazole, and
cis-4,5-diphenyl-2-[2-(4-fluorophenyl)ethylamino]-4,5-dihydro-1H-imidazole.

In yet another embodiment of this invention, the compound of formula (II) having X—Y as —$(CH_2)_a$—Z—$(CH_2)_b$— in which Z is a bond, and a is 0 and b is 2 to 4 is preferred. In this embodiment, the methylene group, $CH_2$, is optionally substituted with hydroxy, methyl or phenyl. Additionally, in this embodiment of the invention, the compound of formula (II) further having $R_1$ and $R_3$ as phenyl or pyridyl, wherein phenyl is optionally substituted with fluorine, and R and $R_4$ as hydrogen and $R_2$ as hydrogen or methyl is particularly preferred. Thus, the compound in accordance with this embodiment may generically be represented by the formula (VII):

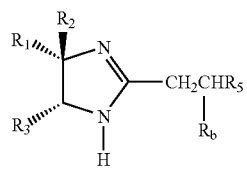

(VII)

In formula (VII), as noted above, $R_b$ is either hydrogen, hydroxy, methyl or phenyl, $R_1$ and $R_3$ are independently phenyl, pyridyl or phenyl substituted with fluorine, $R_2$ is hydrogen or methyl, and $R_5$ is as defined above. Specific compounds in accordance with this embodiment of this invention are listed below:
cis-4,5-diphenyl-2-(2-phenylethyl)-4,5-dihydro-1H-imidazole,
cis-4,5-diphenyl-2-(2-(2-fluorophenyl)ethyl)-4,5-dihydro-1H-imidazole,
cis-4,5-diphenyl-2-(2-(3-fluorophenyl)ethyl)-4,5-dihydro-1H-imidazole,
cis-4,5-diphenyl-2-(2-(4-fluorophenyl)ethyl)-4,5-dihydro-1H-imidazole,
cis-4,5-diphenyl-2-(2-(2-chlorophenylethyl)-4,5-dihydro-1H-imidazole,
cis-4,5-diphenyl-2-(2-(3-chlorophenylethyl)-4,5-dihydro-1H-imidazole,
cis-4,5-diphenyl-2-(2-(4-chlorophenylethyl)-4,5-dihydro-1H-imidazole,
cis-4,5-diphenyl-2-(2-(3,4-dichlorophenylethyl)-4,5-dihydro-1H-imidazole,
cis-4,5-diphenyl-4-methyl-2-(2-phenylethyl)-4,5-dihydro-1H-imidazole,
2-(cis-4,5-diphenyl-4,5-dihydro-1H-imidazol-2-yl)-1-phenylethan-1-ol,
cis-4,5-diphenyl-2-(2-(2-methoxyphenyl)ethyl)-4,5-dihydro-1H-imidazole,
cis-4,5-diphenyl-2-(2-(4-methoxyphenyl)ethyl)-4,5-dihydro-1H-imidazole,
cis-4,5-diphenyl-2-(2-(3,4-dimethoxyphenyl)ethyl)-4,5-dihydro-1H-imidazole,
cis-4,5-diphenyl-2-(2-(2-methylphenyl)ethyl)-4,5-dihydro-1H-imidazole,
cis-4,5-diphenyl-2-(2-(3-methylphenyl)ethyl)-4,5-dihydro-1H-imidazole,
cis-4,5-diphenyl-2-(2-(4-methylphenyl)ethyl)-4,5-dihydro-1H-imidazole,
cis-4,5-diphenyl-2-(2-((2S)-phenyl)propyl)-4,5-dihydro-1H-imidazole,
cis-4,5-diphenyl-2-(2-(3,5-difluorophenyl)ethyl)-4,5-dihydro-1H-imidazole, cis-4,5-diphenyl-2-(2-(4-trifluoromethylphenyl)ethyl)-4,5-dihydro-1H-imidazole,
cis-4,5-diphenyl-2-[2-(2-pyridyl)ethyl)-4,5-dihydro-1H-imidazole,
cis-4,5-diphenyl-4-methyl-2-[2-(2-pyridyl)ethyl)-4,5-dihydro-1H-imidazole,
cis-4,5-diphenyl-2-[2-(3-pyridyl)ethyl)-4,5-dihydro-1H-imidazole,
cis-4,5-diphenyl-2-[2-(4-tetrahydropyranyl)ethyl)-4,5-dihydro-1H-imidazole,
cis-4,5-bis(3-fluorophenyl)-2-[2-(2-fluorophenyl)ethyl]-4,5-dihydro-1H-imidazole,
cis-4,5-bis(3-fluorophenyl)-2-[2-(3-fluorophenyl)ethyl]-4,5-dihydro-1H-imidazole,
cis-4,5-bis(3-fluorophenyl)-2-[2-(4-fluorophenyl)ethyl]-4,5-dihydro-1H-imidazole,
cis-4,5-bis(3-fluorophenyl)-2-[2-(3,4-difluorophenyl)ethyl]-4,5-dihydro-1H-imidazole,
cis-4,5-bis(3-fluorophenyl)-2-[2-(2-chlorophenyl)ethyl]-4,5-dihydro-1H-imidazole,
cis-4,5-bis(3-fluorophenyl)-2-[2-(3,4-dichlorophenyl)ethyl]-4,5-dihydro-1H-imidazole,
cis-4,5-bis(3-fluorophenyl)-2-(2-phenylethyl)-4,5-dihydro-1H-imidazole,
cis-4,5-bis(3-fluorophenyl)-2-[2-(2-methylphenyl)ethyl]-4,5-dihydro-1H-imidazole,
cis-4,5-bis(3-fluorophenyl)-2-[2-(3-methylphenyl)ethyl]-4,5-dihydro-1H-imidazole,
cis-4,5-bis(3-fluorophenyl)-2-[2-(4-methylphenyl)ethyl]-4,5-dihydro-1H-imidazole,
cis-4,5-bis(3-fluorophenyl)-2-[2-(4-trifluoromethylphenyl)ethyl]-4,5-dihydro-1H-imidazole,
cis-4,5-bis(3-fluorophenyl)-2-[2-(3,4-ditrifluoromethylphenyl)ethyl]-4,5-dihydro-1H-imidazole,
cis-4,5-bis(3-fluorophenyl)-2-[2-(2-methoxyphenyl)ethyl]-4,5-dihydro-1H-imidazole,
cis-4,5-bis(3-fluorophenyl)-2-[2-(4-methoxyphenyl)ethyl]-4,5-dihydro-1H-imidazole,
cis-4,5-bis(3-fluorophenyl)-2-[2-(3,4-dimethoxyphenyl)ethyl]-4,5-dihydro-1H-imidazole,
cis-4,5-bis(3-fluorophenyl)-4-methyl-2-(2-phenylethyl)-4,5-dihydro-1H-imidazole,
cis-4,5-bis(3-fluorophenyl)-2-[(2-thiophen-2-yl)ethyl]-4,5-dihydro-1H-imidazole,
cis-4,5-bis(4-fluorophenyl)-2-(2-phenylethyl)-4,5-dihydro-1H-imidazole,
2-phenethyl-cis-4-phenyl-5-(pyridin-3-yl)-4,5-dihydro-1H-imidazole,
2-[2-methyl-(2S)-phenyl)-propyl]-cis-4,5-diphenyl-4,5-dihydro-1H-imidazole trifluoroacetate,
2-[2,2-diphenylethyl]-cis-4,5-diphenyl-4,5-dihydro-1H-imidazole trifluoroacetate,
2-[1-methyl-2-phenylethyl]-cis-4,5-diphenyl-4,5-dihydro-1H-imidazole trifluoroacetate,
2-[3-phenyl-propyl]-cis-4,5-diphenyl-4,5-dihydro-1H-imidazole trifluoroacetate, and
2-[4-phenyl-butyl]-cis-4,5-diphenyl-4,5-dihydro-1H-imidazole trifluoroacetate.

In yet an additional embodiment of this invention, the compound of formula (II) having X—Y as —$(CH_2)_a$—Z—$(CH_2)_b$— in which Z is a bond, and a is 0 and b is 1 is preferred. In this embodiment, the methylene group, $CH_2$, is optionally substituted with hydroxy, methoxy, methyl or phenylaminocarbonyloxy. Furthermore, the ($CH_2$) may optionally be substituted with at least two carbon atoms all of which taken together form a cyclic ring. For instance, when $CH_2$ is substituted with two carbon atoms all of which together form a cyclopropyl ring. Similarly, when the $CH_2$ group is substituted with three carbon atoms all of which together can form a cyclobutyl ring, and so on. The cyclopropyl group is particularly preferred.

Additionally, in this embodiment of the invention, the compound of formula (II) further having $R_1$ and $R_3$ as phenyl or pyridyl, wherein phenyl is optionally substituted with fluorine, and R and $R_4$ as hydrogen and $R_2$ as either hydrogen or methyl is particularly preferred. Thus, the compound in accordance with this embodiment may generically be represented by the formula (VIII):

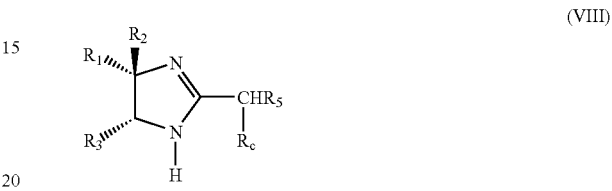

(VIII)

In formula (VIII), as noted above, $R_c$ is either hydrogen, hydroxy, methoxy methyl or phenylaminocarbonyloxy, $R_1$ and $R_3$ are independently phenyl, pyridyl or phenyl substituted with fluorine, $R_2$ is hydrogen or methyl, and $R_5$ is as defined above. In addition, as also noted above, when $R_c$ is a carbon chain of two or more carbon atoms, it can form a cyclic ring with the carbon atom to which it is attached. Thus, when $R_c$ is a two carbon chain it can form a cyclopropyl ring with the carbon to which it is attached. A generic structure of this type may be represented by the formula VIIIA:

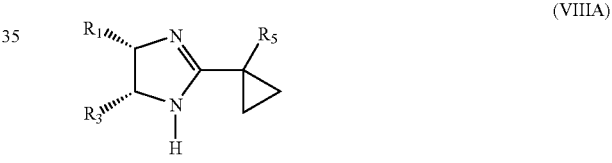

(VIIIA)

Specific compounds in accordance with this embodiment of the invention are listed below:
cis-4,5-diphenyl-2-(2-fluorobenzyl)-4,5-dihydro-1H-imidazole,
cis-4,5-diphenyl-2-(3-fluorobenzyl)-4,5-dihydro-1H-imidazole,
cis-4,5-diphenyl-2-(4-fluorobenzyl)-4,5-dihydro-1H-imidazole,
cis-4,5-diphenyl-2-(3-fluoro-4-methylbenzyl)-4,5-dihydro-1H-imidazole,
cis-4,5-diphenyl-2-(2-methyl-5-fluorobenzyl)-4,5-dihydro-1H-imidazole,
cis-4,5-diphenyl-4-methyl-2-(4-fluorobenzyl)-4,5-dihydro-1H-imidazole,
cis-4,5-diphenyl-2-(2,3-difluorobenzyl)-4,5-dihydro-1H-imidazole,
cis-4,5-diphenyl-2-(2,4-difluorobenzyl)-4,5-dihydro-1H-imidazole,
cis-4,5-diphenyl-2-(2,5-difluorobenzyl)-4,5-dihydro-1H-imidazole,
cis-4,5-diphenyl-2-(2,6-difluorobenzyl)-4,5-dihydro-1H-imidazole,
cis-4,5-diphenyl-2-(2,6-difluoro-3-methylbenzyl)-4,5-dihydro-1H-imidazole,
cis-4,5-diphenyl-2-(3,4-difluorobenzyl)-4,5-dihydro-1H-imidazole, cis-4,5-diphenyl-4-methyl-2-(2,4-difluorobenzyl)-4,5-dihydro-1H-imidazole,
cis-4,5-diphenyl-4-methyl-2-(3,4-difluorobenzyl)-4,5-dihydro-1H-imidazole,
cis-4,5-diphenyl-2-(2-chlorobenzyl)-4,5-dihydro-1H-imidazole,
cis-4,5-diphenyl-2-(3-chlorobenzyl)-4,5-dihydro-1H-imidazole,
cis-4,5-diphenyl-2-(4-chlorobenzyl)-4,5-dihydro-1H-imidazole,
cis-4,5-diphenyl-4-methyl-2-(3-chlorobenzyl)-4,5-dihydro-1H-imidazole,
cis-4,5-diphenyl-2-(2-fluoro-3-chlorobenzyl)-4,5-dihydro-1H-imidazole,
cis-4,5-diphenyl-2-(2-chloro-4-fluorobenzyl)-4,5-dihydro-1H-imidazole,
cis-4,5-diphenyl-2-(2-chloro-6-fluorobenzyl)-4,5-dihydro-1H-imidazole,
cis-4,5-diphenyl-2-(3-chloro-4-fluorobenzyl)-4,5-dihydro-1H-imidazole,
cis-4,5-diphenyl-2-[1-(4-chlorophenyl)-1-ethyl]-4,5-dihydro-1H-imidazole,
cis-4,5-diphenyl-2-[1-{(4-chlorophenyl)-1-methyl}ethyl]-4,5-dihydro-1H-imidazole,
cis-4,5-diphenyl-2-[1-(4-chlorophenyl)-1-cyclopropyl]-4,5-dihydro-1H-imidazole,
cis-4,5-diphenyl-2-[1-(2,4-dichlorophenyl)-1-cyclopropyl]-4,5-dihydro-1H-imidazole,
cis-4,5-diphenyl-2-(2-bromobenzyl)-4,5-dihydro-1H-imidazole,
cis-4,5-diphenyl-2-(4-trifluoromethylbenzyl)-4,5-dihydro-1H-imidazole,
cis-4,5-diphenyl-2-(2-methylbenzyl)-4,5-dihydro-1H-imidazole,
cis-4,5-diphenyl-2-(3-methylbenzyl)-4,5-dihydro-1H-imidazole,
cis-4,5-diphenyl-2-(4-methylbenzyl)-4,5-dihydro-1H-imidazole,
cis-4,5-diphenyl-2-(2,5-dimethylbenzyl)-4,5-dihydro-1H-imidazole,
cis-4,5-diphenyl-2-(2,4,6-trimethylbenzyl)-4,5-dihydro-1H-imidazole,
cis-4,5-diphenyl-2-(2,3-dimethoxybenzyl)-4,5-dihydro-1H-imidazole,
cis-4,5-diphenyl-2-(2,5-dimethoxybenzyl)-4,5-dihydro-1H-imidazole,
cis-4,5-diphenyl-2-(4-methanesulfonylbenzyl)-4,5-dihydro-1H-imidazole,
cis-4,5-diphenyl-2-[(1-phenyl)-(1S)-ethyl]-4,5-dihydro-1H-imidazole,
cis-4,5-diphenyl-2-[(1-phenyl)-(1R)-ethyl]-4,5-dihydro-1H-imidazole,
cis-4,5-diphenyl-2-[1-(4-isobutylphenyl)-1-ethyl]-4,5-dihydro-1H-imidazole,
cis-4,5-diphenyl-4-methyl-2-(1-(4-chlorophenyl)-1-ethyl)-4,5-dihydro-1H-imidazole,
cis-4,5-diphenyl-2-[1-phenyl-1-cyclopropyl]-4,5-dihydro-1H-imidazole,
cis-4,5-diphenyl-2-(2-naphthalen-2-yl)methyl]-4,5-dihydro-1H-imidazole,
cis-4,5-diphenyl-2-(methoxy-phenyl-methyl)-4,5-dihydro-1H-imidazole,
cis-4,5-diphenyl-2-[1-(2-fluorobiphenyl-4-yl)-1-ethyl]-4,5-dihydro-1H-imidazole,
cis-(4,5-diphenyl-4,5-dihydro-1H-imidazol-2-yl)-phenyl-methanol,
phenyl-carbamic acid cis-(4,5-diphenyl-4,5-dihydro-1H-imidazol-2-yl)-phenyl-methyl ester,
1-[(cis-4,5-diphenyl-4,5-dihydro-1H-imidazol-2-yl)methyl]-1H-pyridin-2-one,
cis-4,5-bis-(3-fluorophenyl)-2-(3-chlorobenzyl)-4,5-dihydro-1H-imidazole,
cis-4,5-bis-(3-fluorophenyl)-2-(3,4-difluorobenzyl)-4,5-dihydro-1H-imidazole,
cis-4,5-bis-(3-fluorophenyl)-2-(2,4-difluorobenzyl)-4,5-dihydro-1H-imidazole,
cis-4,5-bis-(3-fluorophenyl)-2-(2-fluorobenzyl)-4,5-dihydro-1H-imidazole,
cis-4,5-bis-(3-fluorophenyl)-2-(4-fluorobenzyl)-4,5-dihydro-1H-imidazole,
cis-4,5-bis-(3-fluorophenyl)-4-methyl-2-(4-fluorobenzyl)-4,5-dihydro-1H-imidazole,
2-methyl-cis-4-phenyl-5-(pyridin-3-yl)-4,5-dihydro-1H-imidazole, and
2-indan-2-ylmethyl-cis-4,5-diphenyl-4,5-dihydro-1H-imidazole trifluoroacetate.

In yet another embodiment of this invention, the compound of formula (II) having X—Y as —(CH$_2$)$_a$—Z—(CH$_2$)$_b$— in which Z is S, and a and b are 0 or 1 is preferred. Additionally, in this embodiment of the invention, the compound of formula (II) further having $R_1$ and $R_3$ as phenyl or pyridyl, and R and $R_4$ as hydrogen and $R_2$ as hydrogen or methyl is particularly preferred. Thus, the compound in accordance with this embodiment may generically be represented by the formula (IX):

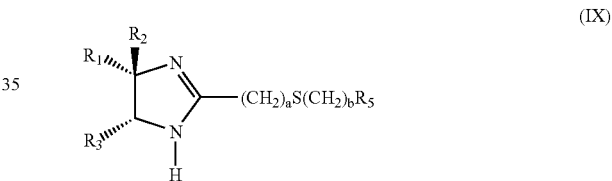

In formula (IX), as noted above, $R_1$ and $R_3$ are independently phenyl or pyridyl, $R_2$ is hydrogen or methyl, a and b are 0 or 1, and $R_5$ is as defined above. Specific compounds encompassed by this aspect of the embodiment may be enumerated as follows:
cis-4,5-diphenyl-2-[(phenylsulfanyl)methyl]-4,5-dihydro-1H-imidazole,
cis-4,5-diphenyl-2-[(benzylsulfanyl)methyl]-4,5-dihydro-1H-imidazole,
cis-4,5-diphenyl-4-methyl-2-[(benzylsulfanyl)methyl]-4,5-dihydro-1H-imidazole,
cis-4,5-diphenyl-2-benzylthio-4,5-dihydro-1H-imidazole,
cis-4,5-diphenyl-2-(2-fluorobenzyl)thio-4,5-dihydro-1H-imidazole,
cis-4,5-diphenyl-2-(3-fluorobenzyl)thio-4,5-dihydro-1H-imidazole,
cis-4,5-diphenyl-2-(4-fluorobenzyl)thio-4,5-dihydro-1H-imidazole,
cis-4,5-diphenyl-2-(3,4-difluorobenzyl)thio-4,5-dihydro-1H-imidazole,
cis-4,5-diphenyl-2-(2-chloro-4-fluorobenzyl)thio-4,5-dihydro-1H-imidazole,
cis-4,5-diphenyl-2-(2-chloro-6-fluorobenzyl)thio-4,5-dihydro-1H-imidazole,
cis-4,5-diphenyl-2-(2-chlorobenzyl)thio-4,5-dihydro-1H-imidazole, cis-4,5-diphenyl-2-(3-chlorobenzyl)thio-4,5-dihydro-1H-imidazole,
cis-4,5-diphenyl-2-(4-chlorobenzyl)thio-4,5-dihydro-1H-imidazole,
cis-4,5-diphenyl-2-(2,4-dichlorobenzyl)thio-4,5-dihydro-1H-imidazole,
cis-4,5-diphenyl-2-(2,5-dichlorobenzyl)thio-4,5-dihydro-1H-imidazole,
cis-4,5-diphenyl-2-(3,4-dichlorobenzyl)thio-4,5-dihydro-1H-imidazole,
cis-4,5-diphenyl-2-(2,6-dichlorobenzyl)thio-4,5-dihydro-1H-imidazole,
cis-4,5-diphenyl-2-(2-bromobenzyl)thio-4,5-dihydro-1H-imidazole,
cis-4,5-diphenyl-2-(3-bromobenzyl)thio-4,5-dihydro-1H-imidazole,
cis-4,5-diphenyl-2-(4-bromobenzyl)thio-4,5-dihydro-1H-imidazole,
cis-4,5-diphenyl-2-(2-iodobenzyl)thio-4,5-dihydro-1H-imidazole,
cis-4,5-diphenyl-2-(2-methylbenzyl)thio-4,5-dihydro-1H-imidazole,
cis-4,5-diphenyl-2-(3-methylbenzyl)thio-4,5-dihydro-1H-imidazole,
cis-4,5-diphenyl-2-(4-methylbenzyl)thio-4,5-dihydro-1H-imidazole,
cis-4,5-diphenyl-2-(2,4-dimethylbenzyl)thio-4,5-dihydro-1H-imidazole,
cis-4,5-diphenyl-2-(2,5-dimethylbenzyl)thio-4,5-dihydro-1H-imidazole,
cis-4,5-diphenyl-2-(2,3,5,6-tetramethylbenzyl)thio-4,5-dihydro-1H-imidazole,
cis-4,5-diphenyl-2-(2,3,4,5,6-pentamethylbenzyl)thio-4,5-dihydro-1H-imidazole,
cis-4,5-diphenyl-2-(4-isopropylbenzyl)thio-4,5-dihydro-1H-imidazole,
cis-4,5-diphenyl-2-(4-tert-butylbenzyl)thio-4,5-dihydro-1H-imidazole,
cis-4,5-diphenyl-2-(2-trifluoromethylbenzyl)thio-4,5-dihydro-1H-imidazole,
cis-4,5-diphenyl-2-(3-trifluoromethylbenzyl)thio-4,5-dihydro-1H-imidazole,
cis-4,5-diphenyl-2-(4-trifluoromethylbenzyl)thio-4,5-dihydro-1H-imidazole,
cis-4,5-diphenyl-2-(3,5-ditrifluoromethylbenzyl)thio-4,5-dihydro-1H-imidazole,
cis-4,5-diphenyl-2-(2-trifluoromethoxybenzyl)thio-4,5-dihydro-1H-imidazole,
cis-4,5-diphenyl-2-(4-trifluoromethoxybenzyl)thio-4,5-dihydro-1H-imidazole,
cis-4,5-diphenyl-2-(3-methoxybenzyl)thio-4,5-dihydro-1H-imidazole,
cis-4,5-diphenyl-2-(4-methoxybenzyl)thio-4,5-dihydro-1H-imidazole,
cis-4,5-diphenyl-2-(3,5-dimethoxybenzyl)thio-4,5-dihydro-1H-imidazole,
cis-4,5-diphenyl-2-(3,4,5-trimethoxybenzyl)thio-4,5-dihydro-1H-imidazole,
cis-4,5-diphenyl-2-(3-phenoxybenzyl)thio-4,5-dihydro-1H-imidazole,
cis-4,5-diphenyl-2-(4-benzyloxybenzyl)thio-4,5-dihydro-1H-imidazole,
cis-4,5-diphenyl-2-(3,4-dibenzyloxybenzyl)thio-4,5-dihydro-1H-imidazole,
cis-4,5-diphenyl-2-(4-phenylbenzyl)thio-4,5-dihydro-1H-imidazole,
cis-4,5-diphenyl-2-[(naphthalen-1-yl)methylthio]-4,5-dihydro-1H-imidazole,
cis-4,5-diphenyl-2-[(2-methylnaphthalen-1-yl)methylthio]-4,5-dihydro-1H-imidazole,
cis-4,5-diphenyl-2-[(anthracen-9-yl)methylthio]-4,5-dihydro-1H-imidazole,
4-[(cis-4,5-diphenyl-4,5-dihydro-1H-imidazol-2-yl)thiomethyl]benzoic acid ethyl ester, and
2-phenylthiomethyl-cis-4-phenyl-5-(pyridin-3-yl)-4,5-dihydro-1H-imidazole.

Still in another embodiment of this invention, the compound of formula (II) having X—Y as —(CH$_2$)$_a$—Z—(CH$_2$)$_b$— in which Z is O, and a and b are 0, 1 or 2 is preferred. Furthermore, in this embodiment the (CH$_2$) is optionally substituted with methyl, n-propyl or cyclopropyl. Additionally, in this embodiment of the invention, the compound of formula (II) further having $R_1$ and $R_3$ as phenyl or phenyl substituted with fluorine or methoxy, and R, $R_2$, $R_4$ as hydrogen or methyl is particularly preferred. Thus, the compound in accordance with this embodiment may generically be represented by the formula (X):

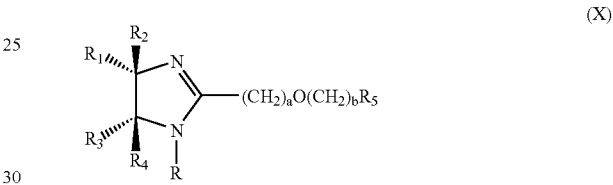

In formula (X), as noted above, $R_1$ and $R_3$ are independently phenyl or phenyl substituted with fluorine or methoxy, R, $R_2$, $R_4$ as hydrogen or methyl, a and b are 0, 1 or 2, and $R_5$ is as defined above. In addition, one or more of the (CH$_2$) group may optionally be substituted with methyl, n-propyl or cyclopropyl. Specific compounds encompassed by this aspect of the embodiment may be enumerated as follows:
cis-4,5-diphenyl-2-[(2-phenethyloxy)methyl]-4,5-dihydro-1H-imidazole,
cis-4,5-diphenyl-2-benzyloxymethyl-4,5-dihydro-1H-imidazole,
cis-4,5-diphenyl-2-(3-fluorobenzyloxy)methyl-4,5-dihydro-1H-imidazole,
cis-4,5-diphenyl-2-(3-methylbenzyloxy)methyl-4,5-dihydro-1H-imidazole,
cis-4,5-diphenyl-2-(3-methoxybenzyloxy)methyl-4,5-dihydro-1H-imidazole,
cis-4,5-diphenyl-2-(3-trifluoromethylbenzyloxy)methyl-4,5-dihydro-1H-imidazole,
cis-4,5-diphenyl-2-phenoxymethyl-4,5-dihydro-1H-imidazole,
cis-4,5-diphenyl-4-methyl-2-phenoxymethyl-4,5-dihydro-1H-imidazole,
cis-4,5-diphenyl-4,5-dimethyl-2-phenoxymethyl-4,5-dihydro-1H-imidazole,
cis-4,5-diphenyl-4-methyl-2-(1-phenoxyethyl)-4,5-dihydro-1H-imidazole,
cis-4,5-diphenyl-2-(2-fluorophenoxy)methyl-4,5-dihydro-1H-imidazole,
cis-4,5-diphenyl-2-(3-fluorophenoxy)methyl-4,5-dihydro-1H-imidazole,
cis-4,5-diphenyl-4-methyl-2-(3-fluorophenoxy)methyl-4,5-dihydro-1H-imidazole,
cis-4,5-diphenyl-2-(4-fluorophenoxy)methyl-4,5-dihydro-1H-imidazole, cis-4,5-diphenyl-4-methyl-2-[(2-chlorophenoxy)methyl]-4,5-dihydro-1H-imidazole,
cis-4,5-diphenyl-2-methoxymethyl-4,5-dihydro-1H-imidazole,
cis-4,5-diphenyl-2-methoxymethyl-4-methyl-4,5-dihydro-1H-imidazole,
cis-4,5-diphenyl-2-isopropoxymethyl-4,5-dihydro-1H-imidazole,
cis-4,5-diphenyl-2-isopropoxymethyl-4-methyl-4,5-dihydro-1H-imidazole,
cis-4,5-diphenyl-4-methyl-2-[(1-ethynyl-1-butoxy)methyl]-4,5-dihydro-1H-imidazole,
cis-4,5-diphenyl-4-methyl-2-[[(cyclopropyl)methoxy]methyl]-4,5-dihydro-1H-imidazole,
cis-4,5-diphenyl-4-methyl-2-[(dicyclopropylmethoxy)methyl]-4,5-dihydro-1H-imidazole,
cis-4,5-diphenyl-4-methyl-2-[(1-cyclopropyl-1-ethoxy)methyl]-4,5-dihydro-1H-imidazole,
cis-4,5-diphenyl-4-methyl-2-[(cyclobutoxy)methyl]-4,5-dihydro-1H-imidazole,
cis-4,5-diphenyl-2-cyclopentyloxymethyl-4-methyl-4,5-dihydro-1H-imidazole,
cis-4,5-diphenyl-4-methyl-2-[(cyclopentylmethoxy)methyl]-4,5-dihydro-1H-imidazole,
cis-4,5-diphenyl-4-methyl-2-[(1-cyclopentyl-1-ethoxy)methyl]-4,5-dihydro-1H-imidazole,
cis-4,5-diphenyl-2-cyclohexyloxymethyl-4,5-dihydro-1H-imidazole,
cis-4,5-diphenyl-2-cyclohexyloxymethyl-4-methyl-4,5-dihydro-1H-imidazole,
cis-4,5-diphenyl-2-cycloheptyloxymethyl-4,5-dihydro-1H-imidazole,
cis-4,5-diphenyl-2-cyclooctyloxymethyl-4,5-dihydro-1H-imidazole,
cis-4,5-diphenyl-4-methyl-2-[[(tetrahydrofuran-2-yl)methoxy]methyl]-4,5-dihydro-1H-imidazole,
cis-4,5-diphenyl-2-[(tetrahydropyran-4-yloxy)methyl]-4,5-dihydro-1H-imidazole,
cis-4,5-diphenyl-4-methyl-2-[(tetrahydropyran-4-yloxy)methyl]-4,5-dihydro-1H-imidazole,
cis-4,5-diphenyl-4-methyl-2-[(1,3-dioxan-5-yl)oxymethyl]-4,5-dihydro-1H-imidazole,
cis-4,5-diphenyl-4-methyl-2-[(1-benzopyran-4-yloxy)methyl]-4,5-dihydro-1H-imidazoline,
cis-4,5-diphenyl-2-(cyclohexylmethoxymethyl)-4,5-dihydro-1H-imidazole,
cis-4,5-diphenyl-4-methyl-2-[(2,3-dihydrobenzo-1,4-dioxan-2-yl)methoxymethyl]-4,5-dihydro-1H-imidazole,
cis-4,5-bis(3-fluorophenyl)-2-(2-fluorophenoxy)methyl-4,5-dihydro-1H-imidazole,
cis-4,5-bis(3-fluorophenyl)-2-(3-fluorophenoxy)methyl-4,5-dihydro-1H-imidazole,
cis-4,5-bis(3-fluorophenyl)-1,4-dimethyl-2-(3-fluorophenoxy)methyl-4,5-dihydro-1H-imidazole,
cis-4,5-bis(3-fluorophenyl)-1,5-dimethyl-2-(3-fluorophenoxy)methyl-4,5-dihydro-1H-imidazole,
cis-4,5-bis(3-fluorophenyl)-2-(4-fluorophenoxy)methyl-4,5-dihydro-1H-imidazole, and
cis-(5-methoxyphenyl-4-phenyl)-2-[[(cyclopentyl)methoxy]methyl]-4,5-dihydro-1H-imidazole.

Finally, in the above embodiment the compound of formula X having $R_1$ and $R_3$ as phenyl, methyl or pyridyl, R as hydrogen, and $R_2$ and $R_4$ as hydrogen or methyl is also preferred. Specific compounds encompassing this preferred embodiment are listed below:

2-(phenoxymethyl)-4,4-dimethyl-5-phenyl-4,5-dihydro-1H-imidazole,
2-(3-fluorophenoxymethyl)-4,4-dimethyl-5-phenyl-4,5-dihydro-1H-imidazole,
2-(benzyloxymethyl)-4,4-dimethyl-5-phenyl-4,5-dihydro-1H-imidazole,
2-(3-fluorobenzyloxymethyl)-4,4-dimethyl-5-phenyl-4,5-dihydro-1H-imidazole,
2-phenoxymethyl-(cis-4-phenyl-5-(pyridin-3-yl)-4,5-dihydro-1H-imidazole,
2-[(3-fluorophenoxy)methyl]-cis-4-phenyl-5-(pyridin-3-yl)-4,5-dihydro-1H-imidazole, and
2-cyclohexyloxymethyl-cis-4-phenyl-5-(pyridin-3-yl)-4,5-dihydro-1H-imidazole.

In another aspect of this invention there is also disclosed a compound including enantiomers, stereoisomers, rotomers and tautomers of said compound and pharmaceutically acceptable salts, solvates or derivatives thereof, with said compound having the general structure shown in formula XI:

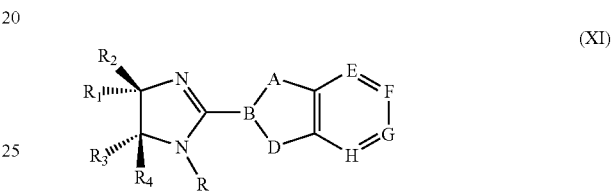

(XI)

wherein:
R is hydrogen, $C_{1-6}$ alkyl, $C_{2-6}$ acyl, $C_{1-6}$ alkoxycarbonyl, or
$C_{6-12}$ aryloxycarbonyl;
$R_1$ and $R_3$ are the same or different and are each independently selected from:
$C_{5-8}$ cycloalkyl,
heterocycle, selected from morpholinyl, piperidinyl, piperazinyl, pyrrolidinyl, tetrahydrofuranyl, tetrahydropyranyl, tetrahydrothiophenyl or thiazolinyl,
aryl, selected from phenyl, biphenyl or naphthyl,
heteroaryl, selected from benzimidazolyl, benzofuranyl, benzooxazolyl, furanyl, imidazolyl, indolyl, isoxazolyl, isoquinolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl or triazolyl,
aryl $C_{1-4}$ alkyl, $C_{5-8}$ cycloalkyl $C_{1-4}$ alkyl, heteroaryl $C_{1-4}$ alkyl, wherein aryl and heteroaryl are as defined above, and
wherein $C_{5-8}$ cycloalkyl, aryl or heteroaryl is optionally substituted with one or more substituents selected from the group consisting of halogen, $C_{1-4}$ alkyl, fluoroalkyl or fluoroalkoxy of the formula $C_nH_xF_y$ or $OC_nH_xF_y$ wherein n is an integer from 1 to 4, x is an integer from 0 to 8, y is an integer from 1 to 9 and sum of x and y is 2n+1, $C_{1-4}$ alkoxy, $C_{1-4}$ thioalkyl, hydroxy, $C_{1-4}$ acyloxy, nitro, amino, $C_{1-4}$ alkylamino, $C_{1-4}$ dialkylamino, amino $C_{1-4}$ alkyl, $C_{1-4}$ alkylamino $C_{1-4}$ alkyl, $C_{1-4}$ dialkylamino $C_{1-4}$ alkyl, —CN, —CO$_2$H,
—CO$_2C_{1-4}$ alkyl, phenyl, phenoxy and benzyloxy; or
$R_1$ and $R_3$ taken together with the carbon atoms to which they are attached form a cyclopentane, cyclohexane, cycloheptane or cyclooctane; and
$R_2$ and $R_4$ are the same or different and are each independently selected from:

hydrogen, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1;

A and D are the same or different and are each independently $CH_2$, NH, O or S;

B is CH or N; and

E, F, G and H are the same or different and are each independently CH or N.

In a preferred aspect of this invention, the compound of this aspect of the invention preferably feature the following substituents:

R is hydrogen;

$R_1$ and $R_3$ are both phenyl;

$R_2$ and $R_4$ are the same or different and are each independently hydrogen or methyl;

A and D are the same or different and are each independently $CH_2$ or NH;

B is CH; and

E, F, G and H are CH.

As an illustrative compound of this aspect of the invention the following can specifically be enumerated:

2-indan-2-yl-4,5-diphenyl-4,5-dihydro-1H-imidazole trifluoroacetate.

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature. See for example, Sharaf, M. A., et al., *J. Chem. Research (S)*, 1996, 322-323, which discloses preparative methods for a few of the precursor compounds. A few of the 2-thiosubstituted-4,5-dihydro-1H-imidazoles are also disclosed in U.S. Pat. Nos. 4,379,159; and 4,308,277. A few other imidazoline derivatives are also disclosed in German Patent Nos. DE 27 01 372; and DE 28 54 428; and EP Patent No. 0 000 208. Each of these references is herein incorporated by reference in its entirety.

Further, a few of the 2-benzylthio-4,5-dihydro-1H-imidazoles have been reported; see, for example, Sharaf, M. A. et al., *Phosphorus, Sulfur, and Silicon,* 1994, 92, 19-27; and Hammouda, H. A., et al., *Gazz. Chim. Ital.,* 1984, 114, 201-204. Similarly, a few derivatives of 2-benzylamino-4,5-dihydro-1H-imidazoles have also been reported; see, for example, Isobe, T., et al., *Chem. Commun.,* 2001, 243-244; and Isobe T., et al., *J. Org. Chem.,* 2000, 65, 7774-7778.

More specifically, the compounds disclosed herein can be synthesized according to the following procedures of Schemes 1-11, wherein the X, Y, Z, $R_1$, $R_2$, $R_3$ and $R_a$ substituents are as defined for Formula (II) or as defined for Formulae (III) to (X) above unless otherwise indicated.

In general, the compounds of this invention, the imidazoline derivatives, can be synthesized from the starting 1,2-diaminoethane derivative, which is prepared following the procedures shown in Scheme 1. Thus, Scheme 1 illustrates a synthesis of a class of 1,2-diphenyl-diaminoethane derivatives, 3, in which both $R_1$ and $R_3$ are the same, i.e., the substituted or unsubstituted phenyl group. The substituents $R_2$ and $R_4$ are hydrogen in this case. In accordance with this procedure, a suitable substituted benzaldehyde, 1 is reacted with ammonium acetate under suitable reaction conditions to form the intermediate 2, which is further reacted with sulfuric acid to form cis-1,2-diaminoethane derivative, 3, the starting material for the synthesis of a variety of 4,5-diphenyl-midazoline compounds of this invention. The coupling reaction as described herein can be effected by any of the methods known in the art. In general, this step is carried out at an elevated temperature typically in the range of from about 80° C. to 150° C. for a sufficient length of time to drive the reaction to completion. Typically, the reaction is carried out for a period of about 8 to 16 hours or longer depending upon the reaction temperature.

The crude, coupling product, 2 is then contacted with a suitable acid such as sulfuric acid at elevated temperature to form the diamino compound, 3. The reaction can again be carried out by any of the procedures known in the art. Typically, the reaction is effected at elevated temperatures in the range of from about 80° C. to 150° C. Various other diamino compounds, 3 in which $R_1$ and $R_3$ groups are the same can be synthesized using the procedures of Scheme 1 and employing the desirable aldehyde.

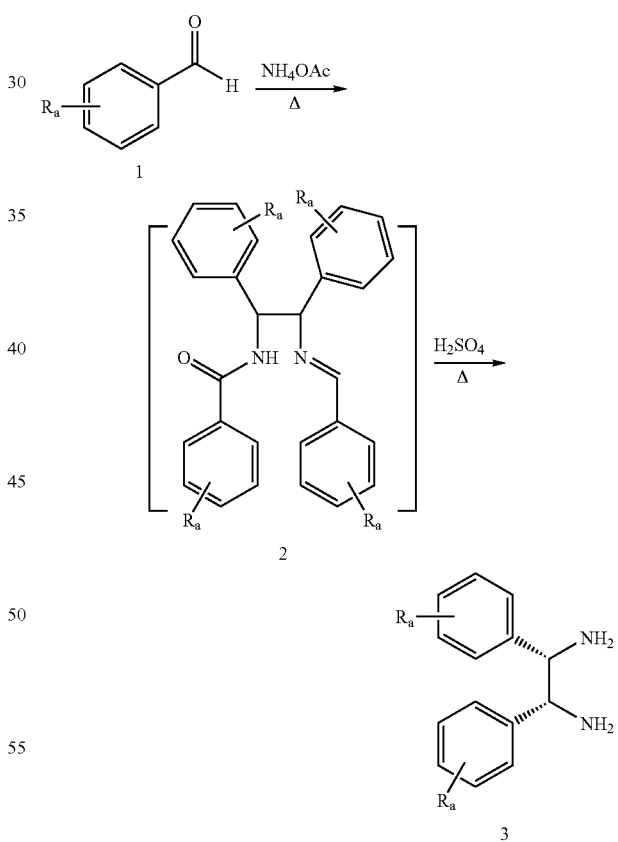

Scheme 1

Alternatively, the starting 1,2-diamino compound can also be synthesized following the steps as set forth in Scheme 2. In accordance with this procedure, a much broader class of diamino compounds, 8 can be prepared.

In Scheme 2, step 1, the 1,2-diketo compound, 4 is first contacted with sulfamide to form the thiadiazole-1,1-dioxide, 5. This reaction is generally carried out in the presence of an acid such as hydrogen chloride and in the presence of any art recognized solvent such as methanol. The reaction can generally be carried out at ambient conditions.

The thiadiazole-1,1-dioxide, 5 can then be substituted with suitable substituents to form the substituted derivative, 6. Generally, the method depicted in Scheme 2 is suitable for the preparation of monosubstituted derivative, 6. Thus, for example, the intermediate, 5 can be contacted with suitable Grignard reagent, such as $R_2MgBr$ to form the alkylated derivative, 6 (i.e., wherein $R_2$ is a suitable alkyl or aryl group and $R_4$ is hydrogen). The substitution reaction using a Grignard agent is carried out using conditions well known in the art such as in an ethereal solvent at a temperature of around $-10°$ C. to $20°$ C. In an analogous manner, the Grignard product can further be treated with another Grignard reagent such as $R_4MgBr$ to form the disubstituted diamine, which can be used to prepare various other disubstituted imidazoline compounds of this invention (i.e., wherein $R_4$ is as defined herein).

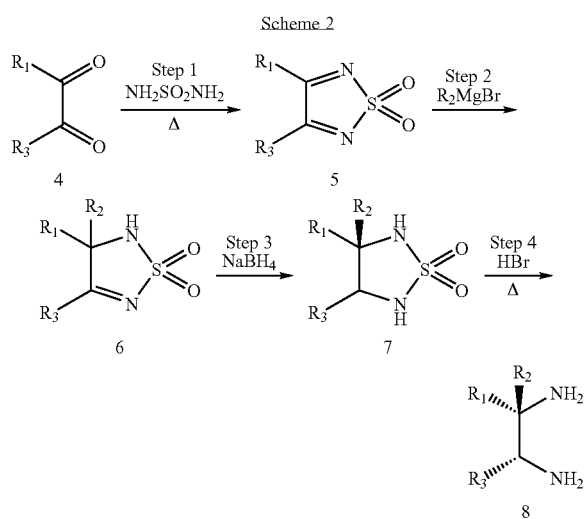

In Scheme 2, step 3, the substituted derivative, 6 is subjected to reductive conditions to form the product 7. For instance, 6 is treated with sodium borohydride in an art recognized solvent such as methanol to form the product 7, which can be cleaved under acidic reaction conditions to form the diamine, 8.

Scheme 2A illustrates a variation of Scheme 2 in which preparation of the tetrasubstituted-1,2-diamine is shown. Thus, the thiadiazole-1,1-dioxide, 5 is contacted with two molar equivalents of Grignard reagent to form the tetrasubstituted-thiadiazole-1,1-dioxide, 7A, which is further cleaved under acidic reaction conditions to form the tetrasubstiuted-1,2-diamine, 8A in which $R_4$ is same as $R_2$.

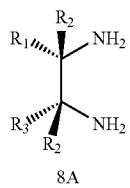

Alternatively, as stated above, the 1,2-diamine having different $R_2$ and $R_4$ groups can also by prepared in an analogous manner following the procedures set forth in Scheme 2 or Scheme 2A by contacting the intermediate, 5 with two different Grignard reagents in two separate sequential steps as shown in Scheme 2B.

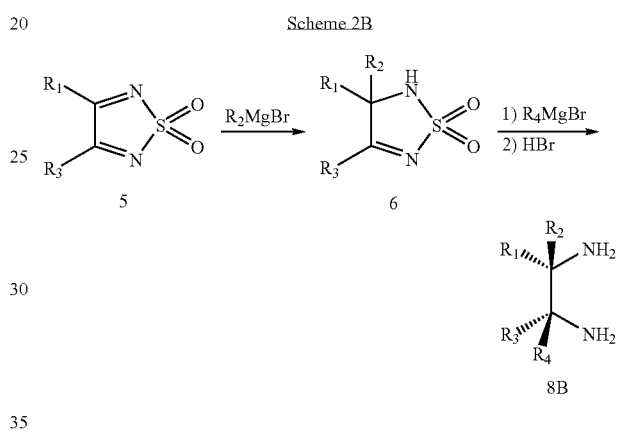

Scheme 3 illustrates general procedures that can be used to prepare a class of imidazoline compounds of this invention in which X—Y is $—(CH_2)_a—Z—(CH_2)_b—$ and wherein Z is $NR_6$ and a is 0. An analogous procedure can be employed for the preparation of various other compounds of this invention with suitable modifications known in the art.

Thus, in Scheme 3, step 1, the diamino compound, 8 is contacted with carbon disulfide under suitable reaction conditions to form the imidazoline-2-thione derivative, 9. The cyclization can be effected by any of the procedures known in the art. Typically, this reaction is carried out at an elevated temperature in the range of from about $80°$ C. to $100°$ C. preferably in the presence of a suitable solvent such as absolute ethanol and the like.

In Scheme 3, step 2, the imidazoline-2-thione derivative, 9 is methylated using any of the known methylating agents such as methyl iodide to form the thiomethyl derivative, 10, which is further contacted with a suitable protective agent to form the N-protected derivative, 11. Various N-protecting groups that are known in the art can be employed in this step, see for example, *Protecting Groups in Organic Synthesis* by T. Greene, John Wiley & Sons, Inc., $2^{nd}$ Ed., 1991. Scheme 2, step 3, shows the N-protection using tert-butoxycarbonyl (Boc) group. This can be effected by treating the thiomethyl derivative, 10 with di-tert-butyl-dicarbonate. This N-protection reaction is typically carried out in the presence of a base such as triethylamine and 4-dimethylamino-pyridine (DMAP) in a suitable organic solvent such as dichloromethane.

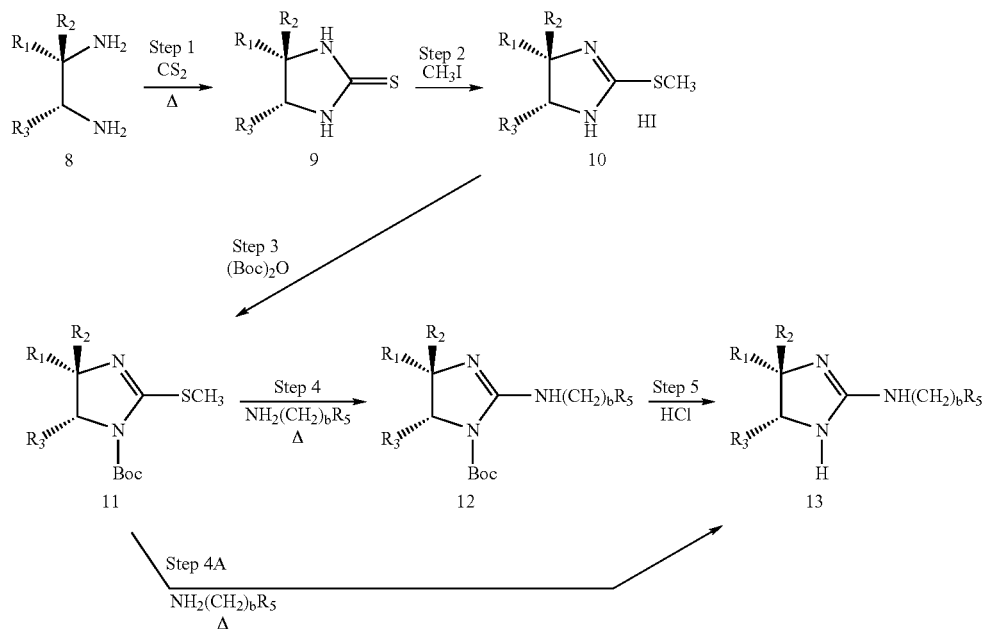

In Scheme 3, step 4, the N-protected thiomethyl-imidazoline derivative, 11 is reacted with a desirable amino compound to form the N-protected-2-amino-imidazoline derivative, 12. This reaction can generally be carried out using any of the methods known in the art. For example, the derivative, 11 is contacted with a suitable amine in an art recognized solvent such as methanol or ethanol at a suitable reaction temperature. In general, the suitable reaction temperature is in the range of from about 80° C. to 120° C., however, lower or higher temperatures can be utilized depending upon the imidazoline compound, 11 and the amino compound that are being employed. Finally, the Boc group is cleaved suitably under acidic reaction conditions such as hydrochloric acid to form the 2-aminosubstituted imidazoline, 13. Alternatively, in certain reaction conditions, the thiomethyl imidazoline, 11 can be aminated and the protective group is cleaved in the same step to form the 2-aminosubstituted imidazoline, 13 as shown in step 4A.

Scheme 4 illustrates an alternative method for the preparation of certain N-substituted imidazoline compounds of this invention. This approach is particularly suitable for those compounds in which X—Y is —NHCO—.

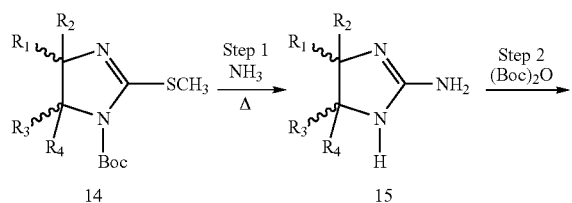

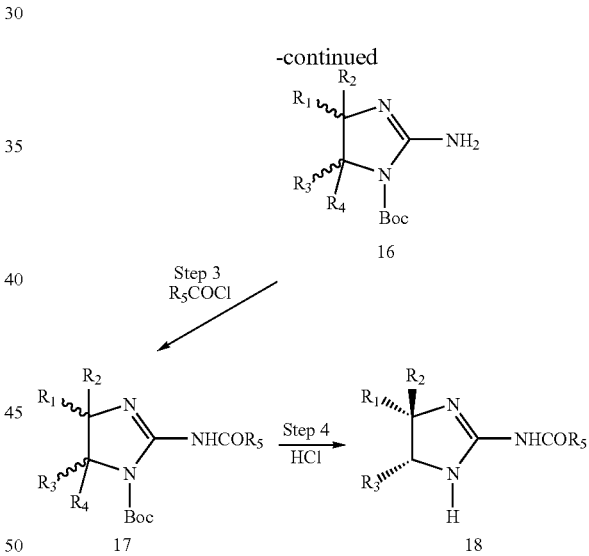

In Scheme 4, step 1, the N-protected thiomethyl derivative, 14 is prepared in an analogous manner as described above for the preparation of derivative, 11. The thiomethyl derivative, 14 is then contacted with ammonia to form the 2-amino imidazoline compound, 15. This reaction can be carried out using any of the procedures known in the art. For example, the amination can be carried out by reacting the N-protected thiomethyl derivative, 14 with ammonia in an organic solvent such as ethylene glycol under pressure at a temperature in the range of from about 100° C. to 130° C. Generally, in this step the N-protected group is also cleaved. Thus, in Scheme 4, step 2, the nitrogen of the imidazoline ring is again protected using the Boc group as described above.

In Scheme 4, step 3, the amino group is amidated using any of the known carboxylating agents. For example, this reaction can be conveniently carried out using a carboxylic acid chloride in the presence of a suitable acid acceptor such as triethylamine. Additional acylating agent activators or a base can be employed such as for example DMAP. The reaction is typically carried out in aprotic organic solvents such as dichloromethane or a hydrocarbon solvent such as hexanes, petroleum ether or mixtures thereof. Finally, the N-protecting group is removed in Scheme 4, step 4 as described above.

Scheme 5 illustrates preparation of various imidazoline compounds of this invention wherein X—Y is —$(CH_2)_a$—Z—$(CH_2)_b$— and wherein Z is O, S NR$_6$, or Z is a bond, and a is 0 or 1 and b is 1 or 2. This approach is particularly suitable for those compounds in which a is 1.

Scheme 5

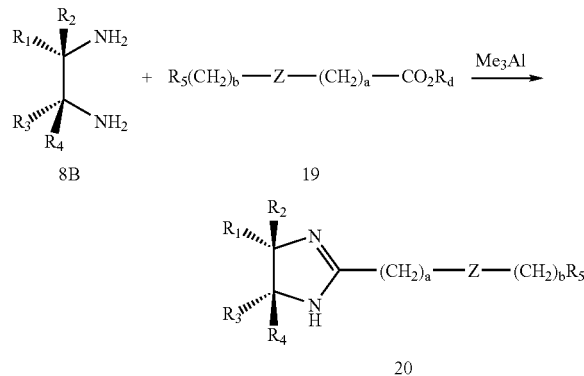

In Scheme 5, the starting 1,2-diaminoethane derivative, 8B can be prepared following the procedures of scheme 2B. The diamine, 8B is then contacted with a carboxylic acid ester derivative, 19 to form the imidazoline compound, 20. In carboxylic acid derivative, 19, R$_d$ is C$_{1-4}$ alkyl, preferably methyl or ethyl. The condensation of 8B with 19 can be carried out using any of the procedures known in the art. However, it has now been found that contacting of 8B with 19 in the presence of an alkyl aluminum reagent such as trimethylaluminum provides a convenient method for the preparation of 20. The condensation can typically be carried out in a hydrocarbon solvent such as toluene in an inert atmosphere at a temperature in the range of from about 50° C. to 80° C. The condensation reaction can also be carried out using various other carboxylic acid ester equivalents such as nitrites, carboxylic acid halides, preferably chlorides or bromides, carboxylic acid anhydrides, mixed anhydrides of carboxylic acids, and the like. One such example of condensation reaction with nitrites is shown in Scheme 5A.

Scheme 5A

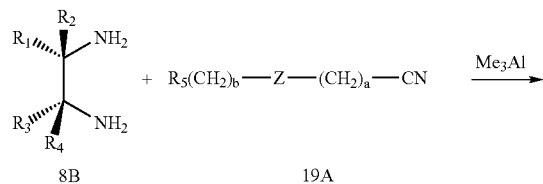

-continued

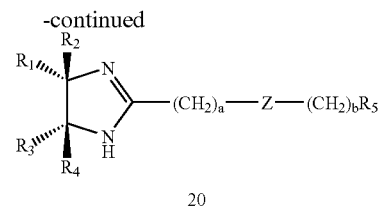

The reaction shown in Scheme 5A is particularly useful for the preparation of imidazoline compound, 20, wherein Z is O, a is 1 and b is 0. The reaction is carried out essentially under similar conditions as described above for Scheme 5.

In Scheme 6, the imidazoline thione, 9A is converted to an imidazoline compound, 21 of this invention, wherein X—Y is —$(CH_2)_a$—Z—$(CH_2)_b$— in which Z is S and a is 0. The starting compound, 9A can be synthesized following the procedures set forth for the preparation of intermediate, 9 in Scheme 3 above and employing the 1,2-diaminoethane compound, 8B.

Scheme 6

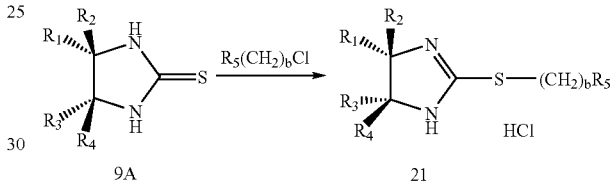

In general, the imidazoline thione, 9A is contacted with a halide compound such as R$_5$(CH$_2$)$_b$Cl in a suitable organic solvent preferably at elevated temperatures to form the product, 21. Suitable organic solvents include alcohols such as ethanol or halogenated solvents such as ethylene chloride and mixtures thereof, ethanol being the preferred solvent. The reaction is suitably carried out at a temperature range of from about 80° C. to 100° C.

Scheme 7 illustrates another method for the preparation of imidazoline compounds, 23 in which X—Y is —$(CH_2)_a$—Z—$(CH_2)_b$— in which Z is a bond and a is 0. In Scheme 7, step 1, one of the starting materials, the nitrile intermediate, 23 is prepared by treating a desirable nitrile compound, 22 with methanol in the presence of a suitable acid such as hydrochloric acid.

In Scheme 7, step 2, the intermediate, 23 is then reacted with 1,2-diaminoethane compound, 8B preferably at superambient temperatures to form the imidazoline compound, 24 of this invention. This reaction is generally carried out in an alcoholic solvent such as ethanol in the temperature range of from about 80° C. to 100° C.

Scheme 7

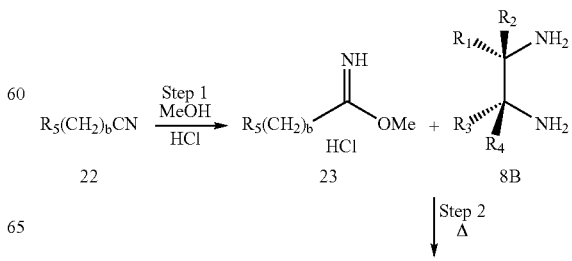

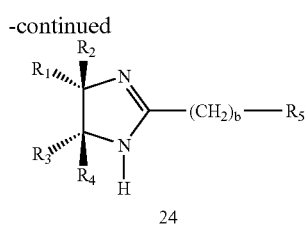

24

Scheme 8 shows preparation of a specific class of imidazoline compounds of this invention in which X—Y is —(CH$_2$)$_a$—Z—(CH$_2$)$_b$— and in which Z is a bond and a is 0, and b is 2, and R$_5$ is phenyl or substituted phenyl, wherein R$_a$ is any of the suitable substituent as defined herein. Additionally, one of the methylene groups is substituted with a hydroxy group.

In Scheme 8, the compound 25 can be prepared following the procedures of scheme 7 and employing acetonitrile as the starting nitrile compound, 22. The nitrogen atom of the imidazoline compound, 25 is then protected with tert-butoxycarbonyl (Boc) using the procedures as described above. The N-protected imidazoline compound, 26 is then contacted with a carbanion donor such as n-butyl lithium and the resulting anion of 26 is reacted with benzaldehyde or substituted benzaldehyde. This reaction is generally carried out at subambient temperature conditions such as for example in the temperature range of from about −70° C. to −40° C., usually in an inert atmosphere of nitrogen or argon. The resulting product, 27 is then contacted with a suitable acid to remove the N-protecting group to form the imidazoline compound, 28.

The imidazoline compounds of this invention can also be prepared by any of the solid phase synthesis known in the art. Optionally, the solid phase synthesis can also involve any of the known parallel or combinatorial methods such that a wide array of imidazoline compounds can be prepared. One such solid phase approach is shown in Scheme 9.

In Scheme 9, the 1,2-diaminoethane compound, 8B is reacted with a solid phase resin to form the intermediate 29, which is then condensed with a desirable carboxylic acid to form the imidazoline compound, 32. Variations of this approach can be employed to prepare various other imidazoline compounds as described herein. More specifically, the imidazoline compounds prepared in accordance with Schemes 1-8 can also be prepared using a solid phase method and utilizing similar steps as set forth therein.

In an analogous fashion N-substituted imidazoline compounds of this invention can also be synthesized using a procedure that is very similar to the one depicted in Scheme 9. This is illustrated in Scheme 9A.

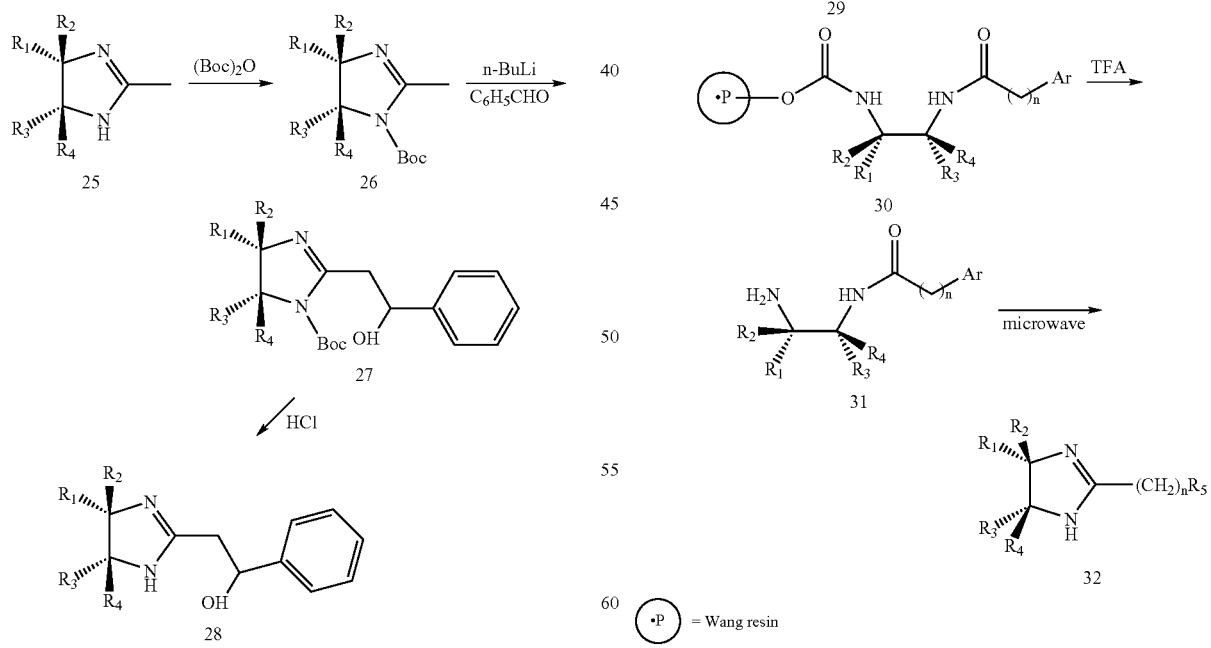

In Scheme 9A, the 1,2-diaminoethane compound, 8B is reacted first with a solid phase resin to form the intermediate 29, which is subsequently reacted with a desirable aldehyde in the presence of a suitable reducing agent such as sodium cyanoborohydride in the presence of an acid such as acetic acid and a suitable solvent or a solvent mixture (e.g., dichloromethane, trimethylorthoformate (TMOF) or mixtures thereof and the like). The N-substituted compound, 30A is then cleaved-off from the solid resin as described herein to obtain compound, 31A which in turn is condensed with a suitable one carbon containing condensating agent such as ethyl formimidate hydrochloride or any other known condensating agent to form the N-substituted imidazoline compound, 32A.

out using the procedures as described in Scheme 5. Additionally any of the known carboxylic acid equivalents as described above can be employed in place of carboxylic acid ester, 37, see Scheme 5A.

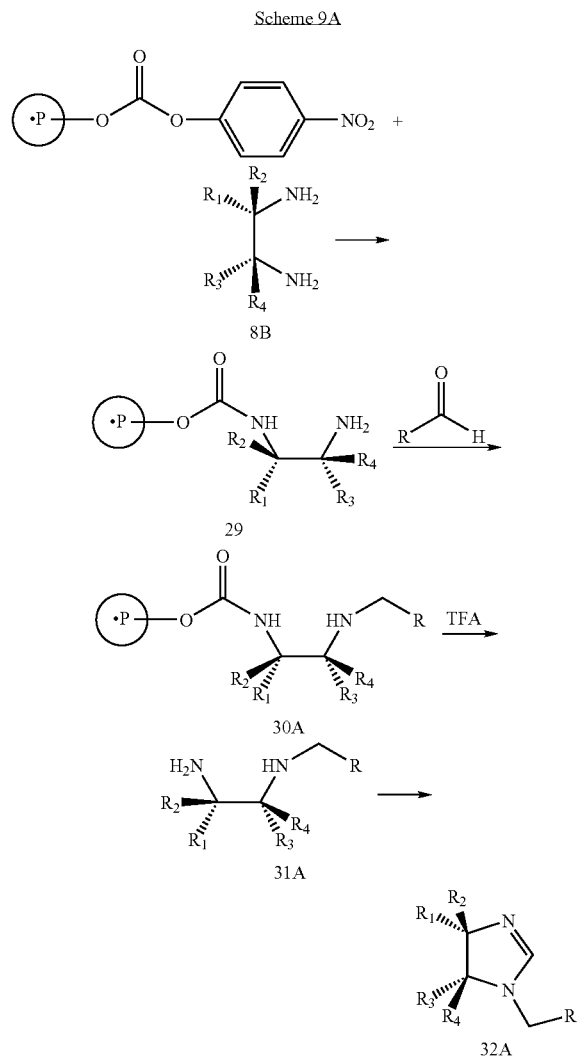

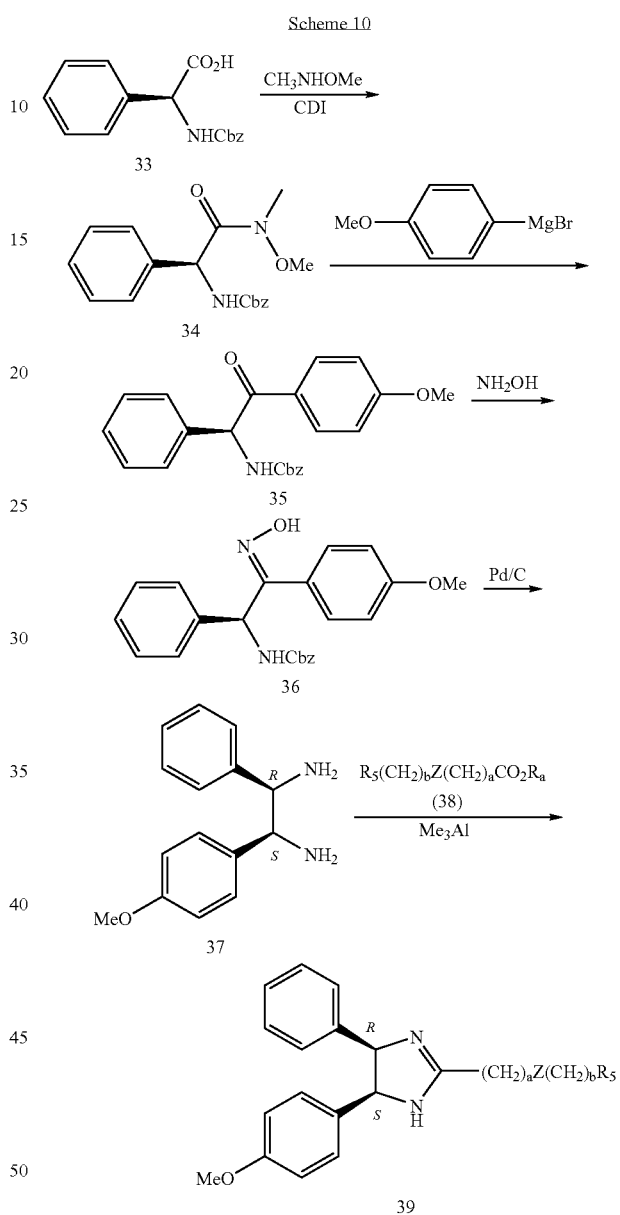

Scheme 10 illustrates a preparation of a specific class of imidazoline compounds of this invention in which substituents $R_1$ and $R_3$ are different. Thus following the series of steps as set forth in Scheme 10, the 1,2-diamino-ethane, 37 can be prepared. In an analogous manner various other 1,2-diamino-ethane compounds can be prepared by starting with the appropriate starting carboxylic acid, 33 and the Grignard reagent. The diamine, 37 is then condensed with the desired carboxylic acid derivative, 38 to form the imidazoline compound, 39 of this invention, in which $R_5$, Z, $R_a$, a and b are as defined herein. The condensation of 37 with 38 can be carried Finally, Scheme 11 shows N-substitution reaction to form the N-substituted imidazoline derivatives of this invention. Any of the N-substitution reactions known in the art can be employed in this method. Thus, the imidazoline compound, IIA prepared in accordance with any of the procedures set forth in Schemes 1-10 is reacted with suitable reagent, R-Hal, to form the N-substituted compound, II of this invention wherein R is as defined herein other than hydrogen. The reagent, R-Hal, is any reagent known in the art which is suitable for a N-substitution reaction. Thus, Hal is preferably a halogen such as chlorine or bromine, but any other suitable leaving group can be used. For example, the imidazoline compound can be reacted with acylating reagents such as carboxylic acid chloride to form N-amide derivative. Similarly, reaction with a wide variety of chloroformates results in carbamate derivatives and reaction with alkyl or aryl halides results in alkyl or aryl derivatives.

Scheme 11

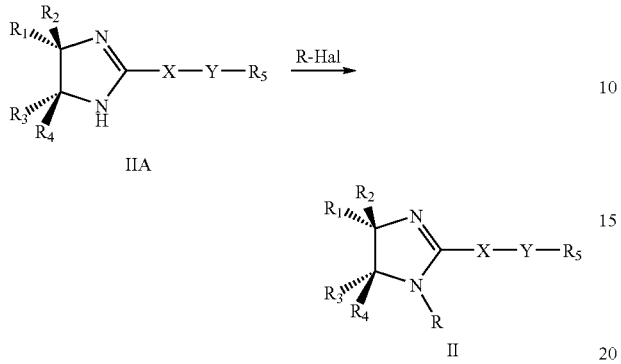

In another aspect of this invention there is also provided a method for the treatment of diseases selected from the group consisting of inflammatory bowel disease, rheumatoid arthritis, and diseases associated with central nervous system, which comprises administering to a patient in need of such treatment a therapeutically effective amount of a compound of the formula (II):

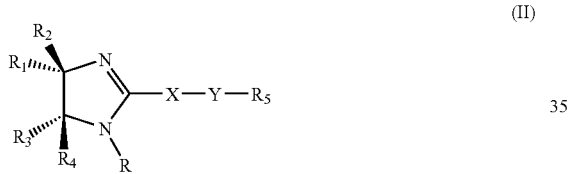

(II)

wherein:

R is hydrogen, $C_{1-6}$ alkyl, $C_{2-6}$ acyl, $C_{1-6}$ alkoxycarbonyl, or $C_{6-12}$ aryloxycarbonyl;

$R_1$ and $R_3$ are the same or different and are each independently selected from:

$C_{5-8}$ cycloalkyl, heterocyclyl, selected from morpholinyl, piperidinyl, piperazinyl, pyrrolidinyl, tetrahydrofuranyl, tetrahydropyranyl, tetrahydrothiophenyl or thiazolinyl, aryl, selected from phenyl, biphenyl or naphthyl, heteroaryl, selected from benzimidazolyl, benzofuranyl, benzooxazolyl, furanyl, imidazolyl, indolyl, isoxazolyl, isoquinolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl or triazolyl, aryl $C_{1-4}$ alkyl, $C_{5-8}$ cycloalkyl $C_{1-4}$ alkyl, heteroaryl $C_{1-4}$ alkyl, wherein aryl and heteroaryl are as defined above, and wherein $C_{5-8}$ cycloalkyl, aryl or heteroaryl is optionally substituted with one or more substituents selected from the group consisting of halogen, $C_{1-4}$ alkyl, fluoroalkyl or fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, $C_{1-4}$ alkoxy, $C_{1-4}$ thioalkyl, hydroxy, $C_{1-4}$ acyloxy, nitro, amino, $C_{1-4}$ alkylamino, $C_{1-4}$ dialkylamino, amino $C_{1-4}$ alkyl, $C_{1-4}$ alkylamino $C_{1-4}$ alkyl, $C_{1-4}$ dialkylamino $C_{1-4}$ alkyl, —CN, —$CO_2H$, —$CO_2C_{1-4}$ alkyl, phenyl, phenoxy and benzyloxy; or $R_1$ and $R_3$ taken together with the carbon atoms to which they are attached form a cyclopentane, cyclohexane, cycloheptane or cyclooctane;

$R_2$ and $R_4$ are the same or different and are each independently selected from:

hydrogen, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1;

$R_5$ is hydrogen, $C_{3-8}$ cycloalkyl, $C_{2-4}$ alkynyl, heterocyclyl, selected from morpholinyl, piperidinyl, piperazinyl, pyrrolidinyl, pyridinonyl, tetrahydrofuranyl, tetrahydropyranyl, dioxanyl, benzopyranyl, dihydrobenzodioxanyl, tetrahydrothiophenyl or thiazolinyl, aryl, selected from phenyl, biphenyl, naphthyl or anthracenyl, heteroaryl, selected from benzimidazolyl, benzofuranyl, benzooxazolyl, furanyl, imidazolyl, indolyl, isoxazolyl, isoquinolyl, isothiazolyl, oxadiazolyl, oxazolyl, pyrazinyl, pyrazolyl, pyridyl, pyrimidyl, pyrrolyl, quinolyl, tetrazolyl, thiadiazolyl, thiazolyl, thienyl or triazolyl, wherein $C_{5-8}$ cycloalkyl, heterocyclyl, aryl or heteroaryl is optionally substituted with one or more substituents selected from the group consisting of halogen, $C_{1-4}$ alkyl, fluoroalkyl fluoroalkoxy of the formula $C_nH_xF_y$ or $OC_nH_xF_y$, wherein n is an integer from 1 to 4, x is an integer from 0 to 8, y is an integer from 1 to 9 and sum of x and y is 2n+1, $C_{1-4}$ alkoxy, $C_{1-4}$ thioalkyl, hydroxy, $C_{1-4}$ acyloxy, nitro, amino, $C_{1-4}$ alkylamino, $C_{1-4}$ dialkylamino, amino $C_{1-4}$ alkyl, $C_{1-4}$ alkylamino $C_{1-4}$ alkyl, $C_{1-4}$ dialkylamino $C_{1-4}$ alkyl, —CN, —$CO_2H$, —$CO_2C_{1-4}$ alkyl, phenyl, phenoxy and benzyloxy;

X—Y is —$(CH_2)_a$—Z—$(CH_2)_b$—, —$(CH_2)_a$—Z—$(CH_2)_b$—$Z^1$— or —NHCO—, wherein wherein $(CH_2)$ is optionally substituted with one or more groups selected independently from:

hydroxy, $C_{1-6}$ alkoxy, arylaminocarbonyloxy, $C_{3-8}$ cycloalkyl, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1, wherein said alkoxy or alkyl or fluoroalkyl is optionally substituted with at least one substituent selected from the group consisting of: hydroxy, —SH, $C_{1-4}$ alkoxy, $C_{1-4}$ thioalkyl, $C_{1-4}$ acyloxy, nitro, amino, $C_{1-4}$ alkylamino, $C_{1-4}$ dialkylamino, —CN, —$CO_2H$, and —$CO_2C_{1-4}$ alkyl, aryl;

Z and $Z^1$ are the same or different and are each independently selected from:

O, S, $NR_6$, $NR_6$—$NR_6$, —OCONH—, —NH—CO—NH—, —$SO_2$—NH—, —$(NR_6)SO_2$— or a bond, wherein $R_6$ is selected from:

hydrogen, $C_{1-6}$ alkoxy, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1, wherein said alkoxy or alkyl or fluoroalkyl is optionally substituted with at least one substituent selected from the group consisting of: hydroxy, —SH, $C_{1-4}$ alkoxy, $C_{1-4}$ thioalkyl, $C_{1-4}$ acyloxy, nitro, amino, $C_{1-4}$ alkylamino, $C_{1-4}$ dialkylamino, —CN, —$CO_2H$, and —$CO_2C_{1-4}$ alkyl, aryl;

a is an integer from 0 to 2 and b is an integer from 0 to 4 provided that sum of a and b is at least 1 or a pharmaceutically acceptable salt thereof, optionally in combination with a pharmaceutically acceptable carrier.

In a specific embodiment of the method of this invention the disease that can be effectively treated with the compounds of this invention is inflammatory bowel disease. In another embodiment the disease state that can be treated in accordance with the method of this invention is rheumatoid arthritis.

In another embodiment various disease states that are associated with central nervous system (CNS) can be treated using the compounds of this invention. Specific CNS disease conditions include, but not limited to, stroke, Alzheimer's disease, multiple sclerosis, septic shock and head trauma.

All of the preferred embodiments of the compounds of this invention as disclosed herein can be used in the method of treating various disease states as described herein. As stated herein, the compounds of this invention are capable of antagonizing the effects of P2X7 receptor and thereby alleviating the inflammatory effects caused due to the P2X7 receptors. In another embodiment of the method of this invention the compounds of this invention can be administered by any of the methods known in the art. Specifically, the compounds of this invention can be administered by oral, intramuscular, subcutaneous, rectal, intratracheal, intranasal, intraperitoneal or topical route.

In yet another aspect of this invention there is also provided a pharmaceutical composition comprising a compound or a pharmaceutically acceptable salt thereof in combination with at least one pharmaceutically acceptable carrier for treating diseases selected from the group consisting of inflammatory bowel disease, rheumatoid arthritis, and diseases associated with central nervous system, wherein said compound is of the formula (II) as described herein, including the pharmaceutically acceptable salt thereof, optionally in combination with a pharmaceutically acceptable carrier. In this aspect of the invention all of the compounds encompassing the generic scope of the formula (II) are used in the composition of this invention.

In a specific embodiment of the composition of this invention the disease that can be effectively treated with the composition of this invention is inflammatory bowel disease. In another embodiment the disease state that can be treated in accordance with the composition of this invention is rheumatoid arthritis.

In another embodiment various disease states that are associated with central nervous system (CNS) can be treated using the compositions of this invention. As stated herein, specific CNS disease conditions include, but not limited to, stroke, Alzheimer's disease, multiple sclerosis, septic shock and head trauma.

All of the preferred embodiments of the compounds of this invention as disclosed herein can be used in preparing the pharmaceutical compositions as described herein. As stated herein, the pharmaceutical compositions comprising the compounds of this invention are capable of antagonizing the effects of P2X7 receptor and thereby alleviating the inflammatory effects caused due to the P2X7 receptors.

Preferably the pharmaceutical compositions of this invention are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Flavored unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The pharmaceutical compositions of this invention can be administered by any of the methods known in the art. In general, the pharmaceutical compositions of this invention can be administered by oral, intramuscular, subcutaneous, rectal, intratracheal, intranasal, intraperitoneal or topical route. The preferred administration of the pharmaceutical composition of this invention is by an intranasal route. Any of the known methods to administer pharmaceutical compositions by an intranasal route can be used to administer the composition of this invention.

In the treatment of various disease states as described herein, a suitable dosage level is about 0.01 to 250 mg/kg per day, preferably about 0.05 to 100 mg/kg per day, and especially about 0.05 to 20 mg/kg per day. The compounds may be administered on a regimen of 1 to 4 times per day.

This invention is further illustrated by the following examples which are provided for illustration purposes and in no way limit the scope of the present invention.

EXAMPLES

General

As used in the examples and preparations that follow, the terms used therein shall have the meanings indicated: "kg" refers to kilograms, "g" refers to grams, "mg" refers to milligrams, "µg" refers to micrograms, "pg" refers to picograms, "mol" refers to moles, "mmol" refers to millimoles, "nmole" refers to nanomoles, "L" refers to liters, "mL" or "ml" refers to milliliters, "µL" refers to microliters, "° C." refers to degrees Celsius, "$R_f$" refers to retention factor, "mp" or "m.p." refers to melting point, "dec" refers to decomposition, "bp" or "b.p." refers to boiling point, "mm of Hg" refers to pressure in millimeters of mercury, "cm" refers to centimeters, "nm" refers to nanometers, "abs." refers to absolute, "conc." refers to concentrated, "$[\alpha]^{20}_D$" refers to specific rotation of the D line of sodium at 20° C. obtained in a 1 decimeter cell, "c" refers to concentration in g/mL, "THF" refers to tetrahydrofuran, "DMF" refers to dimethylformamide, "NMP" refers to 1-methyl-2-pyrrolidinone, "brine" refers to a saturated aqueous sodium chloride solution, "M" refers to molar, "mM" refers to millimolar, "µM" refers to micromolar, "nM" refers to nanomolar, "TLC" refers to thin layer chromatography, "HPLC" refers to high performance liquid chromatography, "HRMS" refers to high resolution mass spectrum, "lb" refers to pounds, "gal" refers to gallons, "L.O.D." refers to loss on drying, "µCi" refers to microcuries, "i.p." refers to intraperitoneally, "i.v." refers to intravenously.

General Analytical Techniques Used for the Characterization: A variety of analytical techniques are used to characterize and isolate the compounds of this invention, which included the following:

The phrase "concentrated in vacuo or rotary evaporated" indicates rotary evaporation using a Buchi apparatus at 20-60° C. and 15-30 torr using a KNF Neuberger diaphragm pump. Room temperature is abbreviated as "RT".

Preparative reversed phase HPLC was carried out on a Rainin SD1 unit using a Dynamax $C_{18}$ column (60 A spherical 13 µm particles). The mobile phase consisted of acetonitrile/buffer mixtures, with buffer composed of distilled water, acetonitrile, and trifluoroacetic acid (TFA) in the ratio listed in the experimental procedures.

$^1$H NMR spectra were recorded on a Varian Gemini 300, Unity 300, Unity 400, or Unity 500 spectrometers with chemical shifts (δ) reported in ppm relative to tetramethylsilane (0.00 ppm) or chloroform (7.26 ppm) as a reference. Signals were designated as s (singlet), d (doublet), t (triplet), q (quartet), p (pentuplet), m (multiplet), br (broad).

Chromatographic (flash) purifications on silica gel were done using pre-packed Isco or Biotage cartridges (32-63 µm, 60 A).

Mass spectra (MS) were obtained on a Finnigan MAT Model TSQ 700 Mass Spectrometer System by chemical ionization at 120 eV using methane (CI, 120 eV). The protonated molecular ion designated as (M$^+$+1) is given in parentheses.

Liquid chromatography with mass spectral analysis (LC/MS): HPLC: column: 50×4.6 mm, Hypersil BDS C18 3u. Mobile Phase: A=water with 0.05% trifluoroacetic acid, B=acetonitrile with 0.05% trifluoroacetic acid, flow rate=1.0 ml/min, gradient=5% B to 100% B in 3 min, stay 100% for 2 min. Mass Spectrometry: Lct API LC/Orthogonal Time of Flight Mass Spectrometer and Masslynx Data System from Micromass. Ionization mode=electrospray (ESI), Source temperature=120° C., Desolvation temperature=250° C., Cone voltage=25 volt, Acquisition mass range nm/z from 145 to 1000. Values were determined for the protonated molecular ions (M$^+$+1).

Several of the intermediates unless otherwise mentioned were obtained by a variety of commercial sources. For instance, meso-1,2-diphenylethane-1,2-diamine (1); (1S, 2S)-(−)-diphenylethane-1,2-diamine (2); (1R,2R)-(+)-diphenylethane-1,2-diamine (3); cis-1,2-diaminocyclohexane (24) were purchased from Aldrich Chemical Co. Various other intermediates used in the syntheses of the compounds of this invention were prepared in accordance with the procedures set forth in the following Preparations 1 to 67.

Preparation 1 meso-1,2-bis-(2-Fluorophenyl)ethane-1,2-diamine (4)

A mixture of 2-fluororobenzaldehyde (40 mL, 0.38 mol) and ammonium acetate (85.0 g, 1.1 mol) is heated at 130° C. for 6 h and then at 100° C. overnight. The mixture is cooled to RT, suspended in abs. EtOH and filtered. The filter cake is washed with abs. EtOH and with 95% EtOH. The crude intermediate, 2-fluoro-N-[2-[(2-fluorobenzylidine)amino]-1,2-cis-bis-(2-fluorophenyl)ethyl]benzamide (28.9 g), is used in the next step without further purification.

The crude intermediate (5.0 g, 10.5 mmol) is suspended in 50% $H_2SO_4/H_2O$ (50 mL) and heated at 180° C. overnight. Water (5 mL portions) is added every 30 min for the first 2 h. The reaction mixture is cooled (ice bath), and water is added slowly. The solution is extracted with ether. The cold aqueous layer is basified with conc. NH$_4$OH, and extracted with ether. The combined ether extracts are dried (MgSO$_4$), filtered, and concentrated in vacuo to yield 2.6 g of the product 4. $^1$H NMR (CDCl$_3$) δ 7.40-7.30 (m, 2 H), 7.30-7.20 (m, 2 H), 7.20-7.10 (m, 2 H), 7.10-7.00 (m, 2 H), 4.45 (s, 2 H), 1.47 (s, 4 H); MS: m/z 249 (M$^+$+1).

Preparation 2 meso-1,2-bis-(3-Fluorophenyl)ethane-1,2-diamine (5)

A mixture of 3-fluororobenzaldehyde (45.38 g, 0.37 mol) and ammonium acetate (92.0 g, 1.2 mol) is heated at 130° C. overnight. The mixture is cooled to RT, suspended in abs. EtOH and filtered. The filter cake is washed with abs. EtOH and with 95% EtOH. The crude intermediate, 3-fluoro-N-[2-[(3-fluorobenzylidine)amino]-1,2-cis-bis-(3-fluorophenyl)-ethyl]benzamide (39.7 g) is used in the next step without further purification.

The crude intermediate (30.0 g, 63 mmol) is suspended in 50% $H_2SO_4/H_2O$ (300 mL) and heated at 170° C. for 10 h. Water (5 mL portions) is added every 30 min for the first 2 h. The reaction mixture is cooled (ice bath), and water is added slowly. The solution is extracted with ether. The cold aqueous layer is basified with conc. NH$_4$OH, and extracted with ether. The combined ether extracts are dried (MgSO$_4$), filtered, and concentrated in vacuo to yield 14.6 g of the product 5. $^1$H NMR (CDCl$_3$) δ 7.35-7.25 (m, 2 H), 7.15-7.05 (m, 4 H), 7.05-6.95 (m, 2 H), 4.02 (s, 2 H), 1.34 (s, 4 H); MS: m/z 249 (M$^+$+1).

Preparation 3 meso-1,2-bis-(4-Fluorophenyl)ethane-1,2-diamine
(6)

A mixture of 4-fluorobenzaldehyde (117.8 g, 0.95 mol) and ammonium acetate (204 g, 2.64 mol) is heated at 130° C. for 5 h. The mixture is cooled to RT, suspended in abs. EtOH and filtered. The filter cake is washed with abs. EtOH and with 95% EtOH. The crude intermediate, 4-fluoro-N-[2-[(4-fluorobenzylidine)amino]-1,2-cis-bis-(4-fluorophenyl)-ethyl]benzamide (80.8 g) is used in the next step without further purification.

The crude intermediate (30 g, 63 mmol) is suspended in 50% H$_2$SO$_4$/H$_2$O (300 mL) and heated at 180° C. for 7 h. The reaction mixture is cooled (ice bath), and water (150 mL) is added slowly. The solution is extracted with ether. The cold aqueous layer is basified with conc. NH$_4$OH, and extracted with ether. The combined ether extracts are dried (MgSO$_4$), filtered, and concentrated in vacuo to yield 8.14 g of the product 6. $^1$H NMR (CDCl$_3$) δ 7.40-7.30 (m, 4 H), 7.10-7.00 (m, 4 H), 3.99 (s, 2 H), 1.52 (s, 4 H); MS: m/z 249 (M$^+$+1).

Preparation 4 meso-1,2-bis-(2-Chlorophenyl)ethane-1,2-diamine
(7)

A mixture of 2-chlorobenzaldehyde (117.8 g, 0.95 mol) and ammonium acetate (204 g, 2.64 mol) is heated at 130° C. overnight. The mixture is cooled to RT, suspended in abs. EtOH and filtered. The filter cake is washed with abs. EtOH and with 95% EtOH. The crude intermediate, 2-chloro-N-[2-[(2-chlorobenzylidine)amino]-1,2-cis-bis-(2-chlorophenyl)-ethyl]benzamide (80.8 g) is used in the next step without further purification The crude intermediate (30 g, 63 mmol) is suspended in 50% H$_2$SO$_4$/H$_2$O (300 mL) and heated at 180° C. for 7 h. The reaction mixture is cooled (ice bath), and water is added slowly. The solution is extracted with ether. The cold aqueous layer is basified with conc. NH$_4$OH, and extracted with ether. The combined ether extracts are dried (MgSO$_4$), filtered, and concentrated in vacuo to yield 8.14 g of the product 7.

Preparation 5 meso-1,2-bis-(3-Chlorophenyl)ethane-1,2-diamine
(8)

A mixture of 3-chlorobenzaldehyde (50 g, 0.36 mol) and ammonium acetate (77 g, 1.0 mol) is heated at 130° C. overnight. The mixture is cooled to RT, suspended in abs. EtOH and filtered. The filter cake is washed with abs. EtOH and with 95% EtOH. The crude intermediate, 3-chloro-N-[2-[(3-chlorobenzylidine)amino]-1,2-cis-bis-(3-chlorophenyl)-ethyl]benzamide (34.3 g) is used in the next step without further purification The crude intermediate (30 g, 55 mmol) is suspended in 50% H$_2$SO$_4$/H$_2$O (300 mL) and heated at 180° C. for 7 h. The reaction mixture is cooled (ice bath), and water is added slowly. The solution is extracted with ether. The cold aqueous layer is basified with conc. NH$_4$OH, and extracted with ether. The combined ether extracts are dried (MgSO$_4$), filtered, and concentrated in vacuo to yield 8.14 g of the product 8.

Preparation 6 meso-1,2-bis-(4-Chlorophenyl)ethane-1,2-diamine
(9)

A mixture of 4-chlorobenzaldehyde (138 g, 0.98 mol) and ammonium acetate (276 g, 3.58 mol) is heated at 130° C. overnight. The mixture is cooled to RT, suspended in abs. EtOH and filtered. The filter cake is washed with abs. EtOH and with 95% EtOH. The crude intermediate, 4-chloro-N-[2-[(4-chlorobenzylidine)amino]-1,2-cis-bis-(4-chlorophenyl)-ethyl]benzamide (107 g) is used in the next step without further purification.

The crude intermediate (107 g, 0.193 mol) is suspended in 50% H$_2$SO$_4$/H$_2$O (500 mL) and heated at 180° C. for 10 h. The reaction mixture is cooled (ice bath), and water is added slowly. The solution is extracted with ether. The cold aqueous layer is basified with conc. NH$_4$OH, and extracted with ether. The combined ether extracts are dried (MgSO$_4$), filtered, and concentrated in vacuo to yield 38.1 g of the product 9. $^1$H NMR (CDCl$_3$) δ 7.35-7.15 (m, 8 H), 3.97 (s, 2 H), 1.38 (s, 4 H); MS: m/z 281 (M$^+$+1).

Preparation 7 meso-1,2-bis-(2-Bromophenyl)ethane-1,2-diamine
(10)

A mixture of 2-bromobenzaldehyde (45 g, 0.24 mol) and ammonium acetate (90 g, 1.2 mol) is heated at 130° C. overnight. The mixture is cooled to RT, and the gummy yellow residue is washed with heptane. The crude intermediate, 2-bromo-N-[2-[(2-bromo-benzylidine)amino]-1,2-cis-bis-(2-bromophenyl)ethyl]benzamide, is used in the next step without further purification.

The crude intermediate from above is suspended in 50% H$_2$SO$_4$/H$_2$O (400 mL) and heated at 170° C. overnight. The reaction mixture is cooled (ice bath), and water (200 mL) is added slowly. The solution is extracted with ether. The cold aqueous layer is basified with conc. NH$_4$OH, and extracted with ether. The combined ether extracts are dried (MgSO$_4$), filtered, and concentrated in vacuo to yield the product 10.

Preparation 8 meso-1,2-bis-(2-Methylphenyl)ethane-1,2-diamine
(11)

A mixture of 2-methylbenzaldehyde (100 g, 0.83 mol) and ammonium acetate (200 g, 2.6 mol) is heated at 135° C. overnight. The mixture is cooled to RT, suspended in abs. EtOH and filtered. The filter cake is washed with abs. EtOH. The crude intermediate, 2-methyl-N-[2-[(2-methylbenzylidine)amino]-1,2-cis-bis-(2-methylphenyl)ethyl]-benzamide (34.7 g) is used in the next step without further purification.

The crude intermediate (34.2 g, 70 mmol) is suspended in 50% H$_2$SO$_4$/H$_2$O (200 mL) and heated at 180° C. for 5 h and then at 150° C. overnight. The reaction mixture is cooled (ice bath), and water (100 mL) is added slowly. The solution is extracted with ether. The cold aqueous layer is basified with conc. NH$_4$OH, and extracted with ether. The combined ether extracts are dried (MgSO$_4$), filtered, and concentrated in vacuo to yield 13.6 g of the product 11. $^1$H NMR (CDCl$_3$) δ

7.45-7.35 (m, 2 H), 7.30-7.10 (m, 6H), 4.44 (s, 2 H), 2.31 (s, 6 H), 1.44 (s, 4 H); MS: m/z 241 (M$^+$+1).

Preparation 9 meso-1,2-bis-(3-Methylphenyl)ethane-1,2-diamine (12)

A mixture of 3-methylbenzaldehyde (100 g, 0.83 mol) and ammonium acetate (200 g, 2.6 mol) is heated at 130° C. overnight. The mixture is cooled to RT, suspended in abs. EtOH and filtered. The filter cake is washed with abs. EtOH and with 95% EtOH. The crude intermediate, 3-methyl-N-[2-[(3-methylbenzylidine)amino]-1,2-cis-bis-(3-methyl-phenyl)-ethyl]benzamide (81.2 g) is used in the next step without further purification.

The crude intermediate (79.7 g, 173 mmol) is suspended in 50% $H_2SO_4/H_2O$ (200 mL) and heated at 180° C. for 5 h. The reaction mixture is cooled (ice bath), and water (200 mL) is added slowly. The solution is extracted with ether. The cold aqueous layer is basified with conc. $NH_4OH$, and extracted with ether. The combined ether extracts are dried ($MgSO_4$), filtered, and concentrated in vacuo to yield 5.18 g of the product 12. $^1H$ NMR (CDCl$_3$) δ 7.35-7.20 (m, 6 H), 7.15-7.10 (m, 2 H), 3.96 (s, 2 H), 2.37 (s, 6 H), 1.43 (s, 4 H); MS: m/z 241 (M$^+$+1).

Preparation 10 meso-1,2-bis-(4-Methylphenyl)ethane-1,2-diamine (13)

A mixture of 4-methylbenzaldehyde (100 mL, 0.85 mol) and ammonium acetate (200 g, 2.6 mol) is heated at 130° C. overnight. The mixture is cooled to RT, suspended in abs. EtOH and filtered. The filter cake is washed with abs. EtOH and with 95% EtOH. The crude intermediate, 4-methyl-N-[2-[(4-methylbenzylidine)amino]-1,2-cis-bis-(4-methylphenyl)-ethyl]benzamide (68.2 g) is used in the next step without further purification.

The crude intermediate (67.8 g, 147 mmol) is suspended in 50% $H_2SO_4/H_2O$ (500 mL) and heated at 180° C. overnight. The reaction mixture is cooled (ice bath), and water (200 mL) is added slowly. The solution is extracted with ether. The cold aqueous layer is basified with conc. $NH_4OH$, and extracted with ether. The combined ether extracts are dried ($MgSO_4$), filtered, and concentrated in vacuo to yield 7.83 g of the product 13.

Preparation 11 cis-1,2-Diphenylpropane-1,2-diamine (16)

Step 1

3,4-Diphenyl-1,2,5-thiadiazole-1,1-dioxide (14)

Hydrogen chloride is bubbled through a solution of benzil (24 g, 0.11 mmol) and sulfamide (11 g, 0.11 mmol) in methanol (120 mL) for 2 h followed by heating to reflux for 2 h. The reaction mixture is cooled to RT, and the precipitate that formed is filtered to give 25.1 g of the product 14.

Step 2 cis-3,4-Diphenyl-3-methyl-2,3-dihydro-1,2,5-thiadiazole-1,1-dioxide (15)

To a cool (10° C.) suspension of 14 (25 g, 92 mmol) in toluene:THF (300:60 mL) is added 3.0M methylmagnesium bromide in Et$_2$O (35 mL, 105 mmol), and the mixture is stirred at ambient temperature for 1 h. The reaction mixture is quenched with saturated ammonium chloride, extracted with EtOAc, and the organic extract is washed with brine, dried (MgSO$_4$), filtered, and the filtrate rotary evaporated. The residue is dissolved in methanol (250 mL), cooled to 0° C., and sodium borohydride (9 g, 238 mmol) is added portionwise. The mixture is stirred at ambient temperature for 45 min, cooled to 0° C., and 5M HCl is added to bring the solution to pH 2. The mixture is extracted with EtOAc, and the organic extract is washed with brine, dried (MgSO$_4$), filtered, and the filtrate rotary evaporated. The residue is crystallized from toluene to give 20.4 g of the product 15.

Step 3 cis-1,2-Diphenylpropane-1,2-diamine (16)

A suspension of 15 (20.4 g, 70 mmol) in 2M HBr (500 mL) containing phenol (32 g) is stirred and heated at reflux for 40 h. The mixture is cooled to RT, extracted with EtOAc, and the aqueous solution is cooled (ice bath) and made basic with sodium hydroxide. The basic solution is extracted with Et$_2$O, and the extract dried (Na$_2$SO$_4$), filtered, and the filtrate rotary evaporated to give 11.1 g of the product 16.

Preparation 12 cis-1,2-bis-(4-Fluorophenyl)propane-1,2-diamine (19)

Step 1

3,4-bis-4-(Fluorophenyl)-1,2,5-thiadiazole-1,1-dioxide (17)

Hydrogen chloride is bubbled through a solution of 4,4'-difluorobenzil (5.0 g, 20.3 mmol) and sulfamide (2.67 g, 27.8 mmol) in methanol (20 mL) for 0.5 min followed by heating to reflux for 2 h. The reaction mixture is cooled to RT, and the precipitate that formed is filtered to give 3 g of the product 17.

Step 2 cis-3,4-bis-(4-Fluorophenyl)-3-methyl-2,3-dihydro-1,2,5-thiadiazole-1,1-dioxide (18)

To a cool (10° C.) suspension of 17 (2.2 g, 7.19 mmol) in toluene:THF (60:6 mL) is added 3.0M methylmagnesium bromide in Et$_2$O (3.59 mL, 10.8 mmol), and the mixture is stirred at ambient temperature for 1 h. The reaction mixture is quenched with saturated ammonium chloride, extracted with EtOAc, and the organic extract is dried (Na$_2$SO$_4$), filtered, and the filtrate rotary evaporated. The residue is dissolved in methanol (20 mL), cooled to 0° C., and sodium borohydride (1.08 g, 28.5 mmol) is added portionwise. The mixture is stirred at 20° C. for 45 min, cooled to 0° C., and 5M HCl is added to bring the solution to pH 2. The mixture is extracted with EtOAc, and the organic extract is washed with brine, dried (Na$_2$SO$_4$), filtered, and the filtrate rotary evaporated. The residue is dissolved in EtOAc, and the addition of heptane precipitates 1.5 g of the product 18.

Step 3 cis-1,2-bis-(4-Fluorophenyl)propane-1,2-diamine (19)

A suspension of 18 (1.5 g, 4.6 mmol) in 2M HBr (56 mL) containing phenol (2.17 g) is stirred and heated at reflux for 24 h. The mixture is cooled to RT, extracted with EtOAc, and the aqueous solution is cooled (ice bath) and made basic with sodium hydroxide. The basic solution is extracted with EtOAc:Et$_2$O (1:1), and the extract is washed with brine, dried (Na$_2$SO$_4$), filtered, and the filtrate rotary evaporated to give 0.7 g of the product 19.

Preparation 13 cis-1,2-bis-(3-Fluorophenyl)propane-1,2-diamine (23)

Step 1

3,3'-Difluorobenzil (20)

To anhydrous THF (80 mL) is added magnesium (2.9 g, 0.120 mol) and 1-bromo-3-fluorobenzene (12.76 g, 0.114 mol) in anhydrous THF (30 mL). The mixture is stirred at 21° C. for 1.5 h. To THF (60 mL) is added lithium bromide (13.22 g, 0.015 mol) and copper (I) bromide (10.9 g, 0.0762 mol) and the mixture is stirred at RT until homogenous, then cooled to 0° C. To this solution is added 3-fluorophenylmagnesium bromide solution followed by a solution of oxalyl chloride (2.76 mL, 0.0317 mol) in THF (20 mL). The solution is stirred at 0° C. for 15 min, then quenched by ammonium chloride solution, and extracted with EtOAc. The organic solution is dried (Na$_2$SO$_4$), filtered, and the filtrate rotary evaporated. The residue is purified by filtration through silica gel; elution with heptane and heptane:EtOAc (9:1) gives 0.70 g of the product 20.

Step 2

3,4-bis-(3-Fluorophenyl)-1,2,5-thiadiazole-1,1-dioxide (21)

Hydrogen chloride is bubbled through a solution of 3,3'-difluorobenzil (20) (3.81 g, 15.7 mmol) and sulfamide (1.53 g, 15.9 mmol) in methanol (15 mL) for 0.5 min followed by heating at 66° C. for 2 h. The reaction mixture is cooled to RT, the solvent rotary evaporated, and the residue triturated from heptane to give 3.50 g of the product 21.

Step 3 cis-3,4-bis-(3-Fluorophenyl)-3-methyl-2,3-dihydro-1,2,5-thiadiazole-1,1-dioxide (22)

To a cool (10° C.) suspension of 21 (1.50 g, 4.90 mmol) in toluene:THF (40:4 mL) is added 3.0M methylmagnesium bromide in Et$_2$O (2.45 mL, 7.35 mmol), and the mixture is stirred at 10° C. for 0.5 h. The reaction mixture is quenched with saturated ammonium chloride, extracted with EtOAc, and the organic extract is washed with brine, dried (Na$_2$SO$_4$), filtered, and the filtrate rotary evaporated. The residue is dissolved in methanol (15 mL), cooled to 0° C., and sodium borohydride (742 mg, 20.1 mmol) is added portionwise. The mixture is stirred at 20° C. for 45 min, and 5M HCl is added to bring the solution to pH 2. The mixture is extracted with EtOAc, and the organic extract is washed with brine, dried (Na$_2$SO$_4$), filtered, and the filtrate rotary evaporated to give 1.5 g of the product 22.

Step 4 cis-1,2-bis-(3-Fluorophenyl)propane-1,2-diamine (23)

A suspension of 22 (1.50 g, 4.62 mmol) in 2M HBr (56 mL) containing phenol (2.17 g) is stirred and heated at reflux (130° C.) for 24 h. The mixture is cooled to RT, extracted with EtOAc, and the aqueous solution is cooled (ice bath) and made basic (pH 14) with sodium hydroxide. The basic solution is extracted with EtOAc, and the extract is washed with water, brine, then dried (Na$_2$SO$_4$), filtered, and the filtrate rotary evaporated to give 1.06 g of the product 23.

Preparation 14 cis-4,5-Diphenylimidazolidine-2-thione (25)

A mixture of cis-1,2-diphenylethane-1,2-diamine (1) (50 g, 0.26 mol) and carbon disulfide (24 mL, 0.40 mol) in abs. EtOH (600 mL) is heated at 95° C. overnight. The reaction mixture is cooled to rt, concentrated in vacuo, and the residue suspended in cold 95% EtOH, and the insoluble material is filtered, to give 58.16 g of the product 25. $^1$H NMR (DMSO-d$_6$) δ 8.73 (s, 2 H), 7.10-6.95 (m, 6 H), 6.95-6.85 (m, 2 H), 5.31 (s, 2 H); MS: m/z 255 (M$^+$+1).

Preparation 15 cis-4,5-bis-(2-Fluorophenyl)imidazolidine-2-thione (26)

A mixture of cis-1,2-bis-(2-fluorophenyl)ethane-1,2-diamine (4) (2.51 g, 0.010 mol) and carbon disulfide (1.21 mL, 0.020 mol) in abs. EtOH (40 mL) is heated at 90° C. for 8 h. The reaction mixture is cooled to RT, concentrated in vacuo, and the residue suspended in abs EtOH, and the insoluble material is filtered to give 2.48 g of the product 26. $^1$H NMR (CDCl$_3$) δ 7.20-7.05 (m, 4 H), 6.95-6.90 (m, 2 H), 6.90-6.75 (m, 2 H), 6.32 (s, 2 H), 5.80 (s, 2 H); MS: m/z 291 (M$^+$+1).

Preparation 16 cis-4,5-bis-(3-Fluorophenyl)imidazolidine-2-thione (27)

A mixture of cis-1,2-bis-(3-fluorophenyl)ethane-1,2-diamine (5) (5.0 g, 0.02 mol) and carbon disulfide (2.46 mL, 0.040 mol) in abs. EtOH (50 mL) is heated at 90° C. overnight. The reaction mixture is cooled to RT, concentrated in vacuo, and the residue suspended in abs EtOH:heptane, and the insoluble material is filtered to give 4.74 g of the product 27. $^1$H NMR (CDCl$_3$) δ 7.15-7.05 (m, 2 H), 6.90-6.80 (m, 2 H), 6.80-6.70 (m, 2H), 6.70-6.60 (m, 2 H), 6.33 (s, 2 H), 5.37 (s, 2 H); MS: m/z 291 (M$^+$+1)

Preparation 17 cis-4,5-bis-(4-Fluorophenyl)imidazolidine-2-thione (28)

A mixture of cis-1,2-bis-(4-fluorophenyl)ethane-1,2-diamine (6) (1.9 g, 0.508 mol) and carbon disulfide (0.92 mL, 1.53 mol) in abs. EtOH (50 mL) is heated at 95° C. overnight. The reaction mixture is cooled to RT, concentrated in vacuo, and the residue suspended in abs EtOH, and the insoluble material is filtered to give 1.8 g of the product 28. ¹H NMR (CDCl₃) δ 6.95-6.75 (m, 8 H), 6.54 (s, 2 H), 5.34 (s, 2 H); MS: m/z 291 (M⁺+1).

Preparation 18 cis-4,5-bis-(2-Methylphenyl)imidazolidine-2-thione (29)

A mixture of cis-1,2-bis-(2-methylphenyl)ethane-1,2-diamine (11) (5.63 g, 0.0234 mol) and carbon disulfide (2.82 mL, 0.0468 mol) in abs. EtOH (50 mL) is heated at 95° C. overnight. The reaction mixture is cooled to RT, concentrated in vacuo, and the residue suspended in abs EtOH:heptane, and the insoluble material is filtered to give 6.10 g of the product 29. ¹H NMR (CDCl₃) δ 7.05-6.95 (m, 6 H), 6.95-6.90 (m, 2 H), 6.11 (s, 2 H), 5.63 (s, 2 H), 2.12 (s, 3 H); MS: m/z 283 (M⁺+1).

Preparation 19 cis-4,5-bis-(3-Methylphenyl)imidazolidine-2-thione (30)

A mixture of cis-1,2-bis-(3-methylphenyl)ethane-1,2-diamine (12) (3.00 g, 0.0125 mol) and carbon disulfide (1.5 mL, 0.025 mol) in abs. EtOH (30 mL) is heated at 90° C. overnight. The reaction mixture is cooled to RT, concentrated in vacuo, and the residue suspended in abs EtOH, and the insoluble material is filtered to give 2.25 g of the product 30. ¹H NMR (CDCl₃) δ 7.05-6.90 (m, 4 H), 6.85-6.80 (m, 4 H), 6.19 (s, 2 H), 5.31 (s, 2 H), 2.15 (s, 6 H); MS: m/z 283 (M⁺+1).

Preparation 20 cis-4,5-bis-(4-Methylphenyl)imidazolidine-2-thione (31) (Scheme 2, Method a)

A mixture of cis-1,2-bis-(4-methylphenyl)ethane-1,2-diamine (13) (5.59 g, 0.233 mol) and carbon disulfide (2.8 mL, 0.0465 mol) in abs. EtOH (30 mL) is heated at 100° C. overnight. The reaction mixture is cooled to RT, concentrated in vacuo, and the residue suspended in abs. EtOH:heptane, and the insoluble material is filtered to give 5.53 g of the product 31. ¹H NMR (CDCl₃) δ 6.95-6.90 (d, 4 H), 6.85-6.75 (d, 4 H), 6.14 (s, 2 H), 5.30 (s, 2 H), 2.21 (s, 6 H); MS: m/z 283 (M⁺+1).

Preparation 21 cis-4,5-bis-(2-Chlorophenyl)imidazolidine-2-thione (32)

A mixture of cis-1,2-bis-(2-chlorophenyl)ethane-1,2-diamine (7) (8.78 g, 0.0312 mol) and carbon disulfide (3.5 mL, 0.0582 mol) in abs. EtOH (120 mL) is heated at 95° C. overnight. The reaction mixture is cooled to RT, concentrated in vacuo to crystallize the product. The material is filtered to give 10.1 g of the product 32. ¹H NMR (DMSO-d₆) δ 8.80 (s, 2H), 7.25-6.95 (m, 8H0), 5.70 (s, 2H); MS: m/z 323 (M⁺+1)

Preparation 22 cis-4,5-bis-(3-Chlorophenyl)imidazolidine-2-thione (33)

A mixture of cis-1,2-bis-(3-chlorophenyl)ethane-1,2-diamine (8) (9.49 g 0.0338 mol) and carbon disulfide (4.06 mL, 0.0675 mol) in abs. EtOH (150 mL) is heated at 95° C. overnight. The reaction mixture is cooled to RT, concentrated in vacuo to crystallize the product. The material is filtered to give 10.1 g of the product 33. ¹H NMR (DMSO-d₆) δ 8.85 (s, 2H), 7.20-7.10 (m, 4H), 7.00-6.80 (m, 4H), 5.35 (s, 2H); MS: m/z 323 (M⁺+1)

Preparation 23 cis-4,5-bis-(4-Chlorophenyl)imidazolidine-2-thione (34)

A mixture of cis-1,2-bis-(4-chlorophenyl)ethane-1,2-diamine (9) (38.1 g, 0.135 mol) and carbon disulfide (16.3 mL, 0.0271 mol) in abs. EtOH (100 mL) is heated at 95° C. for 6 h. The reaction mixture is cooled to RT, and the solid that formed is filtered to give 30 g of the product 34. ¹H NMR (CDCl₃) δ 7.10-7.10 (d, 4 H), 6.95-6.90 (d, 4 H), 6.43 (s, 2 H), 5.33 (s, 2 H); MS: m/z 323 (M⁺+1).

Preparation 24 cis-4,5-bis-(2-Bromophenyl)imidazolidine-2-thione (35)

A mixture of the crude cis-1,2-bis-(2-bromophenyl)ethane-1,2-diamine (10) (4.07 g, 11 mmol) and carbon disulfide (2 mL, 33.3 mmol) in abs. EtOH (100 mL) is heated at 120° C. overnight. The reaction mixture is cooled to RT, and the solid that formed is filtered to give 0.56 g of the crude product 35.

Preparation 25 trans-(4S,5S)-Diphenylimidazolidine-2-thione (36)

A mixture of trans-(1S,2S)-(−)-diphenylethane-1,2-diamine (2) (0.5 g, 2.4 mmol) and carbon disulfide (0.350 mL, 5.80 mmol) in abs. EtOH (20 mL) is heated at 95° C. overnight. The reaction mixture is cooled to RT, the solvent removed by rotary evaporation, and the residue suspended in cold abs. EtOH. The insoluble material is filtered to give 0.5 g of the product 36. ¹H NMR (DMSO-d₆) δ 8.80 (s, 2 H), 7.50-7.20 (m, 10 H), 4.66 (s, 2 H); MS: m/z 255 (M⁺+1).

Preparation 26 trans-(4R,5R)-Diphenylimidazolidine-2-thione (37)

A mixture of trans-(1R,2R)-(+)-diphenylethane-1,2-diamine (3) (5.75 g, 27.1 mmol) and carbon disulfide (5 mL, 81.3 mmol) in abs. EtOH (70 mL) is heated at 95° C. overnight. The reaction mixture is cooled to RT, the solvent removed by rotary evaporation, and the residue suspended in abs. EtOH. The insoluble material is filtered to give 6.87 g of the product 37. ¹H NMR (DMSO-d₆) δ 8.79 (s, 2 H), 7.50-7.20 (m, 10 H), 4.66 (s, 2 H); MS: m/z 255 (M⁺+1).

Preparation 27 cis-4,5-Diphenyl-4-methylimidazolidine-2-thione (38)

A mixture of cis-1,2-diphenylpropane-1,2-diamine (16) (1.0 g, 4.42 mmol) and carbon disulfide (0.293 mL, 4.87 mmol) in abs. EtOH (5 mL) is heated at 95° C. for 6 h. The reaction mixture is cooled to 0° C., and the precipitate that formed is filtered to give 658 mg of the product 38. $^1$H NMR (DMSO-d$_6$) δ 8.85 (s, 1 H), 8.65 (s, 1 H), 7.15-6.75 (m, 10 H), 4.90 (s, 1 H), 1.75 (s, 3 H); MS: m/z 269 (M$^+$+1).

Preparation 28 cis-4,5-bis-(4-Fluorophenyl)-4-methylimidazolidine-2-thione (39)

A mixture of cis-1,2-bis-(4-fluorophenyl)propane-1,2-diamine (19) (1.24 g, 4.73 mmol) and carbon disulfide (0.427 mL, 7.09 mmol) in abs. EtOH (5 mL) is heated at 85° C. overnight. The reaction mixture is cooled to 0° C., and the precipitate that formed is filtered to give 1.2 g of the product 39.

Preparation 29 cis-4,5-bis-(3-Fluorophenyl)-4-methylimidazolidine-2-thione (40)

A mixture of cis-1,2-bis-(3-fluorophenyl)propane-1,2-diamine (23) (858 mg, 3.27 mmol) and carbon disulfide (0.395 mL, 6.81 mmol) in abs. MeOH (5 mL) is heated at 75° C. for 6 h. The reaction mixture is cooled to RT, the solvent evaporated, and the residue triturated with heptane. The insoluble material is filtered and further purified by chromatography on silica gel; elution with heptane:EtOAc (5:1) gives 23 mg of the product 40. $^1$H NMR (CDCl$_3$) δ 7.70-7.00 (m, 2 H), 6.95-6.55 (m, 6 H), 6.47 (s, 1 H), 6.23 (s, 1 H), 4.96 (s, 1 H), 1.90 (s, 3 H); MS: m/z 304 (M$^+$+1).

Preparation 30 cis-1H-Benzimidazol-3a,4,5,6,7,7a-hexahydro-2-thione (41)

A mixture of cis-1,2-diaminocyclohexane (24) (10 g, 87.6 mmol) and carbon disulfide (10.5 mL, 175 mol) in abs. EtOH (100 mL) is heated at 95° C. overnight. The reaction mixture is cooled to RT, the solvent evaporated, and the residue triturated with 95% EtOH. The insoluble material is filtered to give 9.74 g of the product 41. $^1$H NMR (DMSO-d$_6$) δ 8.08 (s, 2 H), 4.75-4.60 (m, 2 H), 1.70-1.15 (m, 8 H); MS: m/z 157 (M$^+$+1).

Preparation 31 cis-4,5-Diphenyl-2-methylthio-4,5-dihydro-1H-imidazole hydroiodide (42)

A mixture of cis-4,5-diphenylimidazolidine-2-thione (25) (58.16 g, 0.229 mol) and methyl iodide (35.6 mL, 0.87 mol) in abs. EtOH (500 mL) is heated at 95° C. overnight. The reaction mixture is cooled to RT, concentrated in vacuo, and the residue suspended in Et$_2$O. The insoluble material is filtered, washed with Et$_2$O to give 88.9 g of the product 42. $^1$H NMR (DMSO-d$_6$) δ 10.75 (s, 2 H), 7.25-6.95 (m, 10 H), 5.85 (s, 2 H), 2.82 (s, 3H); MS: m/z 269 (M$^+$+1).

Preparation 32 cis-4,5-bis-(2-Fluorophenyl)-2-methylthio-4,5-dihydro-1H-imidazole hydroiodide (43)

A mixture of cis-4,5-bis-(2-fluorophenyl)imidazolidine-2-thione (26) (2.45 g, 0.0084 mol) and methyl iodide (0.79 mL, 0.012 mol) in abs. EtOH (30 mL) is heated at 90° C. overnight. The reaction mixture is cooled to rt, concentrated in vacuo, and the residue crystallized from abs EtOH/Et$_2$O to give 3.42 g of the product 43. $^1$H NMR (DMSO-d$_6$) δ 10.85 (s, 2 H), 7.30-7.10 (m, 4 H), 7.10-6.90 (m, 4 H), 6.04 (s, 2 H), 2.80 (s, 3 H); MS: m/z 305 (M$^+$+1).

Preparation 33 cis-4,5-bis-(3-Fluorophenyl)-2-methylthio-4,5-dihydro-1H-imidazole hydroiodide (44)

A mixture of cis-4,5-bis-(3-fluorophenyl)imidazolidine-2-thione (27) (4.5 g, 0.0188 mol) and methyl iodide (1.45 mL, 0.0232 mol) in abs. EtOH (50 mL) is heated at 95° C. overnight. The reaction mixture is cooled to RT, concentrated in vacuo, and the residue suspended in abs EtOH/Et$_2$O. The insoluble material is filtered to give 6.10 g of the product 44. $^1$H NMR (DMSO-d$_6$) δ 10.78 (s, 2 H), 7.30-7.15 (m, 2 H), 7.05-6.90 (m, 6 H); 5.87 (s, 2 H), 2.87 (s, 3 H); MS: m/z 305 (M$^+$+1).

Preparation 34 cis-4,5-bis-(4-Fluorophenyl)-2-methylthio-4,5-dihydro-1H-imidazole hydroiodide (45)

A solution of cis-4,5-bis-(4-fluorophenyl)imidazolidine-2-thione (28) (1.78 g, 0.61 mmol) and methyl iodide (0.620 g, 10.0 mmol) in abs. EtOH (30 mL) is heated at 95° C. for 26 h. The reaction mixture is cooled to rt, concentrated in vacuo, and the residue suspended in abs. EtOH:Et$_2$O. The insoluble material is filtered to give 2.47 g of the product 45. $^1$H NMR (DMSO-d$_6$) δ 10.75 (s, 2 H), 7.15-6.95 (m, 8 H), 5.83 (s, 2 H), 2.81 (s, 3 H); MS: m/z 305 (M$^+$+1).

Preparation 35 cis-4,5-bis-(2-Methylphenyl)-2-methylthio-4,5-dihydro-1H-imidazole hydroiodide (46)

A mixture of cis-4,5-bis-(2-methylphenyl)imidazolidine-2-thione (29) (6.08 g, 0.0215 mol) and methyl iodide (2.01 mL, 0.0323 mol) in abs. EtOH (50 mL) is heated at 85° C. overnight. The reaction mixture is cooled to rt, concentrated in vacuo, and the residue suspended in Et$_2$O. The insoluble material is filtered to give 8.79 g of the product 46. $^1$H NMR (DMSO-d$_6$) δ 10.67 (s, 2 H), 7.10-6.90 (m, 8 H), 6.02 (s, 2 H), 2.79 (s, 3 H), 2.16 (s, 6 H); MS: m/z 297 (M$^+$+1).

Preparation 36 cis-4,5-bis-(3-Methylphenyl)-2-methylthio-4,5-dihydro-1H-imidazole hydroiodide (47)

A mixture of cis-4,5-bis-(3-methylphenyl)imidazolidine-2-thione (30) (2.23 g, 0.00825 mol) and methyl iodide (0.77 mL, 0.0124 mol) in abs. EtOH (30 mL) is heated at 95° C. overnight. The reaction mixture is cooled to rt, concentrated in vacuo, and the residue suspended in Et$_2$O. The insoluble material is filtered to give 3.24 g of the product 47. $^1$H NMR (DMSO-d$_6$) δ 10.71 (s, 2 H), 7.10-7.00 (m, 2 H), 7.00-6.90 (m, 2 H), 6.90-6.75 (m, 4 H), 5.73 (s, 2 H), 2.80 (s, 3 H), 2.13 (s, 6 H); MS: m/z 297 (M$^+$+1).

Preparation 37 cis-4,5-bis-(4-Methylphenyl)-2-methylthio-4,5-dihydro-1H-imidazole hydroiodide (48)

A mixture of cis-4,5-bis-(4-methylphenyl)imidazolidine-2-thione (31) (5.2 g, 0.0184 mol) and methyl iodide (1.72 mL, 0.0276 mol) in abs. EtOH (30 mL) is heated at 90° C. overnight. The reaction mixture is cooled to rt, concentrated in vacuo, and the residue suspended in abs EtOH:Et$_2$O. The insoluble material is filtered to give 7.56 g of the product 48. $^1$H NMR (DMSO-d$_6$) δ 10.68 (s, 2 H), 7.00-6.85 (m, 8 H), 5.72 (s, 2 H), 2.79 (s, 3 H), 2.15 (s, 6 H); MS: m/z 297 (M$^+$+1).

Preparation 38 cis-4,5-bis-(2-Chlorophenyl)-2-methylthio-4,5-dihydro-1H-imidazole hydroiodide (49)

A mixture of cis-4,5-bis-(2-chlorophenyl)imidazolidine-2-thione (32) (10.1 g, 0.0312 mol) and methyl iodide (3.89 mL, 0.0624 mol) in abs. EtOH (15 mL) is heated at 90° C. for 6 h. The reaction mixture is cooled to rt, concentrated in vacuo, and the residue suspended in abs EtOH. The insoluble material is filtered to give 11 g of the product 49.

Preparation 39 cis-4,5-bis-(3-Chlorophenyl)-2-methylthio-4,5-dihydro-1H-imidazole hydroiodide (50)

A mixture of cis-4,5-bis-(3-chlorophenyl)imidazolidine-2-thione (33) (8.23 g, 0.0254 mol) and methyl iodide (3.17 mL, 0.0509 mol) in abs. EtOH (25 mL) is heated at 90° C. for 8 h. The reaction mixture is cooled to rt, concentrated in vacuo, and the residue triturated with abs EtOH. The insoluble material is filtered to give 10.1 g of the product 50.

Preparation 40 cis-4,5-bis-(4-Chlorophenyl)-2-methylthio-4,5-dihydro-1H-imidazole hydroiodide (51)

A mixture of cis-4,5-bis-(4-chlorophenyl)imidazolidine-2-thione (34) (30 g, 0.0928 mol) and methyl iodide (11.5 mL, 0.186 mol) in abs. EtOH (100 mL) is heated at 90° C. for 8 h. The reaction mixture is cooled to rt, concentrated in vacuo, and the residue triturated with abs EtOH. The insoluble material is filtered to give 32.5 g of the product 51.

Preparation 41 cis-4,5-bis-(2-Bromophenyl)-2-methylthio-4,5-dihydro-1H-imidazole hydroiodide (52)

A solution of cis-4,5-bis-(2-bromophenyl)imidazolidine-2-thione (35) (0.51 g, 1.36 mmol) and methyl iodide (0.178 mL, 2.1 mmol) in abs. EtOH (20 mL) is heated at 90° C. overnight. The reaction mixture is cooled to rt, concentrated in vacuo, and the residue suspended in Et$_2$O. The insoluble material is filtered to give 0.51 g of the product 52.

Preparation 42 trans-(4S,5S)-Diphenyl-2-methylthio-4,5-dihydro-1H-imidazole hydroiodide (53)

A mixture of trans-(4S,5S)-diphenylimidazolidine-2-thione (36) (6.93 g, 27.2 mmol) and methyl iodide (4.24 mL, 68.1 mmol) in abs. EtOH (50 mL) is heated at 95° C. overnight. The reaction mixture is cooled to rt, concentrated in vacuo, and the residue triturated with Et$_2$O. The insoluble material is filtered to give 10.5 g of the product 53. $^1$H NMR (DMSO-d$_6$) δ 10.79 (s, 2 H), 7.55-7.35 (m, 10 H), 5.23 (s, 2 H), 2.78 (s, 3 H); MS: m/z 269 (M$^+$+1).

Preparation 43 trans-(4R,5R)-Diphenyl-2-methylthio-4,5-dihydro-1H-imidazole hydroiodide (54)

A mixture of trans-(4R,5R)-diphenylimidazolidine-2-thione (37) (6.87 g, 27.0 mmol) and methyl iodide (4 mL, 64 mmol) in abs. EtOH (50 mL) is heated at 95° C. overnight. The reaction mixture is cooled to rt, concentrated in vacuo, and the residue triturated with Et$_2$O. The insoluble material is filtered to give 9.5 g of the product 54. $^1$H NMR (DMSO-d$_6$) δ 10.80 (d, 2 H), 7.20-6.85 (m, 10 H), 5.37 (s, 1 H), 2.79 (s, 3 H), 1.92 (s, 3 H); MS: m/z 283 (M$^+$+1).

Preparation 44 cis-4,5-Diphenyl-4-methyl-2-methylthio-4,5-dihydro-1H-imidazole hydroiodide (55)

A mixture of cis-4,5-diphenyl-4-methylimidazolidine-2-thione (38) (655 mg, 2.44 mmol) and methyl iodide (0.304 mL, 4.89 mmol) in abs. EtOH (5 mL) is heated at 95° C. for 6 h. The reaction mixture is cooled to rt, concentrated in vacuo, and the residue triturated with heptane. The insoluble material is filtered to give 972 mg of the product 55. $^1$H NMR (DMSO-d$_6$) δ 8.85 (s, 1 H), 8.65 (s, 1 H), 7.15-6.75 (m, 10 H), 4.90 (s, 1 H), 1.75 (s, 3 H); MS: m/z 269 (M$^+$+1).

Preparation 45 cis-4,5-bis-4-Fluorophenyl-4-methyl-2-methylthio-4,5-dihydro-1H-imidazole hydroiodide (56)

A mixture of cis-4,5-bis-(4-fluorophenyl)-4-methylimidazolidine-2-thione (39) (1.2 g, 3.9 mmol) and methyl iodide (0.491 mL, 7.89 mmol) in abs. EtOH (5 mL) is heated to reflux for 3 h. The reaction mixture is cooled to rt, concentrated in vacuo, and the residue triturated with heptane. The insoluble material is filtered to give 1.84 g of the product 56.

Preparation 46 cis-4,5-bis-1-Fluorophenyl-4-methyl-2-methylthio-4,5-dihydro-1H-imidazole hydroiodide (57)

A mixture of cis-4,5-bis-(3-Fluorophenyl)-4-methylimidazolidine-2-thione (40) (900 mg, 2.96 mmol) and methyl iodide (0.368 mL, 6.86 mmol) in abs. EtOH (4 µL) is heated at 88° C. for 6 h. The reaction mixture is cooled to rt, concentrated in vacuo, and the residue triturated with heptane. The insoluble material is filtered to give 1.3 g of the product 57.

Preparation 47 cis-3a,4,5,6,7,7a-Hexahydro-2-methylthio-1H-benzimidazole hydroiodide (58)

A mixture of cis-1H-benzimidazol-3a,4,5,6,7,7a-hexahydro-2-thione (41) (9.0 g, 57.6 mmol) and methyl iodide (5.4 mL, 86.4 mmol) in abs. EtOH (50 mL) is heated at 90° C. for 48 h. The reaction mixture is cooled to rt, concentrated in vacuo, and the residue triturated with Et$_2$O. The insoluble material is filtered to give 16.77 g of the product 58. $^1$H NMR (DMSO-d$_6$) δ 10.11 (s, 2 H), 4.25-4.10 (m, 2 H), 2.65 (s, 3 H), 1.85-1.65 (m, 2H), 1.65-1.55 (m, 2 H), 1.55-1.25 (m, 4 H); MS: m/z 171 (M$^+$+1).

Preparation 48 cis-4,5-Diphenyl-2-methylthio-4,5-dihydro-imidazole-1-carboxylic acid, tert-butyl ester (59)

A solution of imidazoline 42 (5.0 g, 0.0126 mol), di-tert-butyl-dicarbonate (2.75 g, 0.0126 mol), triethylamine (1.94 mL, 0.0139 mol), and 4-dimethylamino-pyridine (50 mg) in dichloromethane (80 mL) is stirred at rt for 3 days. The reaction mixture is extracted with water, and the organic layer is separated, dried ($MgSO_4$), filtered and concentrated in vacuo. The crude solid is purified by chromatography on silica gel, elution with heptane:EtOAc (80:20) gives 4.3 g of the product 59. $^1$H NMR ($CDCl_3$) δ 7.10-6.90 (m, 8 H), 6.90-6.75 (m, 2 H), 5.57 (d, 1 H), 5.47 (d, 1 H), 2.59 (s, 3 H), 1.24 (s, 9 H); MS: m/z 369 ($M^+$+1).

Preparation 49 cis-4,5-bis-(2-Fluorophenyl-2-methylthio-4,5-dihydro-imidazole-1-carboxylic acid, tert-butyl ester (60)

A solution of imidazoline 43 (3.3 g, 0.0076 mol), di-tert-butyl-dicarbonate (2.16 g, 0.0099 mol), triethylamine (1.28 mL, 0.0092 mol), and 4-dimethylamino-pyridine (50 mg) in dichloromethane (30 mL) is stirred at rt overnight. The reaction mixture is extracted with water, and the organic layer is separated, washed with brine, dried ($MgSO_4$), filtered and concentrated in vacuo. The solid residue is triturated with heptane and the insoluble material filtered to give 2.57 g of the product 60. $^1$H NMR ($CDCl_3$) δ 7.30-6.65 (m, 8 H), 6.00-5.80 (m, 2 H), 2.60 (s, 3 H), 1.23 (s, 9 H); MS: m/z 405 ($M^+$+1).

Preparation 50 cis-4,5-bis-(3-Fluorophenyl-2-methylthio-4,5-dihydro-imidazole-1-carboxylic acid, tert-butyl ester (61)

A solution of imidazoline 44 (6.0 g, 0.0139 mol), di-tert-butyl-dicarbonate (3.34 g, 0.0153 mol), triethylamine (1.81 mL, 0.0167 mol), and 4-dimethylamino-pyridine (50 mg) in dichloromethane (30 mL) is stirred at rt overnight. The reaction mixture is extracted with water, and the organic layer is separated, washed with brine, dried ($MgSO_4$), filtered and concentrated in vacuo. The residue is purified by chromatography on silica gel; gradient elution with heptane:EtOAc (80:20-75:25), and the fractions containing the product are triturated with heptane and the insoluble material filtered to give 3.46 g of the product 61. $^1$H NMR ($CDCl_3$) δ 7.10-6.95 (m, 2 H), 6.85-6.70 (m, 4 H), 6.70-6.50 (m, 2 H), 5.57 (d, 1 H), 5.47 (d, 1 H), 2.58 (s, 3 H), 1.25 (s, 9 H); MS: m/z 405 ($M^+$+1).

Preparation 51 cis-4,5-bis-(4-Fluorophenyl)-2-methylthio-4,5-dihydro-imidazole-1-carboxylic acid, tert-butyl ester (62)

A solution of imidazoline 45 (2.45 g, 5.67 mmol), triethylamine (0.948 mL, 6.8 mmol), 4-dimethylaminopyridine (50 mg), and, di-tert-butyl-dicarbonate (1.3 g, 5.9 mmol), in dichloromethane (20 mL) is stirred at rt overnight. The reaction mixture is diluted with dichloromethane, extracted with water, and the organic layer is separated, dried ($MgSO_4$), filtered and concentrated in vacuo. The residue is purified by chromatography on silica gel; gradient elution with heptane:EtOAc (75:25-50:50) gives 2.1 g of the product 62. $^1$H NMR ($CDCl_3$) δ 6.95-6.90 (m, 2 H), 6.85-6.70 (m, 6 H), 5.55 (d, 1 H), 5.45 (d, 1 H), 2.57 (s, 3 H), 1.24 (s, 9 H); MS: m/z 405 ($M^+$+1).

Preparation 52 cis-4,5-Di-(2-methylphenyl)-2-methylthio-4,5-dihydro-imidazole-1-carboxylic acid, tert-butyl ester (63)

A solution of imidazoline 46 (8.6 g, 0.0203 mol), di-tert-butyl-dicarbonate (5.31 g, 0.0243 mol), triethylamine (3.39 mL, 0.0243 mol), and 4-dimethylaminopyridine (50 mg) in dichloromethane (100 mL) is stirred at rt overnight. The reaction mixture is extracted with water, and the organic layer is separated, washed with brine, dried ($MgSO_4$), filtered and concentrated in vacuo. The residue is triturated with heptane and the insoluble material filtered to give 7.43 g of the product 63. $^1$H NMR ($CDCl_3$) δ 7.05-6.75 (m, 8 H), 5.80-5.70 (m, 2 H), 2.57 (s, 3 H), 2.34 (s, 3 H), 2.04 (s, 3 H), 1.18 (s, 9 H); MS: m/z 397 ($M^+$+1)

Preparation 53 cis-4,5-Di-(3-methylphenyl)-2-methylthio-4,5-dihydro-imidazole-1-carboxylic acid, tert-butyl ester (64)

A solution of imidazoline 47 (3.22 g, 0.0076 mol), di-tert-butyl-dicarbonate (1.99 g, 0.0091 mol), triethylamine (1.27 mL, 0.0091 mol), and 4-dimethylaminopyridine (50 mg) in dichloromethane (30 mL) is stirred at rt overnight. The reaction mixture is extracted with water, and the organic layer is separated, washed with brine, dried ($MgSO_4$), filtered and concentrated in vacuo. The residue is triturated with heptane and the insoluble material filtered to give 2.47 g of the product 64. $^1$H NMR ($CDCl_3$) δ 6.95-6.85 (m, 2 H), 6.85-6.70 (m, 4 H), 6.60-6.50 (m, 2 H), 5.50 (d, 1 H), 5.40 (d, 1 H), 2.58 (s, 3 H), 2.13 (s, 6 H), 1.21 (s, 9 H); MS: m/z 397 ($M^+$+1).

Preparation 54 cis-4,5-Di-(4-methylphenyl)-2-methylthio-4,5-dihydro-imidazole-1-carboxylic acid, tert-butyl ester (65)

A solution of imidazoline 48 (7.3 g, 0.0172 mol), di-tert-butyl-dicarbonate (4.53 g, 0.0208 mol), triethylamine (2.87 mL, 0.0208 mol), and 4-dimethylaminopyridine (50 mg) in dichloromethane (50 mL) is stirred at rt overnight. The reaction mixture is extracted with water, the organic layer separated, washed with brine, dried ($MgSO_4$), filtered and concentrated in vacuo. The residue is suspended in heptane and the insoluble material filtered to give 6.33 g of the product 65. $^1$H NMR ($CDCl_3$) δ 6.90-6.80 (m, 6 H), 6.65 (d, 2 H), 5.50 (d, 1 H), 5.40 (d, 1 H), 2.56 (s, 3 H), 2.17 (s, 6 H), 1.22 (s, 9 H); MS: m/z 397 ($M^+$+1).

Preparation 55 cis-4,5-bis-(2-Chlorophenyl)-2-methylthio-4,5-dihydro-imidazole-1-carboxylic acid, tert-butyl ester (66)

A cold (0° C.) solution of imidazoline 49 (11 g, 0.0237 mol), di-tert-butyl-dicarbonate (6.2 g, 0.0285 mol), N,N-diisopropylethylamine (4.95 mL, 0.00285 mol), and 4-dimethylaminopyridine (10 mg) in dichloromethane (75 mL) is stirred for 10 min at 0° C., and then at rt overnight. The reaction mixture is extracted with 0.1N HCl, water, brine and dried ($MgSO_4$). The mixture is filtered and the filtrate concentrated in vacuo. The residue is triturated with dichloromethane:heptane and the insoluble material filtered to give 8.2 g of the product 66.

Preparation 56 cis-4,5-bis-(3-Chlorophenyl)-2-methylthio-4,5-dihydro-imidazole-1-carboxylic acid, tert-butyl ester (67)

A cold (0° C.) solution of imidazoline 50 (10.1 g, 0.0218 mol), di-tert-butyl-dicarbonate (5.23 g, 0.0240 mol), N,N-diisopropylethylamine (4.17 mL, 0.0240 mol), and 4-dimethylaminopyridine (10 mg) in dichloromethane (200 mL) is stirred for 10 min at 0° C., and then at rt overnight. The reaction mixture is extracted with 0.1N HCl, water, brine and then dried (MgSO$_4$). The mixture is filtered and the filtrate concentrated in vacuo. The residue is triturated with heptane and the insoluble material filtered to give 5.19 g of the product 67.

Preparation 57 cis-4,5-bis-(4-Chlorophenyl)-2-methylthio-4,5-dihydro-imidazole-1-carboxylic acid, tert-butyl ester (68)

A cold (0° C.) solution of imidazoline 51 (11 g, 0.0237 mol), di-tert-butyl-dicarbonate (6.2 g, 0.0285 mol), N,N-diisopropylethylamine (4.95 mL, 0.0285 mol), and 4-dimethylaminopyridine (10 mg) in dichloromethane (200 mL) is stirred for 10 min at 0° C., and then at rt overnight. The reaction mixture is extracted with 0.1N HCl, water, brine and then dried (MgSO$_4$). The mixture is filtered and the filtrate concentrated in vacuo. The residue is triturated with heptane and the insoluble material filtered to give 7.95 g of the product 68.

Preparation 58 cis-4,5-bis-(2-Bromophenyl)-2-methylthio-4,5-dihydro-imidazole-1-carboxylic acid, tert-butyl ester (69)

A solution of imidazoline 52 (0.5 g, 0.9 mmol) di-tert-butyl-dicarbonate (236 mg, 1.1 mmol), triethylamine (0.153 mL, 1.1 mmol), and 4-dimethylaminopyridine (10 mg) in dichloromethane (22 mL) is stirred at rt overnight. The reaction mixture is diluted with dichloromethane, extracted with water, the organic layer separated, washed with brine, dried (MgSO$_4$), filtered and concentrated in vacuo. The residue is purified by chromatography on silica gel, eluted with heptane:EtOAc (75:25-60:40) to give 0.33 g of the product 69. $^1$H NMR (CDCl$_3$) δ 7.40-7.10 (m, 4 H), 7.00-6.85 (m, 4 H), 6.10 (d, 1 H), 6.00 (d, 1 H), 2.55 (s, 3 H), 1.22 (s, 9 H); MS: m/z 525 (M++1).

Preparation 59 trans-(4S,5S)-Diphenyl-2-methylthio-4,5-dihydro-imidazole-1-carboxylic acid, tert-butyl ester (70)

A solution of imidazoline 53 (10.0 g, 25.2 mmol) di-tert-butyl-dicarbonate (5.78 g, 26.5 mmol), triethylamine (3.86 mL, 27.8 mmol), and 4-dimethylaminopyridine (50 mg) in dichloromethane (50 mL) is stirred at rt overnight. The reaction mixture is rotary evaporated, and the residue is dissolved in dichloromethane, and purified by chromatography on silica gel; elution with heptane:EtOAc (50:50) to give 7.96 g of the product 70. $^1$H NMR (CDCl$_3$) δ 7.45-7.15 (m, 10 H), 4.99 (d, 1 H), 4.87 (d, 1 H), 2.57 (s, 3 H), 1.19 (s, 9 H); MS: m/z 369 (M$^+$+1).

Preparation 60 trans-(4R,5R)-Diphenyl-2-methylthio-4,5-dihydro-imidazole-1-carboxylic acid, tert-butyl ester (71)

A solution of imidazoline 54 (7.3 g, 18.4 mmol) di-tert-butyl-dicarbonate (4.42 g, 20.3 mmol), triethylamine (3.1 mL, 22 mmol), and 4-dimethylaminopyridine (50 mg) in dichloromethane (40 mL) is stirred at rt overnight. The reaction mixture is rotary evaporated, and the residue is dissolved in dichloromethane, and purified by chromatography on silica gel; elution with heptane:EtOAc (50:50) to give 6.78 g of the product 71. $^1$H NMR (CDCl$_3$) δ 7.45-7.15 (m, 10 H), 4.99 (d, 1 H), 4.87 (d, 1 H), 2.57 (s, 3 H), 1.19 (s, 9 H); MS: m/z 369 (M$^+$+1).

Preparation 61 cis-4,5-Diphenyl-4-methyl-2-methylthio-4,5-dihydro-imidazole-1-carboxylic acid, tert-butyl ester (72)

A solution of imidazoline 55 (972 mg, 2.38 mmol) di-tert-butyl-dicarbonate (570 mg, 2.61 mmol), N,N-diisopropylethylamine (0.828 mL, 4.75 mmol), and 4-dimethyl-aminopyridine (10 mg) in dichloromethane (15 mL) is stirred at rt for 5 h. The reaction mixture is washed with 0.1N HCl, brine, then dried (Na$_2$SO$_4$), filtered, and the filtrate evaporated. The residue is purified by chromatography on silica gel; elution with heptane:EtOAc (3:1) gives 850 mg of the product 72. $^1$H NMR (CDCl$_3$) δ 7.25-7.05 (m, 2 H), 7.05-6.85 (m, 6 H), 6.85-6.70 (m, 2 H), 5.05 (s, 1 H), 2.60 (s, 3 H), 1.75 (s, 3 H), 1.19 (s, 9 H); MS: m/z 383 (M$^+$+1).

Preparation 62 cis-4,5-bis-(4-Fluorophenyl)-4-methyl-2-methylthio-4,5-dihydro-imidazole-1-carboxylic acid, tert-butyl ester (73)

A solution of imidazoline 56 (1.84 g, 3.43 mmol) di-tert-butyl-dicarbonate (899 mg, 4.12 mmol), N,N-diisopropylethylamine (1.79 mL, 10.3 mmol), and 4-dimethylaminopyridine (10 mg) in dichloromethane (15 mL) is stirred at rt overnight. The reaction mixture is washed with 0.1N HCl, brine, then dried (Na$_2$SO$_4$), filtered, and the filtrate evaporated. The residue is purified by chromatography on silica gel; elution with heptane:EtOAc (10:1) gives 1.2 g of the product 73 and 198 mg of a by-product, the corresponding trans-4,5-bis-(4-fluorophenyl)-4-methyl isomer 74. Product 73: $^1$H NMR (CDCl$_3$) δ 7.15-7.00 (m, 2 H), 6.95-6.60 (m, 6 H), 6.85-6.70 (m, 2 H), 5.04 (s, 1 H), 2.60 (s, 3 H), 1.70 (s, 3 H), 1.20 (s, 9 H); MS: m/z 419 (M$^+$+1).

Preparation 63 trans-4,5-bis-(4-Fluorophenyl)-4-methyl-2-methylthio-4,5-dihydro-imidazole-1-carboxylic acid, tert-butyl ester (74)

A solution of imidazoline 56 (1.84 g, 3.43 mmol) di-tert-butyl-dicarbonate (899 mg, 4.12 mmol), N,N-diisopropylethylamine (1.79 mL, 10.3 mmol), and 4-dimethyl-aminopyridine (10 mg) in dichloromethane (15 mL) is stirred at rt overnight. The reaction mixture is washed with 0.1N HCl, brine, then dried (Na$_2$SO$_4$), filtered, and the filtrate evaporated. The residue is purified by chromatography on silica gel;

elution with heptane:EtOAc (10:1) gives two products; 198 mg of the product 74 and 1.2 g of the cis-4,5-bis-(4-fluorophenyl)-4-methyl isomer 73. Product 74: $^1$H NMR (CDCl$_3$) δ 7.40-7.25 (m, 2 H), 7.20-7.00 (m, 6 H), 5.02 (s, 1 H), 2.60 (s, 3 H), 1.15 (s, 9 H), 1.10 (s, 3 H); MS: m/z 419 (M$^+$+1).

Preparation 64 cis-4,5-bis-(3-Fluorophenyl)-4-methyl-2-methylthio-4,5-dihydro-imidazole-1-carboxylic acid, tert-butyl ester (75)

A solution of imidazoline 57 (1.3 g, 2.91 mmol) di-tert-butyl-dicarbonate (763 mg, 3.50 mmol), N,N-diisopropyl-ethylamine (1.52 mL, 8.74 mmol), and 4-dimethylaminopyridine (10 mg) in dichloromethane (20 mL) is stirred at rt 12 h. The reaction mixture is washed with 0.1N HCl, sat. NaHCO$_3$, water, brine, and then dried (Na$_2$SO$_4$). The mixture is filtered, and the filtrate evaporated to give 1.2 g of the product 75. $^1$H NMR (CDCl$_3$) δ 7.10-6.90 (m, 2 H), 6.90-6.80 (m, 2 H), 6.80-6.45 (m, 4 H), 5.03 (s, 1 H), 2.60 (s, 3 H), 1.72 (s, 3 H), 1.22 (s, 9 H); MS: m/z 419 (M$^+$+1).

Preparation 65 cis-3a,4,5,6,7,7a-Hexahydro-2-methylthio-benzimidazole-1-carboxylic acid, tert-butyl ester (76)

A solution of imidazoline 58 (13.0 g, 43.6 mmol), triethylamine (7.9 mL, 56.7 mmol), di-tert-butyl-dicarbonate (11.4 g, 52.3 mmol), and 4-dimethylaminopyridine (50 mg) in dichloromethane (50 mL) is stirred at rt overnight. The reaction mixture is diluted with dichloromethane, washed with brine, dried (Mg$_2$SO$_4$), filtered. The filtrate evaporated to give 8.42 g of the product 76. $^1$H NMR (CDCl$_3$) δ 4.15-4.05 (m, 1 H), 4.00-3.90 (m, 1 H), 2.42 (s, 3 H), 2.25-1.95 (m, 2 H), 1.85-1.10 (m, 15 H); MS: m/z 271 (M$^+$+1).

Preparation 66

3-Phenylpropionimidic acid methyl ester hydrochloride (242)

Hydrogen chloride is bubbled into a cold (0° C.) solution of 3-phenypropionitrile (5.43 g, 41.4 mmol) in methanol (2.5 mL, 62.1 mmol) for 5 min, and the mixture stirred at rt for 3 h. The solid that formed is suspended in Et$_2$O and filtered to give 7.8 g of the product 242. $^1$H NMR (CDCl$_3$) δ 12.65 (s, 1 H), 11.65 (s, 1 H), 7.40-7.15 (m, 5 H), 4.24 (s, 3 H), 3.08 (s, 4 H)

Preparation 67

(cis-4,5-Diphenyl-4,5-dihydro-1H-imidazol-2-yl) amine (122)

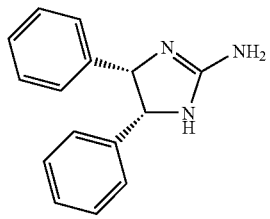

A solution of intermediate 59 (1.0 g, 2.71 mmol) in ethylene glycol (10 mL) is saturated with ammonia and is heated in a pressure tube at 115° C. for 3 h. The reaction mixture is cooled to rt, and saturated with ammonia, and heated is heated at 115° C. overnight. The reaction mixture is cooled to rt, and the product is precipitated by the addition of addition of water to give 226 mg of the product 122. $^1$H NMR (DMSO-d$_6$) δ 7.10-6.80 (m, 10 H), 6.40 (bs, 3 H), 5.10 (s, 2 H); LC/MS: 2.89 min, m/z 238 (M$^+$+1).

Preparation 68

Resolution of 1,2-diphenyl-propane-1,2-diamine

This preparative example of an intermediate illustrate the synthesis of optically enriched isomeric form of 1,2-diphenyl-propane-1,2-diamine that can be employed in the syntheses of various imidazole compounds of the present invention following the synthetic procedures as disclosed herein.

1,2-Diphenyl-propane-1,2-diamine (7.5 grams, 0.033 mol) and (+)-di-p-toluoyl-D-tartaric acid (12.8 grams, 0.33 mol) are dissolved in a refluxing mixture of 200 mL acetonitrile and 40 mL water. The mixture is stirred and cooled to room temperature during 3 hours. The stirring is continued for additional two hours at room temperature. The precipitate so formed is collected by filtration and rinsed with 90% aqueous acetonitrile, 12.1 grams of the salt is isolated with an e.e. of 50% for the diamine. Recrystallization from a mixture of 170 mL acetonitrile and 35 mL water gave 8.5 g salt (chiral yield (c.y.)=42% and enantiomeric excess (e.e.) of 80% for the diamine). Another recrystallization from a mixture of 170 mL acetonitrile and 35 mL water gave 6.8 g salt (c.y.=34% and e.e. of >95% for the diamine). The cis:trans ratio is 6 to 1 based on $^1$H-NMR.

Example 1

(cis-4,5-Diphenyl-4,5-dihydro-1H-imidazol-2-yl) benzylamine hydrochloride (78)

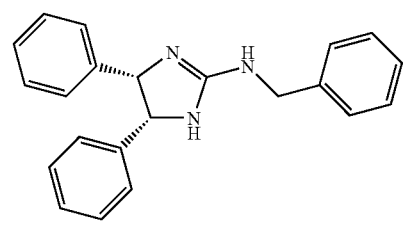

Step 1

2-(Benzylamino)-cis-4,5-diphenyl-4,5-dihydro-imidazole-1-carboxylic acid tert-butyl ester (77)

A mixture of intermediate 59 (5.0 g, 0.0136 mol), benzylamine (4.5 mL, 0.0407 mol) and MeOH (1 mL) is heated at 95° C. for 2 days. The reaction mixture is cooled to RT and purified by chromatography on silica gel; gradient elution with heptane:EtOAc (80:20-50:50) gives 2.81 g of the product 77. $^1$H NMR (CDCl$_3$) δ 7.55-7.25 (m, 6 H), 7.10-6.85 (m, 8 H), 6.85-6.70 (m, 2 H), 5.50-5.30 (m, 2 H), 4.80-4.55 (m, 2 H), 1.14 (s, 9 H)

Step 2

(cis-4,5-Diphenyl-4,5-dihydro-1H-imidazol-2-yl)benzylamine hydrochloride (78)

Hydrogen chloride is bubbled into a solution of 77 (200 mg, 0.47 mmol) in EtOAc (10 mL) for 1 min, and the solution is stirred at RT overnight. The solvent is removed by rotary evaporation, and the residue is crystallized from dichloromethane and Et$_2$O to give 130 mg of the product 78. $^1$H NMR (DMSO-d$_6$) δ 9.80-8.30 (m, 3 H), 7.60-7.30 (m, 5 H), 7.20-7.00 (m, 6 H), 7.00-6.85 (m, 4 H), 5.49 (s, 2 H), 4.59 (d, 2 H); MS: m/z 328 (M$^+$+1).

Example 2

(cis-4,5-Diphenyl-4,5-dihydro-1H-imidazol-2-yl)-(cyclohexylmethyl)amine hydrochloride (80)
(Scheme 5, Method a)

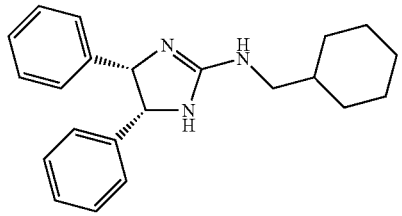

Step 1

2-(Cyclohexylmethylamino)-cis-4,5-diphenyl-4,5-dihydro-imidazole-1-carboxylic acid tert-butyl ester (79)

A mixture of intermediate 59 (0.5 g, 1.36 mmol), cyclohexanemethylamine (0.53 mL, 6.1 mmol) and MeOH (0.11 mL) is heated at 100° C. for 48 h. The reaction mixture is cooled to RT and purified by chromatography on silica gel; gradient elution with heptane:EtOAc (70:30-50:50) gives 0.23 g of the product 79. $^1$H NMR (CDCl$_3$) δ 7.80-7.35 (m, 2 H), 7.18 9s, 1 H), 7.10-6.90 (m, 6 H), 6.90-6.70 (m, 2 H), 5.45-5.30 (m, 2 H), 3.45-3.15 (m, 2 H), 2.00-1.50 (m, 5 H), 1.45-0.95 (m, 15H); MS: m/z 434 (M$^+$+1).

Step 2

(cis-4,5-Diphenyl-4,5-dihydro-1H-imidazol-2-yl)-(cyclohexylmethyl)amine hydrochloride (80)

Hydrogen chloride is bubbled into a solution of 79 (0.23 g, 0.53 mmol) in EtOAc (10 mL) for 1 min, and the solution is stirred at RT overnight. The solvent is removed by rotary evaporation, and the residue triturated with Et$_2$O. The insoluble material is filtered to give 89 mg of the product 80. $^1$H NMR (DMSO-d$_6$) δ 9.08 (m, 1 H), 8.54 (s, 1 H), 7.45 (m, 1 H), 7.15-6.90 (m, 6 H), 6.90-6.70 (m, 4 H), 5.18 (s, 2 H), 3.35-3.10 (m, 2 H), 1.90-1.65 (m, 5 H), 1.40-0.90 (m, 6 H); MS: m/z 334 (M$^+$+1).

Example 3

(cis-4,5-Diphenyl-4,5-dihydro-1H-imidazol-2-yl)-N-methylbenzylamine hydrochloride (82)

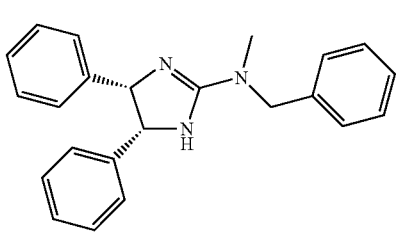

Step 1

2-(N-Methylbenzylamino)-cis-4,5-diphenyl-4,5-dihydro-imidazole-1-carboxylic acid tert-butyl ester (81)

A mixture of intermediate 59 (0.4 g, 0.00109 mol), N-methylbenzylamine (0.42 mL, 0.00326 mol) and MeOH (0.1 mL) is heated at 95° C. for 2 days. The reaction mixture is cooled to RT, dichloromethane is added and the mixture is purified by chromatography on silica gel; gradient elution with heptane:EtOAc (80:20-75:25) gives 110 mg of the product 81. $^1$H NMR (CDCl$_3$) δ 7.50-7.20 (m, 6 H), 7.10-6.90 (m, 7 H), 6.90-6.75 (m, 2 H), 5.52 (q, 2 H), 4.84 (d, 1 H), 4.52 (d, 1 H), 2.97 (s, 3 H), 1.45 (s, 9 H); MS: m/z 442 (M$^+$+1).

Step 2

(cis-4,5-Diphenyl-4,5-dihydro-1H-imidazol-2-yl)-N-methylbenzylamine hydrochloride (82)

Hydrogen chloride is bubbled into a solution of 81 (110 mg, 0.25 mmol) in EtOAc (10 mL) for 1 min, and the solution is stirred at RT for 6 h. The solvent is removed by rotary evaporation, and the residue triturated with Et$_2$O. The insoluble material is dissolved in dichloromethane and Et$_2$O is added, and the precipitate is filtered to give 43 mg of the product 82. $^1$H NMR (DMSO-d$_6$) δ 9.28 (s, 2 H), 7.60-7.30 (m, 5 H), 7.25-6.95 (m, 10 H), 5.58 (s, 2 H), 4.78 (s, 2 H), 3.15 (s, 3 H); MS: m/z 342 (M$^+$+1).

Example 4

(cis-4,5-Diphenyl-4,5-dihydro-1H-imidazol-2-yl)-(3,4,5-trifluorobenzyl)amine hydrochloride (84)

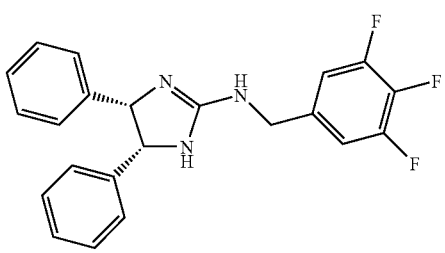

Step 1 cis-4,5-Diphenyl-2-(3,4,5-trifluorobenzylamino)-4,5-dihydro-imidazole-1-carboxylic acid tert-butyl ester (83)

A mixture of intermediate 59 (0.5 g, 1.36 mmol), 3,4,5-trifluorobenzylamine (0.66 g, 4.0 mmol) and MeOH (0.2 mL) is heated at 100° C. for 2 days. The reaction mixture is cooled to RT, and the mixture is purified by chromatography on silica gel; gradient elution with heptane:EtOAc (70:30-50:50) gives 0.44 g of the product 83. $^1$H NMR (CDCl$_3$) δ 7.59 (s, 1 H), 7.20-7.05 (m, 2 H), 7.05-6.90 (m, 8 H), 6.80-6.70 (m, 2 H), 5.45-5.30 (m, 2 H), 4.70-4.50 (m, 2 H), 1.16 (s, 9 H); MS: m/z 482 (M$^+$+1).

Step 2

(cis-4,5-Diphenyl-4,5-dihydro-1H-imidazol-2-yl)-(3,4,5-trifluorobenzyl)amine hydrochloride (84)

Hydrogen chloride is bubbled into a solution of 83 (0.44 g, 0.91 mmol) in EtOAc (15 mL) for 1 min, and the solution is stirred at RT overnight. The solvent is removed by rotary evaporation, and the residue crystallized from dichloromethane and Et$_2$O give 0.21 g of the product 84. $^1$H NMR (DMSO-d$_6$) δ 9.40 (s, 1 H), 9.14 (t, 1 H), 7.88 (s, 1 H), 7.20-6.80 (m, 8 H), 6.80-6.55 (m, 4 H), 5.07 (s, 2 H), 4.70-4.50 (m, 2 H); MS: m/z 382 (M$^+$+1).

Example 5

(cis-4,5-Diphenyl-4,5-dihydro-1H-imidazol-2-yl)-(4-fluorobenzyl)amine hydrochloride (86)

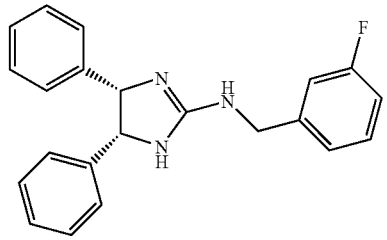

Step 1

2-(4-Fluorobenzylamino)-cis-4,5-diphenyl-4,5-dihydro-imidazole-1-carboxylic acid tert-butyl ester (85)

A mixture of intermediate 59 (1.0 g, 0.0027 mol), 4-fluorobenzylamine (0.372 mL, 0.00321 mol) and MeOH (0.4 mL) is heated at 100° C. for 2 days. The reaction mixture is cooled to RT, and partitioned between dichloromethane and water. The organic solution is separated, dried (MgSO$_4$), and concentrated in vacuo. The residue is purified by chromatography on silica gel; gradient elution with heptane:EtOAc (80:20-40:60) gives 0.50 g of the product 85. $^1$H NMR (CDCl$_3$) δ 7.60-7.35 (m, 3 H), 7.15-6.90 (m, 10 H), 6.85-6.70 (m, 2 H), 5.50-5.30 (m, 2 H), 5.75-5.55 (m, 2 H), 1.12 (s, 9 H); MS: m/z 446 (M$^+$+1).

Step 2

(cis-4,5-Diphenyl-4,5-dihydro-1H-imidazol-2-yl)-(4-fluorobenzyl)amine hydrochloride (86)

Hydrogen chloride is bubbled into a solution of 85 (0.69 g, 1.58 mmol) in EtOAc (40 mL) for 2 min, and the solution is stirred at RT overnight and then at 45° C. for 3 h. The solvent is removed by rotary evaporation, and the residue crystallized from dichloromethane and Et$_2$O to give 0.52 g of the product 86. $^1$H NMR (DMSO-d$_6$) δ 9.80-8.40 (m, 3 H), 7.60-7.45 (m, 2 H), 7.35-7.25 (m, 2 H), 7.15-6.95 (m, 6 H), 6.95-6.80 (m, 4 H), 5.50 (s, 2 H), 4.58 (d, 2 H); MS: m/z 346 (M$^+$+1).

Example 6

(cis-4,5-Diphenyl-4,5-dihydro-1H-imidazol-2-yl)-(3-fluorobenzyl)amine hydrochloride (88)

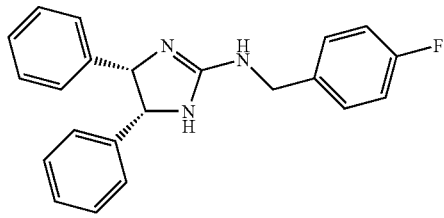

Step 1

2-(3-Fluorobenzylamino)-cis-4,5-diphenyl-4,5-dihydro-imidazole-1-carboxylic acid tert-butyl ester (87)

A mixture of intermediate 59 (2.0 g, 5.42 mmol), 3-fluorobenzylamine (1.86 mL, 16.2 mmol) and MeOH (0.5 mL) is heated at 100° C. for 2 days. The reaction mixture is cooled to RT, and is purified twice by chromatography on silica gel; gradient elution with heptane:EtOAc (70:30-60:40) gives 1.5 g of the product 87. $^1$H NMR (CDCl$_3$) δ 7.50 (s, 1 H), 7.40-7.30 (m, 1 H), 7.30-7.15 (m, 2 H), 7.10-6.90 (m, 9 H), 7.85-7.75 (m, 2 H), 5.50-5.30 (m, 2 H), 4.80-4.55 (m, 2 H), 1.15 (s, 9 H); MS: m/z 446 (M$^+$+1).

Step 2

(cis-4,5-Diphenyl-4,5-dihydro-1H-imidazol-2-yl)-(3-fluorobenzyl)amine hydrochloride (88)

Hydrogen chloride is bubbled into a solution of 87 (1.5 g, 3.37 mmol) in EtOAc (30 mL) for 1 min, and the solution is stirred at RT overnight. The solvent is removed by rotary evaporation, and the residue crystallized from dichloromethane and Et$_2$O to give 1.05 g of the product 88. $^1$H NMR (DMSO-d$_6$) δ 9.28 (t, 1 H), 8.68 (s, 1 H), 8.15 (s, 1 H), 7.35-7.10 (m, 3 H), 7.10-6.80 (m, 7 H), 6.80-6.50 (m, 4 H), 5.03 (s, 1 H), 4.80-4.45 (m, 2 H); MS: m/z 346 (M$^+$+1).

Example 7

(cis-4,5-Diphenyl-4,5-dihydro-1H-imidazol-2-yl)-(3,5-difluorobenzyl)amine hydrochloride (90)

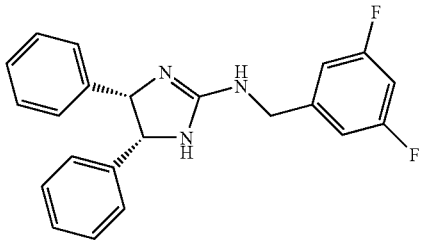

Step 1

2-(3,5-Difluorobenzylamino)-cis-4,5-diphenyl-4,5-dihydro-imidazole-1-carboxylic acid tert-butyl ester (89)

A mixture of intermediate 59 (0.50 g, 1.36 mmol), 3,5-difluorobenzylamine (0.481 mL, 4.07 mmol) and MeOH (0.1 mL) is heated at 100° C. for 3 days. The reaction mixture is cooled to RT, and is purified by chromatography on silica gel; gradient elution with heptane:EtOAc (75:25-60:40) gives 0.28 g of the product 89. $^1$H NMR (CDCl$_3$) δ 7.10-6.60 (m, 14 H), 5.45-5.35 (m, 2 H), 4.75-4.55 (m, 2 H), 1.16 (s, 9 H); MS: m/z 464 (M$^+$+1).

Step 2 cis-4,5-Diphenyl-4,5-dihydro-1H-imidazol-2-yl)-(3,5-difluorobenzyl)amine hydrochloride (90))

Hydrogen chloride is bubbled into a solution of 89 (0.28 g, 0.60 mmol) in EtOAc (10 mL) for 1 min, and the solution is stirred at RT overnight. The solvent is removed by rotary evaporation, and the residue crystallized from dichloromethane and Et$_2$O to give 128 mg of the product 90. $^1$H NMR (DMSO-d$_6$) δ 9.31 (s, 1 H), 9.06 (t, 1 H), 7.93 (s, 1 H), 7.15-6.90 (m, 9 H), 6.80-6.50 (m, 4 H), 5.02 (s, 2 H), 4.75-4.45 (m, 2 H); MS: m/z 364 (M$^+$+1).

Example 8

(cis-4,5-Diphenyl-4,5-dihydro-1H-imidazol-2-yl)-[2-(2-fluorophenyl)ethyl]amine hydrochloride (92)

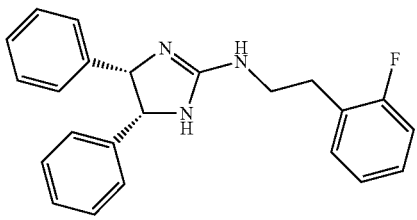

Step 1

2-[2-(2-Fluorophenyl)ethylamino]-cis-4,5-diphenyl-4,5-dihydro-imidazole-1-carboxylic acid tert-butyl ester (91)

A mixture of intermediate 59 (0.5 g, 1.36 mmol), 2-fluorophenethylamine (0.531 mL, 4.07 mmol) and MeOH (0.1 mL) is heated at 100° C. for 3 days. The reaction mixture is cooled to RT, and is purified by chromatography on silica gel; gradient elution with heptane:EtOAc (70:30-60:40) gives 0.27 g of the product 91. $^1$H NMR (CDCl$_3$) δ 7.40-6.85 (m, 13 H), 6.80-6.65 (m, 2 H), 5.45-5.25 (m, 2 H), 3.90-3.60 (m, 2 H), 1.15 (s, 9 H); MS: m/z 460 (M$^+$+1).

Step 2

(cis-4,5-Diphenyl-4,5-dihydro-1H-imidazol-2-yl)-[2-(2-fluorophenyl)ethyl]amine hydrochloride (92)

Hydrogen chloride is bubbled into a solution of 91 (0.37 g, 0.81 mmol) in EtOAc (10 mL) for 1 min, and the solution is stirred at RT overnight. The solvent is removed by rotary evaporation, and the residue crystallized from dichloromethane and Et$_2$O to give 0.21 g of the product 92. $^1$H NMR (DMSO-d$_6$) δ 9.10 (t, 1 H), 8.43 (s, 1 H), 8.58 (s, 1 H), 7.40 (t, 1 H), 7.30-7.15 (m, 1 H), 7.15-6.90 (m, 8 H), 6.80-6.55 (m, 4 H), 5.15 (s, 2 H), 3.80-3.45 (m, 2 H), 3.10-2.85 (m, 2 H); MS: m/z 360 (M$^+$+1).

Example 9

(cis-4,5-Diphenyl-4,5-dihydro-1H-imidazol-2-yl)-2-phenethylamine hydrochloride (94)

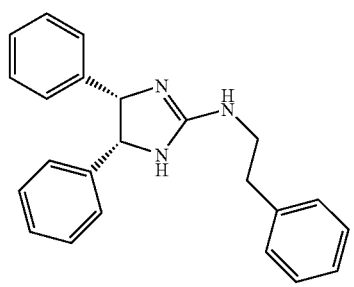

Step 1

2-(Phenethylamino)-cis-4,5-diphenyl-4,5-dihydro-1H-imidazole-1-carboxylic acid tert-butyl ester (93)

A mixture of intermediate 59 (2.0 g, 5.43 mmol), phenethylamine (2.04 mL, 16.3 mmol) and MeOH (0.5 mL) is heated at 100° C. for 2 days. The reaction mixture is cooled to RT, and is purified by chromatography on silica gel; gradient elution with heptane:EtOAc (75:25-60:40) gives 1.06 g of the product 93. $^1$H NMR (CDCl$_3$) δ 7.40-7.30 (m, 4 H), 7.30-7.10 (m, 2 H), 7.10-6.90 (m, 8 H), 6.80-6.65 (m, 2 H), 5.45-5.25 (m, 2 H), 3.90-3.60 (m, 2 H), 3.05 (t, 2 H), 1.13 (s, 9 H); MS: m/z 442 (M$^+$+1).

Step 2

(cis-4,5-Diphenyl-4,5-dihydro-1H-imidazol-2-yl)-2-phenethylamine hydrochloride (94)

Hydrogen chloride is bubbled into a solution of 93 (1.06 g, 2.4 mmol) in EtOAc (30 mL) for 1 min, and the solution is stirred at RT overnight. The solvent is removed by rotary evaporation, and the residue crystallized from dichloromethane and Et$_2$O to give 0.76 g of the product 94. $^1$H NMR (DMSO-d$_6$) δ 8.95 (t, 1 H), 8.23 (s, 1 H), 7.62 (s, 1 H), 7.40-7.15 (m, 6 H), 7.10-6.85 (m, 6 H), 6.80-6.45 (m, 6 H), 4.93 (s, 2 H), 3.85-3.40 (m, 2 H), 3.00-2.75 (m, 2 H); MS: m/z 342 (M$^+$+1).

Example 10

(cis-4,5-Diphenyl-4,5-dihydro-1H-imidazol-2-yl)-(3-methylbenzyl)amine (95)

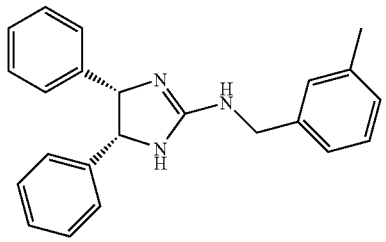

A mixture of intermediate 59 (200 mg, 0.54 mmol), 3-methylbenzylamine (0.5 mL, 3.99 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 21 mg of the product 95. LC/MS: 1.76 min, m/z 342 (M$^+$+1).

Example 11

(cis-4,5-Diphenyl-4,5-dihydro-1H-imidazol-2-yl)-(3,4-difluorobenzyl)amine (96)

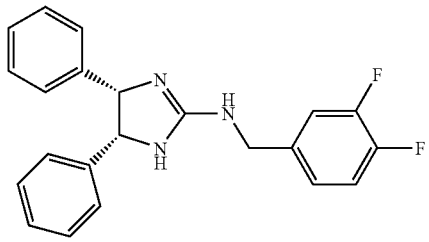

A mixture of intermediate 59 (200 mg, 0.54 mmol), 3,4-difluorobenzylamine (0.5 mL, 4.23 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 72 mg of the product 96. LC/MS: 1.40 min, m/z 364 (M$^+$+1).

Example 12

(cis-4,5-Diphenyl-4,5-dihydro-1H-imidazol-2-yl)-(3-chlorobenzyl)amine (97)

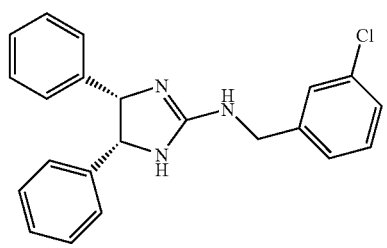

A mixture of intermediate 59 (200 mg, 0.54 mmol), 3-chlorobenzylamine (0.5 mL, 4.09 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 43 mg of the product 97. LC/MS: 1.43 min, nm/z 362 (M$^+$+1).

Example 13

(cis-4,5-Diphenyl-4,5-dihydro-1H-imidazol-2-yl)-(3-bromobenzyl)amine (98)

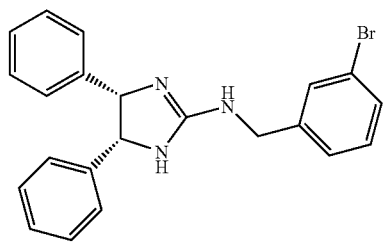

A mixture of intermediate 59 (200 mg, 0.54 mmol), 3-bromobenzylamine (0.5 mL, 4.03 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with

Example 14

(cis-4,5-Diphenyl-4,5-dihydro-1H-imidazol-2-yl)-(2-bromobenzyl)amine (99)

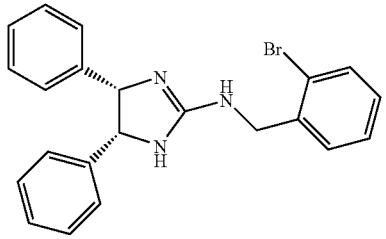

A mixture of intermediate 59 (200 mg, 0.54 mmol), 2-bromobenzylamine (0.5 mL, 4.03 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 52 mg of the product 99. LC/MS: 1.77 min, m/z 407 ($M^+$+1).

Example 15

(cis-4,5-Diphenyl-4,5-dihydro-1H-imidazol-2-yl)-(2-methylbenzyl)amine (100)

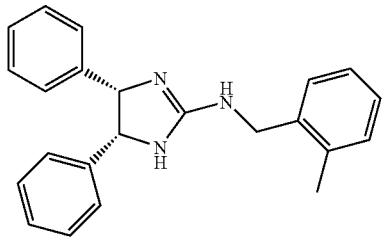

A mixture of intermediate 59 (200 mg, 0.54 mmol), 2-methylbenzylamine (0.5 mL, 4.03 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 43 mg of the product 100. LC/MS: 1.74 min, m/z 342 ($M^+$+1).

Example 16

(cis-4,5-Diphenyl-4,5-dihydro-1H-imidazol-2-yl)-(2-chloro-4-fluorobenzyl)amine (101)

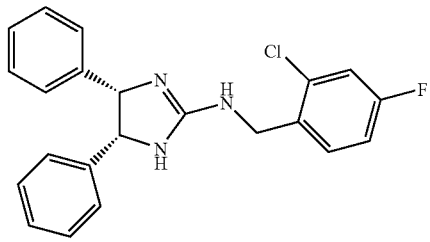

A mixture of intermediate 59 (200 mg, 0.54 mmol), 2-chloro-4-fluorobenzylamine (0.5 mL, 3.76 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 73 mg of the product 101. LC/MS: 1.78 min, m/z 380 ($M^+$+1).

Example 17

(cis-4,5-Diphenyl-4,5-dihydro-1H-imidazol-2-yl)-[2-(4-fluorophenyl)ethyl]amine (102)

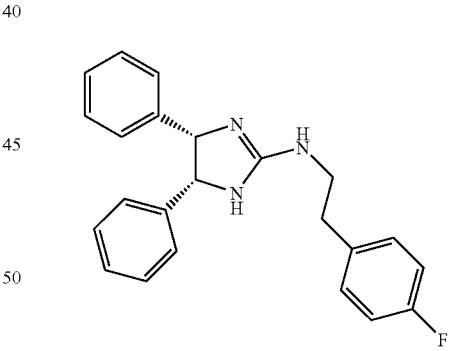

A mixture of intermediate 59 (200 mg, 0.54 mmol), 4-fluorophenethylamine (0.5 mL, 3.81 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 102 mg of the product 102. LC/MS: 1.41 min, m/z 360 ($M^+$+1).

heptane:EtOAc (70:30-50:50) gives 56 mg of the product 98. LC/MS: 1.81 min, m/z 407 ($M^+$+1).

Example 18

(cis-4,5-Diphenyl-4,5-dihydro-1H-imidazol-2-yl)-(2-chlorobenzyl)amine (103)

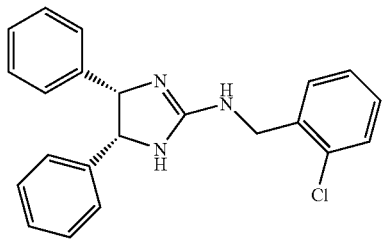

A mixture of intermediate 59 (200 mg, 0.54 mmol), 2-chlorobenzylamine (0.5 mL, 4.14 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 60 mg of the product 103. LC/MS: 1.37 min, m/z 362 ($M^+$+1).

Example 19

(cis-4,5-Diphenyl-4,5-dihydro-1H-imidazol-2-yl)-(2-trifluoromethylbenzyl)amine (104)

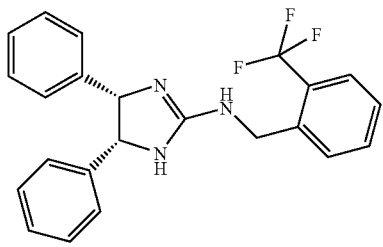

A mixture of intermediate 59 (200 mg, 0.54 mmol), 2-trifluoromethylbenzylamine (0.5 mL, 3.57 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 15 mg of the product 104. LC/MS: 1.41 min, m/z 396 ($M^+$+1).

Example 20

(cis-4,5-Diphenyl-4,5-dihydro-1H-imidazol-2-yl)-(2,4-dichlorobenzyl)amine (105)

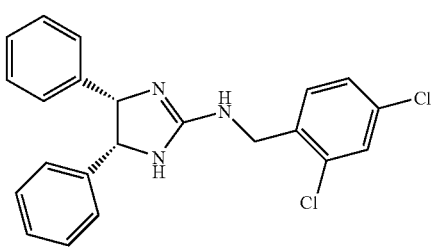

A mixture of intermediate 59 (200 mg, 0.54 mmol), 2,4-dichlorobenzylamine (0.5 mL, 3.74 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 110 mg of the product 105. LC/MS: 1.43 min, m/z 396 ($M^+$+1).

Example 21

(cis-4,5-Diphenyl-4,5-dihydro-1H-imidazol-2-yl)-(3,4-dichlorobenzyl)amine (106)

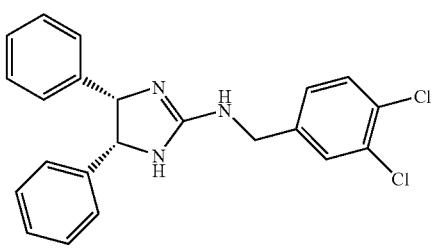

A mixture of intermediate 59 (200 mg, 0.54 mmol), 3,4-dichlorobenzylamine (0.5 mL, 3.77 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 45 mg of the product 106. LC/MS: 1.45 min, m/z 396 ($M^+$+1).

Example 22

(cis-4,5-Diphenyl-4,5-dihydro-1H-imidazol-2-yl)-(2,4-difluorobenzyl)amine (107)

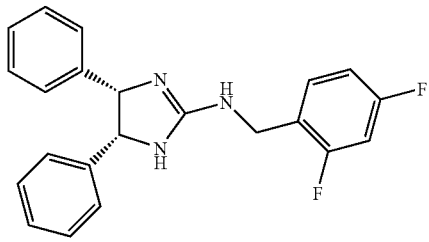

A mixture of intermediate 59 (200 mg, 0.54 mmol), 2,4-difluorobenzylamine (0.5 mL, 4.21 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 155 mg of the product 107. LC/MS: 1.37 min, m/z 364 ($M^+$+1).

Example 23

(cis-4,5-Diphenyl-4,5-dihydro-1H-imidazol-2-yl)-(2,6-difluorobenzyl)amine (108)

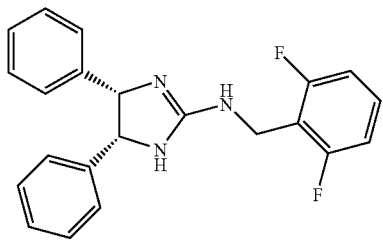

A mixture of intermediate 59 (200 mg, 0.54 mmol), 2,6-difluorobenzylamine (0.5 mL, 4.18 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 30 mg of the product 108. LC/MS: 1.36 min, m/z 364 ($M^+$+1).

Example 24

(cis-4,5-Diphenyl-4,5-dihydro-1H-imidazol-2-yl)-(4-trifluoromethylbenzyl)amine (109)

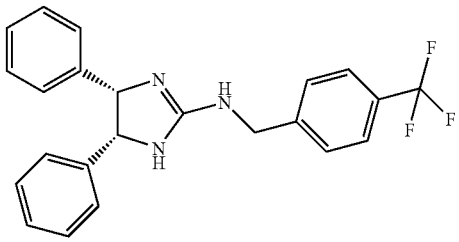

A mixture of intermediate 59 (200 mg, 0.54 mmol), 4-trifluoromethylbenzylamine (0.5 mL, 3.51 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 127 mg of the product 109. LC/MS: 1.43 min, m/z 396 ($M^+$+1).

Example 25

(cis-4,5-Diphenyl-4,5-dihydro-1H-imidazol-2-yl)-(2-fluorobenzyl)amine (110)

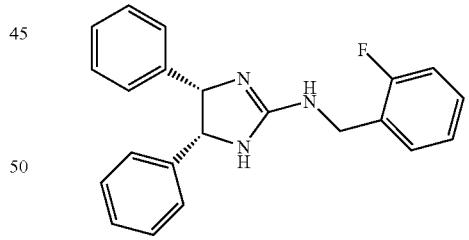

A mixture of intermediate 59 (200 mg, 0.54 mmol), 2-fluorobenzylamine (0.5 mL, 4.37 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 64 mg of the product 110. LC/MS: 1.36 min, m/z 346 ($M^+$+1).

Example 26

(cis-4,5-Diphenyl-4,5-dihydro-1H-imidazol-2-yl)-(4-chloro-2-fluorobenzyl)amine (111)

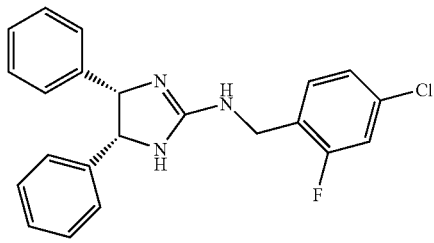

A mixture of intermediate 59 (200 mg, 0.54 mmol), 4-chloro-2-fluorobenzylamine (0.5 mL, 4.39 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 8 mg of the product 111. LC/MS: 1.41 min, m/z 380 ($M^+$+1).

Example 27

(cis-4,5-Diphenyl-4,5-dihydro-1H-imidazol-2-yl)-(4-methylbenzyl)amine (112)

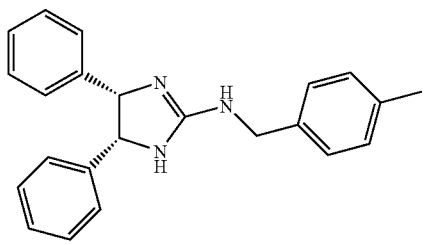

A mixture of intermediate 59 (200 mg, 0.54 mmol), 4-methylbenzylamine (0.5 mL, 3.93 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 38 mg of the product 112. LC/MS: 1.75 min, m/z 342 ($M^+$+1).

Example 28

(cis-4,5-Diphenyl-4,5-dihydro-1H-imidazol-2-yl)-(4-methoxybenzyl)amine (113)

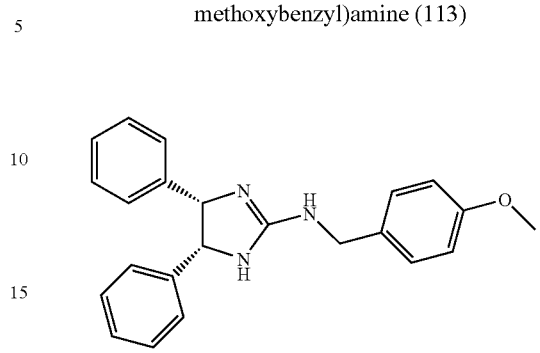

A mixture of intermediate 59 (200 mg, 0.54 mmol), 4-methoxybenzylamine (0.5 mL, 3.83 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 137 mg of the product 113. LC/MS: 1.71 min, m/z 358 ($M^+$+1).

Example 29

(cis-4,5-Diphenyl-4,5-dihydro-1H-imidazol-2-yl)-(3,4,5-trimethoxybenzyl)amine (114)

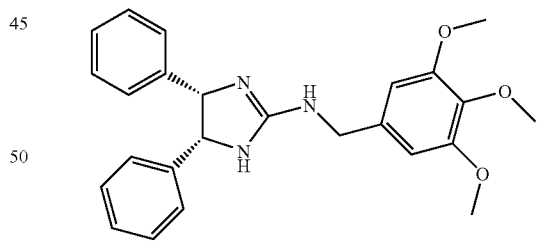

A mixture of intermediate 59 (200 mg, 0.54 mmol), 3,4,5-trimethoxybenzylamine (0.5 mL, 2.93 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 111 mg of the product 114. LC/MS: 1.66 min, m/z 418 ($M^+$+1).

Example 30

(cis-4,5-Diphenyl-4,5-dihydro-1H-imidazol-2-yl)-(4-chlorobenzyl)amine (115)

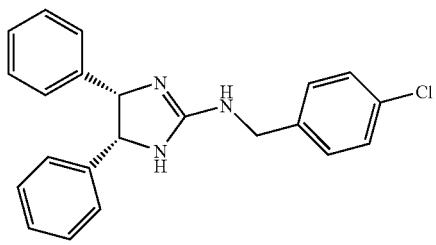

A mixture of intermediate 59 (200 mg, 0.54 mmol), 4-chlorobenzylamine (0.5 mL, 4.11 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 98 mg of the product 115. LC/MS: 1.39 min, m/z 362 ($M^+$+1).

Example 31

(cis-4,5-Diphenyl-4,5-dihydro-1H-imidazol-2-yl)-(2-methoxybenzyl)amine (116)

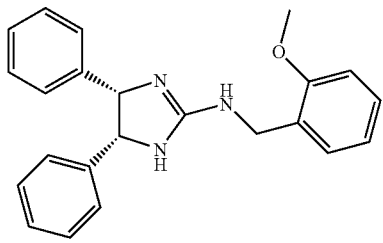

A mixture of intermediate 59 (200 mg, 0.54 mmol), 2-methoxybenzylamine (0.5 mL, 3.83 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 37 mg of the product 116. LC/MS: 1.74 min, m/z 358 ($M^+$+1).

Example 32

(cis-4,5-Diphenyl-4,5-dihydro-1H-imidazol-2-yl)-(3-methoxybenzyl)amine (117)

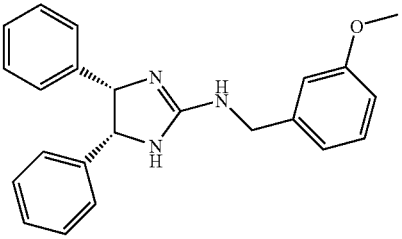

A mixture of intermediate 59 (200 mg, 0.54 mmol), 3-methoxybenzylamine (0.5 mL, 3.91 mmol) is heated at 100° C. (reaction block) for 2 days. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at RT overnight. The reaction mixture is neutralized, the solvent is evaporated, and the residue is purified by chromatography on silica gel; gradient elution with heptane:EtOAc (70:30-50:50) gives 116 mg of the product 117. LC/MS: 1.70 min, m/z 358 ($M^+$+1).

Example 33

2-(4-Fluorobenzylamino)-cis-4,5-diphenyl-4,5-dihydro-imidazole-1-carboxylic acid phenyl ester (123)

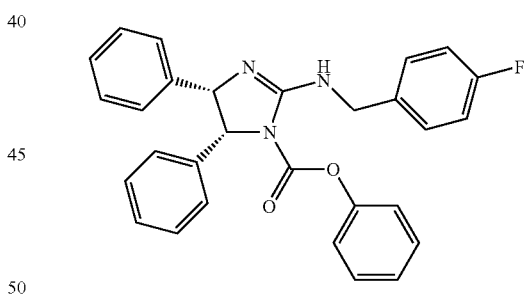

To a solution of (cis-4,5-diphenyl-4,5-dihydro-1H-imidazol-2-yl)-(4-fluorobenzyl)amine (86) (100 mg, 0.26 mmol), triethylamine (0.091 mL, 0.656 mmol), 4-dimethylaminopyridine (10 mg) in dichloromethane (10 mL) is added phenyl chloroformate (0.033 mL, 0.262 mmol), and the mixture is stirred at RT overnight. The reaction mixture is diluted with dichloromethane and washed with water, and the organic layer is dried (MgSO$_4$), filtered, and evaporated. The residue is purified by chromatography on silica gel; gradient elution with heptane:EtOAc (70:30-60:40) gives 100 mg of the product 123. $^1$H NMR (CDCl$_3$) δ 7.50-7.40 (m, 2 H), 7.40-7.10 (m, 6 H), 7.10-6.90 (m, 8 H), 6.90-6.80 (m, 2 H), 6.70-6.60 (m, 2 H), 5.75-5.55 (m, 2 H), 4.75-4.55 (m, 2 H); MS: m/z 466 ($M^+$+1)

Example 34

N-[cis-4,5-Diphenyl-4,5-dihydro-1H-imidazol-2-yl]-4-fluorobenzamide hydrochloride (126)

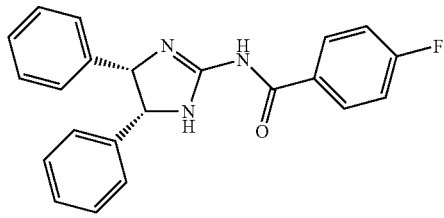

Step 1

2-Amino-cis-4,5-diphenyl-4,5-dihydro-imidazole-1-carboxylic acid tert-butyl ester (124)

A mixture of (cis-4,5-diphenyl-4,5-dihydro-1H-imidazol-2-yl)amine (122) (127 mg, 0.536 mmol) in dichloromethane (5 mL) is added DMF (5 mL) followed by N,N-diisopropylethylamine (0.093 mL, 0.536 mmol) and 4-dimethylaminopyridine (10 mg), and the dropwise addition of di-tert-butyl-dicarbonate (117 mg, 0.536 mmol) in dichloromethane (2 mL). The solution is stirred at RT for 1.5 h, the solvents evaporated, and the residue dissolved in dichloromethane. The solution is washed with 0.1N HCl, NaHCO$_3$, water, and then dried (Na$_2$SO$_4$) and filtered. The filtrate is evaporated and the residue is triturated with Et$_2$O to give 12 mg of the product 124.

Step 2

2-(4-Fluorobenzoylamino)-cis-4,5-diphenyl-4,5-dihydro-imidazole-1-carboxylic acid tert-butyl ester (125)

A mixture of 124 (200 mg, 0.593 mmol), triethylamine (0.082 mL, 0.583 mmol), 4-dimethylaminopyridine (10 mg), and 4-fluorobenzoyl chloride (0.063 mL, 0.533 mmol) in dichloromethane (2 mL) is stirred at RT for 0.5 h. The solution is diluted with dichloromethane and washed with NaHCO$_3$, brine, and then dried (MgSO$_4$). The mixture is filtered, the filtrate evaporated, and residue purified by chromatography on silica gel; gradient elution with heptane:EtOAc (70:30-60:40) gives 123 mg of the product 125. $^1$H NMR (CDCl$_3$) δ 10.00 (s, 1 H), 8.50-8.35 (m, 2 H), 7.20-6.85 (m, 12 H), 6.55-6.40 (m, 2 H), 1.20 (s, 9 H); MS: m/z 460 (M$^+$+1).

Step 3

N-[cis-4,5-Diphenyl-4,5-dihydro-1H-imidazol-2-yl]-4-fluorobenzamide hydrochloride (126) (Scheme 5, Method c)

Hydrogen chloride is bubbled into a solution of 125 (123 mg, 0.267 mmol) in EtOAc (20 mL) for 1 min, and the solution is stirred at RT overnight. The solvent is removed by rotary evaporation, and the residue is triturated with Et$_2$O to give 50 mg of the product 126. $^1$H NMR (DMSO-d$_6$) δ 12.9 (s, 1 H), 9.70 (s, 2 H), 8.35-8.15 (m, 2 H), 7.60-7.40 (m, 2 H), 7.20-6.90 (m, 10), 5.70 (s, 2 H); LC/MS: 3.20 m/z 360 (M$^+$+1).

Example 35

(cis-4,5-bis-(2-Fluorophenyl)-4,5-dihydro-1H-imidazol-2-yl)-benzylamine hydrochloride (127)

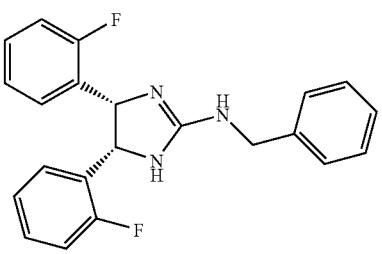

A mixture of intermediate 60 (300 mg, 0.742 mmol), benzylamine (0.5 mL, 4.6 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 67 mg of the product 127. LC/MS: 1.43 min, m/z 364 (M$^+$+1).

Example 36

(cis-4,5-bis-(2-Fluorophenyl)-4,5-dihydro-1H-imidazol-2-yl)-(4-fluorobenzyl)amine hydrochloride (128)

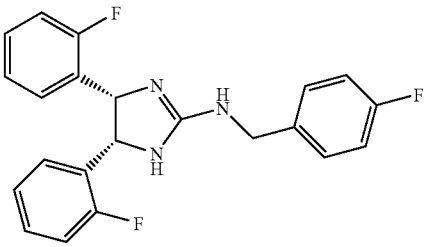

A mixture of intermediate 60 (300 mg, 0.742 mmol), 4-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 107 mg of the product 128. LC/MS: 1.44 min, m/z 382 (M$^+$+1).

Example 37

[cis-4,5-bis-(2-Fluorophenyl)-4,5-dihydro-1H-imidazol-2-yl]-(3,4-difluorobenzyl)-amine hydrochloride (129)

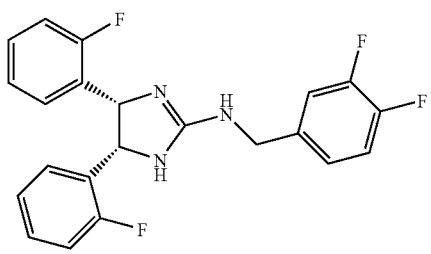

A mixture of intermediate 60 (300 mg, 0.742 mmol), 3,4-difluorobenzylamine (0.5 mL, 4.2 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 188 mg of the product 129. LC/MS: 1.45 min, m/z 400 (M$^+$+1).

Example 38

[cis-4,5-bis-(2-Fluorophenyl)-4,5-dihydro-1H-imidazol-2-yl]-(3-methylbenzyl)amine hydrochloride (130)

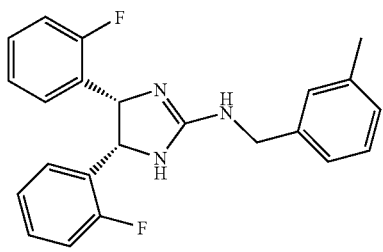

A mixture of intermediate 60 (300 mg, 0.742 mmol), 3-methylbenzylamine (0.5 mL, 3.9 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 80 mg of the product 130. LC/MS: 1.44 min, m/z 382 (M$^+$+1).

Example 39

[cis-4,5-bis-(3-Fluorophenyl)-4,5-dihydro-1H-imidazol-2-yl]-benzylamine hydrochloride (131)

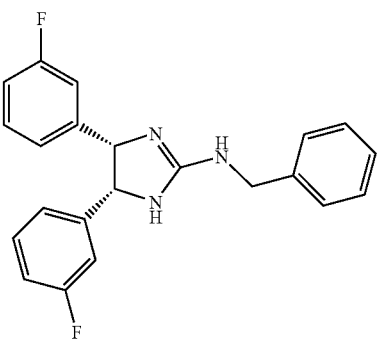

A mixture of intermediate 61 (300 mg, 0.742 mmol), benzylamine (0.5 mL, 4.6 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 110 mg of the product 131. LC/MS: 1.43 min, m/z 364 (M$^+$+1).

Example 40

[cis-4,5-bis-(3-Fluorophenyl)-4,5-dihydro-1H-imidazol-2-yl]-(3-fluorobenzyl)amine hydrochloride (132)

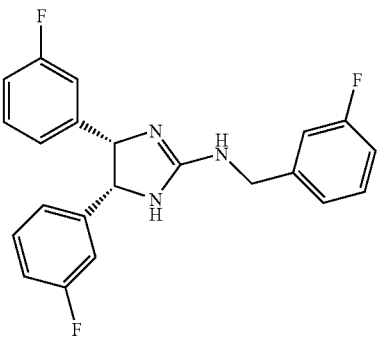

A mixture of intermediate 61 (300 mg, 0.742 mmol), 3-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chroma-

Example 41

[cis-4,5-bis-(3-Fluorophenyl)-4,5-dihydro-1H-imidazol-2-yl]-(4-fluorobenzyl)amine hydrochloride (133)

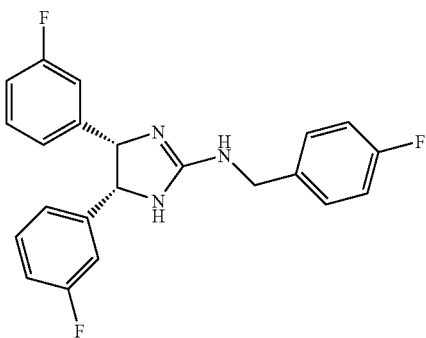

A mixture of intermediate 61 (300 mg, 0.742 mmol), 4-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 160 mg of the product 133. LC/MS: 1.44 min, m/z 382 (M$^+$+1).

Example 42

[cis-4,5-bis-(3-Fluorophenyl)-4,5-dihydro-1H-imidazol-2-yl]-(3,4-difluorobenzyl)-amine hydrochloride (134)

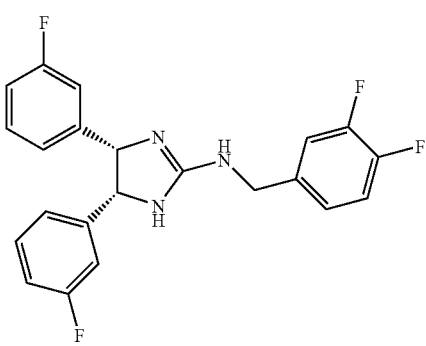

A mixture of intermediate 61 (300 mg, 0.742 mmol), 3,4-difluorobenzylamine (0.5 mL, 4.2 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 210 mg of the product 134. LC/MS: 1.46 min, m/z 400 (M$^+$+1).

Example 43

[cis-4,5-bis-(2-Methylphenyl)-4,5-dihydro-1H-imidazol-2-yl]-benzylamine hydrochloride (135)

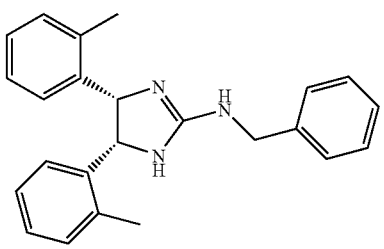

A mixture of intermediate 63 (300 mg, 0.760 mmol), benzylamine (0.5 mL, 4.6 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 150 mg of the product 135. LC/MS: 1.48 min, m/z 356 (M$^+$+1).

Example 44

[cis-4,5-bis-(2-Methylphenyl)-4,5-dihydro-1H-imidazol-2-yl]-(3-fluorobenzyl)amine hydrochloride (136)

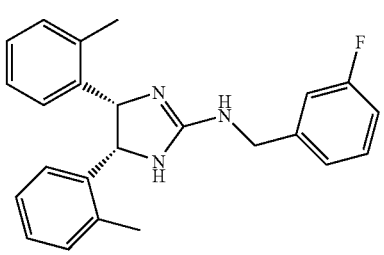

A mixture of intermediate 63 (300 mg, 0.760 mmol), 3-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH: acetic acid (100:4:1) gives 178 mg of the product 136. LC/MS: 1.49 min, m/z 374 (M⁺+1).

Example 45

[cis-4,5-bis-(2-Methylphenyl)-4,5-dihydro-1H-imidazol-2-yl]-(4-fluorobenzyl)amine hydrochloride (137)

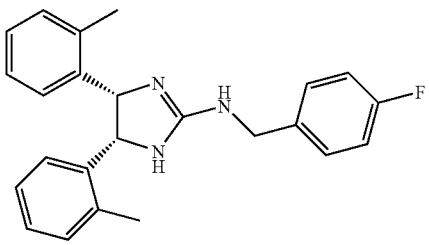

A mixture of intermediate 63 (300 mg, 0.760 mmol), 4-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH: acetic acid (100:4:1) gives 143 mg of the product 137. LC/MS: 1.48 min, m/z 374 (M⁺+1).

Example 46

[cis-4,5-bis-(2-Methylphenyl)-4,5-dihydro-1H-imidazol-2-yl]-(3,4-difluorobenzyl)-amine hydrochloride (138)

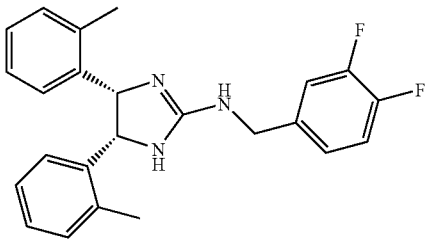

A mixture of intermediate 63 (300 mg, 0.760 mmol), 3,4-difluorobenzylamine (0.5 mL, 4.2 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH: acetic acid (100:4:1) gives 77 mg of the product 138. LC/MS: 1.49 min, m/z 392 (M⁺+1).

Example 47

[cis-4,5-bis-(3-Methylphenyl)-4,5-dihydro-1H-imidazol-2-yl]-benzylamine hydrochloride (139)

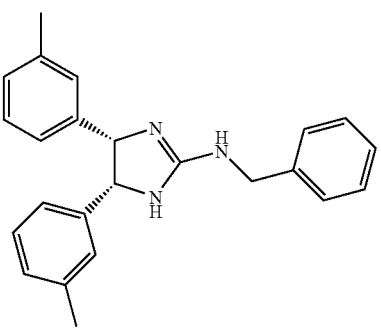

A mixture of intermediate 64 (300 mg, 0.760 mmol), benzylamine (0.5 mL, 4.6 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4: 1) gives 133 mg of the product 139. LC/MS: 1.49 min, m/z 356 (M⁺+1).

Example 48

[cis-4,5-bis-(3-Methylphenyl)-4,5-dihydro-1H-imidazol-2-yl]-(3-fluorobenzyl)amine hydrochloride (140)

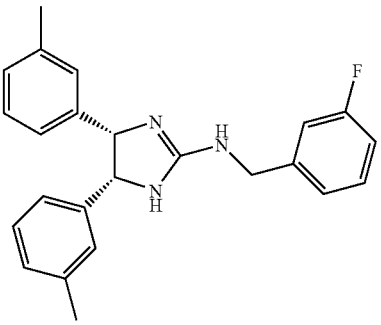

A mixture of intermediate 64 (300 mg, 0.760 mmol), 3-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH: acetic acid (100:4:1) gives 160 mg of the product 140. LC/MS: 1.50 min, m/z 374 (M$^+$+1).

Example 49

[cis-4,5-bis-(3-Methylphenyl)-4,5-dihydro-1H-imidazol-2-yl]-(4-fluorobenzyl)amine hydrochloride (141)

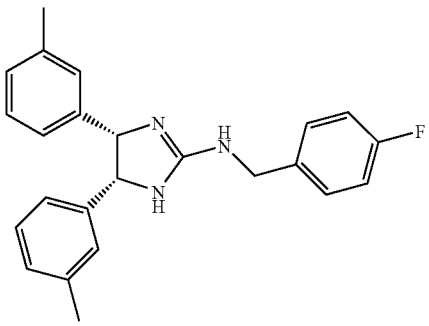

A mixture of intermediate 64 (300 mg, 0.760 mmol), 4-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH: acetic acid (100:4:1) gives 172 mg of the product 141. LC/MS: 1.50 min, m/z 374 (M$^+$+1).

Example 50

[cis-4,5-bis-(3-Methylphenyl)-4,5-dihydro-1H-imidazol-2-yl]-(3,4-difluorobenzyl)-amine hydrochloride (142)

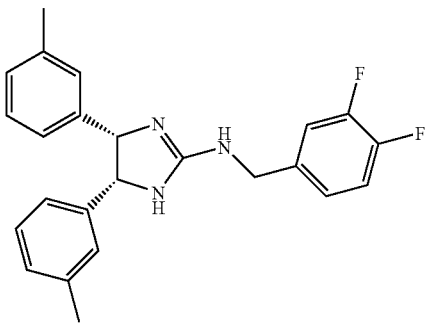

A mixture of intermediate 64 (300 mg, 0.760 mmol), 3,4-difluorobenzylamine (0.5 mL, 4.2 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH: acetic acid (100:4:1) gives 174 mg of the product 142. LC/MS: 1.52 min, m/z 392 (M$^+$+1).

Example 51

[cis-4,5-bis-(4-Methylphenyl)-4,5-dihydro-1H-imidazol-2-yl]-benzylamine hydrochloride (143)
(Scheme 5, Method a)

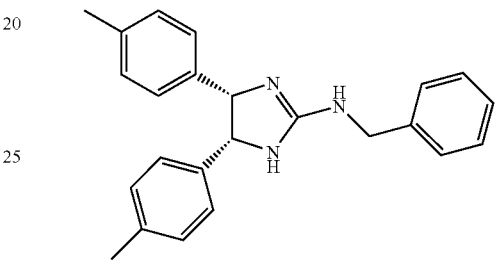

A mixture of intermediate 65 (300 mg, 0.760 mmol), benzylamine (0.5 mL, 4.6 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 135 mg of the product 143. LC/MS: 1.48 min, m/z 356 (M$^+$+1).

Example 52

[cis-4,5-bis-(4-Methylphenyl)-4,5-dihydro-1H-imidazol-2-yl]-(3-fluorobenzyl)amine hydrochloride (144)

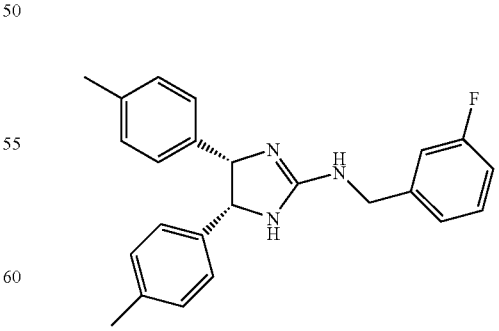

A mixture of intermediate 65 (300 mg, 0.760 mmol), 3-fluorobenzylamine (0.5 mL, 4.4 mmol) is heated at 95° C. (reaction block) overnight. The reaction mixture is cooled to RT. The corresponding N-Boc intermediate is not isolated.

The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH: acetic acid (100:4:1) gives 95 mg of the product 144. LC/MS: 1.50 min, m/z 374 (M$^+$+1).

Example 53

[cis-4,5-bis-(4-Methylphenyl)-4,5-dihydro-1H-imidazol-2-yl]-(4-fluorobenzyl)amine hydrochloride (145)

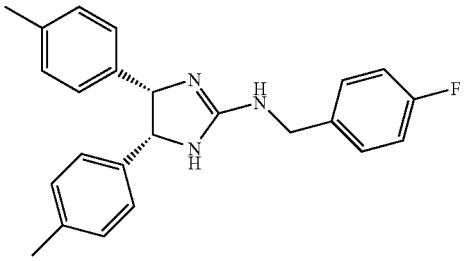

A mixture of intermediate 65 (300 mg, 0.760 mmol), 4-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH: acetic acid (100:4:1) gives 110 mg of the product 145. LC/MS: 1.51 min, m/z 374 (M$^+$+1).

Example 54

[cis-4,5-bis-(4-Methylphenyl)-4,5-dihydro-1H-imidazol-2-yl]-(3,4-difluorobenzyl)-amine hydrochloride (146)

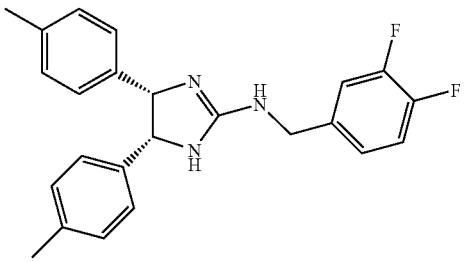

A mixture of intermediate 65 (300 mg, 0.760 mmol), 3,4-difluorobenzylamine (0.5 mL, 4.2 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH: acetic acid (100:4:1) gives 130 mg of the product 146. LC/MS: 1.51 min, m/z 392 (M$^+$+1).

Example 55

[cis-4,5-bis-(3-Chlorophenyl)-4,5-dihydro-1H-imidazol-2-yl]-benzylamine hydrochloride (147)

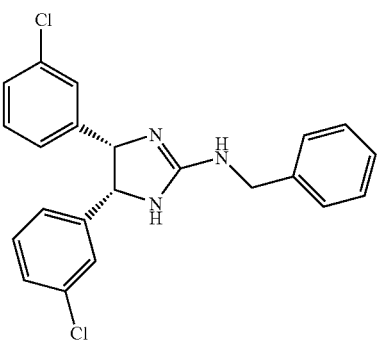

A mixture of intermediate 67 (300 mg, 0.690 mmol), benzylamine (0.5 mL, 4.6 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4: 1) gives 168 mg of the product 147. LC/MS: 1.51 min, nm/z 396 (M$^+$+1).

Example 56

[cis-4,5-bis-(3-Chlorophenyl)-4,5-dihydro-1H-imidazol-2-yl]-(4-fluorobenzyl)amine hydrochloride (148)

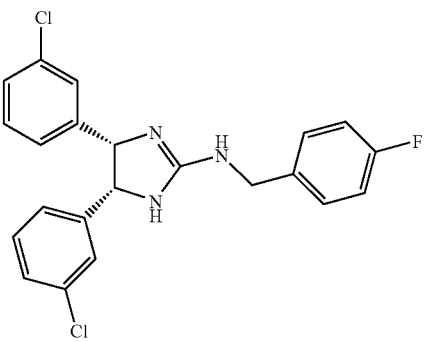

A mixture of intermediate 67 (300 mg, 0.690 mmol), 4-fluorobenzylamine (0.5 mL, 4.4 mmol) is heated at 95° C.

(reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 195 mg of the product 148. LC/MS: 1.51 min, m/z 414 (M⁺+1).

Example 57

[cis-4,5-bis-(3-Chlorophenyl)-4,5-dihydro-1H-imidazol-2-yl]-(3,4-difluorobenzyl)-amine hydrochloride (149)

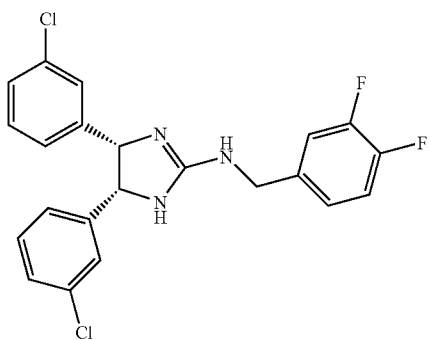

A mixture of intermediate 67 (300 mg, 0.690 mmol), 3,4-difluorobenzylamine (0.5 mL, 4.2 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 135 mg of the product 149. LC/MS: 1.52 min, m/z 432 (M⁺+1).

Example 58

[cis-4,5-bis-(2-Chlorophenyl)-4,5-dihydro-1H-imidazol-2-yl]-benzylamine hydrochloride (150)

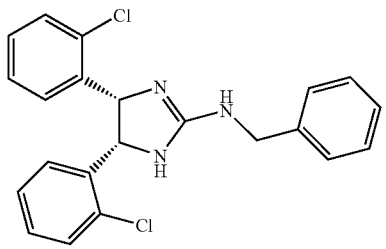

A mixture of intermediate 66 (300 mg, 0.69 mmol), benzylamine (0.5 mL, 4.6 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 170 mg of the product 150. LC/MS: 1.47 min, m/z 396 (M⁺+1).

Example 59

[cis-4,5-bis-(2-Chlorophenyl)-4,5-dihydro-1H-imidazol-2-yl]-(3-fluorobenzyl)amine hydrochloride (151)

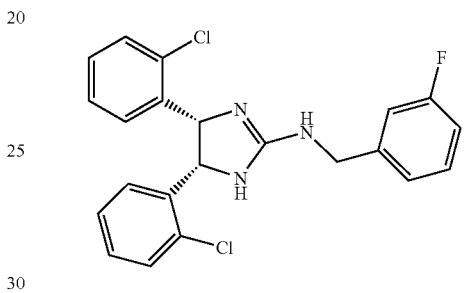

A mixture of intermediate 66 (300 mg, 0.69 mmol), 3-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 216 mg of the product 151. LC/MS: 1.49 min, m/z 414 (M⁺+1).

Example 60

[cis-4,5-bis-(2-Chlorophenyl)-4,5-dihydro-1H-imidazol-2-yl]-(4-fluorobenzyl)amine hydrochloride (152)

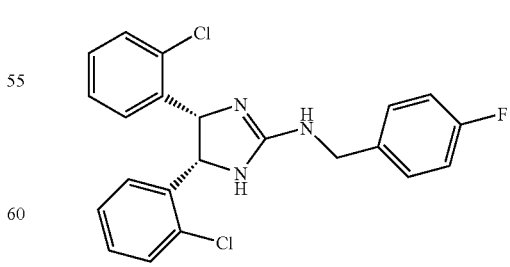

A mixture of intermediate 66 (300 mg, 0.69 mmol), 4-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 216 mg of the product 152. LC/MS: 1.49 min, m/z 414 (M⁺+1).

Example 61

[cis-4,5-bis-(2-Chlorophenyl)-4,5-dihydro-1H-imidazol-2-yl]-(3,4-difluorobenzyl)-amine hydrochloride (153)

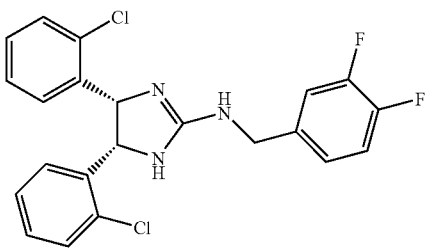

A mixture of intermediate 66 (300 mg, 0.69 mmol), 3,4-difluorobenzylamine (0.5 mL, 4.2 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 100 mg of the product 153. LC/MS: 1.50 min, m/z 432 (M⁺+1).

Example 62

[cis-4,5-bis-(4-Chlorophenyl)-4,5-dihydro-1H-imidazol-2-yl]-benzylamine hydrochloride (154)

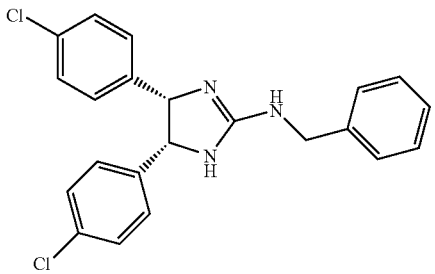

A mixture of intermediate 68 (300 mg, 0.690 mmol), benzylamine (0.5 mL, 4.6 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 170 mg of the product 154. LC/MS: 1.49 min, m/z 396 (M⁺+1).

Example 63

[cis-4,5-bis-(4-Chlorophenyl)-4,5-dihydro-1H-imidazol-2-yl]-(3-fluorobenzyl)amine hydrochloride (155)

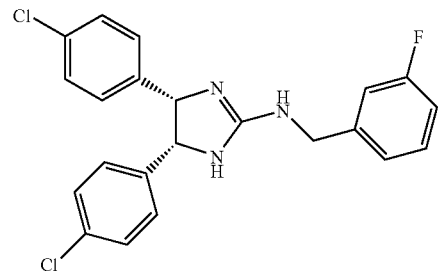

A mixture of intermediate 68 (300 mg, 0.690 mmol), 3-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH: acetic acid (100:4:1) gives 216 mg of the product 155. LC/MS: 1.52 min, m/z 414 (M⁺+1).

Example 64

[cis-4,5-bis-(4-Chlorophenyl)-4,5-dihydro-1H-imidazol-2-yl]-(3,4-difluorobenzyl)-amine hydrochloride (156)

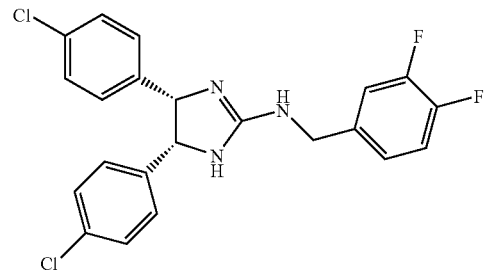

A mixture of intermediate 68 (300 mg, 0.690 mmol), 3,4-difluorobenzylamine (0.5 mL, 4.2 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H₂O, brine, and then dried (MgSO₄).

The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH: acetic acid (100:4:1) gives 100 mg of the product 156. LC/MS: 1.54 min, m/z 432 (M$^+$+1).

Example 65

[cis-4,5-bis-(2-Bromophenyl)-4,5-dihydro-1H-imidazol-2-yl]-(3-fluorobenzyl)amine hydrochloride (157)

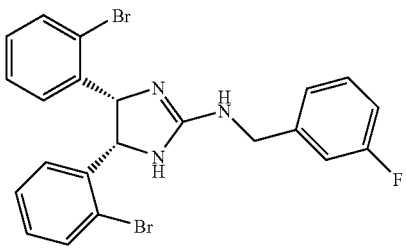

A mixture of intermediate 69 (80 mg, 015 mmol), 3-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 46 mg of the product 157. LC/MS: 1.49 min, m/z 504 (M$^+$+1).

Example 66

[cis-4,5-bis-(2-Bromophenyl)-4,5-dihydro-1H-imidazol-2-yl]-(4-fluorobenzyl)amine hydrochloride (158)

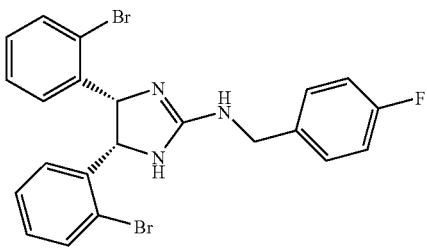

A mixture of intermediate 69 (80 mg, 015 mmol), 4-fluorobenzylamine (0.5 mL, 4.4 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 33 mg of the product 158. LC/MS: 1.49 min, m/z 504 (M$^+$+1).

Example 67

[cis-4,5-bis-(2-Bromophenyl)-4,5-dihydro-1H-imidazol-2-yl]-(3,4-difluorobenzyl)-amine hydrochloride (159)

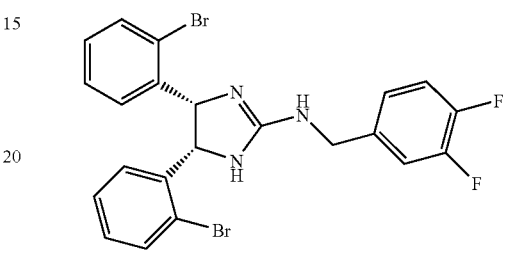

A mixture of intermediate 69 (80 mg, 015 mmol), 3,4-difluorobenzylamine (0.5 mL, 4.2 mmol) is heated at 95° C. (reaction block) overnight. The reaction mixture is cooled to RT. The corresponding N-Boc intermediate is not isolated. The reaction mixture is dissolved in dichloromethane, washed with 0.1N HCl, H$_2$O, brine, and then dried (MgSO$_4$). The mixture is filtered and evaporated, and the residue dissolved in EtOAc. Hydrogen chloride is bubbled into the solution for 5 min, and the solution is stirred at RT overnight. The solvent is evaporated, and the residue is purified by chromatography on silica gel; elution with dichloromethane:MeOH:acetic acid (100:4:1) gives 58 mg of the product 159. LC/MS: 1.53 min, m/z 522 (M$^+$+1).

Example 68

[cis-4,5-bis-(4-Fluorophenyl)-4,5-dihydro-1H-imidazol-2-yl]-benzylamine hydrochloride (161)

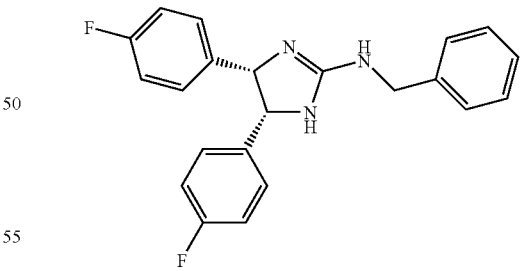

Step 1

2-(Benzylamino)-cis-4,5-bis-(4-fluorophenyl)-4,5-dihydro-imidazole-1-carboxylic acid tert-butyl ester (160)

A mixture of intermediate 62 (0.5 g, 1.24 mmol), benzylamine (0.680 mL, 6.2 mmol) and MeOH (0.1 mL) is heated at 100° C. overnight. The reaction mixture is cooled to RT and purified by chromatography on silica gel; gradient elution with heptane:EtOAc (75:25-60:40) gives 0.354 g of the product 160. $^1$H NMR (CDCl$_3$) δ 7.55-7.25 (m, 6 H), 6.95-6.85 (m, 2 H), 6.80-6.60 (m, 6 H), 5.45-5.20 (m, 2 H), 4.75-4.55 (m, 2 H), 1.16 (s, 9 H)

Step 2

[cis-4,5-bis-(4-Fluorophenyl)-4,5-dihydro-1H-imidazol-2-yl]-benzylamine hydrochloride (161)

Hydrogen chloride is bubbled into a solution of 160 (350 mg, 0.76 mmol) in EtOAc (20 mL) for 0.5 min, and the solution is stirred at RT overnight. The solvent is removed by rotary evaporation, and the residue is triturated with Et$_2$O to give 230 mg of the product 161. $^1$H NMR (DMSO-d$_6$) δ 9.50-8.40 (m, 3 H), 7.55-7.250 (m, 5 H), 7.05-6.85 (m, 8 H), 5.48 (s, 2 H), 4.55 (d, 2 H); MS: m/z 364 (M$^+$+1).

Example 69 cis-4,5-bis-(4-Fluorophenyl)-4,5-dihydro-1H-imidazol-2-yl]-(4-fluorobenzyl)amine hydrochloride (163)

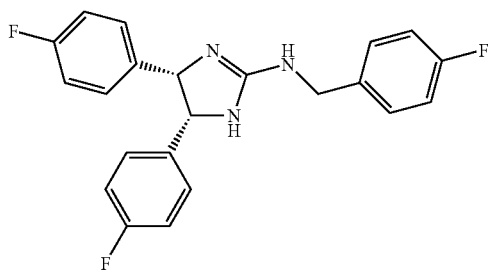

Step 1

2-(4-Fluorobenzyamino)-cis-4,5-bis-(4-fluorophenyl)-4,5-dihydro-imidazole-1-carboxylic acid tert-butyl ester (162)

A mixture of intermediate 62 (0.5 g, 1.24 mmol), 4-fluorobenzylamine (0.71 mL, 6.2 mmol) and MeOH (0.2 mL) is heated at 110° C. overnight. The reaction mixture is cooled to RT diluted with dichloromethane (3 mL), and purified by chromatography on silica gel; gradient elution with heptane:EtOAc (70:30-50:50) gives 0.326 g of the product 162. $^1$H NMR (CDCl$_3$) δ 7.55-7.35 (m, 2 H), 7.10-7.00 (m, 2 H), 6.95-6.85 (m, 2 H), 6.80-6.65 (m, 6 H), 5.45-5.25 (m, 2 H), 4.75-4.55 (m, 2 H), 1.16 (s, 9 H).

Step 2 cis-4,5-bis-(4-Fluorophenyl)-4,5-dihydro-1H-imidazol-2-yl]-(4-fluorobenzyl)-amine hydrochloride (163)

Hydrogen chloride is bubbled into a solution of intermediate 162 (320 mg, 0.66 mmol) in EtOAc (20 mL) for 0.5 min, and the solution is stirred at RT overnight. The solvent is removed by rotary evaporation, and the residue is crystallized from dichloromethane:Et$_2$O to give 89 mg of the product 163. $^1$H NMR (DMSO-d$_6$) δ 9.80-8.20 (m, 3 H), 7.60-7.40 (m, 2 H), 7.35-7.20 (m, 2 H), 5.50 (s, 2 H), 4.58 (s, 2 H); MS: m/z 382 (M$^+$+1).

Example 70 cis-4,5-bis-(4-Fluorophenyl)-4,5-dihydro-1H-imidazol-2-yl]-(3,4-difluorobenzyl)-amine hydrochloride (165)

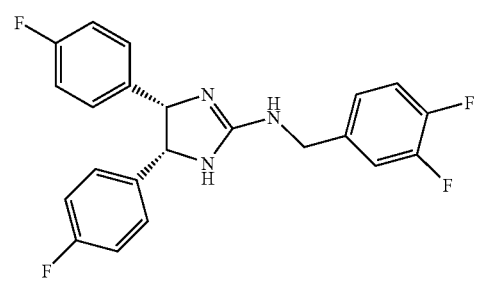

Step 1

2-(3,4-Difluorobenzyamino)-cis-4,5-bis-(4-fluorophenyl)-4,5-dihydro-imidazole-1-carboxylic acid tert-butyl ester (164)

A mixture of intermediate 62 (0.5 g, 1.24 mmol), 3,4-difluorobenzylamine (0.731 mL, 6.20 mmol) and MeOH (0.1 mL) is heated at 100° C. overnight. The reaction mixture is cooled to RT, and purified by chromatography on silica gel; gradient elution with heptane:EtOAc (75:25-50:50) gives 0.348 g of the product 164. $^1$H NMR (CDCl$_3$) δ 7.52 (s, 1 H), 7.35-7.25 (m, 1 H), 7.20-7.10 (m, 2 H), 6.90-6.85 (m, 2 H), 6.80-6.85 (m, 6 H), 5.45-5.30 (m, 2 H), 4.70-4.50 (m, 2 H), 1.17 (s, 9 H).

Step 2 cis-4,5-bis-(4-Fluorophenyl)-4,5-dihydro-1H-imidazol-2-yl]-(3,4-difluorobenzyl)-amine hydrochloride (165)

Hydrogen chloride is bubbled into a solution of 164 (348 mg, 0.67 mmol) in EtOAc (20 mL) for 0.5 min, and the solution is stirred at RT overnight. The solvent is removed by rotary evaporation, and the residue is triturated with Et$_2$O to give 199 mg of the product 165. $^1$H NMR (DMSO-d$_6$) δ 9.70-8.40 (m, 3 H), 7.65-7.20 (m, 3 H), 7.10-6.80 (m, 8 H), 5.51 (s, 2 H), 4.60 (d, 2 H); MS: m/z 400 (M$^+$+1).

Example 71

(cis-4,5-Diphenyl-4-methyl-4,5-dihydro-1H-imidazol-2-yl)-(4-fluorobenzyl)amine hydrochloride (185)

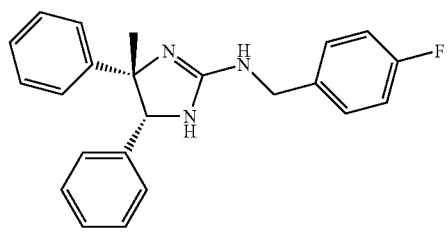

A mixture of intermediate 72 (850 mg, 2.22 mmol), 4-fluorobenzylamine (1 mL, 8.35 mmol) is heated at 140° C. overnight. The reaction mixture is cooled to RT. The reaction mixture is diluted with dichloromethane, washed with 0.1N HCl, brine, and then dried ($Na_2SO_4$). The mixture is filtered, the filtrate evaporated, and the residue crystallized from dichloromethane:heptane gives 365 mg of the product 185. $^1$H NMR (DMSO-$d_6$) δ 9.80-8.40 (m, 3 H), 7.65-7.45 (m, 2 H), 7.40-7.30 (m, 2 H), 7.15-6.95 (m, 6H), 6.95-6.75 (m, 4 H), 5.10 (s, 1 H), 4.70-4.50 (m, 2 H), 1.85 (s, 3 H); MS: m/z 360 ($M^+$+1).

Example 72

[4,5-cis-bis-(4-Fluorophenyl)-4-methyl-4,5-dihydro-1H-imidazol-2-yl]-(4-fluoro-benzyl)amine (186)

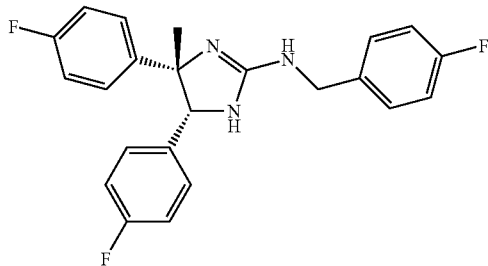

A mixture of intermediate 73 (200 mg, 0.478 mmol), 4-fluorobenzylamine (0.5 mL, 4.4 mmol) is heated at 145° C. overnight. The reaction mixture is cooled to RT. The reaction mixture is diluted with dichloromethane, washed with 3M HCl, brine, and then dried ($Na_2SO_4$). The mixture is filtered, the filtrate evaporated, and the residue triturated with dichloromethane, and the insoluble material filtered to give 133 mg of the product 186. $^1$H NMR (DMSO-$d_6$) δ 9.80-8.40 (m, 3 H), 7.60-7.40 (m, 2 H), 7.40-7.20 (m, 2 H), 7.15-6.80 (m, 8H), 5.10 (s, 1 H), 4.70-4.40 (m, 2 H), 1.85 (s, 3 H); MS: m/z 396 ($M^+$+1).

Example 73 cis-4,5-bis-(3-Fluorophenyl)-4-methyl-4,5-dihydro-1H-imidazol-2-yl]-(4-fluoro-benzyl)amine (188)

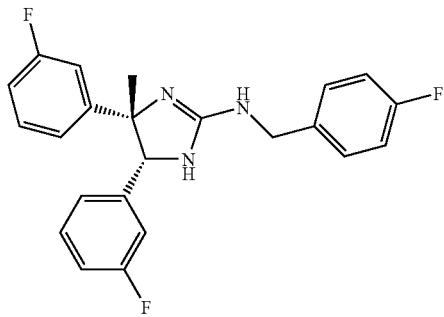

A mixture of intermediate 75 (200 mg, 0.478 mmol), 4-fluorobenzylamine (0.5 mL, 4.4 mmol) is heated at 150° C. overnight. The reaction mixture is cooled to RT. The reaction mixture is diluted with dichloromethane, washed with 3M HCl, brine, and then dried ($Na_2SO_4$). The mixture is filtered, the filtrate evaporated, and the residue purified by chromatography on silica gel; gradient elution with dichloromethane:MeOH:HOAc (100:2:0.5-100:4:1) gives 90 mg of the product 188. $^1$H NMR (CDCl$_3$) δ 9.80-7.60 (m, 2 H), 7.60-7.30 (m, 2 H), 7.15-6.85 (m, 4 H), 6.85-6.70 (m, 2 H), 6.70-6.20 (m, 4 H), 4.75 (s, 1 H), 4.70-4.40 (m, 2 H), 1.90 (s, 3 H); MS: m/z 396 ($M^+$+1).

Example 74

(cis-3a,4,5,6,7,7a-Hexahydro-1H-benzimidazol-2-yl)-benzylamine hydrochloride (190)

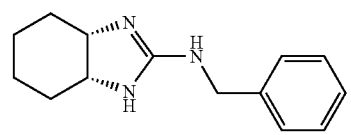

Step 1

2-(Benzylamino)-cis-3a,4,5,6,7,7a-hexahydro-1H-benzimidazol-1-carboxylic acid tert-butyl ester (189)

A mixture of intermediate 76 (200 mg, 0.0.740 mmol), benzylamine (0.5 mL, 4.6 mmol) is heated at 100° C. (reaction block) overnight. The reaction mixture is cooled to RT. The reaction mixture is diluted with dichloromethane, washed with 0.1N HCl, and brine. The solvent is evaporated, and the residue triturated with EtOAc, and the insoluble material filtered to give 207 mg of the product 189. $^1$H NMR (CDCl$_3$) δ 8.56 (s, 1 H), 7.50-7.20 (m, 5 H), 5.15-4.95 (m, 2 H), 4.35-4.05 (m, 2 H), 2.85-2.55 (m, 1 H), 2.25-2.05 (m, 1 H), 1.90-1.05 (m, 15 H); MS: m/z 330 ($M^+$+1).

Step 2 cis-3a,4,5,6,7,7a-Hexahydro-1H-benzimidazol-2-yl)-benzylamine hydrochloride (190)

A solution of intermediate 189 (150 mg, 0.455 mmol) in EtOAc (5 mL) is saturated with hydrogen chloride for 3 min, and stirred at RT overnight. The solvent is evaporated, and the residue is triturated with dichloromethane and the insoluble material filtered to give 35 mg of the product 190. $^1$H NMR (CDCl$_3$) δ 8.62 (s, 1 H), 8.40 (s, 1 H), 7.70 (s, 1H), 7.45-7.05 (m, 5 H), 4.50 (s, 2 H), 3.75 (s, 2 H), 2.00-1.00 (m, 8 H); MS: m/z 230 ($M^+$+1).

Example 75 cis-3a,4,5,6,7,7a-Hexahydro-1H-benzimidazol-2-yl)-(3-fluorobenzyl)amine hydrochloride (192)

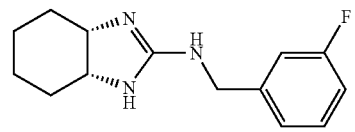

Step 1

2-[(3-Fluorobenzyl)amino]-cis-3a,4,5,6,7,7a-hexahydro-1H-benzimidazol-1-carboxylic acid tert-butyl ester (191)

A mixture of intermediate 76 (200 mg, 0.0.740 mmol), 3-fluorobenzylamine (0.5 mL, 4.4 mmol) is heated at 100° C. (reaction block) overnight. The reaction mixture is cooled to RT. The reaction mixture is diluted with dichloromethane, washed with 0.1N HCl, and brine. The solvent is evaporated, and the residue triturated with EtOAc, and the insoluble material filtered to give 188 mg of the product 191. $^1$H NMR (CDCl$_3$) δ 8.56 (s, 1 H), 7.45-7.20 (m, 3 H), 7.20-6.95 (m, 2 H), 5.20-4.95 (m, 2 H), 4.35-4.10 (m, 2 H), 2.75-2.55 (m, 1 H), 2.20-2.05 (m, 1 H), 1.80-1.05 (m, 15 H); MS: m/z 348 (M$^+$+1).

Step 2 cis-3a,4,5,6,7,7a-Hexahydro-1H-benzimidazol-2-yl)-(3-fluorobenzyl)amine hydrochloride (192)

A solution of 191 (150 mg, 0.432 mmol) in EtOAc (5 mL) is saturated with hydrogen chloride for 3 min, and stirred at RT overnight. The solvent is evaporated, and the residue is triturated with dichloromethane and the insoluble material filtered to give 90 mg of the product 192. $^1$H NMR (CDCl$_3$) δ 8.80 (s, 1 H), 8.65 (s, 1 H), 7.55 (s, 1 H), 7.25-6.75 (m, 4 H), 4.55 (s, 2 H), 3.80 (s, 2 H), 2.00-1.05 (m, 8 H); MS: m/z 248 (M$^+$+1).

Example 76 cis-3a,4,5,6,7,7a-Hexahydro-1H-benzimidazol-2-yl)-(4-fluorobenzyl)amine hydrochloride (194)

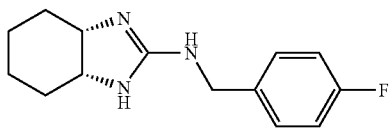

Step 1

2-[(4-Fluorobenzyl)amino]-cis-3a,4,5,6,7,7a-hexahydro-1H-benzimidazol-1-carboxylic acid tert-butyl ester (193)

A mixture of intermediate 76 (200 mg, 0.0.740 mmol), 4-fluorobenzylamine (0.5 mL, 4.4 mmol) is heated at 100° C. (reaction block) overnight. The reaction mixture is cooled to RT. The reaction mixture is diluted with dichloromethane, washed with 0.1N HCl, and brine. The solvent is evaporated, and the residue triturated with EtOAc, and the insoluble material filtered to give 252 mg of the product 193. $^1$H NMR (CDCl$_3$) δ 8.55 (s, 1 H), 7.55-7.35 (m, 2 H), 7.10-7.00 (m, 2 H), 5.10-4.90 (m, 2 H), 4.30-4.10 (m, 2 H), 2.70-2.55 (m, 1 H), 2.20-2.05 (m, 1 H), 1.80-1.05 (m, 15 H); MS: m/z 348 (M$^+$+1)

Step 2 cis-3a,4,5,6,7,7a-Hexahydro-1H-benzimidazol-2-yl)-(3-fluorobenzyl)amine hydrochloride (194)

A solution of 193 (150 mg, 0.432 mmol) in EtOAc (5 mL) is saturated with hydrogen chloride for 3 min, and stirred at RT overnight. The solvent is evaporated, and the residue is triturated with dichloromethane and the insoluble material filtered to give 30 mg of the product 194. $^1$H NMR (CDCl$_3$) δ 9.20-7.40 (m, 3 H), 7.40-7.15 (m, 2 H), 7.05-6.85 (m, 2 H), 4.50 (s, 2 H), 3.80 (s, 2 H), 1.90-1.15 (m, 8 H); MS: m/z 248 (M$^+$+1).

Example 77 cis-3a,4,5,6,7,7a-Hexahydro-1H-benzimidazol-2-yl)-(3,4-difluorobenzyl)amine hydrochloride (196)

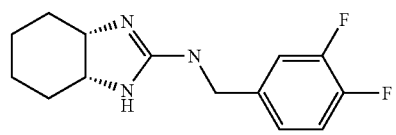

Step 1

2-[(3,4-Difluorobenzyl)amino]-cis-3a,4,5,6,7,7a-hexahydro-1H-benzimidazol-1-carboxylic acid tert-butyl ester (195)

A mixture of intermediate 76 (200 mg, 0.740 mmol), 3,4-difluorobenzylamine (0.5 mL, 4.2 mmol) is heated at 100° C. (reaction block) overnight. The reaction mixture is cooled to RT. The reaction mixture is diluted with dichloromethane, washed with 0.1N HCl, and brine. The solvent is evaporated, and the residue triturated with EtOAc, and the insoluble material filtered to give 270 mg of the product 195. $^1$H NMR (CDCl$_3$) δ 8.60 (s, 1 H), 7.40-7.10 (m, 3 H), 5.15-4.90 (m, 2 H), 4.30-4.10 (m, 2 H), 2.70-2.55 (m, 1 H), 2.20-2.05 (m, 1 H), 1.85-1.10 (m, 15 H); MS: m/z 366 (M$^+$+1).

Step 2 cis-3a,4,5,6,7,7a-Hexahydro-1H-benzimidazol-2-yl)-(3,4-difluorobenzyl)amine hydrochloride (196)

A solution of intermediate 195 (150 mg, 0.410 mmol) in EtOAc (5 mL) is saturated with hydrogen chloride for 3 min, and stirred at RT overnight. The solvent is evaporated, and the residue is triturated with dichloromethane and the insoluble material filtered to give 35 mg of the product 196. $^1$H NMR (CDCl$_3$) δ 8.80 (s, 2 H), 7.50 (s, 1 H), 7.40-6.90 (m, 3 H), 4.55 (s, 2 H), 3.80 (s, 2 H), 2.00-1.10 (m, 8 H); MS: m/z 266 (M$^+$+1).

Example 78

2-[(4-Fluorobenzyl)thio]-cis-4,5-diphenyl-4,5-dihydro-1H-imidazole hydrochloride (197)

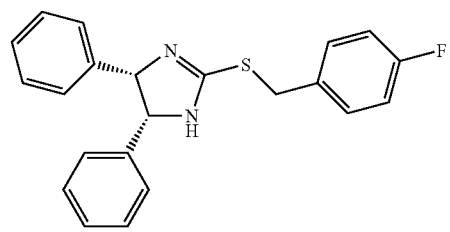

A mixture of intermediate 25 (0.50 g, 1.9 mmol) and 4-fluorobenzyl chloride (0.47 mL, 0.3.93 mmol) in abs. EtOH (20 mL) is heated at 90° C. for 24 h. The reaction mixture is cooled to RT, evaporated to dryness, and the residue suspended in Et$_2$O. The insoluble material is filtered to give 0.70 g of the product 197. $^1$H NMR (DMSO-d$_6$) δ 11.37 (s, 2H), 7.75-7.65 (m, 2 H), 7.40-7.25 (m, 2 H), 7.15-6.95 (m, 6 H), 6.90-6.70 (m, 4 H), 5.78 (s, 2 H), 4.84 (s, 2 H); MS: m/z 363 (M$^+$+1).

Example 79

[4-tert-Butylbenzyl)thio]-cis-4,5-diphenyl-4,5-dihydro-1H-imidazole hydrochloride (198)

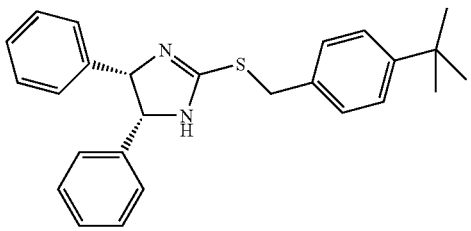

A mixture of intermediate 25 (200 mg, 0.786 mmol) and 4-tert-butylbenzyl chloride (0.304 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 112 mg of the product 198. $^1$H NMR (DMSO-d$_6$) δ 11.20 (s, 2 H), 7.60-7.40 (m, 4 H), 7.15-6.90 (m, 6 H), 6.90-6.70 (m, 4 H), 5.78 (s, 2 H), 4.75 (s, 2 H), 1.35 (s, 9 H); MS: m/z 401 (M$^+$+1).

Example 80

2-[(2,4-Dichlorobenzyl)thio]-cis-4,5-diphenyl-4,5-dihydro-1H-imidazole hydrochloride (199)

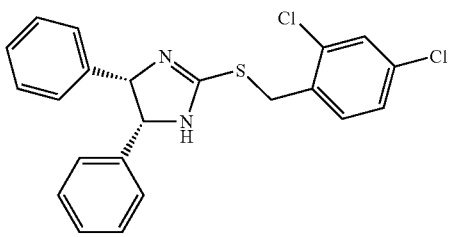

A mixture of intermediate 25 (200 mg, 0.786 mmol) and 2,4-dichlorobenzyl chloride (0.218 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 287 mg of the product 199. $^1$H NMR (DMSO-d$_6$) δ 11.38 (s, 2 H), 7.95-7.75 (m, 2 H), 7.65-7.50 (m, 1 H), 7.20-7.00 (m, 6 H), 7.00-6.80 (m, 4 H), 5.83 (s, 2 H), 4.90 (s, 2 H); MS: m/z 413 (M$^+$+1).

Example 81

2-[(4-Chlorobenzyl)thio]-cis-4,5-diphenyl-4,5-dihydro-1H-imidazole hydrochloride (200)

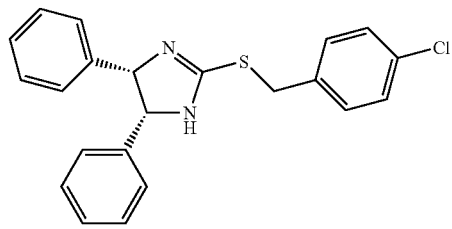

A mixture of intermediate 25 (200 mg, 0.786 mmol) and 4-chlorobenzyl chloride (0.253 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 151 mg of the product 200. $^1$H NMR (DMSO-d$_6$) δ 11.30 (s, 2 H), 7.75-7.60 (d, 2 H), 7.60-7.55 (d, 2 H), 7.20-6.90 (m, 6 H), 6.85-6.65 (m, 4 H), 5.78 (s, 2 H), 4.90 (s, 2 H); MS: m/z 379 (M$^+$+1).

Example 82

2-(Benzylthio)-cis-4,5-diphenyl-4,5-dihydro-1H-imidazole hydrochloride (201)

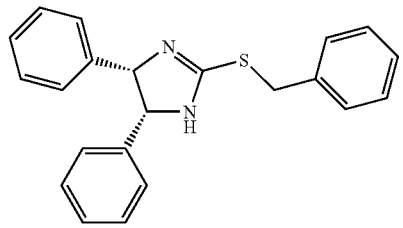

A mixture of intermediate 25 (200 mg, 0.786 mmol) and benzyl chloride (0.184 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 128 mg of the product 201. $^1$H NMR (DMSO-d$_6$) δ 11.30 (s, 2H), 7.70-7.50 (m, 2 H), 7.50-7.35 (m, 3 H), 7.20-6.95 (m, 6 H), 6.90-6.70 (m, 4 H), 5.78 (s, 2H), 4.90 (s, 2 H); MS: m/z 345 (M$^+$+1).

Example 83

2-[(3-Trifluoromethylbenzyl)thio]-cis-4,5-diphenyl-4,5-dihydro-1H-imidazole hydrochloride (202)

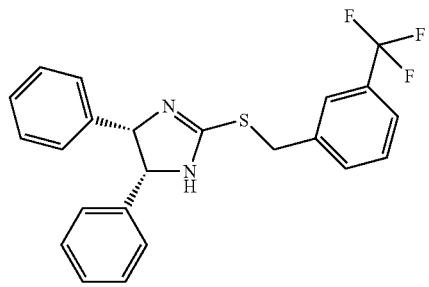

A mixture of intermediate 25 (200 mg, 0.786 mmol) and 3-trifluoromethylbenzyl chloride (0.243 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 196 mg of the product 202. $^1$H NMR (DMSO-d$_6$) δ 11.32 (s, 2 H), 8.10-7.65 (m, 4 H), 7.15-6.95 (m, 6 H), 6.90-6.60 (m, 4 H), 5.78 (s, 2 H), 4.93 (s, 2 H); MS: m/z 413 (M$^+$+1).

Example 84

2-[(3-Chlorobenzyl)thio]-cis-4,5-diphenyl-4,5-dihydro-1H-imidazole hydrochloride (203)

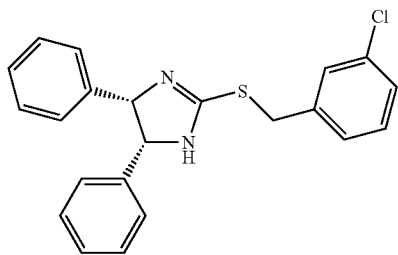

A mixture of intermediate 25 (200 mg, 0.786 mmol) and 3-chlorobenzyl chloride (0.199 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 196 mg of the product 203. $^1$H NMR (DMSO-d$_6$) δ 11.37 (s, 2 H), 7.85-7.45 (m, 4 H), 7.20-6.90 (m, 6 H), 6.90-6.60 (m, 4 H), 5.78 (s, 2 H), 4.93 (s, 2 H); MS: m/z 379 (M$^+$+1).

Example 85

2-[(3,4-Dichlorobenzyl)thio]-cis-4,5-diphenyl-4,5-dihydro-1H-imidazole hydrochloride (204)

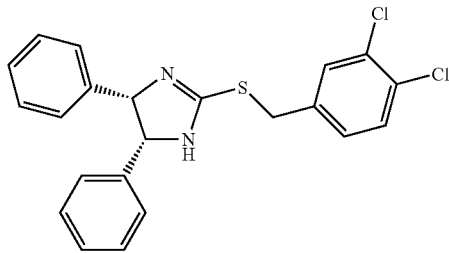

A mixture of intermediate 25 (200 mg, 0.786 mmol) and 3,4-dichlorobenzyl chloride (0.218 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 217 mg of the product 204. $^1$H NMR (DMSO-d$_6$) δ 11.40 (s, 2 H), 7.95 (d, 1 H), 7.78 (d, 1 H), 7.65 (d, 1 H), 7.20-6.90 (m, 6 H), 6.90-6.60 (m, 4 H), 5.78 (s, 2 H), 4.85 (s, 2 H); MS: m/z 413 (M$^+$+1).

Example 86

4-[(cis-4,5-Diphenyl-4,5-dihydro-1H-imidazol-2-yl)thiomethyl]benzoic acid ethyl ester hydrochloride (205)

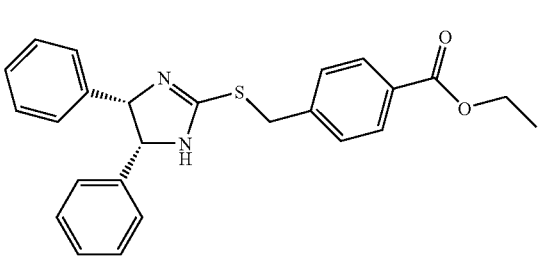

A mixture of intermediate 25 (200 mg, 0.786 mmol) and 4-chloromethylbenzoic acid ethyl ester (0.268 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 278 mg of the product 205. $^1$H NMR (DMSO-d$_6$) δ 11.20 (s, 2 H), 8.00 (d, 2 H), 7.75 (d, 2 H), 7.15-6.90 (m, 6 H), 6.90-6.65 (m, 4 H), 5.78 (s, 2 H), 4.90 (s, 2 H), 4.35 (q, 2 H), 1.32 (t, 3 H); MS: m/z 417 (M$^+$+1).

Example 87

2-[(3,5-Dimethoxybenzyl)thio]-cis-4,5-diphenyl-4,5-dihydro-1H-imidazole hydrochloride (206)

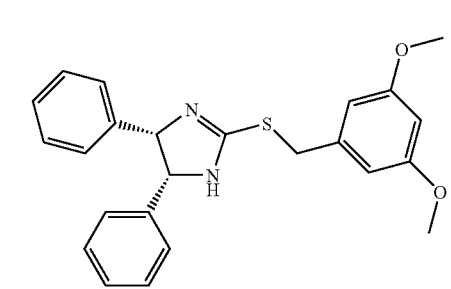

A mixture of intermediate 25 (200 mg, 0.786 mmol) and 3,5-dimethoxybenzyl chloride (0.293 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 189 mg of the product 206. $^1$H NMR (DMSO-d$_6$) δ 11.37 (s, 2 H), 7.85-7.45 (m, 4 H), 7.20-6.90 (m, 6 H), 6.90-6.60 (m, 4 H), 5.78 (s, 2 H), 4.70 (s, 2 H), 3.78 (s, 6 H); MS: m/z 405 (M$^+$+1).

Example 88

2-[(4-Phenylbenzyl)thio]-cis-4,5-diphenyl-4,5-dihydro-1H-imidazole hydrochloride (207)

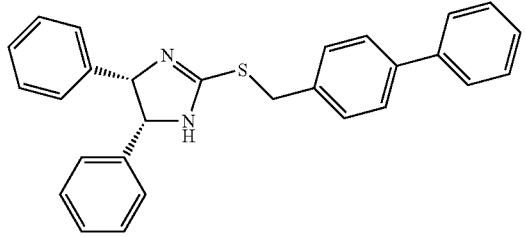

A mixture of intermediate 25 (200 mg, 0.786 mmol) and 4-phenylbenzyl chloride (0.318 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 205 mg of the product 207. $^1$H NMR (DMSO-d$_6$) δ 11.24 (s, 2 H), 7.90-7.60 (m, 6 H), 7.60-7.30 (m, 3 H), 7.20-6.90 (m, 6 H), 6.90-6.65 (m, 4 H), 5.79 (s, 2 H), 4.85 (s, 2 H); MS: m/z 421 (M$^+$+1).

Example 89

2-[(2-Chlorobenzyl)thio]-cis-4,5-diphenyl-4,5-dihydro-1H-imidazole hydrochloride (208)

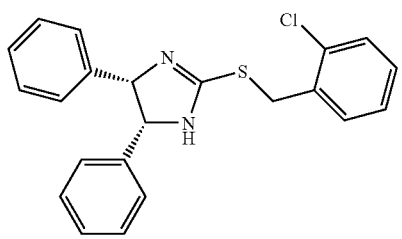

A mixture of intermediate 25 (200 mg, 0.786 mmol) and 2-chlorobenzyl chloride (0.198 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 105 mg of the product 208. $^1$H NMR (DMSO-d$_6$) δ 11.38 (s, 2 H), 7.90-7.70 (m, 1 H), 7.70-7.55 (m, 1 H), 7.55-7.35 (m, 2 H), 7.20-7.00 (m, 6 H), 7.00-6.85 (m, 4 H), 5.81 (s, 2 H), 4.88 (s, 2 H); MS: m/z 379 (M++1).

Example 90

2-[(2,6-Dichlorobenzyl)thio]-cis-4,5-diphenyl-4,5-dihydro-1H-imidazole hydrochloride (209)

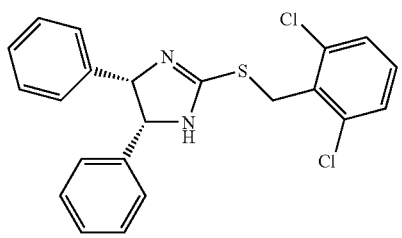

A mixture of intermediate 25 (200 mg, 0.786 mmol) and 2,6-dichlorobenzyl chloride (0.307 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 296 mg of the product 209. $^1$H NMR (DMSO-d$_6$) δ 11.47 (s, 2 H), 7.75-7.60 (m, 2 H), 7.60-7.40 (m, 1 H), 7.30-6.85 (m, 10 H), 5.90 (s, 2 H), 4.98 (s, 2 H); MS: m/z 413 (M$^+$+1).

Example 91

2-[(2-Fluorobenzyl)thio]-cis-4,5-diphenyl-4,5-dihydro-1H-imidazole hydrochloride (210)

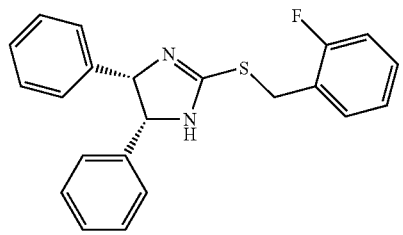

A mixture of intermediate 25 (200 mg, 0.786 mmol) and 2-fluorobenzyl chloride (0.187 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 141 mg of the product 210. $^1$H NMR (DMSO-d$_6$) δ 11.28 (s, 2 H), 7.80-7.65 (m, 1 H), 7.60-7.40 (m, 1 H), 7.40-7.20 (m, 2 H), 7.20-7.00 (m, 6 H), 7.00-6.80 (m, 4 H), 5.80 (s, 2 H), 4.85 (s, 2 H); MS: m/z 363 (M$^+$+1).

Example 92

2-[(4-Methylbenzyl)thio]-cis-4,5-diphenyl-4,5-dihydro-1H-imidazole hydrochloride (211)

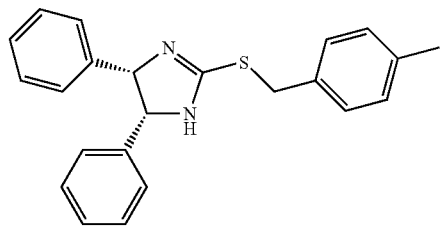

A mixture of intermediate 25 (200 mg, 0.786 mmol) and 4-methylbenzyl chloride (0.208 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 199 mg of the product 211. $^1$H NMR (DMSO-d$_6$) δ 11.18 (s, 2 H), 7.45 (d, 2 H), 7.25 (d, 2 H), 7.20-6.90 (m, 6 H), 6.90-6.65 (m, 4 H), 5.77 (s, 2 H), 4.73 (s, 2 H), 2.35 (s, 3 H); MS: m/z 359 (M++1).

Example 93

2-[(3-Methylbenzyl)thio]-cis-4,5-diphenyl-4,5-dihydro-1H-imidazole hydrochloride (212)

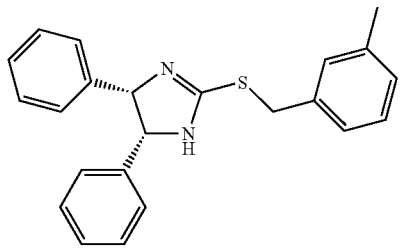

A mixture of intermediate 25 (200 mg, 0.786 mmol) and 3-methylbenzyl chloride (0.207 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 180 mg of the product 212. $^1$H NMR (DMSO-d$_6$) δ 11.21 (s, 2 H), 7.50-7.20 (m, 4 H), 7.20-6.90 (m, 6 H), 6.90-6.65 (m, 4 H), 5.73 (s, 2 H), 4.75 (s, 2 H), 2.32 (s, 3 H); MS: m/z 359 (M$^+$+1).

Example 94

2-[(Naphthalen-1-yl)methylthio]-cis-4,5-diphenyl-4,5-dihydro-1H-imidazole hydrochloride (213)

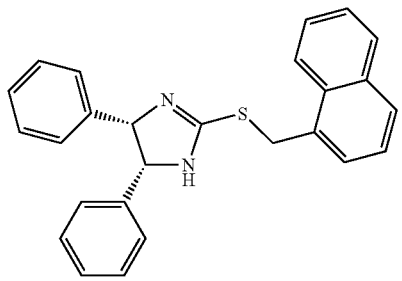

A mixture of intermediate 25 (200 mg, 0.786 mmol) and 1-chloromethylnaphthalene (0.277 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 67 mg of the product 213. $^1$H NMR (DMSO-d$_6$) δ 11.20 (s, 2 H), 8.40-8.25 (m, 1 H), 8.10-7.90 (m, 2 H), 7.90-7.80 (m, 1 H), 7.80-7.50 (3, H), 7.20-6.70 (m, 10 H), 5.79 (s, 2 H), 4.85 (s, 2 H); MS: m/z 395 (M$^+$+1).

Example 95

2-[(3,4-Difluorobenzyl)thio]-cis-4,5-diphenyl-4,5-dihydro-1H-imidazole hydrochloride (214)

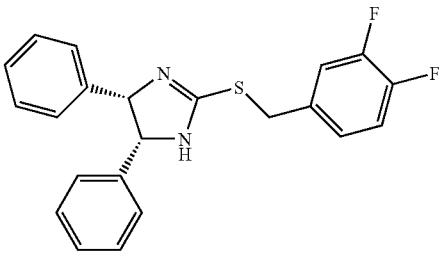

A mixture of intermediate 25 (200 mg, 0.786 mmol) and 3,4-difluorobenzyl chloride (0.255 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 207 mg of the product 214. $^1$H NMR (DMSO-d$_6$) δ 11.38 (s, 2 H), 7.90-7.65 (m, 1 H), 7.65-7.40 (m, 2 H), 7.20-6.90 (m, 6 H), 6.90-6.65 (m, 4 H), 5.79 (s, 2 H), 4.85 (s, 2 H); MS: m/z 381 (M$^+$+1).

Example 96

2-[(2-Trifluoromethoxybenzyl)thio]-cis-4,5-diphenyl-4,5-dihydro-1H-imidazole hydrochloride (215)

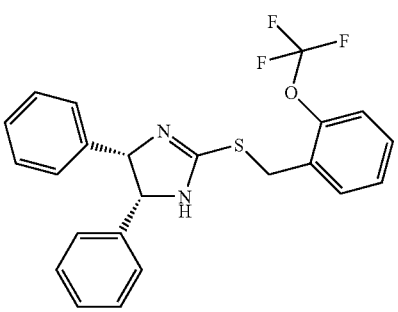

A mixture of intermediate 25 (200 mg, 0.786 mmol) and 2-trifluoromethoxybenzyl chloride (0.331 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 202 mg of the product 215. $^1$H NMR (DMSO-d$_6$) δ 11.32 (s, 2 H), 7.85 (d, 1 H), 7.70-7.40 (m, 3 H), 7.20-6.70 (m, 10 H), 5.80 (s, 2 H), 4.85 (s, 2 H); MS: m/z 429 (M$^+$+1).

Example 97

2-[(4-Trifluoromethoxybenzyl)thio]-cis-4,5-diphenyl-4,5-dihydro-1H-imidazole hydrochloride (216)

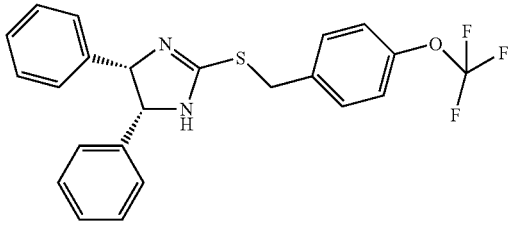

A mixture of intermediate 25 (200 mg, 0.786 mmol) and 4-trifluoromethoxybenzyl chloride (0.331 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 229 mg of the product 216. $^1$H NMR (DMSO-d$_6$) δ 11.30 (s, 2 H), 7.75 (d, 2 H), 7.45 (d, 2 H), 7.20-6.90 (m, 6 H), 6.90-6.60 (m, 4 H), 5.79 (s, 2 H), 4.85 (s, 2 H); MS: m/z 429 (M$^+$+1).

Example 98

2-[(3,4,5-Trimethoxybenzyl)thio]-cis-4,5-diphenyl-4,5-dihydro-1H-imidazole hydrochloride (217)

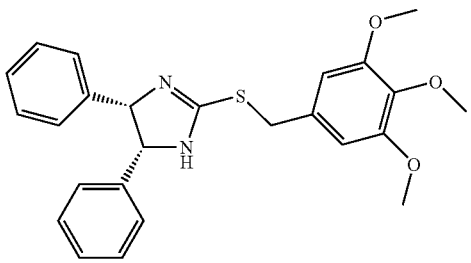

A mixture of intermediate 25 (200 mg, 0.786 mmol) and 3,4,5-trimethoxybenzyl chloride (0.340 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 93 mg of the product 217. $^1$H NMR (DMSO-d$_6$) δ 11.10 (m, 2 H), 7.25-6.90 (m, 8 H), 6.90-6.70 (m, 4 H), 5.80 (d, 2 H), 4.70 (s, 1 H), 3.78 (s, 6 H), 3.70 (s, 1 H)

Example 99

2-[(3-Methoxybenzyl)thio]-cis-4,5-diphenyl-4,5-dihydro-1H-imidazole hydrochloride (218)

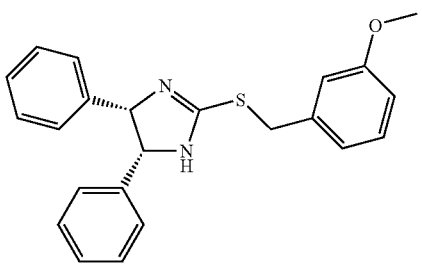

A mixture of intermediate 25 (200 mg, 0.786 mmol) and 3-methoxybenzyl chloride (0.288 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 212 mg of the product 218. $^1$H NMR (DMSO-d$_6$) δ 11.26 (s, 2 H), 7.40 (t, 1 H), 7.30-7.10 (m, 2 H), 7.10-6.90 (m, 7 H), 6.90-6.65 (m, 4 H), 5.78 (s, 2 H), 4.80 (s, 2 H); MS: m/z 375 (M$^+$+1).

Example 100

2-[(3-Fluorobenzyl)thio]-cis-4,5-diphenyl-4,5-dihydro-1H-imidazole hydrochloride (219)

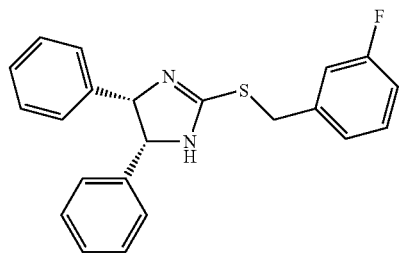

A mixture of intermediate 25 (200 mg, 0.786 mmol) and 3-fluorobenzyl chloride (0.190 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 169 mg of the product 219. $^1$H NMR (DMSO-d$_6$) δ 11.39 (s, 2 H), 7.65-7.40 (m, 3 H), 7.35-7.20 (m, 1 H), 7.20-6.90 (m, 6 H), 6.90-6.65 (m, 4 H), 5.80 (s, 2 H), 4.85 (s, 2 H); MS: m/z 363 (M$^+$+1).

Example 101

2-[(3-Bromobenzyl)thio]-cis-4,5-diphenyl-4,5-dihydro-1H-imidazole hydrochloride (220)

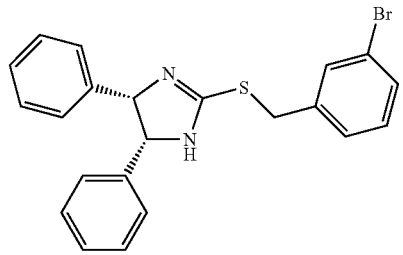

A mixture of intermediate 25 (200 mg, 0.786 mmol) and 3-bromobenzyl chloride (0.201 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 298 mg of the product 220. $^1$H NMR (DMSO-d$_6$) δ 11.30 (s, 2 H), 7.95-7.80 (m, 1 H), 7.75-7.50 (m, 2 H), 7.50-7.35 (m, 1 H), 7.15-6.90 (m, 6 H), 6.90-6.60 (m, 4 H), 5.78 (s, 2 H), 4.80 (s, 2 H); MS: m/z 423 (M$^+$+1).

Example 102

2-[(3,5-Ditrifluoromethylbenzyl)thio]-cis-4,5-diphenyl-4,5-dihydro-1H-imidazole hydrochloride (221)

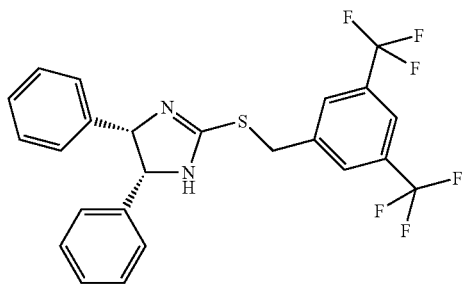

A mixture of intermediate 25 (200 mg, 0.786 mmol) and 3,5-ditrifluoromethylbenzyl chloride (417 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 278 mg of the product 221. $^1$H NMR (DMSO-d$_6$) δ 11.43 (s, 2 H), 8.40 (s, 2 H), 8.20 (s, 1 H), 7.15-6.85 (m, 6 H), 6.90-6.55 (m, 4 H), 5.77 (s, 2 H), 4.82 (s, 2 H); MS: m/z 481 (M$^+$+1).

Example 103

2-[(2-Iodobenzyl)thio]-cis-4,5-diphenyl-4,5-dihydro-1H-imidazole hydrochloride (222)

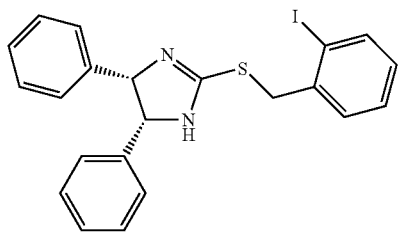

A mixture of intermediate 25 (200 mg, 0.786 mmol) and 2-iodobenzyl chloride (396 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 270 mg of the product 222. $^1$H NMR (DMSO-d$_6$) δ 11.43 (s, 2 H), 8.00 (d, 1 H), 7.82 (d, 1 H), 7.48 (t, 1 H), 7.30-7.00 (m, 7 H), 7.00-6.80 (m, 4 H), 5.82 (s, 2 H), 4.88 (s, 2 H); MS: m/z 471 (M$^+$+1).

Example 104

2-[(4-Methoxybenzyl)thio]-cis-4,5-diphenyl-4,5-dihydro-1H-imidazole hydrochloride (223)

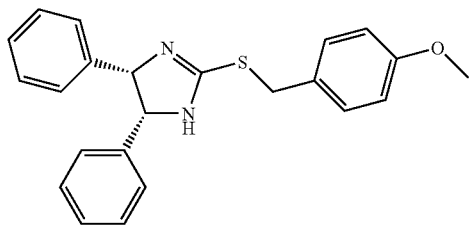

A mixture of intermediate 25 (200 mg, 0.786 mmol) and 4-methoxybenzyl chloride (0.213 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 167 mg of the product 223. $^1$H NMR (DMSO-d$_6$) δ 11.24 (s, 2 H), 7.50 (d, 2 H), 7.20-6.90 (m, 8 H), 6.90-6.65 (m, 4 H), 5.78 (s, 2 H), 4.78 (s, 2 H), 3.78 (s, 3 H); MS: m/z 375 (M$^+$+1).

Example 105

2-[(4-Benzyloxybenzyl)thio]-cis-4,5-diphenyl-4,5-dihydro-1H-imidazole hydrochloride (224)

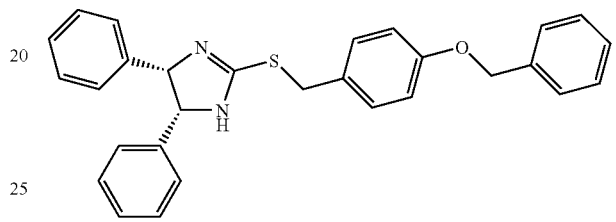

A mixture of intermediate 25 (200 mg, 0.786 mmol) and 4-benzyloxybenzyl chloride (365 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 194 mg of the product 224. $^1$H NMR (DMSO-d$_6$) δ 11.28 (s, 2 H), 7.60-7.25 (m, 7 H), 7.20-6.95 (m, 8 H), 6.95-6.70 (m, 4 H), 5.75 (s, 2 H), 5.25 (s, 2 H), 4.80 (s, 2 H); MS: m/z 451 (M$^+$+1).

Example 106

2-[(3,4-Dibenzyloxybenzyl)thio]-cis-4,5-diphenyl-4,5-dihydro-1H-imidazole hydrochloride (225)

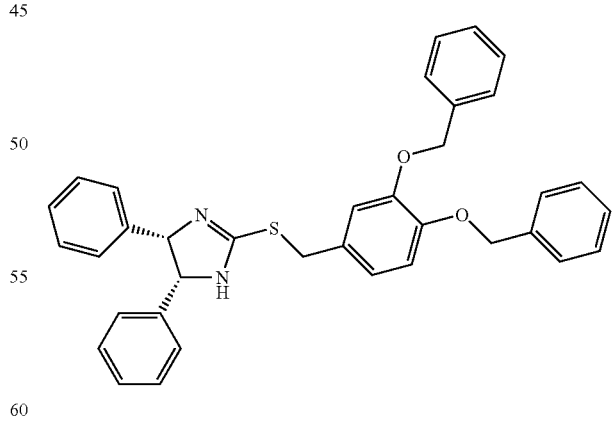

A mixture of intermediate 25 (200 mg, 0.786 mmol) and 3,4-dibenzyloxybenzyl chloride (532 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 149 mg of the product 225. MS: m/z 557 (M$^+$+1).

Example 107

2-[(2-Methylnaphthalen-1-yl)methylthio]-cis-4,5-diphenyl-4,5-dihydro-1H-imidazole hydrochloride (226)

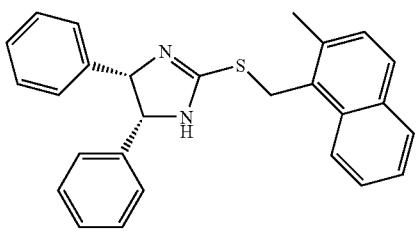

A mixture of intermediate 25 (200 mg, 0.786 mmol) and 1-chloromethyl-2-methyl-naphthalene (299 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 229 mg of the product 226. $^1$H NMR (DMSO-d$_6$) δ 11.40 (s, 2 H), 8.36 (d, 1 H), 8.10-7.80 (m, 2 H), 7.80-7.30 (m, 3 H), 7.30-6.75 (m, 10 H), 5.90 (s, 2 H), 5.30 (s, 2 H), 2.62 (s, 3 H); MS: m/z 409 (M$^+$+1).

Example 108

2-[(2-Methylbenzyl)thio]-cis-4,5-diphenyl-4,5-dihydro-1H-imidazole hydrochloride (227)

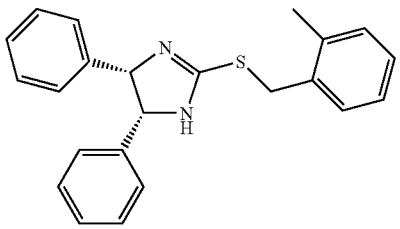

A mixture of intermediate 25 (200 mg, 0.786 mmol) and 2-methylbenzyl chloride (0.204 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 174 mg of the product 227. $^1$H NMR (DMSO-d$_6$) δ 11.28 (s, 2 H), 7.68 (m, 1 H), 7.55-7.20 (m, 3 H), 7.20-7.00 (m, 6 H), 7.00-6.90 (m, 4 H), 5.82 (s, 2 H), 4.81 (s, 2 H), 2.44 (s, 3 H); MS: m/z 359 (M$^+$+1).

Example 109

2-[(4-Trifluoromethylbenzyl)thio]-cis-4,5-diphenyl-4,5-dihydro-1H-imidazole hydrochloride (228)

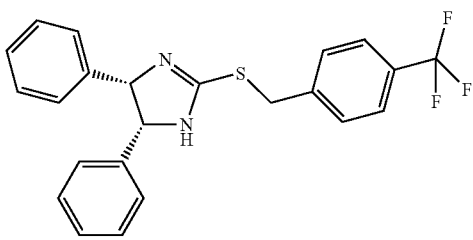

A mixture of intermediate 25 (200 mg, 0.786 mmol) and 4-trifluoromethylbenzyl chloride (0.232 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 262 mg of the product 228. $^1$H NMR (DMSO-d$_6$) δ 11.42 (s, 2 H), 7.95-7.90 (m, 4 H), 7.15-6.90 (m, 6 H), 6.90-6.65 (m, 4 H), 5.77 (s, 2 H), 4.92 (s, 2 H); MS: m/z 413 (M$^+$+1).

Example 110

2-[(2-Chloro-4-fluorobenzyl)thio]-cis-4,5-diphenyl-4,5-dihydro-1H-imidazole hydrochloride (229)

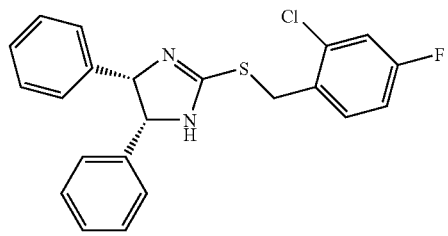

A mixture of intermediate 25 (200 mg, 0.786 mmol) and 2-chloro-4-fluorobenzyl chloride (281 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 249 mg of the product 229. $^1$H NMR (DMSO-d$_6$) δ 11.35 (s, 2 H), 8.00-7.80 (m, 1 H), 7.75-7.60 (m, 1 H), 7.55-7.35 (m, 1 H), 7.20-7.00 (m, 6 H), 7.00-6.85 (m, 4 H), 5.80 (s, 2 H), 4.90 (s, 2 H); MS: m/z 397 (M$^+$+1).

Example 111

2-[(2,5-Dimethylbenzyl)thio]-cis-4,5-diphenyl-4,5-dihydro-1H-imidazole hydrochloride (230)

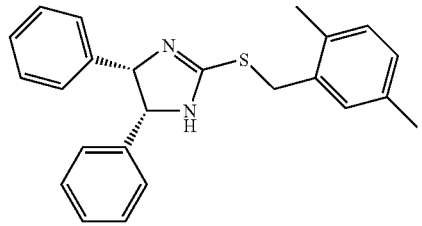

A mixture of intermediate 25 (200 mg, 0.786 mmol) and 2,5-dimethylbenzyl chloride (0.269 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 171 mg of the product 230. $^1$H NMR (DMSO-d$_6$) δ 11.20 (s, 2 H), 7.38 (s, 1 H), 7.30-7.00 (m, 8 H), 7.00-6.85 (m, 4 H), 5.82 (s, 2 H), 4.75 (s, 2 H), 2.40 (s, 3 H), 2.30 (s, 3 H); MS: m/z 373 (M$^+$+1).

Example 112

2-[(2-Chloro-6-fluorobenzyl)thio]-cis-4,5-diphenyl-4,5-dihydro-1H-imidazole hydrochloride (231)

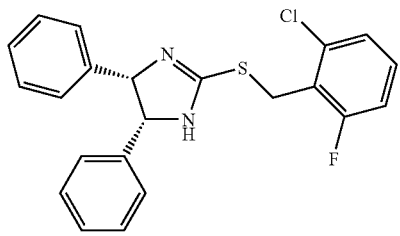

A mixture of intermediate 25 (200 mg, 0.786 mmol) and 2-chloro-6-fluorobenzyl chloride (0.204 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 174 mg of the product 231. $^1$H NMR (DMSO-d$_6$) δ 11.40 (s, 2 H), 7.70-7.30 (m, 3 H), 7.25-6.90 (m, 10 H), 5.88 (s, 2 H), 4.90 (s, 2 H); MS: m/z 397 (M$^+$+1).

Example 113

2-[(Anthracen-9-yl)methylthio]-cis-4,5-diphenyl-4,5-dihydro-1H-imidazole hydrochloride (232)

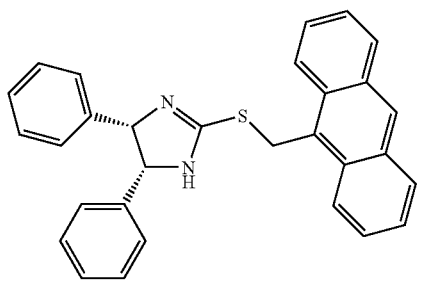

A mixture of intermediate 25 (200 mg, 0.786 mmol) and 9-chloromethylanthracene (256 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 179 mg of the product 232. $^1$H NMR (DMSO-d$_6$) δ 11.35 (s, 2 H), 8.80 (s, 1 H), 8.64 (d, 2 H), 7.85-7.50 (m, 4 H), 7.38 (d, 1 H), 7.30-6.80 (m, 10 H), 6.80-6.65 (m, 4 H), 5.92 (s, 4 H); MS: m/z 445 (M$^+$+1).

Example 114

2-[(2-Trifluoromethylbenzyl)thio]-cis-4,5-diphenyl-4,5-dihydro-1H-imidazole hydrochloride (233)

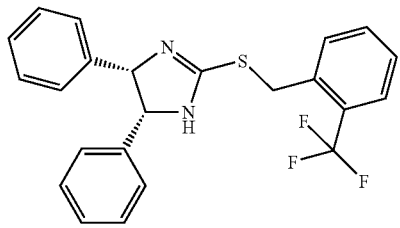

A mixture of intermediate 25 (200 mg, 0.786 mmol) and 2-trifluoromethylbenzyl chloride (0.229 mL, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 224 mg of the product 233. $^1$H NMR (DMSO-d$_6$) δ 11.41 (s, 2 H), 7.95 (d, 1 H), 7.90-7.75 (m, 2 H), 7.65 (t, 1 H), 7.25-6.90 (m, 10 H), 5.85 (s, 2 H), 4.98 (s, 2 H); MS: m/z 413 (M$^+$+1).

Example 115

2-[(2,3,4,5,6-Pentamethylbenzyl)thio]-cis-4,5-diphenyl-4,5-dihydro-1H-imidazole hydrochloride (234)

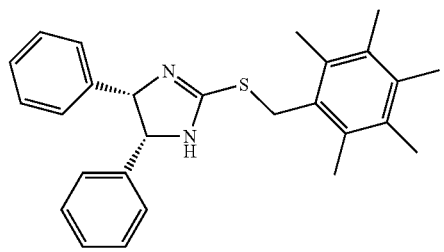

A mixture of intermediate 25 (200 mg, 0.786 mmol) and 2,3,4,5,6-pentamethylbenzyl chloride (309 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 186 mg of the product 234. $^1$H NMR (DMSO-d$_6$) δ 11.20 (s, 2 H), 7.25-6.95 (m, 10 H), 5.85 (s, 2 H), 4.84 (s, 2 H), 2.38 (s, 6 H), 2.20 (s, 9 H); MS: m/z 415 (M$^+$+1).

Example 116

2-[(2-Bromobenzyl)thio]-cis-4,5-diphenyl-4,5-dihydro-1H-imidazole hydrochloride (235)

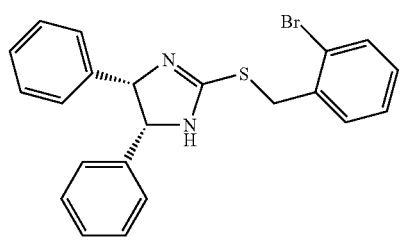

A mixture of intermediate 25 (200 mg, 0.786 mmol) and 2-bromobenzyl chloride (327 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 400 mg of the product 235. $^1$H NMR (DMSO-d$_6$) δ 11.52 (s, 2 H), 7.86 (d, 1 H), 7.78 (d, 1 H), 7.55-7.30 (m, 2 H), 7.20-7.00 (m, 6 H), 7.00-6.85 (m, 4 H), 5.83 (s, 2 H), 4.95 (s, 2 H); MS: m/z 424 (M$^+$+1).

Example 117

2-[(2,3,5,6-Tetramethylbenzyl)thio]-cis-4,5-diphenyl-4,5-dihydro-1H-imidazole hydrochloride (236)

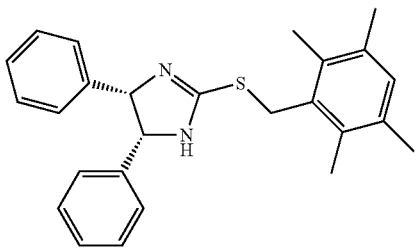

A mixture of intermediate 25 (200 mg, 0.786 mmol) and 2,3,5,6-tetramethylbenzyl chloride (287 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 177 mg of the product 236. $^1$H NMR (DMSO-d$_6$) δ 11.33 (s, 2 H), 7.25-6.95 (m, 11 H), 5.86 (s, 2 H), 4.84 (s, 2 H), 2.35 (s, 6 H), 2.21 (s, 6 H); MS: m/z 401 (M$^+$+1).

Example 118

2-[(4-Bromobenzyl)thio]-cis-4,5-diphenyl-4,5-dihydro-1H-imidazole hydrochloride (237)

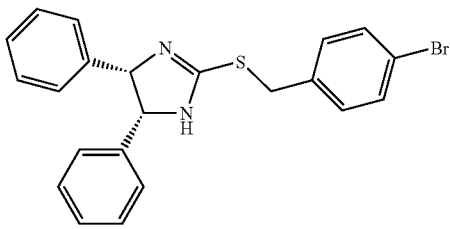

A mixture of intermediate 25 (200 mg, 0.786 mmol) and 4-bromobenzyl chloride (327 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 290 mg of the product 237. $^1$H NMR (DMSO-d$_6$) δ 11.30 (s, 2 H), 7.65 (d, 2 H), 7.58 (d, 2 H), 7.15-6.95 (m, 6 H), 6.90-6.65 (m, 4 H), 5.78 (s, 2 H), 4.80 (s, 2 H); MS: m/z 424 (M$^+$+1).

Example 119

2-[(2,5-Dichlorobenzyl)thio]-cis-4,5-diphenyl-4,5-dihydro-1H-imidazole hydrochloride (238)

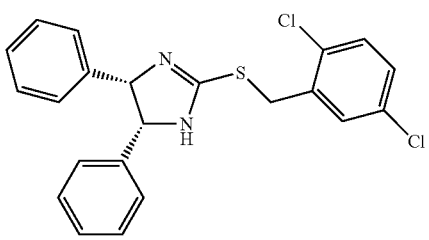

A mixture of intermediate 25 (200 mg, 0.786 mmol) and 2,5-dichlorobenzyl chloride (327 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 175 mg of the product 238. $^1$H NMR (DMSO-d$_6$) δ 11.50 (s, 2 H), 8.00 (s, 1 H), 7.70-7.50 (m, 2 H), 7.20-7.00 (m, 6 H), 6.95-6.80 (m, 4 H), 5.81 (s, 2 H), 4.90 (s, 2 H); MS: m/z 413 (M$^+$+1).

Example 120

2-[(4-Isopropylbenzyl)thio]-cis-4,5-diphenyl-4,5-dihydro-1H-imidazole hydrochloride (239)

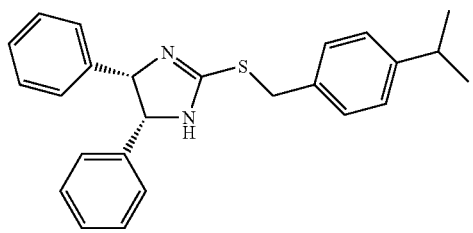

A mixture of intermediate 25 (200 mg, 0.786 mmol) and 4-isopropylbenzyl chloride (264 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 249 mg of the product 239. $^1$H NMR (DMSO-d$_6$) δ 11.24 (s, 2 H), 7.52 (d, 2 H), 7.32 (d, 2 H), 7.20-6.90 (m, 6 H), 6.90-6.70 (m, 4 H), 5.77 (s, 2 H), 4.78 (s, 2 H), 3.02-3.85 (m, 1 H), 1.22 (d, 6 H); MS: m/z 387 (M$^+$+1).

Example 121

2-[(2,4-Dimethylbenzyl)thio]-cis-4,5-diphenyl-4,5-dihydro-1H-imidazole hydrochloride (240)

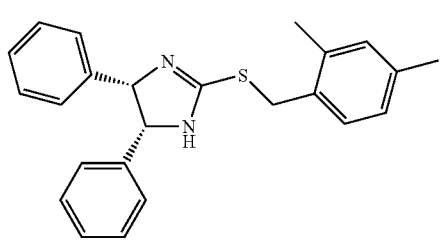

A mixture of intermediate 25 (200 mg, 0.786 mmol) and 2,4-dimethylbenzyl chloride (243 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 177 mg of the product 240. $^1$H NMR (DMSO-d$_6$) δ 11.18 (s, 2 H), 7.20-6.80 (m, 13 H), 5.80 (s, 2 H), 4.88 (s, 2 H), 2.41 (s, 3H), 2.30 (s, 3 H); MS: m/z 373 (M$^+$+1).

Example 122

2-[(3-Phenoxybenzyl)thio]-cis-4,5-diphenyl-4,5-dihydro-1H-imidazole hydrochloride (241)

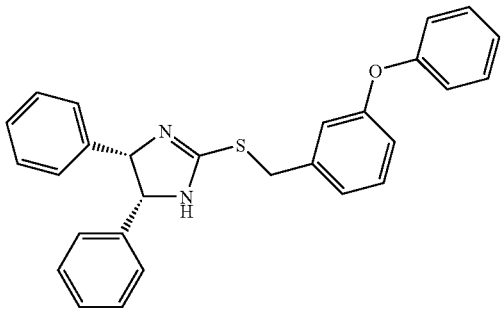

A mixture of intermediate 25 (200 mg, 0.786 mmol) and 3-phenoxybenzyl chloride (343 mg, 1.57 mmol) in abs. EtOH (2 mL) is heated at 95° C. for 24 h. The reaction mixture is cooled to RT, evaporated to dryness, and the residue suspended in Et$_2$O. The insoluble material is filtered to give 350 mg of the product 241. $^1$H NMR (DMSO-d$_6$) δ 11.25 (s, 2 H), 7.55-7.30 (m, 6 H), 7.30-7.25 (m, 1 H), 7.25-7.10 (m, 1 H), 7.15-6.90 (m, 6H), 6.90-6.70 (m, 4 H), 5.79 (s, 2 H), 4.81 (s, 2 H); MS: m/z 437 (M$^+$+1).

Example 123

2-Phenethyl-cis-4,5-diphenyl-4,5-dihydro-1H-imidazole hydrochloride (243)

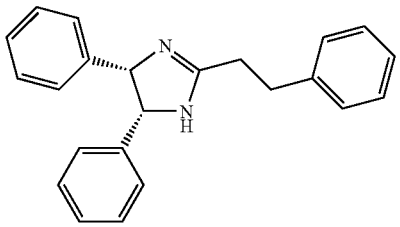

A mixture of cis-1,2-diphenylethane-1,2-diamine (1) (1.0 g, 4.7 mmol) and 3-phenyl-propionimidic acid methyl ester hydrochloride (242) (0.94 g, 4.7 mmol) in EtOH (10 mL) is heated at 80° C. overnight. The solvent is removed by rotary evaporation, and the residue dissolved in dichloromethane, and the solution washed with sodium carbonate, brine, then dried (MgSO$_4$) and filtered. The filtrate is rotary evaporated to give 1.2 g of impure product 243.

A mixture of impure product (1.0 g, 2.76 mmol), diethylamine (0.442 mL, 3.03 mmol), 4-dimethylaminopyridine (10 mg), and di-tert-butyl-dicarbonate (0.66 g, 3.03 mmol) in dichloromethane (50 mL) is stirred at RT for 2 days. The mixture is washed with water, brine, then dried (MgSO$_4$) and filtered. The filtrate is rotary evaporated and the residue purified by chromatography on silica gel; gradient elution with heptane:EtOAc (70:30-60:40) gives 0.84 g of the N-Boc derivative of the product. $^1$H NMR (CDCl$_3$) δ 7.50-7.20 (m, 5 H), 7.10-6.90 (m, 6 H), 6.90-6.85 (m, 2 H), 6.75-6.65 (m, 2 H), 5.55-5.35 (m, 2 H), 3.50-3.10 (m, 4 H), 1.19 (s, 9 H); MS: m/z 427 (M$^+$+1).

Hydrogen chloride is bubbled into a solution of the above N-Boc derivative (0.84 g, 1.97 mmol) in EtOAc (50 mL) for 1 min, and the mixture stirred at RT overnight. The solvent is rotary evaporated, and the residue recrystallized from dichloromethane:Et$_2$O to give 0.54 g of the product 243. $^1$H NMR (DMSO-d$_6$) δ 10.90 (s, 2 H), 7.60-7.30 (m, 5 H), 7.15-6.90 (m, 6 H), 6.90-6.65 (m, 4 H), 5.71 (s, 2 H), 3.25-3.05 (m, 4 H); LC/MS: 3.15 min, m/z 327 (M$^+$+1).

Example 124

2-Phenethyl-cis-4,5-bis-(3-fluorophenyl)-4,5-dihydro-1H-imidazole hydrochloride (244)

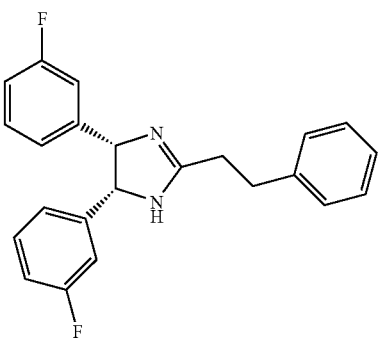

A mixture of cis-1,2-bis-(3-fluorophenyl)ethane-1,2-diamine (5) (0.5 g, 2.01 mmol) and 3-phenylpropionimidic acid methyl ester hydrochloride (242) (0.402 g, 2.01 mmol) in EtOH (20 mL) is heated at 90° C. for 2 days. The solvent is removed by rotary evaporation to give impure product 244.

A mixture of the above impure product, triethylamine (0.310 mL, 2.23 mmol), 4-dimethylaminopyridine (10 mg), and di-tert-butyl-dicarbonate (0.486 g, 2.21 mmol) in dichloromethane (50 mL) is stirred at RT for 3 days. The mixture is washed with water, brine, dried (MgSO$_4$), and filtered. The filtrate is rotary evaporated and the residue purified by chromatography on silica gel; elution with heptane:EtOAc (70:30) gives 0.78 g of the N-Boc derivative of the product. $^1$H NMR (CDCl$_3$) δ 7.45-7.30 (m, 3 H), 7.30-7.15 (m, 2 H), 7.05-6.90 (m, 2 H), 6.75-6.35 (m, 6 H), 5.55-5.30 (m, 2 H), 3.55-3.05 (m, 4 H), 1.23 (s, 9 H); MS: m/z 463 (M$^+$+1).

Hydrogen chloride is bubbled into a solution of the above N-Boc derivative (0.78 g, 1.69 mmol) in EtOAc (25 mL) for 1 min, and the mixture stirred at RT overnight. The solvent is rotary evaporated, and the residue recrystallized from dichloromethane:Et$_2$O to give 0.52 g of the product 244. $^1$H NMR (DMSO-d$_6$) δ 10.98 (s, 2 H), 7.20-7.05 (m, 2 H), 7.00-6.85 (m, 2 H), 6.80-6.60 (m, 4 H), 5.77 (s, 2 H), 3.25-3.10 (m, 4 H); MS: m/z 363 (M$^+$+1).

Example 125

2-Phenethyl-cis-4,5-bis-(4-fluorophenyl)-4,5-dihydro-1H-imidazole hydrochloride (245)

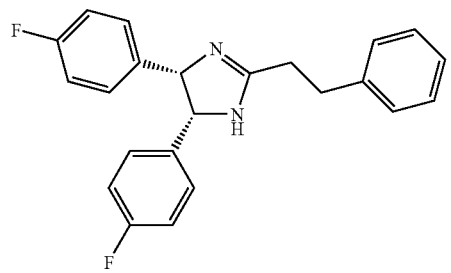

A mixture of cis-1,2-bis-(4-fluorophenyl)ethane-1,2-diamine (6) (0.5 g, 2.01 mmol) and 3-phenylpropionimidic acid methyl ester hydrochloride (242) (0.402 g, 2.01 mmol) in EtOH (20 mL) is heated at 90° C. overnight. The solvent is removed by rotary evaporation, and the residue is dissolved in dichloromethane, and the solution is washed with water, brine, then dried (MgSO$_4$) and filtered. The filtrate is rotary evaporated to give 0.78 g of impure product 245.

A mixture of the above impure product (0.78 g, 2.15 mmol), triethylamine (0.300 mL, 2.15 mmol), 4-dimethylaminopyridine (10 mg), and di-tert-butyl-dicarbonate (0.520 g, 2.37 mmol) in dichloromethane (10 mL) is stirred at RT for 4 h. The mixture is washed with water, brine, then dried (MgSO$_4$) and filtered. The filtrate is rotary evaporated and the residue purified by chromatography on silica gel; elution with heptane:EtOAc (70:30) gives 0.65 g of the N-Boc derivative of the product. $^1$H NMR (CDCl$_3$) δ 7.45-7.20 (m, 5H), 6.85-6.55 (m, 8 H), 5.55-5.30 (m, 2 H), 3.50-3.10 (m, 4 H), 1.22 (s, 9 H)

Hydrogen chloride is bubbled into a solution of the above N-Boc derivative (0.64 g, 1.38 mmol) in EtOAc (20 mL) for 0.5 min, and the mixture stirred at RT overnight. The solvent is rotary evaporated, and the residue recrystallized from dichloromethane:Et$_2$O to give 0.409 g of the product 245. $^1$H NMR (CDCl$_3$) δ 11.09 (s, 2 H), 7.50-7.40 (m, 2 H), 7.40-7.30 (m, 3 H), 6.70-6.55 (t, 4 H), 6.50-6.35 (m, 4 H), 5.25 (s, 2 H), 3.28 (m, 4 H); MS: m/z 363 (M$^+$+1).

Example 126

2-Phenethyl-cis-4,5-diphenyl-4-methyl-4,5-dihydro-1H-imidazole hydrochloride (246)

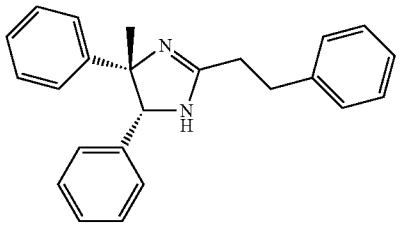

A mixture of cis-1,2-diphenylpropane-1,2-diamine (16) (0.300 g, 1.33 mmol) and 3-phenylpropionimidic acid methyl ester hydrochloride (242) (0.246 g, 1.33 mmol) in EtOH (30 mL) is heated at 90° C. for 2 days. The solvent is removed by rotary evaporation to give impure product 246.

A mixture of the above impure product, triethylamine (0.203 mL, 1.46 mmol), 4-dimethylaminopyridine (10 mg), and di-tert-butyl-dicarbonate (0.319 g, 1.46 mmol) in dichloromethane (50 mL) is stirred at RT for 3 days. The mixture is washed with water, brine, then dried (MgSO$_4$) and filtered. The filtrate is rotary evaporated and the residue purified by chromatography on silica gel; elution with heptane:EtOAc (70:30) gives 0.49 g of the N-Boc derivative of the product. $^1$H NMR (CDCl$_3$) δ 7.45-7.20 (m, 5 H), 7.05-6.90 (m, 8 H), 6.90-6.80 (m, 2 H), 4.97 (s, 1 H), 3.50-3.10 (m, 4 H), 1.71 (s, 3 H), 1.18 (s, 9 H); LC/MS: 3.62 min, m/z 441 (M$^+$+1).

Hydrogen chloride is bubbled into a solution of the above N-Boc derivative (0.49 g, 1.11 mmol) in EtOAc (50 mL) for 1 min, and the mixture stirred at RT overnight. The solvent is rotary evaporated, and the residue recrystallized from dichloromethane:Et$_2$O to give 0.290 g of the product 246. $^1$H NMR (CDCl$_3$) δ 11.35 (s, 1 H), 10.78 (s, 1 H), 7.50-7.30 (m, 2 H), 7.30-7.15 (m, 3 H), 7.00-6.80 (m, 6 H), 6.70-6.55 (D, 2 H), 6.50-6.35 (d, 2 H), 4.75 (s, 1 H), 3.30-3.10 (m, 4 H), 1.61 (s, 3 H); LC/MS: 2.83 min, m/z 341 (M$^+$+1).

Example 127

2-Phenethyl-cis-4,5-bis-(3-fluorophenyl)-4-methyl-4,5-dihydro-1H-imidazole hydrochloride (248)

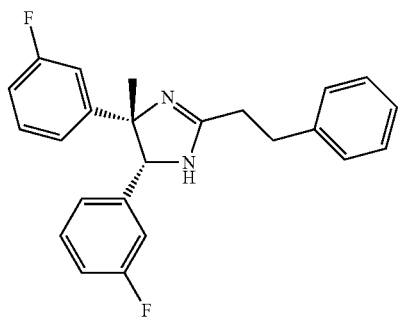

Step 1

A mixture of cis-1,2-di-(3-fluorophenyl)propane-1,2-diamine (23) (0.202 g, 0.77 mmol) and 3-phenylpropionimidic acid methyl ester hydrochloride (242) (0.169 g, 847 mmol) in EtOH (30 mL) is heated at 90° C. for overnight. The solvent is removed by rotary evaporation to give impure product 248.

Step 2

2-Phenethyl-cis-4,5-bis-(3-fluorophenyl)-4-methyl-4,5-dihydroimidazole-1-carboxylic acid, tert-butyl ester (247)

A mixture of the above impure product, triethylamine (0.128 mL, 0.924 mmol), 4-dimethylaminopyridine (10 mg), and di-tert-butyl-dicarbonate (0.202 g, 0.924 mmol) in dichloromethane (30 mL) is stirred at RT overnight. The mixture is washed with water, brine, then dried (MgSO$_4$) and filtered. The filtrate is rotary evaporated and the residue purified by chromatography on silica gel; elution with heptane:EtOAc (70:30) gives 0.33 g of the product 247. $^1$H NMR (CDCl$_3$) δ 7.45-7.15 (m, 5 H), 7.05-6.90 (m, 2 H), 6.85-6.55 (m, 4 H), 6.55-6.35 (m, 2 H), 4.93 (s, 1 H), 3.50-3.10 (m, 4 H), 1.68 (s, 3 H), 1.21 (s, 9 H); LC/MS: 3.30 min, m/z 477 (M$^+$+1).

Step 3

2-Phenethyl-cis-4,5-bis-(3-fluorophenyl)-4-methyl-4,5-dihydro-1H-imidazole hydrochloride (248)

Hydrogen chloride is bubbled into a solution of 247 (0.31 g, 0.65 mmol) in EtOAc (30 mL) for 0.5 min, and the mixture stirred at RT overnight. The solvent is rotary evaporated, and the residue recrystallized from dichloromethane:Et$_2$O to give 0.186 g of the product 248. $^1$H NMR (DMSO-d$_6$) δ 11.14 (s, 1 H), 10.93 (s, 1 H), 7.50-7.30 (m, 5 H), 7.20-7.00 (m, 2 H), 7.00-6.50 (m, 6 H), 5.27 (s, 1 H), 3.15-3.10 (m, 4 H), 1.82 (s, 3 H); LC/MS: 2.80 min, m/z 377 (M++1).

Example 128

2-[2-(3,4-Difluorophenyl)ethyl]-cis-4,5-bis-(3-fluorophenyl)-4,5-dihydro-1H-imidazole (250)

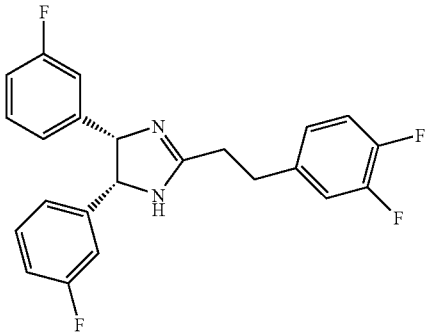

Step 1

3-(3,4-Difluorophenyl)propionic acid, ethyl ester (249)

To a solution of 3-(3,4-difluorophenyl)propionic acid (1.0 g, 5.4 mmol) in EtOH (10 mL) is added dropwise acetyl chloride (1.0 mL, 14.1 mmol), and the solution is stirred at RT for 2 h. The solvent is rotary evaporated, and the residue purified by chromatography on silica gel; elution with heptane:EtOAc (4:1) gives 0.99 g of the product 249. $^1$H NMR (CDCl$_3$) δ 7.10-6.85 (m, 3 H), 4.13 (q, 2 H), 2.90 (t, 2 H), 3.35-2.59 (t, 2 H), 1.23 (t, 2 H); MS: m/z 215 (M$^+$+1).

Step 2

2-[2-(3,4-Difluorophenyl)ethyl]-cis-4,5-bis-(3-fluorophenyl)-4,5-dihydro-1H-imidazole (250)

To a solution of cis-1,2-bis-(3-fluorophenyl)ethane-1,2-diamine (5) (248 mg 1.0 mmol) in toluene (6 mL) is added 2.0M trimethylaluminum in toluene (1.0 mL, 2.0 mmol). The solution is stirred at RT for 20 min, and intermediate 249 (214 mg, 1 mmol) is added, and the solution is heated at 80° C. overnight. The reaction is quenched by the addition of sat. sodium bicarbonate solution, and water and EtOAc are added. The organic layer is separated, washed with brine, then dried (Na$_2$SO$_4$), and filtered. The filtrate is evaporated, and the residue triturated with Et$_2$O to give 118 mg of the product 250. $^1$H NMR (CDCl$_3$) δ 7.70 (s, 2 H), 7.30-6.40 (m, 10 H), 5.55-5.00 (m, 2 H), 3.35-3.05 (m, 2 H), 2.75 (t, 2 H); MS: m/z 399 (M$^+$+1).

Example 129

2-[2-(2-Chlorophenyl)ethyl]-cis-4,5-bis-(3-fluorophenyl)-4,5-dihydro-1H-imidazole (251)

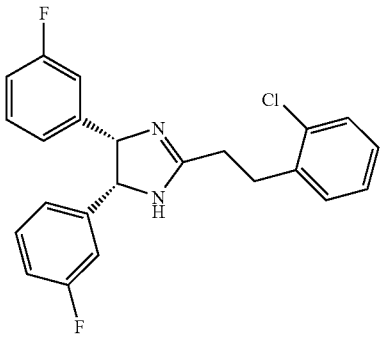

To a solution of cis-1,2-bis-(3-fluorophenyl)ethane-1,2-diamine (5) (248.3 mg 1 mmol) in toluene (6 mL) is added 2.0 M trimethylaluminum in toluene (1.0 mL, 2.0 mmol). The solution is stirred at RT for 20 min, and 3-(2-chlorophenyl) propionitrile (0.145 mL, 1 mmol) is added, and the solution is heated at 70° C. for 18 h. The reaction is quenched by the addition of sat. sodium bicarbonate solution, and water and EtOAc are added. The organic layer is separated, washed with brine, dried (Na$_2$SO$_4$), and filtered. The filtrate is evaporated, and the residue is purified by chromatography on silica gel; elution with heptane:EtOAc (5:1) and then with dichloromethane:MeOH (95:5) gives 12 mg of the product 251. $^1$H NMR (CDCl$_3$) δ 7.70 (s, 2 H), 7.50-7.10 (m, 3 H), 7.10-6.80 (m, 2 H), 6.80-6.40 (m, 5 H), 5.35 (s, 3 H), 3.23 (t, 2 H), 2.90 (t, 2 H); MS: m/z 397 (M$^+$+1).

Example 130

2-(cis-4,5-Diphenyl-4,5-dihydro-1H-imidazol-2-yl)-1-phenylethan-1-ol (255)

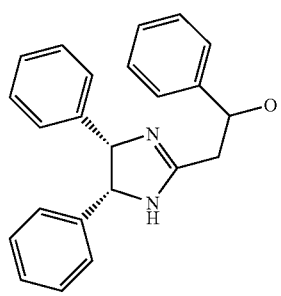

Step 1

2-Methyl-cis-4,5-diphenyl-4,5-dihydro-imidazole-1-carboxylic acid, tert-butyl ester (253)

To a solution of 2-methyl-cis-4,5-diphenyl-4,5-dihydro-1H-imidazole (252) (4.27 g, 18.1 mmol) in dichloromethane (20 mL) is added triethylamine (5.2 mL, 37.8 mmol), di-tert-butyl-dicarbonate (5.2 mL, 22.7 mmol), and 4-dimethylaminopyridine (50 mg), and the mixture is stirred at RT overnight. The reaction mixture is washed with water, brine, then dried (MgSO$_4$), filtered, and the filtrate is rotary evaporated. The residue is crystallized from Et$_2$O to give 5.4 g of the product 253. $^1$H NMR (CDCl$_3$) δ 7.10-6.85 (m, 10 H), 6.85-6.70 (m, 2 H), 5.60-5.30 (m, 2 H), 2.60 (s, 3 H), 1.20 (s, 9 H); MS: m/z 337 (M$^+$+1).

Step 2

2-[(2-Hydroxy-2-phenyl)ethyl]-cis-4,5-diphenyl)-4,5-dihydroimidazole-1-carboxylic acid, tert-butyl ester (254)

To a cold (−70° C.) solution of 253 (336 mg, 1 mmol) in THF is added 2.5M n-butyl lithium in hexane (0.44 mL, 1.1 mmol), and the mixture is stirred for 1 h at −70° C. To the reaction mixture is added benzaldehyde (0.11 mL, 1.1 mmol), and the mixture is stirred for 1 h at −70° C. and 0.5 h at RT. To the reaction mixture is added ammonium chloride solution, EtOAc, and the organic layer is separated, and washed with brine, dried (MgSO$_4$), and filtered. The filtrate is rotary evaporated, and the residue purified by chromatography on silica gel; elution with dichloromethane:EtOAc (9:1) gives 230 mg of the product 254. $^1$H NMR (CDCl$_3$) δ 7.60-7.50 (m, 2 H), 7.50-7.25 (m, 3 H), 7.15-6.90 (m, 8 H), 6.80-6.70 (m, 2 H), 5.70-5.50 (m, 1 H), 5.50-5.20 (m, 3 H), 3.65-3.40 (m, 1 H), 3.30-3.20 (m, 1 H), 1.17 (s, 9 H); MS: m/z 443 (M$^+$+1).

Step 3

2-(cis-4,5-Diphenyl-4,5-dihydro-1H-imidazol-2-yl)-1-phenylethan-1-ol (255)

To a cold (0° C.) solution of 254 (442 mg, 1 mmol) in THF is added 4N HCl in dioxane (2.0 mL, 8.0 mmol), and the mixture is stirred at 0° C. for 20 min and at RT for 2 days. To the reaction mixture is added EtOAc, and the mixture washed with NaHCO$_3$, the organic layer is separated, and washed with brine, dried (MgSO$_4$), and filtered. The filtrate is rotary evaporated, and the residue purified by chromatography on silica gel; elution with dichloromethane:MeOH:NH$_4$OH (9:1:0.1) gives 130 mg of the product 255. $^1$H NMR (CDCl$_3$) δ 7.60-7.20 (m, 5 H), 7.10-6.70 (m, 11 H), 5.45-5.20 (m, 3 H), 2.82 (d, 2 H); MS: m/z 343 (M$^+$+1).

Example 131

2-(cis-4,5-Diphenyl-4,5-dihydro-1H-imidazol-2-yl)-1-(4-fluorophenyl)ethan-1-one (258)

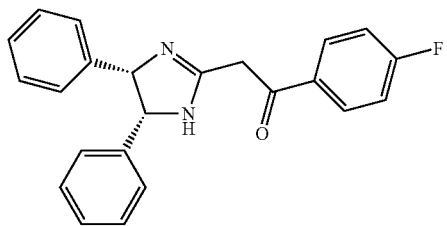

Step 1

2-[2-(4-Fluorophenyl)-2-hydroxyethyl]-cis-4,5-diphenyl-4,5-dihydro-imidazole-1-carboxylic acid, tert-butyl ester (256)

To a cold (−70° C.) solution of 2-methyl-cis-4,5-diphenyl-4,5-dihydro-imidazole-1-carboxylic acid, tert-butyl ester (253) (3.36 g, 10.0 mmol) in THF is added 1.6M n-butyl lithium in hexane (6.9 mL, 11.0 mmol), and the mixture is stirred for 1 h at −70° C. To the reaction mixture is added 4-fluorobenzaldehyde (1.18 mL, 11.0 mmol), and the mixture is stirred for 1 h at −70° C. and 1 h at RT. To the reaction mixture is added ammonium chloride solution, EtOAc, and the organic layer is separated, and washed with brine, dried (MgSO$_4$), and filtered. The filtrate is rotary evaporated, and the residue purified by chromatography on silica gel; elution with dichloromethane:EtOAc (9:1) gives 2.11 g of the product 256. $^1$H NMR (CDCl$_3$) δ 7.60-7.45 (m, 2 H), 7.15-6.90 (m, 10 H), 6.85-6.60 (m, 2 H), 5.70-5.20 (m, 4 H), 3.60-3.10 (m, 2 H), 1.18 (s, 9 H); MS: m/z 461 (M$^+$+1).

Step 2

2-[2-(4-Fluorophenyl)-2-oxoethyl]-cis-4,5-diphenyl-4,5-dihydro-imidazole-1-carboxylic acid, tert-butyl ester (257)

To a cold (−70° C.) solution of oxalyl chloride (0.27 mL, 3.06 mmol) in dichloromethane (15 mL) is added DMSO (0.32 mL, 6.11 mmol) followed by the alcohol 256 (1.28 g, 2.48 mmol) in dichloromethane (5 mL). The mixture is stirred for at −70° C. solution 15 min., and triethylamine (1.03 mL, 13.9 mmol) is added and the mixture is allowed to come to RT and is stirred for 4 h. The reaction mixture is washed with water, brine, then dried (MgSO$_4$), and filtered. The filtrate is rotary evaporated, and the residue is recrystallized from Et$_2$O to give 1.02 g of the product 257. $^1$H NMR (CDCl$_3$) δ 10.60 (s, 1 H), 8.10-7.95 (m, 2 H), 7.10-6.90 (m, 12 H), 6.90-6.70 (m, 2 H), 5.40 (s, 2 H), 1.25 (s, 9 H); MS: m/z 459 (M$^+$+1).

Step 3

2-(cis-4,5-Diphenyl-4,5-dihydro-1H-imidazol-2-yl)-1-(4-fluorophenyl)ethan-1-one (258)

To a cold (0° C.) solution of 257 (458 mg, 1.0 mmol) in dichloromethane (25 mL) is added TFA (1.5 mL). The reaction mixture is stirred for 20 min. at 0° C., and at RT for 30 min. The solution is poured into cold sat. sodium bicarbonate solution, and the mixture extracted with EtOAc. The organic layer is separated, dried (MgSO$_4$), and filtered. The filtrate is rotary evaporated, and the residue is recrystallized from Et$_2$O to give 170 mg of the product 258. $^1$H NMR (CDCl$_3$) δ 10.60-8.80 (bs, 1 H), 8.00-7.80 (m, 2 H), 7.20-7.00 (m, 9 H), 7.00-6.85 (m, 4 H), 5.50 (bs, 1 H), 5.30 (s, 2 H); MS: m/z 359 (M$^+$+1).

Example 132

2-[2(E)-(4-Fluorophenyl)vinyl]-cis-4,5-diphenyl-4,5-dihydro-1H-imidazole (259)

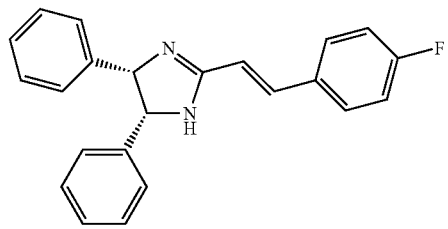

To a cold (0° C.) solution of 2-[2-(4-fluorophenyl)-2-hydroxyethyl]-cis-4,5-diphenyl-4,5-dihydro-imidazole-1-carboxylic acid, tert-butyl ester (256) (690 mg, 1.5 mmol) in dichloromethane (2 mL) is added TFA (2 mL). The reaction mixture is stirred at RT overnight. Reaction mixture is rotary evaporated and the residue purified by chromatography on silica gel; elution with dichloromethane:MeOH (9:1) gives 110 mg of the product 259. $^1$H NMR (CDCl$_3$) δ 8.10 (d, 1 H), 7.60-7.35 (m, 2 H), 7.15-6.85 (m, 9 H), 6.85-6.60 (m, 4 H), 5.20 (s, 2 H); MS: m/z 343 (M$^+$+1).

Example 133

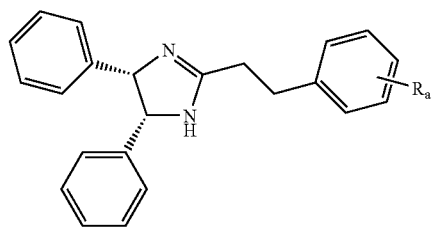

This Example illustrates the syntheses of a few of the compounds of this invention by way of a solid phase synthetic techniques. In this Example, the following procedure is employed to make a variety of compounds of this invention following the steps as set forth in Scheme 9.

A mixture of cis-1,2-diphenylethane-1,2-diamine (1) (5 mmol) in dichloromethane and p-nitrophenyl carbonate Wang resin (1 g, 1.32 mmol/g) is shaken overnight, the resin filtered and washed with dichloromethane. A suspension of the monocarbamoylated resin (0.20 g, 0.26 mmol) is treated with a substituted 3-phenylpropionic acid (0.78 mmol), 1-(dimethylaminopropyl)-3-ethylcarbodiimide hydrochloride (0.78 mmol) in DMF (6 mL), and the mixture is shaken overnight at RT. The resin is filtered, washed with DMF, and the substituted 3-phenylpropanamide derivative is cleaved from the resin with 50% TFA/DMF (or methylene chloride) at RT for 1.5 h. The solvents are evaporated, and the residue is dissolved in trimethylsilyl polyphosphate/dichloromethane solution (1:4), and the solution is microwaved at 140° C. for 2×4 min to effect imidazoline ring formation. The mixture is diluted with dichloromethane, washed with water, sat. sodium bicarbonate, brine, then dried ($Na_2SO_4$), and filtered. The filtrate is rotary evaporated, and the residue purified by chromatography on silica gel; elution with dichloromethane: MeOH (8:2) or on reversed phase silica gel; elution with acetonitrile:water/0.5% TFA (80:20) gives the product.

The compounds so prepared are summarized in Table 1, which are also identified by a compound number. Also summarized in Table 1 are the amounts of the compound formed, the LC/MS retention time, m/e ion peak, and the substituted 3-phenylpropionic acid employed to make the respective compound. Also listed are two examples which utilized respectively, 5-phenyl-butanoic acid and 5-phenyl-pentanoic acid to make the corresponding imidazoline derivatives, Compound Nos. 267D and 267E.

TABLE 1

| # | Compound<br>Amount (mg) | LC/MS retention time | LC/MS m/e ($M^+$ + 1).<br>Substituted ($R_a$) 3-phenylpropionic acid |
|---|---|---|---|
| 260 | | 2-[2-(2-Methoxyphenyl)ethyl]-cis-4,5-diphenyl-4,5-dihydro-1H-imidazole trifluoroacetate | |
| | 20 mg | 2.89 min | 357 |
| | | 3-(2-methoxyphenyl)propionic acid | |
| 261 | | 2-[2-(3,4-Dimethoxyphenyl)ethyl]-cis-4,5-diphenyl-4,5-dihydro-1H-imidazole trifluoroacetate | |
| | 26 mg | 2.54 min | 387 |
| | | 3-(3,4-dimethoxyphenyl)propionic acid | |
| 262 | | 2-[2-(4-Methylphenyl)ethyl]-cis-4,5-diphenyl-4,5-dihydro-1H-imidazole | |
| | 17 mg | 2.77 min | 341 |
| | | 3-(4-methylphenyl)propionic acid | |
| 263 | | 2-[2-(2-Methylphenyl)ethyl]-cis-4,5-diphenyl-4,5-dihydro-1H-imidazole | |
| | 21 mg | 2.74 min | 341 |
| | | 3-(2-methylphenyl)propionic acid | |
| 264 | | 2-[2-(4-Methoxyphenyl)ethyl]-cis-4,5-diphenyl-4,5-dihydro-1H-imidazole trifluoroacetate | |
| | 7 mg | 2.70 min | 357 |
| | | 3-(4-methoxyphenyl)propionic acid | |
| 265 | | 2-[2-(3,4-Difluorophenyl)ethyl]-cis-4,5-diphenyl-4,5-dihydro-1H-imidazole | |
| | 26 mg | 2.72 min | 363 |
| | | 3-(3,4-difluorophenyl)propionic acid | |
| 266 | | 2-[2-(4-Trifluoromethylphenyl)ethyl]-cis-4,5-diphenyl-4,5-dihydro-1H-imidazole trifluoroacetate | |
| | 35 mg | 3.25 min | 395 |
| | | 3-(4-trifluoromethylphenyl)propionic acid | |
| 267 | | 2-[2-[(2S)-Phenyl)propyl]-cis-4,5-diphenyl-4,5-dihydro-1H-imidazole trifluoroacetate | |
| | 58 mg | 3.15 min | 341 |
| | | (3S)-3-phenylbutanoic acid | |

TABLE 1-continued

| # | Compound<br>Amount (mg) | LC/MS retention time | LC/MS m/e ($M^+$ + 1).<br>Substituted ($R_a$) 3-phenylpropionic acid |
|---|---|---|---|
| 267A | | 2-[2-Methyl-(2S)-phenyl)-propyl]-cis-4,5-diphenyl-4,5-dihydro-1H-imidazole trifluoroacetate | |
| | n.a. | n.a. | 355 |
| | | 3-Methyl-(3S)-3-phenylbutanoic acid | |
| 267B | | 2-[2,2-Diphenylethyl]-cis-4,5-diphenyl-4,5-dihydro-1H-imidazole trifluoroacetate | |
| | n.a. | n.a. | 403 |
| | | 3,3-Diphenylpropanoic acid | |
| 267C | | 2-[1-Methyl-2-phenylethyl]-cis-4,5-diphenyl-4,5-dihydro-1H-imidazole trifluoroacetate | |
| | n.a. | n.a. | 341 |
| | | 2-Methyl-3-phenylpropanoic acid | |
| 267D | | 2-[3-Phenyl-propyl]-cis-4,5-diphenyl-4,5-dihydro-1H-imidazole trifluoroacetate | |
| | n.a. | n.a. | 341 |
| | | 4-phenyl-butanoic acid | |
| 267E | | 2-[4-Phenyl-butyl]-cis-4,5-diphenyl-4,5-dihydro-1H-imidazole trifluoroacetate | |
| | n.a. | n.a. | 355 |
| | | 4-phenyl-pentanoic acid | |
| 268 | | 2-[2-(2-Fluorophenyl)ethyl]-cis-4,5-diphenyl-4,5-dihydro-1H-imidazole trifluoroacetate | |
| | 56 mg | 2.70 min | 345 |
| | | 3-(2-fluorophenyl)propionic acid | |
| 269 | | 2-[2-(3-Fluorophenyl)ethyl]-cis-4,5-diphenyl-4,5-dihydro-1H-imidazole trifluoroacetate | |
| | 60 mg | 2.68 min | 345 |
| | | 3-(3-fluorophenyl)propionic acid | |
| 270 | | 2-[2-(4-Fluorophenyl)ethyl]-cis-4,5-diphenyl-4,5-dihydro-1H-imidazole trifluoroacetate | |
| | 61 mg | 2.70 min | 345 |
| | | 3-(4-fluorophenyl)propionic acid | |
| 271 | | 2-[2-(2-Chlorophenyl)ethyl]-cis-4,5-diphenyl-4,5-dihydro-1H-imidazole trifluoroacetate | |
| | 11 mg | 2.80 min | 361 |
| | | 3-(2-chlorophenyl)propionic acid | |
| 271A | | 2-[2-(3-Chlorophenyl)ethyl]-cis-4,5-diphenyl-4,5-dihydro-1H-imidazole trifluoroacetate | |
| | n.a. | n.a. | 361 |
| | | 3-(3-chlorophenyl)propionic acid | |
| 271B | | 2-[2-(4-Chlorophenyl)ethyl]-cis-4,5-diphenyl-4,5-dihydro-1H-imidazole trifluoroacetate | |
| | n.a. | n.a. | 361 |
| | | 3-(4-chlorophenyl)propionic acid | |
| 272 | | 2-[2-(3,4-Dichlorophenyl)ethyl]-cis-4,5-diphenyl-4,5-dihydro-1H-imidazole trifluoroacetate | |
| | 28 mg | 2.99 min | 395 |
| | | 3-(3,4-dichlorophenyl)propionic acid | |
| 273 | | 2-[2-(3-Methylphenyl)ethyl]-cis-4,5-diphenyl-4,5-dihydro-1H-imidazole trifluoroacetate | |
| | 66 mg | 2.81 min | 341 |
| | | 3-(3-methylphenyl)propionic acid | | n.a. = not available

Example 134

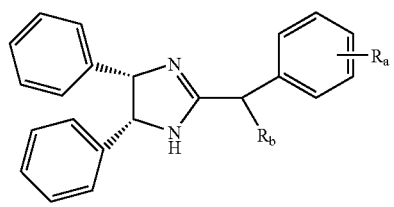

The procedure as set forth in Example 133 is essentially repeated in this Example except that a substituted phenylacetic acid (0.78 mmol) is employed in the place of a substituted 3-phenylpropionic acid. The substituted phenylacetamide derivative so formed is then cleaved in accordance with the procedures of Example 133 and the product is isolated.

The compounds so prepared are summarized in Table 2, which are also identified by a compound number. Also summarized in Table 2 are the amounts of the compound formed, the LC/MS retention time, m/e ion peak, and the substituted phenylacetic acid employed to make the respective compound. An example has also been included in this Table which utilized 2-indanyl carboxylic acid to make the corresponding imidazoline, compound 283D.

TABLE 2

| # | Compound / Amount (mg) / LC/MS retention time / LC/MS m/e (M$^+$ + 1) / Substituted phenylacetic acid |
|---|---|
| 274 | 2-(3-Chlorobenzyl)-cis-4,5-diphenyl-4,5-dihydro-1H-imidazole trifluoroacetate |
|  | 14 mg  2.95 min  347 |
|  | 3-chlorophenylacetic acid |
| 274A | 2-(2-Chlorobenzyl)-cis-4,5-diphenyl-4,5-dihydro-1H-imidazole trifluoroacetate |
|  | n.a.  n.a.  347 |
|  | 2-chlorophenylacetic acid |
| 274B | 2-(4-Chlorobenzyl)-cis-4,5-diphenyl-4,5-dihydro-1H-imidazole trifluoroacetate |
|  | n.a.  n.a.  347 |
|  | 4-chlorophenylacetic acid |
| 275 | 2-(4-Trifluoromethylbenzyl)-cis-4,5-diphenyl-4,5-dihydro-1H-imidazole trifluoroacetate |
|  | 18 mg  2.90 min  381 |
|  | 4-trifluoromethylphenylacetic acid |
| 276 | 2-(2,5-Dimethoxybenzyl)-cis-4,5-diphenyl-4,5-dihydro-1H-imidazole trifluoroacetate |
|  | 35 mg  3.85 min  373 |
|  | 2,5-dimethoxyphenylacetic acid |
| 277 | 2-(2,3-Dimethoxybenzyl)-cis-4,5-diphenyl-4,5-dihydro-1H-imidazole trifluoroacetate |
|  | 36 mg  2.90 min  373 |
|  | 2,3-dimethoxyphenylacetic acid |
| 278 | 2-(2-Fluorobenzyl)-cis-4,5-diphenyl-4,5-dihydro-1H-imidazole trifluoroacetate |
|  | 10 mg  2.85 min  331 |
|  | 2-fluorophenylacetic acid |
| 278A | 2-(3-Fluorobenzyl)-cis-4,5-diphenyl-4,5-dihydro-1H-imidazole trifluoroacetate |
|  | n.a.  n.a.  331 |
|  | 3-fluorophenylacetic acid |
| 279 | 2-(4-Fluorobenzyl)-cis-4,5-diphenyl-4,5-dihydro-1H-imidazole trifluoroacetate |
|  | 27 mg  2.87 min  331 |
|  | 4-fluorophenylacetic acid |
| 280 | 2-(2-Bromobenzyl)-cis-4,5-diphenyl-4,5-dihydro-1H-imidazole trifluoroacetate |
|  | 19 mg  4.14 min  393 |
|  | 2-bromophenylacetic acid |
| 281 | 2-(2,4-Difluorobenzyl)-cis-4,5-diphenyl-4,5-dihydro-1H-imidazole trifluoroacetate |
|  | 10 mg  3.95 min  349 |
|  | 2,4-difluorophenylacetic acid |
| 282 | 2-(3,4-Difluorobenzyl)-cis-4,5-diphenyl-4,5-dihydro-1H-imidazole trifluoroacetate |
|  | 6 mg  2.87 min  349 |
|  | 3,4-difluorophenylacetic acid |
| 282A | 2-(2,3-Difluorobenzyl)-cis-4,5-diphenyl-4,5-dihydro-1H-imidazole trifluoroacetate |
|  | n.a.  n.a.  349 |
|  | 2,3-difluorophenylacetic acid |
| 283 | 2-(2-Methylbenzyl)-cis-4,5-diphenyl-4,5-dihydro-1H-imidazole trifluoroacetate |
|  | 28 mg  3.77 min  327 |
|  | 2-methylphenylacetic acid |

TABLE 2-continued

| # | Compound / Amount (mg) / LC/MS retention time / LC/MS m/e (M$^+$ + 1) / Substituted phenylacetic acid |
|---|---|
| 283A | 2-(4-Methylbenzyl)-cis-4,5-diphenyl-4,5-dihydro-1H-imidazole trifluoroacetate |
|  | n.a.  n.a.  327 |
|  | 4-methylphenylacetic acid |
| 283B | 2-(1-phenyl-(1R)-ethyl)-cis-4,5-diphenyl-4,5-dihydro-1H-imidazole trifluoroacetate |
|  | n.a.  n.a.  327 |
|  | 1-phenyl-ethanoic acid |
| 283C | 2-Indan-2-ylmethyl-cis-4,5-diphenyl-4,5-dihydro-1H-imidazole trifluoroacetate |
|  | n.a.  n.a.  353 |
|  | 2-Indanylacetic acid |
| 283D | 2-Indan-2-yl-4,5-diphenyl-4,5-dihydro-1H-imidazole trifluoroacetate |
|  | n.a.  n.a.  339 |
|  | 2-Indanyl-carboxylic acid | n.a. = not available

Example 135

The procedure as set forth in Example 133 is essentially repeated in this Example except that a mixture of cis-1,2-bis-(3-fluorophenyl)ethane-1,2-diamine (5) (5 mmol) is employed in the place of a mixture of cis-1,2-diphenylethane-1,2-diamine (1) (5 mmol). The substituted 3-phenylpropionamide derivative so formed is then cleaved in accordance with the procedures of Example 133 and the compound is isolated.

The compounds so prepared are summarized in Table 3, which are also identified by a compound number. Also summarized in Table 3 are the amounts of the compound formed, the LC/MS retention time, m/e ion peak, and the substituted 3-phenylpropionic acid employed to make the respective compound.

TABLE 3

| # | Product / Amount (mg) / LC/MS retention time / LC/MS m/e (M$^+$ + 1) / Substituted 3-phenylpropionic acid |
|---|---|
| 284 | 2-[2-(2-Fluorophenyl)ethyl]-cis-4,5-bis-(3-fluorophenyl)-4,5-dihydro-1H-imidazole trifluoroacetate |
|  | 7 mg  3.15 min  381 |
|  | 3-(2-fluorophenyl)propionic acid |
| 285 | 2-[2-(3-Fluorophenyl)ethyl]-cis-4,5-bis-(3-fluorophenyl)-4,5-dihydro-1H-imidazole trifluoroacetate |
|  | 10 mg  3.15 min  381 |
|  | 3-(3-fluorophenyl)propionic acid |
| 286 | 2-[2-(4-Fluorophenyl)ethyl]-cis-4,5-bis-(3-fluorophenyl)-4,5-dihydro-1H-imidazole trifluoroacetate |
|  | 16 mg  3.14 min  381 |
|  | 3-(4-fluorophenyl)propionic acid |
| 287 | 2-[2-(4-Methylphenyl)ethyl]-cis-4,5-bis-(3-fluorophenyl)-4,5-dihydro-1H-imidazole trifluoroacetate |
|  | 21 mg  3.20 min  377 |
|  | 3-(4-methylphenyl)propionic acid |
| 288 | 2-[2-(3-Methylphenyl)ethyl]-cis-4,5-bis-(3-fluorophenyl)-4,5-dihydro-1H-imidazole trifluoroacetate |
|  | 15 mg  3.22 min  377 |
|  | 3-(3-methylphenyl)propionic acid |
| 289 | 2-[2-(2-Methylphenyl)ethyl]-cis-4,5-bis-(3-fluorophenyl)-4,5-dihydro-1H-imidazole trifluoroacetate |
|  | 17 mg  3.20 min  377 |
|  | 3-(2-methylphenyl)propionic acid |

TABLE 3-continued

| | Product | | |
|---|---|---|---|
| # | Amount (mg) | LC/MS retention time Substituted 3-phenylpropionic acid | LC/MS m/e (M+ + 1). |
| 290 | | 2-[2-(4-Methoxyphenyl)ethyl]-cis-4,5-bis-(3-fluorophenyl)-4,5-dihydro-1H-imidazole trifluoroacetate | |
| | 13 mg | 3.12 min | 393 |
| | | 3-(4-methoxyphenyl)propionic acid | |
| 291 | | 2-[2-(2-Methoxyphenyl)ethyl]-cis-4,5-bis-(3-fluorophenyl)-4,5-dihydro-1H-imidazole trifluoroacetate | |
| | 7 mg | 2.92 min | 393 |
| | | 3-(2-methoxypheny)propionic acid | |
| 292 | | 2-[2-(3,4-Dichlorophenyl)ethyl]-cis-4,5-bis-(3-fluorophenyl)-4,5-dihydro-1H-imidazole trifluoroacetate | |
| | 9 mg | 2.97 min | 431 |
| | | 3-(3,4-dichlorophenyl)propionic acid | |
| 293 | | 2-[2-(3,4-Dimethoxyphenyl)ethyl]-cis-4,5-bis-(3-fluorophenyl)-4,5-dihydro-1H-imidazole trifluoroacetate | |
| | 5 mg | 2.70 min | 423 |
| | | 3-(3,4-dimethoxyphenyl)propionic acid | |
| 294 | | 2-[(2-Thiophen-2-yl)ethyl]-cis-4,5-bis-(3-fluorophenyl)-4,5-dihydro-1H-imidazole trifluoroacetate | |
| | 2 mg | 4.07 min | 369 |
| | | 3-(Thiophen-2-yl)propionic acid | |
| 295 | | 2-[2-(4-Trifluoromethylphenyl)ethyl]-cis-4,5-bis-(3-fluorophenyl)-4,5-dihydro-1H-imidazole trifluoroacetate | |
| | 15 mg | 4.15 min | 431 |
| | | 3-(4-trifluoromethylphenyl)propionic acid | |
| 296 | | 2-[2-(3,5-Ditrifluoromethylphenyl)ethyl]-cis-4,5-bis-(3-fluorophenyl)-4,5-dihydro-1H-imidazole trifluoroacetate | |
| | 13 mg | 4.50 min | 499 |
| | | 3-(3,5-ditrifluoromethylphenyl)propionic acid | |

Example 136

2-[(cis-4,5-Diphenyl-4,5-dihydro-1H-imidazol-2-yl)-2-ethyl]pyridine (299)

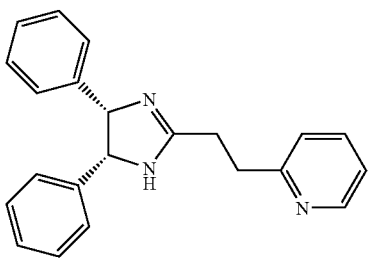

Step 1

3-(Pyridin-2-yl)prop-2(E)-enoic acid methyl ester (297)

To a solution of 2-pyridinecarboxaldehyde (0.476 mL, 5.0 mmol) in toluene (25 mL) is added methyl (triphenylphosphoranylidine)acetate (1.84 g, 5.5 mmol), and the solution is stirred and heated at 90° C. for 4 h. The reaction mixture is cooled to RT, diluted with EtOAc, and washed with water, brine, then dried (MgSO$_4$), and filtered. The filtrate is rotary evaporated, and the residue is purified by chromatography on silica gel; elution with EtOAc:MeOH:heptane (25:5:70) gives 0.658 g of the product 297 as the mostly trans isomer. $^1$H NMR (CDCl$_3$) δ 8.70 (d, 1 H), 7.75-7.70 (m, 2 H), 7.41 (d, 1 H), 7.30 (t, 1 H), 6.90 (d, 1 H), 3.85 (s, 3 H); MS: m/z 164 (M$^+$+1).

Step 2

3-(Pyridin-2-yl)propionic acid methyl ester (298)

To a solution of 297 (0.658 g, 4.0 mmol) in 1:1 THF:MeOH (14 mL) is added 10% palladium-on-carbon (98 mg), and the mixture is stirred at RT under hydrogen for 18 h. The mixture is filtered, and the filtrate is evaporated, and the residue purified by chromatography on silica gel; elution with EtOAc:MeOH:heptane (25:5:70) gives 0.554 g of the product 298. $^1$H NMR (CDCl$_3$) δ 8.55 (d, 1 H), 7.59 (t, 1 H), 7.20 (d, 1 H), 7.14 (m, 1 H), 3.70 (s, 3 H), 3.13 (t, 2 H), 2.82 (t, 2 H); MS: m/z 166 (M$^+$+1).

Step 3

2-[(cis-4,5-Diphenyl-4,5-dihydro-1H-imidazol-2-yl)-2-ethyl]pyridine (299)

To a solution of 298 (165 mg, 1.0 mmol) in toluene (8 mL) is added the diamine 1 (212 mg 1.0 mmol) followed by 2.0M trimethylaluminum in toluene (1.2 mL, 1.2 mmol), and the solution is heated at 70° C. for 6 h. The reaction is cooled to RT and quenched by the addition of sat. sodium bicarbonate solution, followed by the addition of water and EtOAc. The organic layer is separated, and washed with brine, dried (MgSO$_4$), and filtered. The filtrate is evaporated, and the residue is purified by chromatography on silica gel; elution with dichloromethane:MeOH (9:1) gives 99 mg of the product 299. $^1$H NMR (CDCl$_3$) δ 8.56 (d, 1 H), 7.65 (t, 1 H), 7.32 (d, 1 H), 7.17 (m, 1 H), 7.0-6.9 (m, 6 H), 6.82-6.80 (m, 4 H), 5.4-5.1 (bs, 2 H), 3.34 (t, 2 H), 3.00 (t, 2 H); MS: m/z 328 (M$^+$+1).

Example 137

3-[(cis-4,5-Diphenyl-4,5-dihydro-1H-imidazol-2-yl)-2-ethyl]pyridine (302)

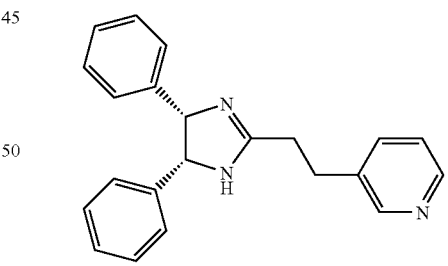

Step 1

3-(Pyridin-3-yl)prop-2(E)-enoic acid methyl ester (300)

To a solution of 3-pyridinecarboxaldehyde (0.472 mL, 5.0 mmol) in toluene (25 mL) is added methyl (triphenylphosphoranylidine)acetate (1.84 g, 5.5 mmol), and the solution is stirred and heated at 90° C. for 3 h. The reaction mixture is cooled to RT, diluted with EtOAc, and washed with water, brine, then dried (MgSO$_4$), and filtered. The filtrate is rotary evaporated, and the residue is purified by chromatography on silica gel; elution with EtOAc:MeOH:heptane (25:5:70) gives 0.355 g of the product 300. $^1$H NMR (CDCl$_3$) δ 7.82 (d, 1 H), 7.70-7.60 (m, 2 H), 7.50 (m, 1 H), 7.35 (m, 1 H), 6.50 (d, 1 H), 3.80 (s, 3 H); MS: m/z 164 (M$^+$+1).

Step 2

3-(Pyridin-3-yl)propionic acid methyl ester (301)

To a solution of 300 (0.355 g, 2.2 mmol) in 1:1 THF:MeOH (7 mL) is added 10% palladium-on-carbon (53 mg), and the mixture is stirred at RT under hydrogen for 20 h. The mixture is filtered, and the filtrate is evaporated, and the residue purified by chromatography on silica gel; elution with EtOAc:MeOH:heptane (45:5:50) gives 0.124 g of the product 301. $^1$H NMR (CDCl$_3$) δ 8.50 (s, 1 H), 7.65 (m, 1 H), 7.45 (m, 1 H), 7.20 (m, 1 H), 3.65 (s, 3 H), 2.95 (t, 2 H), 2.65 (t, 2 H); MS: m/z 166 (M$^+$+1).

Step 3

3-[(cis-4,5-Diphenyl-4,5-dihydro-1H-imidazol-2-yl)-2-ethyl]pyridine (302)

To a solution of the diamine 1 (159 mg 0.75 mmol) in toluene (5 mL) is added 2.0M trimethylaluminum in toluene (0.95 mL, 1.9 mmol), followed by 301 (124 mg, 0.75 mmol), and the solution is heated at 65° C. for 6 h. The reaction is cooled to RT and quenched by the addition of sat. sodium bicarbonate solution, followed by the addition of water and EtOAc. The organic layer is separated, and washed with brine, dried (MgSO$_4$), and filtered. The filtrate is evaporated, and the residue is purified by chromatography on silica gel; elution with dichloromethane:7M ammonia in MeOH (95:5) gives 104 mg of the product 302. $^1$H NMR (CDCl$_3$) δ 8.62 (s, 1 H), 8.52 (d, 1 H), 7.67 (d, 1 H), 7.28 (m, 1 H), 7.05-7.00 (m, 6 H), 6.8-6.7 (m, 4 H), 5.27 (bs, 2 H), 3.19 (t, 2 H), 2.82 (t, 2 H); MS: m/z 328 (M$^+$+1).

Example 138

2-[(Tetrahydropyran-4-yl)methyl]-cis-4,5-diphenyl-4,5-dihydro-1H-imidazole trifluoroacetate (305)

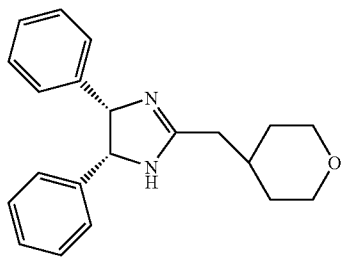

Step 1

(Tetrahydropyran-4-ylidine)acetic acid methyl ester (303)

To a solution of tetrahydro-4H-pyran-4-one (0.462 mL, 5.0 mmol) in toluene (25 mL) is added methyl (triphenylphosphoranylidine)acetate (1.84 g, 5.5 mmol), and the solution is stirred and heated at 110° C. for 24 h. The reaction mixture is cooled to RT, diluted with Et$_2$O, and washed with water, brine, then dried (MgSO$_4$), and filtered. The filtrate is rotary evaporated, and the residue is purified by chromatography on silica gel; elution with EtOAc:heptane (40:60) gives 0.496 g of the product 303. $^1$H NMR (CDCl$_3$) δ 5.70 (s, 1 H), 3.80-3.75 (m, 4 H), 3.70 (s, 3 H), 3.00 (t, 2 H), 2.35 (t, 2 H); MS: m/z 157 (M$^+$+1).

Step 2

(Tetrahydropyran-4-yl)acetic acid methyl ester (304)

To a solution of 303 (490 mg, 3.1 mmol) in 1:1 THF:MeOH (10 mL) is added 10% palladium-on-carbon (74 mg), and the mixture is stirred at RT under hydrogen for 16 h. The mixture is filtered, and the filtrate is evaporated to give 481 mg of the product 304. $^1$H NMR (CDCl$_3$) δ 4.0-3.9 (m, 2 H), 3.70 (s, 3 H), 3.40 (t, 2 H), 2.25 (d, 2 H), 2.01 (m, 1 H), 1.65-1.60 (m, 2 H), 1.40-1.25 (m, 2 H); MS: m/z 159 (M$^+$+1).

Step 3

2-[(Tetrahydropyran-4-yl)methyl]-cis-4,5-diphenyl-4,5-dihydro-1H-imidazole trifluoroacetate (305)

To a solution of the diamine 1 (584 mg 2.75 mmol) in toluene (15 mL) is added 2.0M trimethylaluminum in toluene (3.44 mL, 6.88 mmol), followed by 304 (473 mg, 3.0 mmol), and the solution is heated at 65° C. for 12 h. The reaction is cooled to 20° C. and quenched by the addition of sat. sodium bicarbonate solution, and filtered. The filtrate is evaporated, and the residue is purified by reverse phase HPLC; gradient elution with acetonitrile/0.1% TFA:water/0.1% TFA (25:75-100:0) gives 178 mg of the product 305. $^1$H NMR (DMSO-d$_6$) δ 10.72 (s, 2 H), 7.2-7.1 (m, 6 H), 7.05-7.0 (m, 4 H), 5.80 (s, 2 H), 3.95-3.90 (m, 2 H), 3.36 (t, 2 H), 2.74 (d, 2 H), 2.15 (m, 1 H), 1.75-1.70 (m, 2 H), 1.45-1.30 (m, 2 H); MS: m/z 321 (M$^+$+1).

Example 139

2-[(cis-4,5-Diphenyl-4-methyl-4,5-dihydro-1H-imidazol-2-yl)-2-ethyl]pyridine ditrifluoroacetate (306)

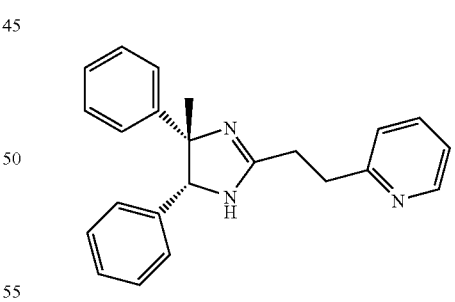

To a solution of the diamine 16 (170 mg 0.75 mmol) in toluene (2 mL) is added 2.0M trimethylaluminum in toluene (0.980 mL, 1.95 mmol), followed by 3-(pyridin-2-yl)-propionic acid methyl ester (298) (124 mg, 0.75 mmol), and the solution is heated at 90° C. for 12 h. The reaction is cooled to 20° C. and quenched by the addition of sat. sodium bicarbonate solution, followed by the addition of water and EtOAc. The organic layer is separated, washed with brine, dried (MgSO$_4$), and filtered. The filtrate is evaporated, and the residue is purified by reverse phase HPLC; gradient elution with acetonitrile/0.1% TFA:water/0.1% TFA (20:80-100:0)

gives 55 mg of the product 306. ¹H NMR (DMSO-d₆) δ 10.84 (s, 1 H), 10.67 (s, 1 H), 8.65 (m, 1 H), 7.88 (t, 1 H), 7.46 (d, 1 H), 7.40 (m, 1 H), 7.1-7.0 (m, 5 H), 6.93-6.90 (m, 2 H), 6.85-6.80 (m, 2 H), 5.26 (s, 1 H), 3.40 (t, 2 H), 3.26 (t, 2 H), 1.88 (s, 3 H); LC/MS: 2.60 min, m/z 342 (M⁺+1).

Example 140

[4,5-cis-bis-(3-Fluorophenyl)-4-methyl-4,5-dihydro-1H-imidazol-2-yl]-(3-fluoro-benzyl)amine (381)

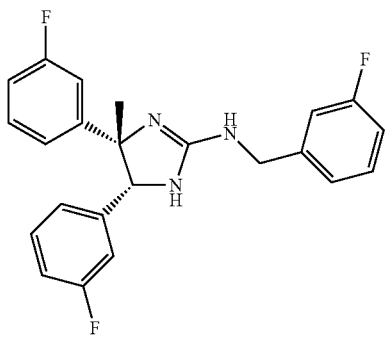

A mixture of intermediate 75 (200 mg, 0.478 mmol), 3-fluorobenzylamine (0.400 mL, 3.51 mmol) is heated at 150° C. overnight. The reaction mixture is cooled to RT. The reaction mixture is diluted with dichloromethane, washed with 3M HCl, brine, and then dried (Na₂SO₄), and filtered. The filtrate is evaporated, and the residue purified by chromatography on silica gel; elution with dichloromethane:MeOH:HOAc (100:4:1) gives 100 mg of the product 381. ¹H NMR (CDCl₃) δ 9.80-7.60 (m, 2 H), 7.50-7.10 (m, 4 H), 7.10-6.85 (m, 4 H), 6.85-6.65 (m, 2 H), 6.65-6.20 (m, 4 H), 4.75 (s, 1 H), 4.60 (s, 2 H), 1.90 (s, 3 H); LC/MS: 2.75 min, m/z 396 (M⁺+1).

Example 141

[4,5-cis-bis-(4-Fluorophenyl)-4-methyl-4,5-dihydro-1H-imidazol-2-yl]-(3-fluoro-benzyl)amine (382)

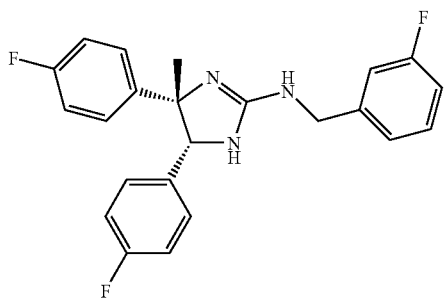

A mixture of intermediate 73 (200 mg, 0.478 mmol), 3-fluorobenzylamine (0.400 mL, 3.51 mmol) is heated at 150° C. overnight. The reaction mixture is cooled to RT. The reaction mixture is diluted with dichloromethane, washed with 3M HCl, and brine. The precipitate that formed during drying is filtered to give 46 mg of the product 382. ¹H NMR (DMSO-d₆) δ 9.20 (m, 2 H), 7.60-7.40 (m, 1 H), 7.40-7.10 (m, 3 H), 7.10-6.80 (m, 8 H), 5.15 (s, 1 H), 4.60 (s, 2 H), 1.95 (s, 3 H); LC/MS: 2.79 min, m/z 396 (M⁺+1).

Example 142

2-[(Phenoxy)methyl]-cis-4,5-diphenyl-4,5-dihydro-1H-imidazole (383)

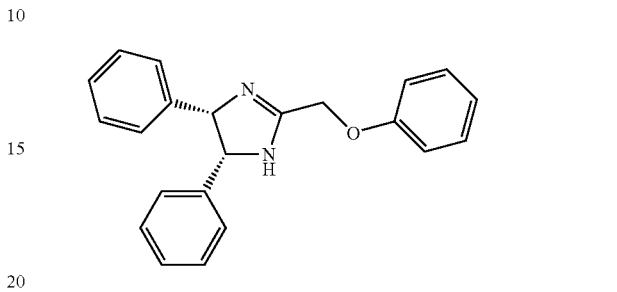

To a solution of the diamine 1 (212 mg, 1.0 mmol) in toluene (6 mL) is added 2.0M trimethylaluminum in toluene (1.0 mL, 2.0 mmol) followed by a solution of phenoxyacetonitrile (133 mg, 1.0 mmol) in toluene (1 mL). The solution is heated at 60° C. for 2 h, then cooled to RT. The reaction mixture is quenched with sat. sodium bicarbonate solution (2 mL) and EtOAc is added, and the solution filtered. The filtrate is evaporated, and the residue purified by chromatography on silica gel; elution with dichloromethane:MeOH (9:1) gives 119 mg of the product 383. ¹H NMR (CDCl₃) δ 7.37 (t, 2H), 7.1-6.9 (m, 9H), 6.88 (bs, 4H), 5.4 (bd, 2H), 5.01 (bs, 2H); MS: m/z 329 (M⁺+1).

Example 143

2-[(2-Fluorophenoxy)methyl]-cis-4,5-diphenyl-4,5-dihydro-1H-imidazole (385)

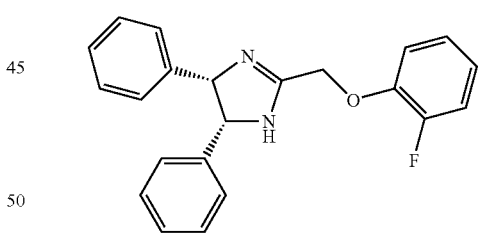

Step 1.

(2-Fluorophenoxy)acetonitrile (384)

To a solution of 2-fluorophenol (560 mg, 5.0 mmol) in DMF (10 mL) is added potassium carbonate (828 mg, 6.0 mmol) followed by chloroacetonitrile (0.315 mL, 50.0 mmol). The reaction mixture is stirred and heated at 50° C. for 14 h. The reaction mixture is cooled to RT, diluted with EtOAc, and washed with water, brine, then dried (MgSO₄), and filtered. The filtrate is evaporated, and the residue purified by chromatography on silica gel; elution with dichloromethane gives 736 mg of the product 384.

Step 2.

2-[(2-Fluorophenoxy)methyl]-cis-4,5-diphenyl-4,5-dihydro-1H-imidazole (385)

To a solution of the diamine 1 (212 mg, 1.0 mmol) in toluene (6 mL) is added 2.0M trimethylaluminum in toluene (1.0 mL, 2.0 mmol) followed by a solution of 384 (151 mg, 1.0 mmol) in toluene (1 mL). The solution is heated at 60° C. for 2 h, then cooled to RT. The reaction mixture is quenched with sat. sodium bicarbonate solution (2 mL) and EtOAc is added, and the solution filtered. The filtrate is evaporated, and the residue purified by chromatography on silica gel; elution with dichloromethane:MeOH (9:1) gives 59 mg of the product 385. $^1$H NMR (CDCl$_3$) δ 7.40-7.25 (m, 1H), 7.24-7.11 (m, 3H), 7.00 (m, 6H), 6.88 (m, 4H), 5.37 (bs, 2H), 5.06 (bs, 2H); MS: m/z 347 (M$^+$+1).

Example 144

2-[(3-Fluorophenoxy)methyl]-cis-4,5-diphenyl-4,5-dihydro-1H-imidazole trifluoroacetate (387)

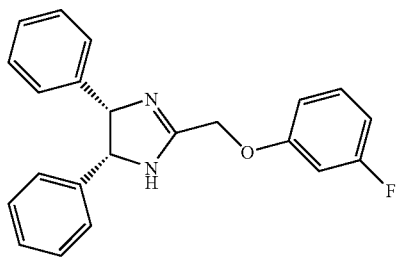

Step 1.

3-Fluorophenoxyacetonitrile (386)

To a solution of 3-fluorophenol (560 mg, 5.0 mmol) in DMF (10 mL) is added potassium carbonate (828 mg, 6.0 mmol) followed by chloroacetonitrile (0.315 mL, 50.0 mmol). The reaction mixture is stirred and heated at 50° C. for 14 h. The reaction mixture is cooled to RT, diluted with EtOAc, and washed with water, brine, then dried (MgSO$_4$), and filtered. The filtrate is evaporated, and the residue purified by chromatography on silica gel; elution with dichloromethane gives 712 mg of the product 386.

Step 2.

2-[(3-Fluorophenoxy)methyl]-cis-4,5-diphenyl-4,5-dihydro-1H-imidazole trifluoroacetate (387)

To a solution of the diamine 1 (212 mg, 1.0 mmol) in toluene (6 μL) is added 2.0M trimethylaluminum in toluene (1.0 mL, 2.0 mmol) followed by a solution 386 (151 mg, 1.0 mmol) in toluene (1 mL). The solution is heated at 60° C. for 2 h, then cooled to RT. The reaction mixture is quenched with sat. sodium bicarbonate solution (2 mL) and EtOAc is added, and the solution filtered. The filtrate is evaporated, and the residue purified by chromatography on reversed phase silica gel; gradient elution with acetonitrile:water/1% TFA (30:70-100:0) gives 63 mg of the product 387. $^1$H NMR (CDCl$_3$) δ 7.31 (q, 1H), 7.7.1-7.0 (m, 6H), 7.9-7.7 (m, 7H), 5.59 (s, 2H), 5.42 (s, 2H); MS: m/z 347 (M$^+$+1).

Example 145

2-[(4-Fluorophenoxy)methyl]-cis-4,5-diphenyl-4,5-dihydro-1H-imidazole trifluoroacetate (389)

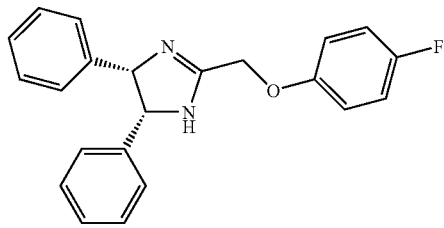

Step 1.

(4-Fluorophenoxy)acetonitrile (388)

To a solution of 4-fluorophenol (560 mg, 5.0 mmol) in DMF (10 mL) is added potassium carbonate (828 mg, 6.0 mmol) followed by chloroacetonitrile (0.315 mL, 50.0 mmol). The reaction mixture is stirred and heated at 50° C. for 14 h. The reaction mixture is cooled to RT, diluted with EtOAc, and washed with water, brine, then dried (MgSO$_4$), and filtered. The filtrate is evaporated, and the residue purified by chromatography on silica gel; elution with dichloromethane gives 721 mg of the product 388.

Step 2.

2-[(4-Fluorophenoxy)methyl]-cis-4,5-diphenyl-4,5-dihydro-1H-imidazole trifluoroacetate (389)

To a solution of the diamine 1 (212 mg, 1.0 mmol) in toluene (6 mL) is added 2.0M trimethylaluminum in toluene (1.0 mL, 2.0 mmol) followed by a solution 388 (151 mg, 1.0 mmol) in toluene (1 mL). The solution is heated at 60° C. for 2 h, then cooled to RT. The reaction mixture is quenched with sat. sodium bicarbonate solution (2 mL) and EtOAc is added, and the solution filtered. The filtrate is evaporated, and the residue purified by chromatography on reversed phase silica gel; gradient elution with acetonitrile:water/1% TFA (30:70-100:0) gives 48 mg of the product 389. $^1$H NMR (CDCl$_3$) δ 7.1-6.9 (m, 10H), 6.82 (m, 4H), 5.59 (bs, 2H), 5.42 (bs, 2H); MS: m/z 347 (M$^+$+1).

Example 146

2-[(Benzyloxy)methyl]-cis-4,5-diphenyl-4,5-dihydro-1H-imidazole (391)

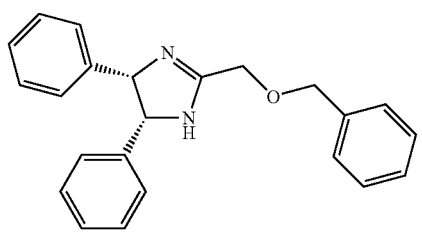

Step 1.

Benzyloxyacetic acid ethyl ester (390)

To a solution of benzyl alcohol (1.04 mL, 10.0 mmol) in dichloromethane (30 mL) is added rhodium (II) acetate dimer (40 mg) followed by ethyl diazoacetate (1.14 g, 10.0 mmol). The reaction mixture is stirred at RT for 20 min. The reaction mixture is rotary evaporated, and the residue is vacuum distilled at 110° C. to give 1.81 g of the product 390. $^1$H NMR (CDCl$_3$) δ 7.4-7.26 (m, 5H), 4.65 (s, 2H), 4.23 (q, 2H), 4.10 (s, 2H), 1.30 (t, 3H).

Step 2.

2-[(Benzyloxy)methyl]-cis-4,5-diphenyl-4,5-dihydro-1H-imidazole (391)

To a solution of the diamine 1 (106 mg, 0.5 mmol) in toluene (3 mL) is added 2.0M trimethylaluminum in toluene (0.6 mL, 1.2 mmol) followed by 390 (100 mg, 0.5 mmol), and the solution is heated at 60° C. for 6 h, then cooled to rt. The reaction mixture is quenched with sat. sodium bicarbonate solution (0.5 mL) and EtOAc is added, and the solution is dried (MgSO$_4$), and filtered. The filtrate is evaporated, and the residue purified by chromatography on silica gel; elution with dichloromethane:MeOH (92:8) gives 49 mg of the product 391. $^1$H NMR (CDCl$_3$) δ 7.4-7.26 (m, 5H), 7.01 (m, 6H), 6.92 (m, 4H), 5.31 (bs, 2H), 4.70 (s, 2H), 4.48 (s, 2H); MS: m/z 343 (M$^+$).

Example 147

2-[(3-Fluorobenzyloxy)methyl]-cis-4,5-diphenyl-4,5-dihydro-1H-imidazole hydrochloride (393)

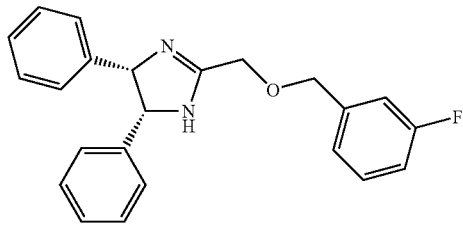

Step 1.

3-Fluorobenzyloxyacetic acid ethyl ester (392)

To a solution of 3-fluorobenzyl alcohol (1.12 g, 10.0 mmol) in dichloromethane (20 mL) is added rhodium (II) acetate dimer (10 mg) followed by ethyl diazoacetate (0.95 mL, 9.0 mmol). The reaction mixture is stirred at RT for 30 min. The reaction mixture is diluted with heptane, filtered through Celite, and the filtrate is evaporated and the residue is vacuum distilled at 150° C. to give 1.88 g of the product 392. $^1$H NMR (CDCl$_3$) δ 7.30 (m, 1H), 7.12 (m, 2H), 6.99 (dt, 1H), 4.63 (s, 2H), 4.28 (q, 2H), 4.11 (s, 2H), 1.30 (t, 3H); MS: m/z 213 (M$^+$+1).

Step 2.

2-[(3-Fluorobenzyloxy)methyl]-cis-4,5-diphenyl-4,5-dihydro-1H-imidazole hydrochloride (393) (Scheme 11, Method b)

To a solution of the diamine 1 (106 mg, 0.5 mmol) in toluene (3 mL) is added 2.0M trimethylaluminum in toluene (0.6 mL, 1.2 mmol) followed by 392 (106 mg, 0.53 mmol), and the solution is heated at 60° C. for 6 h, then cooled to rt. The reaction mixture is quenched with sat. sodium bicarbonate solution (0.2 mL) and EtOAc is added, and the solution filtered. The filtrate is evaporated, and the residue purified by chromatography on silica gel; elution with dichloromethane:MeOH (94:6) followed by treatment with hydrogen chloride in Et$_2$O gives 17 mg of the product 393. $^1$H NMR (CDCl$_3$) δ 10.3 (bs, 2H), 7.37 (m, 1H), 7.26-7.0 (m, 9H), 6.88 (m, 4H), 5.68 (s, 2H), 5.17 (s, 2H), 4.73 (s, 2H)

Example 148

2-[(3-Trifluoromethylbenzyloxy)methyl]-cis-4,5-diphenyl-4,5-dihydro-1H-imidazole hydrochloride (395)

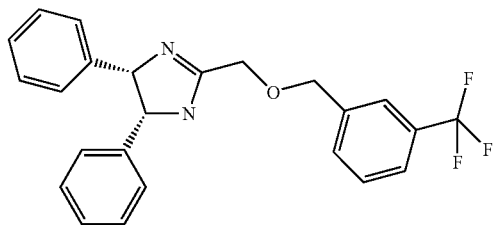

Step 1.

(3-Trifluoromethylbenzyloxy)acetic acid ethyl ester (394)

To a solution of 3-trifluoromethylbenzyl alcohol (1.62 g, 10.0 mmol) in dichloromethane (20 mL) is added rhodium (II) acetate dimer (10 mg) followed by ethyl diazoacetate (0.95 mL, 9.0 mmol). The reaction mixture is stirred at RT for 30 min. The reaction mixture is diluted with heptane, filtered through Celite, and the filtrate is evaporated and the residue is vacuum distilled at 150° C. to give 2.31 g of the product 394. $^1$H NMR (CDCl$_3$) δ 7.65 (bs, 1H), 7.57 (m, 2H), 7.48 (t, 1H), 4.69 (s, 2H), 4.24 (q, 2H), 4.14 (s, 2H), 1.30 (t, 3H); MS: m/z 263 (M$^+$).

Step 2.

2-[(3-Trifluoromethylbenzyloxy)methyl]-cis-4,5-diphenyl-4,5-dihydro-1H-imidazole hydrochloride (395)

To a solution of the diamine 1 (106 mg, 0.5 mmol) in toluene (3 mL) is added 2.0M trimethylaluminum in toluene (0.6 mL, 1.2 mmol) followed by 394 (131 mg, 0.53 mmol), and the solution is heated at 60° C. for 6 h, then cooled to rt. The reaction mixture is quenched with sat. sodium bicarbonate solution (0.2 mL) and EtOAc is added, and the solution filtered. The filtrate is evaporated, and the residue purified by chromatography on silica gel; elution with dichloromethane:MeOH (94:6) followed by treatment with hydrogen chloride in Et$_2$O gives 14 mg of the product 395. $^1$H NMR (DMSO-d$_6$) δ 10.90 (s, 2H), 7.85 (bs, 1H), 7.81-7.64 (m, 31H), 7.15-7.0 (m, 10H), 5.81 (s, 2H), 4.87 (s, 4H); MS: m/z 411 (M$^+$+1).

Example 149

2-[(3-Methylbenzyloxy)methyl]-cis-4,5-diphenyl-4,5-dihydro-1H-imidazole hydrochloride (397)

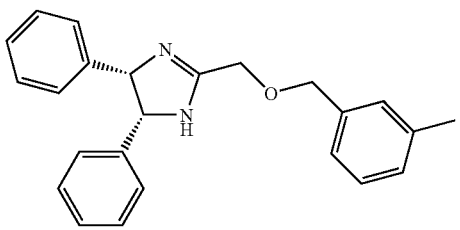

Step 1.

(3-Methylbenzyloxy)acetic acid ethyl ester (396)

To a solution of 3-methylbenzyl alcohol (1.08 g, 10.0 mmol) in dichloromethane (20 mL) is added rhodium (II) acetate dimer (10 mg) followed by ethyl diazoacetate (0.95 mL, 9.0 mmol). The reaction mixture is stirred at RT for 30 min. The reaction mixture is diluted with heptane, filtered through Celite, and the filtrate is evaporated and the residue is vacuum distilled at 150° C. to give 1.91 g of the product 396. $^1$H NMR (CDCl$_3$) δ 7.3-7.1 (m, 4H), 4.60 (s, 2H), 4.23 (q, 2H), 4.09 (s, 2H), 2.36 (s, 3H), 1.29 (t, 311); MS: m/z 209 (M$^+$+1).

Step 2.

2-[(3-Methylbenzyloxy)methyl]-cis-4,5-diphenyl-4,5-dihydro-1H-imidazole hydrochloride (397)

To a solution of the diamine 1 (106 mg, 0.5 mmol) in toluene (3 mL) is added 2.0M trimethylaluminum in toluene (0.6 mL, 1.2 mmol) followed by 396 (194 mg, 0.53 mmol), and the solution is heated at 60° C. for 6 h, then cooled to rt. The reaction mixture is quenched with sat. sodium bicarbonate solution (0.2 mL) and EtOAc is added, and the solution filtered. The filtrate is evaporated, and the residue purified by chromatography on silica gel; elution with dichloromethane:MeOH (94:6) followed by treatment with hydrogen chloride in Et$_2$O gives 40 mg of the product 397. $^1$H NMR (DMSO-d$_6$) δ 10.91 (s, 2H), 7.34-6.99 (m, 14H), 5.79 (s, 2H), 4.79 (s, 21H), 4.72 (s, 2H), 2.34 (s, 3H); MS: m/z 357 (M$^+$+1).

Example 150

2-[(3-Methoxybenzyloxy)methyl]-cis-4,5-diphenyl-4,5-dihydro-1H-imidazole hydrochloride (399)

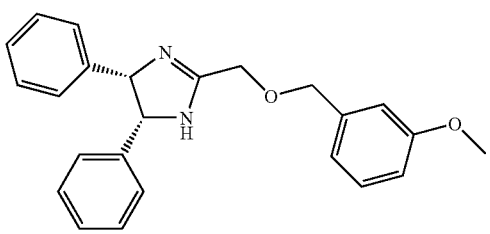

Step 1.

(3-Methoxybenzyloxy)acetic acid ethyl ester (398)

To a solution of 3-methoxybenzyl alcohol (1.24 g, 10.0 mmol) in dichloromethane (20 mL) is added rhodium (II) acetate dimer (10 mg) followed by ethyl diazoacetate (0.95 mL, 9.0 mmol). The reaction mixture is stirred at RT for 30 min. The reaction mixture is diluted with heptane, filtered through Celite, and the filtrate is evaporated and the residue is vacuum distilled at 150° C. to give 2.00 g of the product 398. $^1$H NMR (CDCl$_3$) δ 7.26 (t, 1H), 6.93 (m, 2H), 6.85 (m, 1H), 4.62 (s, 2H), 4.23 (q, 2H), 4.09 (s, 2H), 3.81 (s, 3H), 1.29 (t, 3H); MS: m/z 224 (M$^+$+1).

Step 2.

2-[(3-Methoxybenzyloxy)methyl]-cis-4,5-diphenyl-4,5-dihydro-1H-imidazole hydrochloride (399)

To a solution of the diamine 1 (106 mg, 0.5 mmol) in toluene (3 mL) is added 2.0M trimethylaluminum in toluene (0.6 mL, 1.2 mmol) followed by 398 (210 mg, 0.53 mmol), and the solution is heated at 60° C. for 6 h, then cooled to rt. The reaction mixture is quenched with sat. sodium bicarbonate solution (0.2 mL) and EtOAc is added, and the solution filtered. The filtrate is evaporated, and the residue purified by chromatography on silica gel; elution with dichloromethane:MeOH (94:6) followed by treatment with hydrogen chloride in Et$_2$O gives 34 mg of the product 399. $^1$H NMR (DMSO-d$_6$) δ 10.87 (s, 2H), 7.34 (t, 1H), 7.13-6.96 (m, 12H), 6.92 (m, 1H), 5.79 (s, 2H), 4.79 (s, 2H), 4.74 (s, 2H), 3.78 (s, 3H); MS: m/z 373 (M$^+$+1).

Example 151

2-[(Phenylsulfanyl)methyl]-cis-4,5-diphenyl-4,5-dihydro-1H-imidazole trifluoroacetate (401)

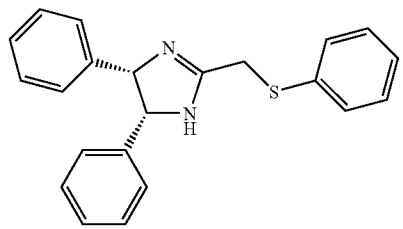

Step 1

(Phenylthio)acetic acid ethyl ester (400)

To a solution of thiophenol (1 mL, 9.7 mmol) in DMF (20 mL) is added potassium carbonate (1.51 g, 10.9 mmol) and ethyl bromoacetate (1.17 mL, 10.6 mmol), and the mixture is stirred at RT for 25 min. Et$_2$O is added, and the mixture is washed with water, brine, then dried (MgSO$_4$), and filtered. The filtrate is evaporated, and the residue is vacuum distilled (130-140° C.) to give 1.71 g of the product 400. $^1$H NMR (CDCl$_3$) δ 7.41 (d, 2H), 7.33-7.2 (m, 4H), 4.16 (q, 2H), 3.63 (s, 2H), 1.22 (t, 3H); MS: m/z 196 (M$^+$+1).

Step 2

2-[(Phenylsulfanyl)methyl]-cis-4,5-diphenyl-4,5-dihydro-1H-imidazole trifluoroacetate (401)

To a solution of the diamine 1 (106 mg, 0.5 mmol) in toluene (1.5 mL) is added 2.0M trimethylaluminum in toluene (0.65 mL, 1.3 mmol) followed by 400 (98 mg, 0.50 mmol), and the solution is heated at 80° C. for 2.5 h, then cooled to rt. The reaction mixture is quenched with sat. sodium bicarbonate solution (0.6 mL) and EtOAc:dichloromethane is added, and the solution filtered. The filtrate is evaporated, and the residue purified by chromatography on reversed phase silica gel; elution with acetonitrile:water/ 0.1% TFA gives 96 mg of the product 401. $^1$H NMR (CDCl$_3$) δ 10.8 (bs, 2H), 7.60 (m, 2H), 7.45-7.3 (m, 3H), 7.05-6.9 (m, 6H), 6.58 (m, 4H), 5.52 (s, 2H), 4.50 (s, 2H); LC/MS: 3.24 min, nm/z 345 (M$^+$+1).

Example 152

2-[(Benzylsulfanyl)methyl]-cis-4,5-diphenyl-4,5-dihydro-1H-imidazole trifluoroacetate (403)

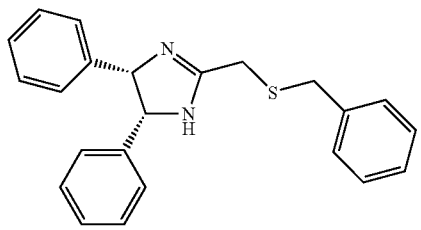

Step 1

(Benzylsulfanyl)acetic acid ethyl ester (402)

To a solution of benzyl mercaptan (1.18 mL, 10.0 mmol) in DMF (20 mL) is added potassium carbonate (1.51 g, 10.9 mmol) and ethyl bromoacetate (1.17 mL, 10.6 mmol), and the mixture is stirred at RT for 25 min. Et$_2$O is added, and the mixture is washed with water, brine, then dried (MgSO$_4$), and filtered. The filtrate is evaporated, and the residue is vacuum distilled (130-140° C.) to give 1.05 g of the product 402.

Step 2

2-[(Benzylsulfanyl)methyl]-cis-4,5-diphenyl-4,5-dihydro-1H-imidazole trifluoroacetate (403)

To a solution of the diamine 1 (106 mg, 0.5 mmol) in toluene (2 mL) is added 2.0M trimethylaluminum in toluene (0.65 mL, 1.3 mmol) followed by 402 (105 mg, 0.50 mmol), and the solution is heated at 80° C. for 2.5 h, then cooled to rt. The reaction mixture is quenched with sat. sodium bicarbonate solution (0.6 mL) and EtOAc:dichloromethane is added, and the solution filtered. The filtrate is evaporated, and the residue purified by chromatography on reversed phase silica gel; elution with acetonitrile:water/0.1% TFA gives 96 mg of the product 403. $^1$H NMR (CDCl$_3$) δ 10.8 (bs, 2H), 7.44-7.3 (m, 5H), 7.05 (m, 6H), 6.73 (m, 4H), 5.23 (s, 2H), 4.08 (s, 2H), 3.98 (s, 2H); LC/MS: 3.35 min, m/z 359 (M$^+$+1).

Example 153

2-[(Methoxy)methyl]-cis-4,5-diphenyl-4,5-dihydro-1H-imidazole trifluoroacetate (404)

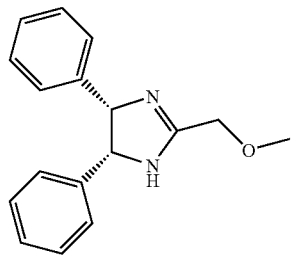

To a solution of the diamine 1 (159 mg, 0.75 mmol) in toluene (2.5 mL) is added 2.0M trimethylaluminum in toluene (0.980 mL, 1.96 mmol) followed by methoxyacetic acid methyl ester (0.74 mL, 0.75 mmol), and the solution is heated at 90° C. for 3 h, then cooled to rt. The reaction mixture is quenched with sat. sodium bicarbonate solution (1.5 mL) and EtOAc is added, and the mixture is dried (MgSO$_4$), and filtered. The filtrate is evaporated, and the residue purified by chromatography on reversed phase silica gel; elution with acetonitrile/0.1% TFA:water/0.1% TFA gives 63 mg of the product 404. $^1$H NMR (DMSO-d$_6$) δ 10.85 (s, 1 H), 7.1-7.0 (m, 10 H), 5.80 (s, 2 H), 4.71 (s, 2 H), 3.51 (s, 3 H); LC/MS: 2.80 min, m/z 267 (M$^+$+1).

Example 154

2-[(Isopropoxy)methyl]-cis-4,5-diphenyl-4,5-dihydro-1H-imidazole trifluoroacetate (406)

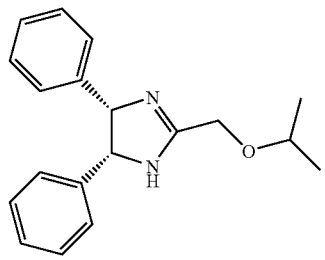

Step 1

Isopropoxyacetic acid ethyl ester (405)

To a solution of 2-propanol (0.776 mL, 10.0 mmol) in dichloromethane (33 mL) is added rhodium (II) acetate dimer (22 mg) followed by ethyl diazoacetate (1.05 mL, 10.0 mmol). The reaction mixture is stirred at RT for 30 min. The reaction mixture is filtered through Celite, and the filtrate is evaporated and the residue is vacuum distilled at 150° C. to give 750 mg of the product 405. $^1$H NMR (CDCl$_3$) δ 4.21 (q, 2 H), 4.06 (s, 2 H), 3.73 (m, 1 H), 1.29 (t, 3 H), 1.22 (s, 3 H), 1.19 (s, 3 H); MS: m/z 147 (M$^+$+1).

Step 2

2-[(Isopropoxy)methyl]-cis-4,5-diphenyl-4,5-dihydro-1H-imidazole trifluoroacetate (406)

To a solution of the diamine 1 (159 mg, 0.75 mmol) in toluene (2.5 mL) is added 2.0M trimethylaluminum in toluene (0.980 mL, 1.96 mmol) followed by 405 (110 mg, 0.75 mmol), and the solution is heated at 90° C. for 3 h, then cooled to rt. The reaction mixture is quenched with sat. sodium bicarbonate solution (1.5 mL) and EtOAc is added, and the mixture is dried (MgSO$_4$), and filtered. The filtrate is evaporated, and the residue purified by chromatography on reversed phase silica gel; elution with acetonitrile/0.1% TFA: water/0.1% TFA gives 56 mg of the product 406. $^1$H NMR (DMSO-d$_6$) δ 10.73 (s, 1 H), 7.2-7.0 (m, 10 H), 5.79 (s, 2 H), 4.72 (s, 2H), 3.86 (m, 1 H), 1.25 (s, 3 H), 1.23 (s, 3H); LC/MS: 3.05 min, m/z 295 (M$^+$+1).

Example 155

2-[(Cyclohexyloxy)methyl]-cis-4,5-diphenyl-4,5-dihydro-1H-imidazole trifluoroacetate (408)

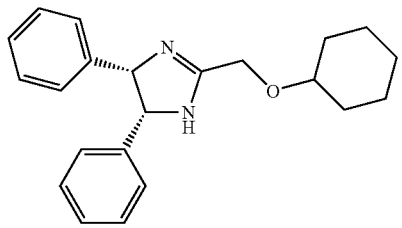

Step 1

Cyclohexyloxyacetic acid ethyl ester (407)

To a solution of cyclohexanol (1.0 g, 0.95 mmol) in dichloromethane (30 mL) is added rhodium (II) acetate dimer (44 mg) followed by ethyl diazoacetate (1.14 g, 10.0 mmol). The reaction mixture is stirred at RT for 20 min. The reaction mixture is diluted with Et$_2$O, filtered through Celite, and the filtrate is evaporated and the residue is vacuum distilled at 150° C. to give 1.57 g of the product 407. $^1$H NMR (CDCl$_3$) δ 4.23 (q, 2H), 4.10 (s, 2H), 3.33 (m, 1H), 1.93 (m, 2H), 1.74 (m, 2H), 1.54 (m, 1H), 1.4-1.1 (m, 8H)

Step 2

2-(Cyclohexyloxy)methyl-cis-4,5-diphenyl-4,5-dihydro-1H-imidazole trifluoroacetate (408)

To a solution of the diamine 1 (212 mg, 1.0 mmol) in toluene (6 mL) is added 2.0M trimethylaluminum in toluene (1.0 mL, 2.0 mmol) followed by a solution of 407 (186 mg, 1.0 mmol) in toluene (1 mL). The solution is heated at 60° C. for 2 h, then cooled to RT. The reaction mixture is quenched with sat. sodium bicarbonate solution (1.5 mL) and EtOAc is added, and the mixture is dried (MgSO$_4$), and filtered. The filtrate is evaporated, and the residue purified by chromatography on reversed phase silica gel; gradient elution with acetonitrile:water/0.1% TFA (30:70-100:0) gives 54 mg of the product 408. $^1$H NMR (CDCl$_3$) δ 7.10 (m, 6H), 6.89 (m, 4H), 5.67 (s, 2H), 4.96 (s, 2H), 3.53 (m, 1H), 1.99 (m, 2H), 1.76 (m, 2H), 1.57 (m, 1H), 1.2-1.05 (m, 5H); MS: m/z 335 (M$^+$+1).

Example 156

2-[(Tetrahydropyran-4-yloxy)methyl]-cis-4,5-diphenyl-4,5-dihydro-1H-imidazole trifluoroacetate (410)

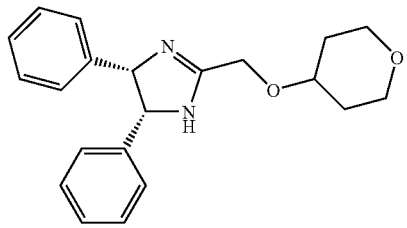

Step 1

(Tetrahydropyran-4-yloxy)acetic acid ethyl ester (409)

To a solution of tetrahydro-4H-pyran-4-one (1.0 g, 10.0 mmol) in cold (0° C.) THF is added 1.0M lithium aluminum hydride in THF (5 mL, 5.0 mmol). The reaction mixture is stirred at 0° C. for 15 min. followed by the sequential addition of water (0.190 mL), 5M sodium hydroxide (0.190 mL), and water (0.190 mL) and Et$_2$O. The mixture is filtered, and the filtrate is evaporated to give tetrahydro-4H-pyran-4-ol, which is dissolved in dichloromethane (30 mL). To the solution is added rhodium (II) acetate dimer (44 mg) followed by ethyl diazoacetate (1.25 g, 11.0 mmol). The reaction mixture is stirred at RT for 40 min. The reaction mixture is diluted with ethanol, filtered through Celite, and the filtrate is evaporated and the residue is vacuum distilled at 150° C. to give 1.67 g of the product 409. $^1$H NMR (CDCl$_3$) δ 4.21 (q, 2H), 4.11 (s, 2H), 3.95 (dt, 2H), 3.59 (m, 1H), 3.42 (dt, 2H), 1.91 (m, 2H), 1.62 (m, 2H), 1.28 (t, 3H); MS: m/z 189 (M$^+$+1).

Step 2

2-[(Tetrahydropyran-4-yloxy)methyl]-cis-4,5-diphenyl-4,5-dihydro-1H-imidazole trifluoroacetate (410)

To a solution of the diamine 1 (106 mg, 0.5 mmol) in toluene (4 mL) is added 2.0M trimethylaluminum in toluene (0.6 mL, 1.2 mmol) followed by a solution of 409 (95 mg, 0.5 mmol) in toluene (1 mL). The solution is heated at 70° C. for 6 h, then cooled to RT. The reaction mixture is quenched with sat. sodium bicarbonate solution (1 mL) and EtOAc is added, and the mixture is filtered. The filtrate is evaporated, and the residue purified by chromatography on reversed phase silica gel; gradient elution with acetonitrile:water/0.1% TFA (30:70-100:0) gives 109 mg of the product 410. $^1$H NMR (DMSO-d$_6$) δ 10.76 (s, 2H), 7.15-7.00 (m, 10H), 5.80 (s, 2H), 4.80 (s, 2H), 3.9-3.75 (m, 3H), 3.39 (dt, 2H), 1.96 (m, 2H), 1.56 (m, 2H); MS: m/z 337 (M$^+$+1).

Example 157

2-[(Cycloheptyloxy)methyl]-cis-4,5-diphenyl-4,5-dihydro-1H-imidazole trifluoroacetate (412)

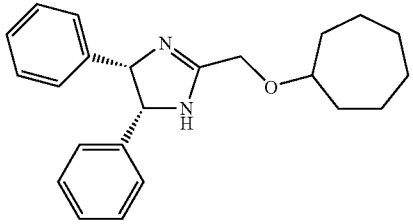

Step 1

Cycloheptyloxyacetic acid ethyl ester (411)

To a solution of cycloheptanol (0.600 mL, 5.0 mmol) in dichloromethane (15 mL) is added rhodium (II) acetate dimer (21 mg) followed by ethyl diazoacetate (0.60 g, 5.7 mmol). The reaction mixture is stirred at RT for 10 min. The reaction mixture is rotary evaporated, and the residue dissolved in Et$_2$O, filtered through Celite, and the filtrate is evaporated and the residue is vacuum distilled at 150° C. to give 0.960 g of the product 411. $^1$H NMR (CDCl$_3$) δ 4.21 (q, 2H), 4.06 (s, 2H), 3.50 (m, 1H), 1.93 (m, 2H), 1.7-1.4 (m, 8H), 1.4-1.3 (m, 2H), 1.28 (t, 3H); MS: m/z 201 (M$^+$+1).

Step 2

2-[(Cycloheptyloxy)methyl]-cis-4,5-diphenyl-4,5-dihydro-1H-imidazole trifluoroacetate (412)

To a solution of the diamine 1 (106 mg, 0.5 mmol) in toluene (4 mL) is added 2.0M trimethylaluminum in toluene (0.6 mL, 1.2 mmol) followed by a solution of 411 (100 mg, 0.5 mmol) in toluene (1 mL). The solution is heated at 70° C. for 6 h, then cooled to RT. The reaction mixture is quenched with sat. sodium bicarbonate solution (1 mL) and EtOAc is added, and the mixture is filtered. The filtrate is evaporated, and the residue purified by chromatography on reversed phase silica gel; gradient elution with acetonitrile:water/0.1% TFA (30:70-100:0) gives 58 mg of the product 412. $^1$H NMR (DMSO-d$_6$) δ 10.70 (s, 2H), 7.15-7.00 (m, 10H), 5.79 (s, 2H), 4.70 (s, 2H), 3.73 (m, 1H), 1.94 (m, 2H), 1.95 (m, 2H), 1.73-1.6 (m, 4H), 1.6-1.5 (m, 4H), 1.5-1.3 (m, 2H); MS: m/z 349 (M$^+$+1).

Example 158

2-[(Cyclooctyloxy)methyl]-cis-4,5-diphenyl-4,5-dihydro-1H-imidazole trifluoroacetate (414)

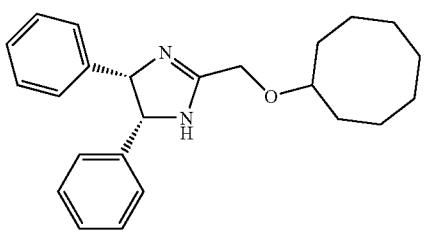

Step 1

Cyclooctyloxyacetic acid ethyl ester (413)

To a solution of cyclooctanol (640 mg, 4.9 mmol) in dichloromethane (15 mL) is added rhodium (II) acetate dimer (21 mg) followed by ethyl diazoacetate (0.60 g, 5.7 mmol). The reaction mixture is stirred at RT for 10 min. The reaction mixture is rotary evaporated, and the residue dissolved in Et$_2$O, filtered through Celite, and the filtrate is evaporated and the residue is vacuum distilled at 150° C. to give 397 mg of the product 413. $^1$H NMR (CDCl$_3$) δ 4.21 (q, 2H), 4.06 (s, 2H), 3.50 (m, 1H), 1.93 (m, 2H), 1.7-1.4 (m, 8H), 1.4-1.3 (m, 2H), 1.28 (t, 3H); MS: m/z 215 (M$^+$+1).

Step 2

2-[(Cyclooctyloxy)methyl]-cis-4,5-diphenyl-4,5-dihydro-1H-imidazole trifluoroacetate (414)

To a solution of the diamine 1 (106 mg, 0.5 mmol) in toluene (4 mL) is added 2.0M trimethylaluminum in toluene (0.6 mL, 1.2 mmol) followed by a solution of 413 (107 mg, 0.5 mmol) in toluene (1 mL). The solution is heated at 70° C. for 6 h, then cooled to RT. The reaction mixture is quenched with sat. sodium bicarbonate solution (1 mL) and EtOAc is added, and the mixture is filtered. The filtrate is evaporated, and the residue purified by chromatography on reversed phase silica gel; gradient elution with acetonitrile:water/0.1% TFA (30:70-100:0) gives 53 mg of the product 414. $^1$H NMR (CDCl$_3$) δ 7.15-7.0 (m, 6H), 6.88 (m, 4H), 5.67 (s, 2H), 4.93 (s, 2H), 3.71 (m, m, 1H), 1.95-1.8 (m, 2H), 1.8-1.6 (m, 4H), 1.6-1.4 (m, 8H); MS: m/z 363 (M$^+$+1).

Example 159

2-(Cyclohexylmethoxymethyl)-cis-4,5-diphenyl-4,5-dihydro-1H-imidazole (420)

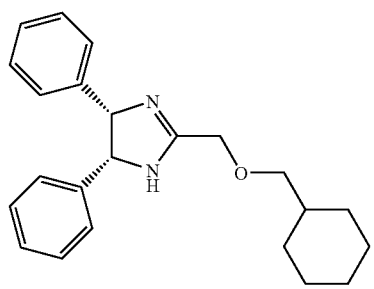

Step 1

(Cyclohexylmethoxy)acetic acid ethyl ester (419)

To a solution of cyclohexylmethanol (1.23 mL, 10.0 mmol) in dichloromethane (30 mL) is added rhodium (II) acetate dimer (11 mg) followed by ethyl diazoacetate (1.05 mL, 10.0 mmol). The reaction mixture is stirred at RT for 30 min. To the reaction mixture is added MeOH, and the reaction mixture is rotary evaporated, and the residue dissolved in Et$_2$O, filtered through Celite, and the filtrate is evaporated and the residue is vacuum distilled at to give 2.02 g of the product 419. $^1$H NMR (CDCl$_3$) δ 4.22 (q, 2 H), 4.05 (s, 2 H), 3.33 (d, 2 H), 1.8-1.5 (m, 7 H), 1.4-1.1 (m, 5 H), 1.1-0.9 (m, 2 H); MS: m/z 200 (M$^+$+1).

Step 2

2-(Cyclohexylmethoxymethyl)-cis-4,5-diphenyl-4,5-dihydro-1H-imidazole (420)

To a solution of the diamine 1 (276 mg, 1.3 mmol) in toluene (4 mL) is added 2.0M trimethylaluminum in toluene (1.62 mL, 3.24 mmol) followed by a solution of 419 (260 mg, 1.3 mmol) in toluene (1 mL). The solution is heated at 65° C. for 4 h, then cooled to RT. The reaction mixture is quenched with sat. sodium bicarbonate solution (3 mL) and EtOAc is added, and the mixture is filtered, dried (MgSO$_4$), and filtered. The filtrate is evaporated, and the residue purified by chromatography on silica gel; elution with EtOAc:MeOH:heptane (65:5:30) gives 31 mg of the product 420. $^1$H NMR (DMSO-d$_6$) δ 7.1 (bs, 1 H), 7.0-6.9 (m, 10 H), 5.22 (bs, 2 H), 4.21 (s, 2 H), 3.41-3.39 (d, 2 H), 1.8-1.6 (m, 5 H), 1.2-1.1 (m, 4 H), 1.0-0.9 (m, 2 H); LC/MS: 3.50 min, m/z 349 (M$^+$+1).

Example 160

[(cis-4,5-Diphenyl-4,5-dihydro-1H-imidazol-2-yl)methyl]benzylamine ditrifluoroacetate (422)

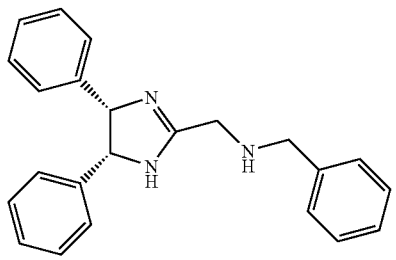

Step 1

(Benzylamino)acetic acid ethyl ester (421)

To a solution of ethyl bromoacetate (2.22 mL, 20.0 mmol) in 1,4-dioxane (40 mL) is added N,N-diisopropylethylamine (7.0 mL, 40.0 mol) and benzylamine (3.3 mL, 30.0 mmol), and the mixture is heated at 90° C. for 3 h. The reaction mixture is cooled to RT, dichloromethane is added, and the solution is washed with water, brine, then dried (MgSO$_4$), and filtered. The filtrate is evaporated, and the residue is residue purified by chromatography on silica gel; elution with EtOAc:MeOH:heptane (35:5:60) gives 2.9 g of the product 421. $^1$H NMR (CDCl$_3$) δ 7.4-7.3 (m, 6 H), 4.19 (q, 2 H), 3.80 (s, 2 H), 3.40 (s, 2 H), 1.25 (t, 3 H); MS: m/z 194 (M$^+$+1).

Step 2

[(cis-4,5-Diphenyl-4,5-dihydro-1H-imidazol-2-yl)methyl]benzylamine ditrifluoroacetate (422)

To a solution of the diamine 1 (637 mg, 3.0 mmol) in toluene (11 mL) is added 2.0M trimethylaluminum in toluene (3.9 mL, 7.8 mmol) followed by a solution of 421 (580 mg, 3.0 mmol) in toluene (2 mL). The solution is heated at 90° C. for 6.5 h, then cooled to RT. The reaction is quenched with sat. sodium bicarbonate solution (4 mL) and EtOAc:dichloromethane is added, and the mixture is filtered, and the filtrate is dried (MgSO$_4$), and filtered. The filtrate is evaporated, and the residue purified by chromatography on reversed phase silica gel; gradient elution with acetonitrile/0.1% TFA:water/0.1% TFA (30:70-100:0) gives 166 mg of the product 422. $^1$H NMR (DMSO-d$_6$) δ 10.61 (bs, 1 H), 7.5-7.3 (m, 5 H), 7.1-7.0 (m, 10 H), 5.75 (s, 2H), 4.04 (s, 2H), 4.00 (s, 2H); LC/MS: 2.95 min, m/z 342 (M$^+$+1).

Example 161

2-[(2-Phenethyloxy)methyl]-cis-4,5-diphenyl-4,5-dihydro-1H-imidazole (424)

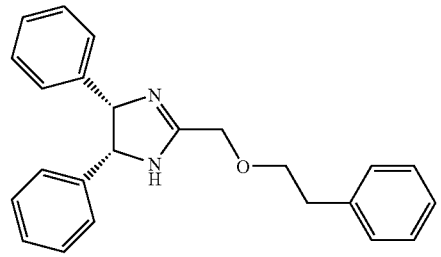

Step 1

(2-Phenethyloxy)acetic acid ethyl ester (423)

To a solution of 2-phenethyl alcohol (0.597 mL, 5.0 mmol) in dichloromethane (15 mL) is added rhodium (II) acetate dimer (6 mg) followed by ethyl diazoacetate (0.526 mL, 5.0 mmol). The reaction mixture is stirred at RT for 30 min. To the reaction mixture is added MeOH, and the reaction mixture is rotary evaporated, and the residue purified by chromatography on silica gel; elution with EtOAc:heptane (20:80) gives 713 mg of the product 423. $^1$H NMR (CDCl$_3$) δ 7.3-7.2 (m, 5 H), 4.20 (q, 2 H), 4.09 (s, 2 H), 3.75 (t, 2 H), 2.95 (t, 2 H), 1.29 (t, 3 H); MS: m/z 209 (M$^+$+1).

Step 2

2-[(2-Phenethyloxy)methyl]-cis-4,5-diphenyl-4,5-dihydro-1H-imidazole (424)

To a solution of the diamine 1 (318 mg, 1.5 mmol) in toluene (6 mL) is added 2.0M trimethylaluminum in toluene (2.25 mL, 4.5 mmol) followed by a solution of 423 (312 mg, 1.5 mmol) in toluene (2 mL). The solution is heated at 65° C. for 6 h, then cooled to RT. The reaction is quenched with sat. sodium bicarbonate solution (3 mL) and EtOAc: is added, and the mixture is filtered, and the filtrate is dried (MgSO$_4$), and filtered. The filtrate is evaporated, and the residue purified by chromatography on silica gel; elution with EtOAC:MeOH:heptane (70:10:20) gives 84 mg of the product 424. $^1$H NMR (DMSO-d$_6$) δ 7.27 (d, 4 H), 7.2-7.1 (m, 1 H), 7.0-6.9 (m, 11 H), 5.19 (bs, 2 H), 4.24 (s, 2 H), 3.78 (t, 2 H), 2.89 (t, 2 H); LC/MS: 3.33 min, m/z 357 (M$^+$+1).

Example 162

1-[(cis-4,5-Diphenyl-4,5-dihydro-1H-imidazol-2-yl)methyl]-1H-pyridin-2-one (426)

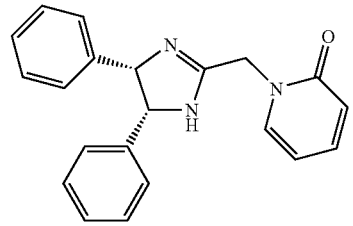

Step 1

(2-Oxo-2H-pyridin-1-yl)acetic acid ethyl ester (425)

To a suspension of 60% sodium hydride dispersion in mineral oil (220 mg, 5.5 mmol) in cold (0° C.) THF is added 2-pyridone (475 mg, 5.0 mmol) in THF (4 mL) and DMPU (2 mL) followed by ethyl bromoacetate (0.556 mL, 5.0 mmol), and the reaction is stirred at RT for 1 h. The reaction is quenched with water, and extracted with EtOAc. The organic layer is separated, evaporated, and the residue purified by chromatography on silica gel; elution with EtOAC:dichloromethane:heptane (50:30:20) gives 690 mg of the product 425. $^1$H NMR (CDCl$_3$) δ 7.35 (m, 1H), 7.21 (d, 1H), 6.57 (d, 1H), 6.19 (t, 1H), 4.62 (s, 2H), 4.23 (q, 2H), 1.28 (t, 3H); MS: m/z 182 (M$^+$+1).

Step 2

1-[(cis-4,5-Diphenyl-4,5-dihydro-1H-imidazol-2-yl) methyl]-1H-pyridin-2-one (426)

To a solution of the diamine 1 (106 mg, 0.5 mmol) in toluene (4 mL) is added 2.0M trimethylaluminum in toluene (0.6 mL, 1.2 mmol) followed by a solution of 425 (90 mg, 0.5 mmol) in toluene (1 mL). The solution is heated at 70° C. for 6 h, then cooled to RT. The reaction mixture is quenched with sat. sodium bicarbonate solution (1 mL) and EtOAc is added, and the mixture is filtered. The filtrate is evaporated, and the residue purified by chromatography on silica gel; elution with dichloromethane:MeOH (95:5) gives 23 mg of the product 426. $^1$H NMR (DMSO-d$_6$) δ 10.97 (s, 2H), 7.84 (dd, 1H) 7.58 (dt, 1H), 7.15-7.0 (m, 10H), 6.60 (d, 1H), 6.39 (t, 1H), 5.79 (s, 2H), 5.25 (s, 2H); MS: m/z 330 (M$^+$+1).

Example 163

2-[(2-Fluorophenoxy)methyl]-cis-4,5-bis-(3-fluorophenyl)-4,5-dihydro-1H-imidazole (427)

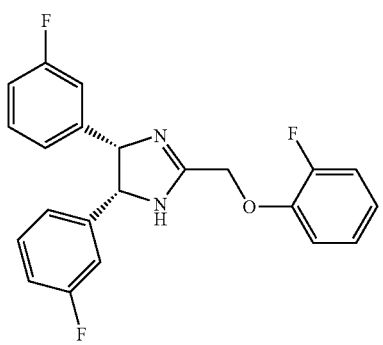

To a solution of the diamine 5 (248 mg, 1.0 mmol) in toluene (6 mL) is added 2.0M trimethylaluminum in toluene (1.0 mL, 2.0 mmol) followed by a solution of (2-fluorophenoxy)acetonitrile (384) (151 mg, 1.0 mmol) in toluene (1 mL). The solution is heated at 90° C. overnight, then cooled to RT. The reaction mixture is quenched with sat. sodium bicarbonate solution (2 mL) and EtOAc and water are added, and the organic solution is separated, washed with brine, dried (MgSO$_4$), and filtered. The filtrate is evaporated, and the residue purified by chromatography on silica gel; gradient elution with EtOAc:heptane (1:5-1:1) followed by trituration with Et$_2$O gives 17 mg of the product 427. LC/MS: 1.45 min, m/z 383 (M$^+$+1).

Example 164

2-[(3-Fluorophenoxy)methyl]-cis-4,5-bis-(3-fluorophenyl)-4,5-dihydro-1H-imidazole (428)

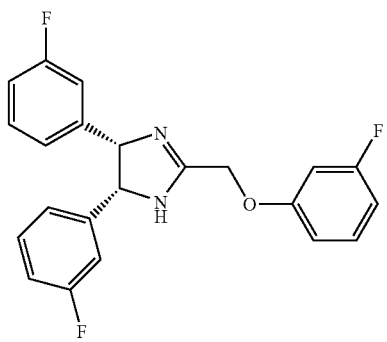

To a solution of the diamine 5 (248 mg, 1.0 mmol) in toluene (6 mL) is added 2.0M trimethylaluminum in toluene (1.0 mL, 2.0 mmol) followed by a solution of 3-fluorophenoxyacetonitrile (386) (151 mg, 1.0 mmol) in toluene (1 mL). The solution is heated at 70° C. overnight, then cooled to RT. The reaction mixture is quenched with sat. sodium bicarbonate solution (2 mL) and EtOAc and water are added, and the organic solution is separated, washed with brine, dried (MgSO$_4$), and filtered. The filtrate is evaporated, and the residue triturated with heptane:Et$_2$O to give 44 mg of the product 428. LC/MS: 1.46 min, m/z 383 (M$^+$+1).

Example 165

2-[(4-Fluorophenoxy)methyl]-cis-4,5-bis-(3-fluorophenyl)-4,5-dihydro-1H-imidazole (429)

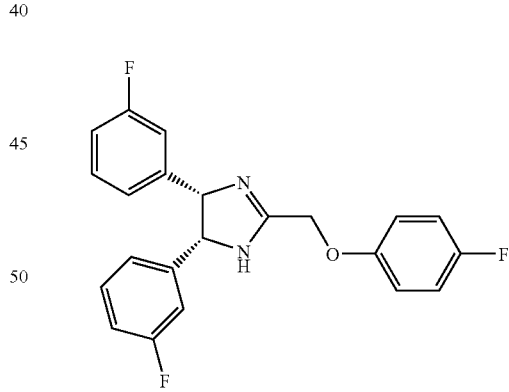

To a solution of the diamine 5 (248 mg, 1.0 mmol) in toluene (6 mL) is added 2.0M trimethylaluminum in toluene (1.0 mL, 2.0 mmol) followed by a solution of (4-fluorophenoxy)acetonitrile (388) (151 mg, 1.0 mmol) in toluene (1 mL). The solution is heated at 60° C. for 2.5 h, then cooled to RT. The reaction mixture is quenched with sat. sodium bicarbonate solution (2 mL) and EtOAc and water are added, and the organic solution is separated, washed with brine, dried (MgSO$_4$), and filtered. The filtrate is evaporated, and the residue crystallized from Et$_2$O to give 70 mg of the product 429. LC/MS: 1.44 min, m/z 383 (M$^+$+1).

Example 166

2-[(Phenoxy)methyl]-cis-4,5-diphenyl-4-methyl-4,5-dihydro-1H-imidazole trifluoroacetate (431)

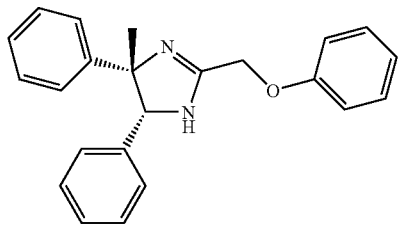

Step 1

Phenoxyacetic acid ethyl ester (430)

To a solution of phenol (1.88 g, 20.0 mmol) in DMF (40 mL) is added potassium carbonate (3.03 g, 22.0 mmol) and ethyl bromoacetate (2.34 mL, 21.0 mmol), and the mixture is stirred at 70° C. for 18 h. The mixture is cooled to RT, Et$_2$O is added, and the mixture is washed with water, brine, then dried (MgSO$_4$), and filtered. The filtrate is evaporated, and the residue is vacuum distilled to give 3.39 g of the product 430.

Step 2

2-[(Phenoxy)methyl]-cis-4,5-diphenyl-4-methyl-4,5-dihydro-1H-imidazole trifluoroacetate (431)

To a solution of the diamine 16 (226 mg, 1.0 mmol) in toluene (3 mL) is added 2.0M trimethylaluminum in toluene (1.3 mL, 2.6 mmol) followed by a solution of phenoxyacetic acid ethyl ester (430) (186 mg, 1.0 mmol) in toluene (1 mL). The solution is heated at 90° C. for 2 h, then cooled to RT. The reaction mixture is quenched with sat. sodium bicarbonate solution (0.5 mL), EtOAc is added, and the mixture is filtered. The filtrate is evaporated, and the residue is purified by chromatography on reversed phase silica gel; gradient elution with acetonitrile:water/0.1% TFA (30:70-100:0) gives 233 mg of the product 431. $^1$H NMR (CDCl$_3$) δ 7.35 (t, 2H), 7.11-7.0 (m, 9H), 6.86 (m, 2H, 6.77 (d, 2H), 5.50 (s, 2H), 5.15 (s, 1H), 1.98 (s, 3H); LC/MS: 3.26 min, m/z 343 (M$^+$+1).

Example 167

2-[(3-Fluorophenoxy)methyl]-cis-4,5-diphenyl-4-methyl-4,5-dihydro-1H-imidazole trifluoroacetate (433)

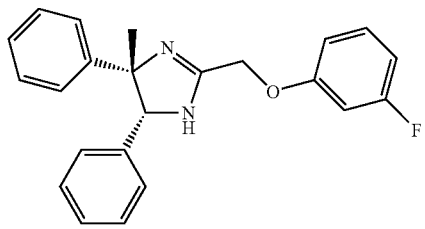

Step 1

3-Fluorophenoxyacetic acid ethyl ester (432)

To a solution of 3-fluorophenol (2.24 g, 20.0 mmol) in DMF (40 mL) is added potassium carbonate (3.03 g, 22.0 mmol) and ethyl bromoacetate (2.34 mL, 21.0 mmol), and the mixture is stirred at 70° C. for 18 h. The mixture is cooled to RT, Et$_2$O is added, and the mixture is washed with water, brine, then dried (MgSO$_4$), and filtered. The filtrate is evaporated, and the residue is vacuum distilled to give 3.2 g of the product 432.

Step 2

2-[(3-Fluorophenoxy)methyl]-cis-4,5-diphenyl-4-methyl-4,5-dihydro-1H-imidazole trifluoroacetate (433)

To a solution of the diamine 16 (113 mg, 0.5 mmol) in toluene (1.5 mL) is added 2.0M trimethylaluminum in toluene (0.65 mL, 1.30 mmol) followed by a solution of 432 (106 mg, 0.5 mmol) in toluene (1 mL). The solution is heated at 90° C. for 2 h, then cooled to RT. The reaction mixture is quenched with sat. sodium bicarbonate solution (0.4 mL), EtOAc is added, and the mixture is filtered. The filtrate is evaporated, and the residue is purified by chromatography on reversed phase silica gel; gradient elution with acetonitrile:water/0.1% TFA (30:70-100:0) gives 183 mg of the product 433. $^1$H NMR (CDCl$_3$) δ 7.27 (t, 1H), 7.1-6.9 (m, 6H), 6.82-6.72 (m, 7H), 5.31 (s, 2H), 5.12 (s, 1H), 1.93 (s, 3H); LC/MS: 3.32 min, m/z 361 (M$^+$+1).

Example 168

2-(Cyclohexylmethoxy)-cis-4,5-diphenyl-4-methyl-4,5-dihydro-1H-imidazole trifluoroacetate (434)

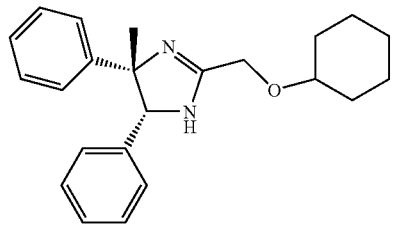

To a solution of the diamine 16 (113 mg, 0.5 mmol) in toluene (1.5 mL) is added 2.0M trimethylaluminum in toluene (0.65 mL, 1.30 mmol) followed by a solution of cyclohexyloxyacetic acid ethyl ester (407) (100 mg, 0.5 mmol) in toluene (1 mL). The solution is heated at 90° C. for 2 h, then cooled to RT. The reaction mixture is quenched with sat. sodium bicarbonate solution (0.4 mL), EtOAc is added, and the mixture is filtered. The filtrate is evaporated, and the residue is purified by chromatography on reversed phase silica gel; gradient elution with acetonitrile:water/0.1% TFA (30:70-100:0) gives 163 mg of the product 434. $^1$H NMR (CDCl$_3$) δ 11.0 (bs, 1H), 9.6 (bs, 1H), 7.13-7.05 (m, 6H), 6.87 (m, 2H), 6.83 (m, 2H), 5.20 (s, 1H), 4.95 (d, 1H), 4.93 (d, 1H), 3.50 (m, 1H), 2.03 (s, 3H), 2.0 (m, 2H), 1.76 (m, 2H), 1.59 (m, 1H), 1.4-1.1 (m, 5H); LC/MS: 3.42 min, m/z 349 (M$^+$+1).

Example 169

Mixture of 2-[(3-Fluorophenoxy)methyl]-cis-4,5-bis-(3-fluorophenyl)-1,4-dimethyl-4,5-dihydro-1H-imidazole trifluoroacetate and 2-[(3-Fluorophenoxy)methyl]-cis-4,5-bis-(3-fluorophenyl)-1,5-dimethyl-4,5-dihydro-1H-imidazole trifluoroacetate (435)

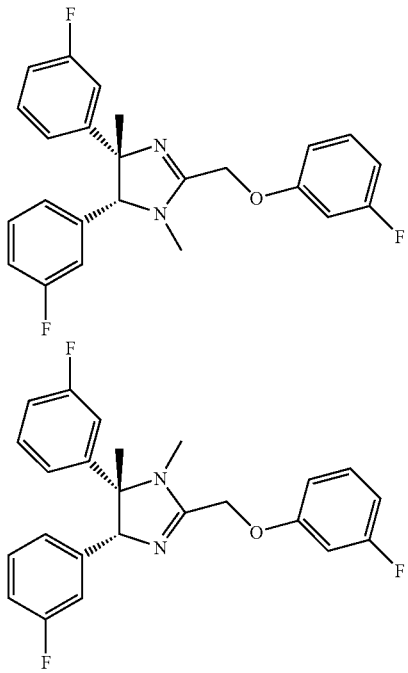

To a solution of 2-[(3-fluorophenoxy)methyl]-cis-4,5-bis-(3-fluorophenyl)-4-methyl-4,5-dihydro-1H-imidazole (433) (104 mg, 0.29 mmol) in cold (0° C.) DMF (1 mL) is added sodium hydride (60% dispersion in mineral oil) (12 mg, 0.3 mmol), and then methyl iodide (0.018 mL, 0.29 mmol). The reaction mixture is stirred for 1 h, quenched with ammonium chloride solution, diluted with EtOAc, and the organic layer is separated, washed with water, brine, then dried (MgSO$_4$), and filtered. The filtrate is evaporated, and the residue is purified by chromatography on reversed phase silica gel; gradient elution with acetonitrile:water/0.1% TFA (35:65-100:0) gives 92 mg of the product 435 as a 3:1 mixture of 1-methyl and 3-methyl diastereomers.

Example 170

2-[2-(2-Chlorophenoxy)ethoxymethyl]-1-[(cis-4,5-diphenyl-4-methyl-4,5-dihydro-1H-imidazole trifluoroacetate (437)

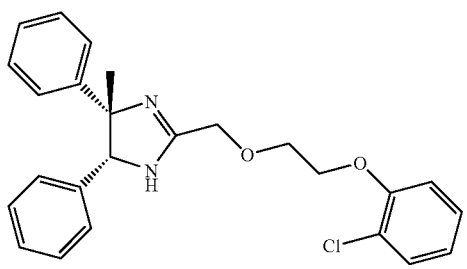

Step 1

2-[2-(2-Chlorophenoxy)ethoxy]acetic acid ethyl ester (436)

To a solution of 2-(2-chlorophenoxy)ethanol (1.73 mL, 10.0 mmol) in dichloromethane (20 mL) is added rhodium (II) acetate dimer (11 mg) followed by ethyl diazoacetate (1.05 mL, 10.0 mmol). The reaction mixture is stirred at rt for 20 min. To the reaction mixture is added MeOH followed by rotary evaporated, and the residue is purified by chromatography on silica gel; elution with EtOAc:heptane (25:75) gives 1.36 g of the product 436. $^1$H NMR (CDCl$_3$) δ 7.35 (d, 1 H), 7.19 (d, 1 H), 6.95-6.90 (m, 2 H), 4.30 (s, 2 H), 4.25-4.15 (m, 4 H), 4.0 (t, 2 H), 1.2 (t, 3 H); MS: m/z 259 (M$^+$+1).

Step 2

2-[2-(2-Chlorophenoxy)ethoxymethyl]-1-[(cis-4,5-diphenyl-4-methyl-4,5-dihydro-1H-imidazole trifluoroacetate (437) (Scheme 11, Method b)

To a solution of the diamine 16 (113 mg, 0.5 mmol) in toluene (2 mL) is added 2.0M trimethylaluminum in toluene (0.65 mL, 1.30 mmol) followed by a solution of 436 (129 mg, 0.5 mmol) in toluene (1 mL). The solution is heated at 90° C. for 9 h, then cooled to rt. The reaction mixture is quenched with sat. sodium bicarbonate solution (0.4 mL), EtOAc is added, and the mixture is dried (MgSO$_4$), and filtered. The filtrate is evaporated, and the residue is purified by chromatography on reversed phase silica gel; gradient elution with acetonitrile/0.1% TFA:water/0.1% TFA (40:60-85:15) gives 32 mg of the product 437. $^1$H NMR (DMSO-d$_6$) δ 11.02 (s, 1 H), 10.81 (s, 1 H), 7.46 (d, 1 H), 7.34 (m, 1 H), 7.03 (m, 11 H), 5.34 (s, 1 H), 4.97 (s, 2 H), 4.34 (m, 2 H), 4.10 (m, 2 H), 1.93 (s, 3 H); LC/MS: 3.29 min, m/z 421 (M$^+$+1).

Example 171

2-[(2,3-Dihydrobenzo-1,4-dioxan-2-yl)methoxymethyl]-cis-4,5-diphenyl-4-methyl-4,5-dihydro-1H-imidazole trifluoroacetate (439)

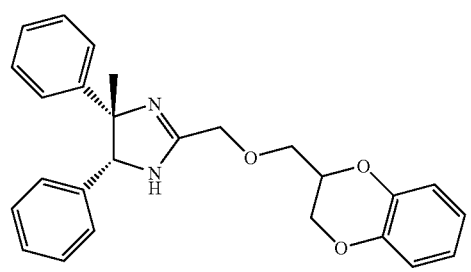

Step 1

(2,3-Dihydrobenzo-1,4-dioxan-2-yl)acetic acid ethyl ester (438)

To a solution of 2-hydroxymethyl-1,4-benzodioxan (1.66 mL, 10.0 mmol) in dichloromethane (20 mL) is added rhodium (II) acetate dimer (11 mg) followed by ethyl diazoacetate (1.05 mL, 10.0 mmol). The reaction mixture is stirred at rt for 20 min. To the reaction mixture is added MeOH, and the reaction mixture is rotary evaporated, and the residue purified by chromatography on silica gel; elution with EtOAc:heptane (25:75) gives 0.242 g of the product 438. $^1$H NMR (CDCl$_3$) δ 6.9-6.8 (m, 4 H), 4.4-4.1 (m, 7 H), 3.9-3.8 (m, 2 H), 1.30 (t, 3 H); MS: m/z 253 (M$^+$+1).

Step 2

2-[(2,3-Dihydrobenzo-1,4-dioxan-2-yl)methoxymethyl]-cis-4,5-diphenyl-4-methyl-4,5-dihydro-1H-imidazole trifluoroacetate (439)

To a solution of the diamine 16 (113 mg, 0.5 mmol) in toluene (2 mL) is added 2.0M trimethylaluminum in toluene (0.65 mL, 1.30 mmol) followed by a solution of 438 (126 mg, 0.5 mmol) in toluene (1 mL). The solution is heated at 90° C. for 9 h, then cooled to rt. The reaction mixture is quenched with sat. sodium bicarbonate solution (0.4 mL), EtOAc is added, and the mixture is dried (MgSO$_4$), and filtered. The filtrate is evaporated, and the residue is purified by chromatography on reversed phase silica gel; gradient elution with acetonitrile/0.1% TFA:water/0.1% TFA (40:60-85:15) gives 36 mg of the product 439. $^1$H NMR (DMSO-d$_6$) δ 11.00 (s, 1H), 10.80 (s, 1 H), 7.1-7.0 (m, 10 H), 6.9-6.8 (m, 4 H), 5.35 (m, 1 H), 4.89 (s, 2 H), 4.5-3.7 (m, 5 H), 1.94 (s, 3 H); LC/MS: 2.82 min, m/z 415 (M$^+$+1).

Example 172

2-[[(Phenoxy)ethoxy]methyl]-cis-4,5-diphenyl-4-methyl-4,5-dihydro-1H-imidazole hydrochloride (441)

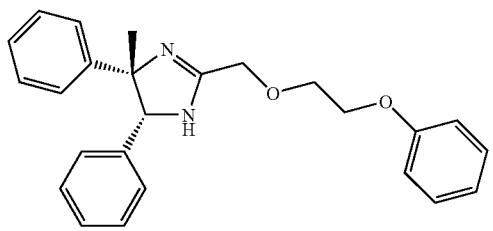

Step 1

(2-Phenoxy)ethoxyacetic acid ethyl ester (440)

To a solution of 2-phenoxyethan-1-ol (1.5 mL, 12.7 mmol) in dichloromethane (50 mL) is added rhodium (II) acetate dimer (10 mg) followed by ethyl diazoacetate (1.1 mL, 10.5 mmol). The reaction mixture is stirred at rt overnight. The reaction mixture is diluted with heptane, and filtered. The filtrate is evaporated, and the residue vacuum distilled to give 1.95 g of the product 440. $^1$H NMR (CDCl$_3$) δ 7.40-7.25 (m, 2 H), 7.10-6.90 (m, 3 H), 4.30-4.15 (m, 5 H), 4.15-4.05 (m, 1 H), 4.05-3.90 (s, 2 H), 1.28 (t, 3 H)

Step 2

2-[[(Phenoxy)ethoxy]methyl]-cis-4,5-diphenyl-4-methyl-4,5-dihydro-1H-imidazole hydrochloride (441)

To a solution of the diamine 16 (452 mg, 2.0 mmol) in toluene (6 mL) is added 2.0M trimethylaluminum in toluene (2.5 mL, 5.0 mmol) followed by a solution of 440 (448 mg, 2.0 mmol) in toluene (1 mL). The solution is heated at 110° C. for 2 h, then cooled to rt. The reaction mixture is quenched with sat. sodium bicarbonate solution (0.4 mL), EtOAc is added, and the mixture is filtered, washed with brine, then dried (MgSO$_4$), and filtered. The filtrate is evaporated, and the residue is purified by chromatography on silica gel; elution with dichloromethane:MeOH:NH$_4$OH (95:5:1) followed by treatment with hydrogen chloride in Et$_2$O gives 151 mg of the product 441. $^1$H NMR (CDCl$_3$) δ 7.30-7.10 (m, 4 H), 7.10-6.70 (m, 12 H), 4.81 (bs, 1 H), 4.65-4.45 (m, 2 H), 4.30-4.10 (m, 2 H), 4.10-3.90 (m, 2 H), 1.90 (s, 3 H); MS: m/z 387 (M$^+$+1).

Example 173

2-[(Benzylsulfanyl)methyl]-cis-4,5-diphenyl-4-methyl-4,5-dihydro-1H-imidazole (442)

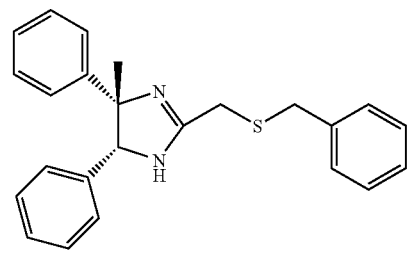

To a solution of the diamine 16 (170 mg, 0.75 mmol) in toluene (2 mL) is added 2.0M trimethylaluminum in toluene (0.980 mL, 1.95 mmol) followed by a solution of (benzylsulfanyl)acetic acid ethyl ester (402) (158 mg, 0.75 mmol) in toluene (1 mL). The solution is heated at 90° C. for 2 h, then cooled to rt. The reaction mixture is quenched with sat. sodium bicarbonate solution (0.4 mL), EtOAc is added, and the mixture is filtered, and the filtrate is dried (MgSO$_4$), and filtered. The filtrate is evaporated, and the residue is purified by chromatography on silica gel; elution with dichloromethane:MeOH (95:5) gives 20 mg of the product 442. $^1$H NMR (DMSO-d$_6$) δ 7.4-7.3 (m, 5 H), 7.0-6.9 (m, 10 H), 4.77 (bs, 1 H), 3.91 (s, 2 H), 3.50 (s, 2 H), 1.79 (s, 3 H); LC/MS: 3.32 min, m/z 373 (M$^+$+1).

Example 174

2-[(Cyclopentyloxy)methyl]-cis-4,5-diphenyl-4-methyl-4,5-dihydro-1H-imidazole hydrochloride (445)

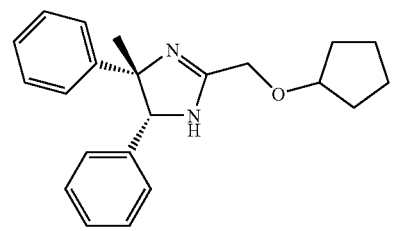

Step 1

Cyclopentyloxyacetic acid ethyl ester (444)

To a solution of cyclopentanol (0.91 mL, 9.5 mmol) in dichloromethane (20 mL) is added rhodium (II) acetate dimer (10 mg) followed by ethyl diazoacetate (0.95 mL, 9.0 mmol). The reaction mixture is stirred at rt overnight. The reaction mixture is diluted with heptane, and filtered. The filtrate is evaporated, and the residue vacuum distilled at 150° C. to give 1.04 g of the product 444. $^1$H NMR (CDCl$_3$) δ 4.21 (q, 2 H), 4.04 (s, 2 H), 1.85-1.45 (m, 8 H), 1.29 (t, 3 H)

Step 2

2-[(Cyclopentyloxy)methyl]-cis-4,5-diphenyl-4-methyl-4,5-dihydro-1H-imidazole hydrochloride (445)

To a solution of the diamine 16 (226 mg, 1.0 mmol) in toluene (3 mL) is added 2.0M trimethylaluminum in toluene (1.3 mL, 2.6 mmol) followed by a solution of 444 (172 mg, 1.0 mmol) in toluene (1 mL). The solution is heated at 110° C. overnight, then cooled to rt. The reaction mixture is quenched with sat. sodium bicarbonate solution (1 mL), EtOAc is added, and the mixture is filtered, and the filtrate dried (MgSO$_4$), and filtered. The filtrate is evaporated, and the residue is purified by chromatography on silica gel; elution with dichloromethane:MeOH:NH$_4$OH (95:5:1) followed by treatment with hydrogen chloride in Et$_2$O gives 60 mg of the product 445. $^1$H NMR (CDCl$_3$) δ 7.50-7.25 (m, 2 H), 7.10-6.80 (m, 8 H), 4.95-4.70 (m, 1 H), 4.50-4.30 (m, 2 H), 4.20-4.05 (m, 1 H), 2.00-1.40 (m, 11 H); MS: m/z 335 (M$^+$+1).

Example 175

2-[(1-Ethynyl-1-butoxy)methyl]-cis-4,5-diphenyl-4-methyl-4,5-dihydro-1H-imidazole hydrochloride (447)

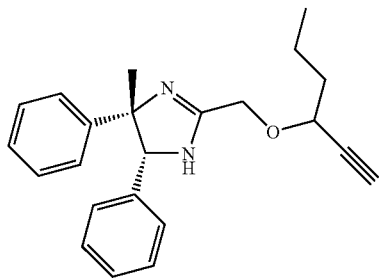

Step 1

(1-Ethynylbutoxy)acetic acid ethyl ester (446)

To a solution of 1-hexyn-3-ol (981 mg, 10.0 mmol) in dichloromethane (20 mL) is added rhodium (II) acetate dimer (10 mg) followed by ethyl diazoacetate (1.0 mL, 9.0 mmol). The reaction mixture is stirred at rt for 6 h. The reaction mixture is diluted with heptane, and filtered. The filtrate is evaporated, and the residue purified by chromatography on silica gel: elution with EtOAc:heptane (25:75) gives 900 mg of the product 446. $^1$H NMR (CDCl$_3$) δ 4.35-4.10 (m, 5 H), 2.43 (s, 1 H), 1.90-1.65 (m, 2 H), 1.65-1.40 (m, 2 H), 1.40-1.20 (m, 3 H), 0.95 (t, 3 H)

Step 2

2-[(1-Ethynyl-1-butoxy)methyl]-cis-4,5-diphenyl-4-methyl-4,5-dihydro-1H-imidazole hydrochloride (447)

To a solution of the diamine 16 (226 mg, 1.0 mmol) in toluene (3 mL) is added 2.0M trimethylaluminum in toluene (1.25 mL, 2.5 mmol) followed by a solution of 446 (184 mg, 1.0 mmol) in toluene (1 mL). The solution is heated at 110° C. for 3 h, then cooled to rt. The reaction mixture is quenched with sat. sodium bicarbonate solution (1 mL), EtOAc is added, and the mixture is filtered, and the filtrate dried (MgSO$_4$), and filtered. The filtrate is evaporated, and the residue is purified by chromatography on silica gel; elution with dichloromethane:MeOH:NH$_4$OH (95:5:1) followed by treatment with hydrogen chloride in Et$_2$O gives 131 mg of the product 447. $^1$H NMR (CDCl$_3$) δ 7.10-6.80 (m, 10 H), 4.82 (bs, 1 H), 4.70 (t, 1 H), 4.43 (t, 1 H), 4.23 (t, 1 H), 2.50 (s, 1 H), 1.95-1.65 (m, 5 H), 1.65-1.40 (m, 2 H), 1.10-0.95 (m, 3 H); MS: m/z 346 (M$^+$+1).

Example 176

2-[(Dicyclopropylmethoxy)methyl]-cis-4,5-diphenyl-4-methyl-4,5-dihydro-1H-imidazole hydrochloride (449)

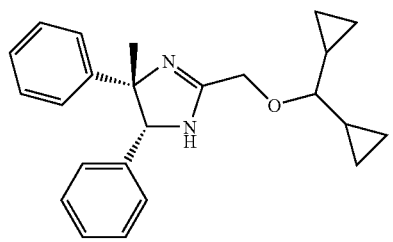

Step 1

(Dicyclopropylmethoxy)acetic acid ethyl ester (448)

To a solution of dicyclopropylmethan-1-ol (1.5 mL, 12.7 mmol) in dichloromethane (20 mL) is added rhodium (II) acetate dimer (10 mg) followed by ethyl diazoacetate (1.26 mL, 12.0 mmol). The reaction mixture is stirred at rt for 48 h. The reaction mixture is diluted with heptane, and filtered. The filtrate is evaporated, and the residue is vacuum distilled at 170° C. to give 1.24 g of the product 448.

Step 2

2-[(Dicyclopropylmethoxy)methyl]-cis-4,5-diphenyl-4-methyl-4,5-dihydro-1H-imidazole hydrochloride (449)

To a solution of the diamine 16 (452 mg, 2.0 mmol) in toluene (6 mL) is added 2.0M trimethylaluminum in toluene (2.5 mL, 5.0 mmol) followed by a solution of 448 (396 mg, 2.0 mmol) in toluene (1 mL). The solution is heated at 110° C. overnight, then cooled to rt. The reaction mixture is quenched with sat. sodium bicarbonate solution (1 mL), EtOAc is added, and the mixture is filtered, and the filtrate is washed with brine, dried (MgSO$_4$), and filtered. The filtrate is evaporated, and the residue is purified by chromatography on silica gel; elution with dichloromethane:MeOH:NH$_4$OH (95:5:1) followed by treatment with hydrogen chloride in Et$_2$O gives 118 mg of the product 449. LC/MS: 2.90 min, m/z 361 (M$^+$+1).

Example 177

2-[(Cyclopentylmethoxy)methyl]-cis-4,5-diphenyl-4-methyl-4,5-dihydro-1H-imidazole hydrochloride (451)

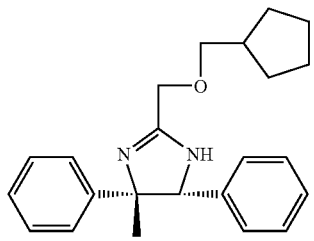

Step 1

(Cyclopentylmethoxy)acetic acid ethyl ester (450)

To a solution of cyclopentanemethan-1-ol (1.2 mL, 11.1 mmol) in dichloromethane (30 mL) is added rhodium (II) acetate dimer (10 mg) followed by ethyl diazoacetate (1.23 mL, 11.6 mmol). The reaction mixture is stirred at rt overnight. The reaction mixture is diluted with heptane, and filtered. The filtrate is evaporated, and the residue is vacuum distilled at 150° C. to give 1.42 g of the product 450. $^1$H NMR (CDCl$_3$) δ 4.22 (q, 2 H), 4.07 (s, 2 H), 3.40 (d, 2 H), 2.30-2.10 (m, 1 H), 11.90-1.65 (m, 2 H), 1.65-1.45 (m, 4 H), 1.40-1.15 (m, 5 H).

Step 2

2-[(Cyclopentylmethoxy)methyl]-cis-4,5-diphenyl-4-methyl-4,5-dihydro-1H-imidazole hydrochloride (451)

To a solution of the diamine 16 (452 mg, 2.0 mmol) in toluene (6 mL) is added 2.0M trimethylaluminum in toluene (2.6 mL, 5.2 mmol) followed by a solution of 450 (372 mg, 2.0 mmol) in toluene (1 mL). The solution is heated at 110° C. for 6 h, then cooled to rt. The reaction mixture is quenched with sat. sodium bicarbonate solution (1 mL), EtOAc:MeOH: dichloromethane (8:1:1) is added, and the mixture is filtered, and the filtrate is washed with brine, dried (MgSO$_4$), and filtered. The filtrate is evaporated, and the residue is purified by chromatography on silica gel; elution with dichloromethane:MeOH:NH$_4$OH (95:5:1) followed by treatment with hydrogen chloride in Et$_2$O gives 153 mg of the product 451. $^1$H NMR (CDCl$_3$) δ 7.20-6.80 (m, 10 H), 5.19 (s, 1 H), 5.05 (s, 2 H), 3.56 (d, 2 H), 1.75-1.45 (m, 10 H), 1.35-1.20 (m, 3 H); LC/MS: 3.34 min, m/z 349 (M$^+$+1).

Example 178

2-[(1-Cyclopentyl-1-ethoxy)methyl]-cis-4,5-diphenyl-4-methyl-4,5-dihydro-1H-imidazole hydrochloride (453)

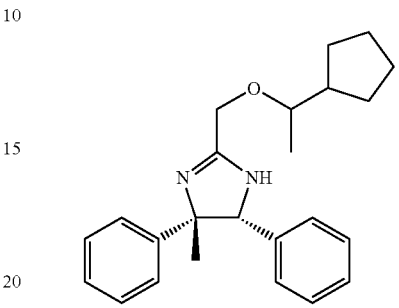

Step 1

(1-Cyclopentylethoxy)acetic acid ethyl ester (452)

To a solution of 1-cyclopentylethan-1-ol (1.14 g, 10.0 mmol) in dichloromethane (20 mL) is added rhodium (II) acetate dimer (10 mg) followed by ethyl diazoacetate (0.95 mL, 9.03 mmol). The reaction mixture is stirred at rt for 0.5 h. The reaction mixture is diluted with heptane, and filtered. The filtrate is evaporated, and the residue is purified by chromatography on silica gel; elution with EtOAc:heptane (1:9) gives 0.81 g of the product 452. $^1$H NMR (CDCl$_3$) δ 4.30-4.15 (m, 2 H), 4.09 (d, 2 H), 3.25-3.15 (m, 1 H), 2.00-1.78 (m, 2 H), 1.75-1.35 (m, 6 H), 1.29 (t, 3 H), 1.15 (d, 3 H).

Step 2

2-[(1-Cyclopentyl-1-ethoxy)methyl]-cis-4,5-diphenyl-4-methyl-4,5-dihydro-1H-imidazole hydrochloride (453)

To a solution of the diamine 16 (226 mg, 1.0 mmol) in toluene (3 μL) is added 2.0M trimethylaluminum in toluene (1.30 mL, 2.6 mmol) followed by a solution of 452 (200 mg, 1.0 mmol) in toluene (0.5 mL). The solution is heated at 100° C. for 4 h, then cooled to rt. The reaction mixture is quenched with sat. sodium bicarbonate solution (1 mL), EtOAc:MeOH: dichloromethane (10:1:2) is added, and the mixture is filtered. The filtrate is evaporated, and the residue is purified by chromatography on silica gel; elution with dichloromethane: MeOH: (94:6) followed by treatment with hydrogen chloride in Et$_2$O gives 180 mg of the product 453. $^1$H NMR (CDCl$_3$) δ 7.20-6.85 (m, 10 H), 5.30-5.05 (m, 3 H), 3.55-3.45 (m, 1 H), 2.05-1.95 (m, 4 H), 1.80-1.55 (m, 6 H), 1.35-0.90 (m, 6 H); LC/MS: 3.44 min, m/z 363 (M$^+$+1).

Example 179

2-[(1,3-Dioxan-5-yl)oxymethyl]-cis-4,5-diphenyl-4-methyl-4,5-dihydro-1H-imidazole hydrochloride (455)

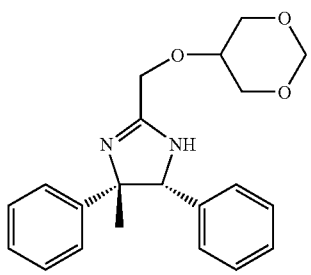

Step 1

(1,3-Dioxan-5-yl)acetic acid ethyl ester (454)

To a solution of 1,3-dioxan-5-ol (1.04 g, 10.0 mmol) in dichloromethane (20 mL) is added rhodium (II) acetate dimer (10 mg) followed by ethyl diazoacetate (0.95 mL, 9.03 mmol). The reaction mixture is stirred at rt for 4 h. The reaction mixture is diluted with heptane and filtered. The filtrate is evaporated, and the residue is purified by chromatography on silica gel; elution with EtOAc:heptane (1:4) gives 0.65 g of the product 454. $^1$H NMR (CDCl$_3$) δ 5.04 (s, 1 H), 4.89 (s, 1 H), 4.25-4.20 (m, 5 H), 3.98 (dd, 1 H), 3.78 (dd, 1 H), 3.65 (d, 1 H), 1.29 (t, 3 H).

Step 2

2-[(1,3-Dioxan-5-yl)oxymethyl]-cis-4,5-diphenyl-4-methyl-4,5-dihydro-1H-imidazole hydrochloride (455)

To a solution of the diamine 16 (226 mg, 1.0 mmol) in toluene (3 mL) is added 2.0M trimethylaluminum in toluene (1.30 mL, 2.6 mmol) followed by a solution of 454 (190 mg, 1.0 mmol) in toluene (0.5 mL). The solution is heated at 100° C. for 6 h, then cooled to rt. The reaction mixture is quenched with sat. sodium bicarbonate solution (1 µL), EtOAc:MeOH:dichloromethane (10:1:1) is added, and the mixture is filtered, and the filtrate is washed with brine, dried (MgSO$_4$), and filtered. The filtrate is evaporated, and the residue is purified by chromatography on silica gel; elution with dichloromethane:MeOH:NH$_4$OH (95:5:1) followed by treatment with hydrogen chloride in Et$_2$O gives 162 mg of the product 455. $^1$H NMR (CDCl$_3$) δ 7.05-6.85 (m, 10 H), 5.30-5.05 (m, 3 H), 4.90 (d, 1 H), 4.75 (d, 1 H), 4.32 (s, 1 H), 3.95-3.50 (m, 5 H), 2.00-1.90 (m, 3 H); LC/MS: 2.35 min, m/z 353 (M$^+$+1).

Example 180

2-(Methoxymethyl)-cis-4,5-diphenyl-4-methyl-4,5-dihydro-1H-imidazole trifluoroacetate (456)

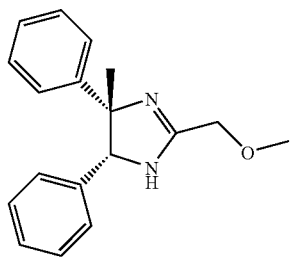

To a solution of the diamine 16 (170 mg, 0.75 mmol) in toluene (2.5 mL) is added 2.0M trimethylaluminum in toluene (0.980 mL, 1.96 mmol) followed by methoxyacetic acid methyl ester (0.74 mL, 0.75 mmol), and the solution is heated at 90° C. for 2.5 h, then cooled to rt. The reaction mixture is quenched with sat. sodium bicarbonate solution (1.5 mL) and EtOAc is added, and the mixture is filtered, and the filtrate dried (MgSO$_4$), and filtered. The filtrate is evaporated, and the residue purified by chromatography on reversed phase silica gel; gradient elution with acetonitrile/0.1% TFA:water/0.1% TFA (20:80-100:0) gives 51 mg of the product 456. $^1$H NMR (DMSO-d$_6$) δ 8.0 (d, 1 H), 7.4-7.0 (m, 10 H), 5.48 (d, 1 H), 3.78 (s, 2 H), 3.15 (s, 3 H), 1.62 (s, 3 H); LC/MS: 2.63 min, m/z 282 (M$^+$+1).

Example 181

2-(Isopropoxymethyl)-cis-4,5-diphenyl-4-methyl-4,5-dihydro-1H-imidazole trifluoroacetate (457)

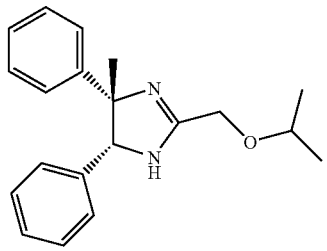

To a solution of the diamine 16 (170 mg, 0.75 mmol) in toluene (2.5 mL) is added 2.0M trimethylaluminum in toluene (0.980 mL, 1.96 mmol) followed by isopropoxyacetic acid ethyl ester (405) (110 mg, 0.75 mmol), and the solution is heated at 90° C. for 2.5 h, then cooled to rt. The reaction mixture is quenched with sat. sodium bicarbonate solution (1.5 mL) and EtOAc is added, and the mixture is filtered, and the filtrate dried (MgSO$_4$), and filtered. The filtrate is evaporated, and the residue purified by chromatography on reversed phase silica gel; gradient elution with acetonitrile/0.1% TFA:water/0.1% TFA (20:80-100:0) gives 44 mg of the product 457. $^1$H NMR (DMSO-d$_6$) δ 7.1-6.8 (m, 10 H), 4.73 (bs, 1 H), 4.21 (s, 2 H), 3.80 (m, 1 H), 3.32 (s, 3 H), 1.2-1.9 (m, 6 H); LC/MS: 3.12 min, m/z 309 (M$^+$+1).

Example 182

2-[[(Tetrahydropyran-2-yl)methoxy]methyl]-cis-4,5-diphenyl-4-methyl-4,5-dihydro-1H-imidazole trifluoroacetate (459)

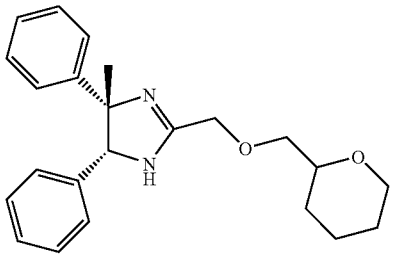

Step 1

(Tetrahydropyran-2-yl)methoxyacetic acid ethyl ester (458).

To a solution of tetrahydropyran-2-methanol (1.13 mL, 10.0 mmol) in dichloromethane (20 mL) is added rhodium (II) acetate dimer (11 mg) followed by ethyl diazoacetate (1.05 mL, 10.0 mmol). The reaction mixture is stirred at rt for 20 min. To the reaction mixture is added MeOH (0.5 mL), and the solvents rotary evaporated. The residue is purified by chromatography on silica gel; elution with EtOAc:heptane (30:70) gives 1.66 g of the product 458. $^1$H NMR (CDCl$_3$) δ 4.3-4.1 (m, 4 H), 4.0 (m, 1 H), 3.6-3.4 (m, 4 H), 1.85 (m, 1 H), 1.6-1.3 (m, 5 H), 1.25 (t, 3 H); MS: m/z 203 (M$^+$+1).

Step 2

2-[[(Tetrahydropyran-2-yl)methoxy]methyl]-cis-4,5-diphenyl-4-methyl-4,5-dihydro-1H-imidazole trifluoroacetate (459)

To a solution of the diamine 16 (136 mg, 0.60 mmol) in toluene (2.5 mL) is added 2.0M trimethylaluminum in toluene (0.78 mL, 1.56 mmol) followed by 458 (121 mg, 0.6 mmol), and the solution is heated at 90° C. for 4 h, then cooled to rt. The reaction mixture is quenched with sat. sodium bicarbonate solution (1 mL) and EtOAc is added, and the mixture is filtered, and the filtrate dried (MgSO$_4$), and filtered. The filtrate is evaporated, and the residue purified by chromatography on reversed phase silica gel; gradient elution with acetonitrile/0.1% TFA:water/0.1% TFA (40:60-100:0) gives 89 mg of the product 459. $^1$H NMR (DMSO-d$_6$) δ 10.75 (s, 1 H), 7.1-6.9 (m, 10 H), 5.35 (s, 1 H), 4.8 (s, 2 H), 3.9-3.5 (m, 4 H), 3.4 (m, 1 H), 1.94 (s, 3 H), 1.80 (m, 1 H), 1.6-1.4 (m, 4 H), 1.30 (m, 1 H); LC/MS: 2.64 min, m/z 365 (M$^+$+1).

Example 183

2-[[(Cyclopropyl)methoxy]methyl]-cis-4,5-diphenyl-4-methyl-4,5-dihydro-1H-imidazole trifluoroacetate (463)

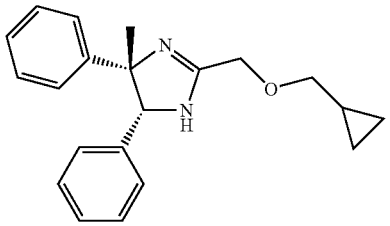

Step 1

(Cyclopropyl)methoxyacetic acid ethyl ester (462)

To a solution of cyclopropylmethanol (720 mg, 10.0 mmol) in dichloromethane (20 mL) is added rhodium (II) acetate dimer (10 mg) followed by ethyl diazoacetate (0.95 mL, 9.0 mmol). The reaction mixture is stirred at rt for 5 min. The reaction mixture is diluted with heptane, filtered through Celite, and the filtrate is evaporated and the residue is vacuum distilled at 150° C. to give 1.22 g of the product 462. $^1$H NMR (CDCl$_3$) δ 4.2 (q, 2H), 4.09 (s, 2H), 3.37 (d, 2H), 1.27 (t, 3H), 1.09 (m, 1H), 0.56-0.51 (m, 2H), 0.25-0.2 (m, 2H); MS: m/z 191 (M$^+$)

Step 2

2-[[(Cyclopropyl)methoxy]methyl]-cis-4,5-diphenyl-4-methyl-4,5-dihydro-1H-imidazole trifluoroacetate (463)

To a solution of the diamine 16 (113 mg, 0.50 mmol) in toluene (2 mL) is added 2.0M trimethylaluminum in toluene (0.65 mL, 1.30 mmol) followed by 462 (79 mg, 0.50 mmol), and the solution is heated at 80° C. for 3 h, then cooled to rt. The reaction mixture is quenched with sat. sodium bicarbonate solution (0.4 mL) and EtOAc:dichloromethane:MeOH (2:2:1) is added, and the mixture is filtered. The filtrate is evaporated, and the residue purified by chromatography on reversed phase silica gel; elution with acetonitrile:water/0.1% TFA gives 102 mg of the product 463. $^1$H NMR (DMSO-d$_6$) δ 11.0 (s, 1H), 10.79 (s, 1H), 7.1-6.9 (m, 10H), 5.35 (s, 1H), 4.77 (s, 2H), 3.52 (d, 2H), 1.94 (s, 3H), 1.15 (m, 1H), 0.58 (m, 2H), 0.31 (m, 2H); LC/MS: 2.62 min, nm/z 321 (M$^+$+1).

Example 184

2-[(2-Chlorophenoxy)methyl]-cis-4,5-diphenyl-4-methyl-4,5-dihydro-1H-imidazole hydrochloride (466)

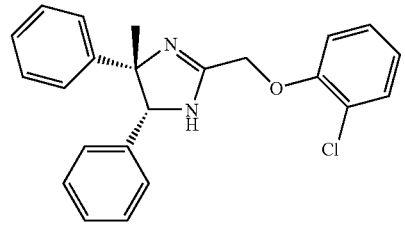

Step 1

(2-Chlorophenoxy)acetic acid ethyl ester (465)

To a solution of 2-chlorophenol (2.06 mL, 19.9 mmol) in DMF (40 mL) is added potassium carbonate (3.03 g, 21.9 mmol) and ethyl bromoacetate (2.3 mL, 20.7 mmol), and the mixture is stirred at 80° C. for 18 h. Et$_2$O is added, and the mixture is washed with water, brine, dried (MgSO$_4$), and filtered. The filtrate is evaporated, and the residue is purified by chromatography in silica gel; elution with EtOAc:dichloromethane:hexane (10:5:85) gives 4.17 g of the product 465. $^1$H NMR (CDCl$_3$) δ 7.38 (d, 1H), 7.21 (t, 1H), 6.92 (t, 1H), 6.84 (d, 1H), 4.70 (s, 2H), 4.27 (q, 2H), 1.29 (t, 3H); MS: m/z 215, 217 (M$^+$+1).

Step 2

2-[(2-Chlorophenoxy)methyl]-cis-4,5-diphenyl-4-methyl-4,5-dihydro-1H-imidazole hydrochloride (466)

To a solution of the diamine 16 (113 mg, 0.50 mmol) in toluene (1.5 mL) is added 2.0M trimethylaluminum in toluene (0.65 mL, 1.30 mmol) followed by 465 (103 mg, 0.50 mmol), and the solution is heated at 80° C. for 2.5 h, then cooled to rt. The reaction mixture is quenched with sat. sodium bicarbonate solution (0.4 mL) and EtOAc:dichloromethane:MeOH (2:2:1) is added, and the mixture is filtered. The filtrate is evaporated, and the residue purified by chromatography on silica gel; elution with dichloromethane:MeOH (95:5) followed by treatment with hydrogen chloride in Et$_2$O gives 141 mg of the product 466. $^1$H NMR (DMSO-d$_6$) δ 11.4 (bs, 1H), 11.2 (bs, 1H), 7.57 (dd, 1H), 7.5-7.35 (m, 2H), 7.2-6.95 (m, 11H), 5.53 (s, 2H), 5.41 (s, 1H), 1.96 (s, 3H); LC/MS: 2.77 min, m/z 377, 379 (M$^+$+1).

Example 185

2-(1-Phenoxyethyl)-cis-4,5-diphenyl-4-methyl-4,5-dihydro-1H-imidazole trifluoroacetate (468)

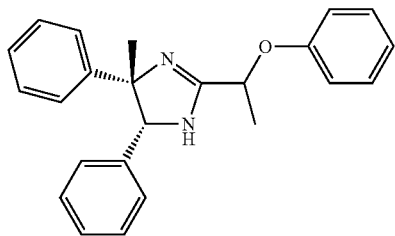

Step 1

N-(2-Amino-1,2-diphenylethyl)-2-phenoxypropionamide (467)

To a solution of 2-phenoxypropanoic acid (84 mg, 0.5 mmol) in dichloromethane (2 mL) is added DMF (0.010 mL) followed by oxalyl chloride (0.126 mL, 1.44 mmol), and the solution is stirred at rt for 30 min., then concentrated under nitrogen. The residue is dissolved in dichloromethane (1 mL), and is added to a solution of the diamine 16 (113 mg, 0.5 mmol) in dichloromethane (1.5 mL), and the reaction mixture is stirred at rt for 2 h. The reaction mixture is made basic with sat. sodium bicarbonate solution, and the organic layer is separated and evaporated. The residue is purified by chromatography on silica gel; elution with dichloromethane:MeOH (95:5) gives 166 mg of the product 467. $^1$H NMR (CDCl$_3$ Diastereomer A) δ 7.78 (bd, 1H), 7.4-6.8 (m, 13H), 6.40 (d, 2H), 5.16 (d, 1H), 4.76 (q, 1H), 1.57 (s, 3H), 1.53 (d, 3H); $^1$H NMR (CDCl$_3$ Diastereomer B) δ 7.63 (bd, 1H), 7.4-6.8 (m, 13H), 6.78 (d, 2H), 5.13 (d, 1H), 4.69 (q, 1H), 1.67 (d, 3H), 1.22 (s, 3H); LC/MS: 3.00 min, m/z 375 (M$^+$+1).

Step 2

2-(1-Phenoxyethyl)-cis-4,5-diphenyl-4-methyl-4,5-dihydro-1H-imidazole trifluoroacetate (468)

To a solution of 467 (160 mg, 0.44 mmol) in toluene (2.5 mL) is added 2.0M trimethylaluminum in toluene (0.65 mL, 1.30 mmol), and the solution heated at 93° C. for 2.5 h, then cooled to rt. The reaction mixture is quenched with sat. sodium bicarbonate solution (0.4 mL) and EtOAc:dichloromethane:MeOH (2:2:1) is added, and the mixture is filtered. The filtrate is evaporated, and the residue purified by chromatography on reversed phase silica gel; elution with acetonitrile:water/0.1% TFA gives 105 mg of the product 468. $^1$H NMR (DMSO-d$_6$) δ 11.25 (bd, 1H), 11.07 (bs, 1H), 7.45-7.38 (m, 2H), 7.2-6.9 (m, 10H), 6.9-6.74 (m, 3H), 5.73 (q, 1H), 5.34 (d, 1H), 1.90 (s, 3H), 1.79 (d, 3H); LC/MS: 3.13 min, m/z 357 (M$^+$+1).

Example 186

2-[(Cyclobutoxy)methyl]-cis-4,5-diphenyl-4-methyl-4,5-dihydro-1H-imidazole trifluoroacetate (470)

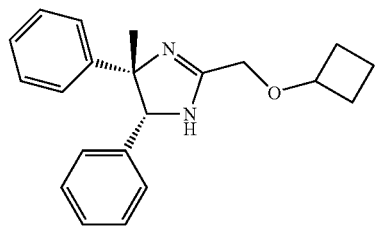

Step 1

Cyclobutoxyacetic acid ethyl ester (469)

To a solution of cyclobutanol (720 mg, 10.0 mmol) in dichloromethane (20 mL) is added rhodium (II) acetate dimer (10 mg) followed by ethyl diazoacetate (0.95 mL, 9.0 mmol). The reaction mixture is stirred at rt for 30 min. The reaction mixture is diluted with heptane, filtered through Celite, and the filtrate is evaporated and the residue is vacuum distilled at 140° C. to give 1.00 g of the product 469. $^1$H NMR (CDCl$_3$) δ 4.21 (q, 2H), 4.03 (m, 1H), 3.98 (s, 2H), 2.28-2.15 (m, 2H), 2.08-1.95 (m, 2H), 1.7 (q, 1H), 1.50 (m, 1H), 1.28 (t, 3H)

Step 2

2-[(Cyclobutoxy)methyl]-cis-4,5-diphenyl-4-methyl-4,5-dihydro-1H-imidazole trifluoroacetate (470)

To a solution of the diamine 16 (113 mg, 0.50 mmol) in toluene (1.5 mL) is added 2.0M trimethylaluminum in toluene (0.65 mL, 1.30 mmol) followed by 469 (79 mg, 0.50 mmol), and the solution is heated at 90° C. for 11 h, then cooled to rt. The reaction mixture is quenched with sat. sodium bicarbonate solution (0.4 mL) and EtOAc:dichloromethane:MeOH (2:2:1) is added, and the mixture is filtered. The filtrate is evaporated, and the residue purified by chromatography on reversed phase silica gel; elution with acetonitrile:water/0.1% TFA gives 89 mg of the product 470. $^1$H NMR (DMSO-d$_6$) δ 11.01 (bs, 1H), 10.79 (bs, 1H), 7.1-6.9 (m, 10H), 5.34 (s, 1H), 4.64 (s, 2H), 4.20 (m, 1H), 2.3-2.2 (m, 2H), 2.09-1.95 (m, 2H), 1.93 (s, 3H), 1.72 (m, 1H), 1.51 (m, 1H); LC/MS: 3.05 min, m/z 321 (M$^+$+1).

Example 187

2-[(1-Cyclopropyl-1-ethoxy)methyl]-cis-4,5-diphenyl-4-methyl-4,5-dihydro-1H-imidazole trifluoroacetate (472)

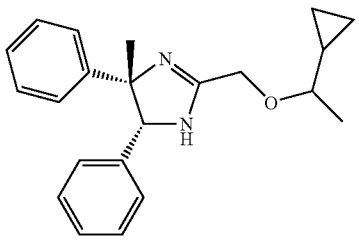

Step 1

(1-Cyclopropyl-1-ethoxy)acetic acid ethyl ester (471)

To a solution of cyclopropyl-1-ethanol (860 mg, 10.0 mmol) in dichloromethane (20 mL) is added rhodium (II) acetate dimer (10 mg) followed by ethyl diazoacetate (0.95 mL, 9.0 mmol). The reaction mixture is stirred at rt for 30 min. The reaction mixture is diluted with heptane, filtered through Celite, and the filtrate is evaporated and the residue is vacuum distilled at 130° C. to give 1.11 g of the product 471. $^1$H NMR (CDCl$_3$) δ 4.12 (s, 2H), 4.10 (q, 2H), 2.86 (m, 1H), 1.25-1.15 (m, 6H), 0.8-0.7 (m, 1H), 0.55-0.3 (m, 3H), 0.05-0.02 (m, 1H); MS: m/z 173 (M$^+$+1).

Step 2

2-[(1-Cyclopropyl-1-ethoxy)methyl]-cis-4,5-diphenyl-4-methyl-4,5-dihydro-1H-imidazole trifluoroacetate (472)

To a solution of the diamine 16 (113 mg, 0.50 mmol) in toluene (1.5 mL) is added 2.0M trimethylaluminum in toluene (0.65 mL, 1.30 mmol) followed by 471 (86 mg, 0.50 mmol), and the solution is heated at 90° C. for 11 h, then cooled to rt. The reaction mixture is quenched with sat. sodium bicarbonate solution (0.4 mL) and EtOAc:dichloromethane:MeOH (2:2:1) is added, and the mixture is filtered. The filtrate is evaporated, and the residue purified by chromatography on reversed phase silica gel; elution with acetonitrile:water/0.1% TFA gives 76 mg of the product 472. $^1$H NMR (DMSO-d$_6$) δ 10.93 (s, 1H), 10.72 (s, 1H), 7.1-6.9 (m, 10H), 5.35 (s, 1H), 4.82 (s, 2H), 3.08 (m, 1H), 1.30 and 1.29 (two d, 3H combined), 0.93 (m, 1H), 0.62 (m, 1H), 0.50 (m, 2H), 0.18 (m, 1H); LC/MS: 3.10 min, m/z 335 (M$^+$+1).

Example 188

2-[(2-Methoxy-1-methylethoxy)methyl]-cis-4,5-diphenyl-4-methyl-4,5-dihydro-1H-imidazole trifluoroacetate (474)

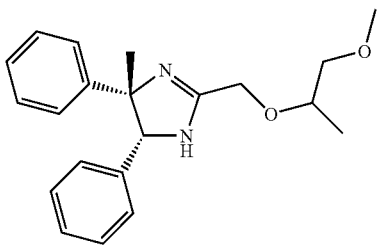

Step 1

(2-Methoxy-1-methylethoxy)acetic acid ethyl ester (473)

To a solution of 1-methoxy-2-propanol (900 mg, 10.0 mmol) in dichloromethane (20 mL) is added rhodium (II) acetate dimer (10 mg) followed by ethyl diazoacetate (0.95 mL, 9.0 mmol). The reaction mixture is stirred at rt for 30 min. The reaction mixture is diluted with heptane, filtered through Celite, and the filtrate is evaporated and the residue is vacuum distilled at 133° C. to give 1.03 g of the product 473. $^1$H NMR (CDCl$_3$) δ 4.20 (q, 2H), 3.72 (m, 1H), 3.45 (dd, 1H), 3.37 (dd, 1H), 3.35 (s, 3H), 1.27 (t, 3H), 1.19 (d, 3H).

Step 2

2-[(2-Methoxy-1-methylethoxy)methyl]-cis-4,5-diphenyl-4-methyl-4,5-dihydro-1H-imidazole trifluoroacetate (474)

To a solution of the diamine 16 (113 mg, 0.50 mmol) in toluene (1.5 mL) is added 2.0M trimethylaluminum in toluene (0.65 mL, 1.30 mmol) followed by 473 (88 mg, 0.50 mmol), and the solution is heated at 90° C. for 11 h, then cooled to rt. The reaction mixture is quenched with sat. sodium bicarbonate solution (0.4 mL) and EtOAc:dichloromethane:MeOH (2:2:1) is added, and the mixture is filtered. The filtrate is evaporated, and the residue purified by chromatography on reversed phase silica gel; elution with acetonitrile:water/0.1% TFA gives 56 mg of the product 474. $^1$H NMR (DMSO-d$_6$) δ 7.05-6.85 (m, 10H), 4.80 (s, 1H), 4.35 (s, 1H), 3.83 (m, 1H), 3.42 (m, 1H), 3.35 (m, 1H), 3.28 (s, 3H), 1.66 (s, 3H), 1.17 and 1.18 (two d, 3H combined); LC/MS: 2.95 min, m/z 339 (M$^+$+1).

Example 189

2-[(1-Benzopyran-4-yloxy)methyl]-cis-4,5-diphenyl-4-methyl-4,5-dihydro-1H-imidazoline hydrochloride (476)

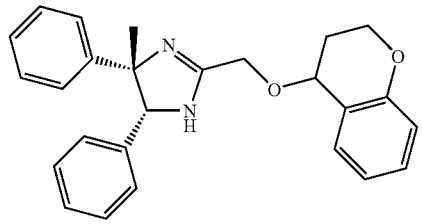

Step 1

[(1-Benzopyran-4-yloxy)methyl]acetic acid ethyl ester (475)

To a solution of 4-chromanol (1.5 g, 10.0 mmol) in dichloromethane (20 mL) is added rhodium (II) acetate dimer (10 mg) followed by ethyl diazoacetate (0.95 mL, 9.0 mmol). The reaction mixture is stirred at rt for 30 min. The reaction mixture is diluted with heptane, filtered through Celite, and the filtrate is evaporated and the residue purified by chromatography on silica gel; elution with EtOAc:dichloromethane:hexane (10:20:70) gives 1.81 g of the product 475. $^1$H NMR (CDCl$_3$) δ 7.35 (dd, 1H), 7.22 (dt, 1H), 6.90 (t, 1H), 6.84 (d, 1H), 4.56 (m, 1H), 4.36 (dd, 1H), 4.29 (dd, 1H), 4.23 (q, 2H), 4.19 (s, 2H), 2.18 (m, 1H), 2.05 (m, 1H), 1.30 (t, 3H); MS: m/z 236 (M$^+$+1).

Step 2

2-[(1-Benzopyran-4-yloxy)methyl]-cis-4,5-diphenyl-4-methyl-4,5-dihydro-1H-imidazoline hydrochloride (476)

To a solution of the diamine 16 (113 mg, 0.50 mmol) in toluene (2 mL) is added 2.0M trimethylaluminum in toluene (0.65 mL, 1.30 mmol) followed by 475 (118 mg, 0.50 mmol), and the solution is heated at 80° C. for 3 h, then cooled to rt. The reaction mixture is quenched with sat. sodium bicarbonate solution (0.4 mL) and EtOAc:dichloromethane:MeOH (2:2:1) is added, and the mixture is filtered. The filtrate is evaporated, and the residue purified by chromatography on silica gel; elution with dichloromethane:MeOH (95:5) followed by treatment with hydrogen chloride in Et$_2$O gives 65 mg of the product 476. $^1$H NMR (DMSO-d$_6$) δ 11.0 (d, 1H), 10.77 (s, 1H), 7.45 (m, 2H), 7.29 (m, 2H), 7.06-6.9 (m, 9H), 6.85 (dd, 1H), 5.30 (s, 1H), 5.00 (d, 1H), 4.87 (d, 1H), 4.75 (m, 1H), 4.3 (m, 2H), 2.3-2.2 (m, 1H), 2.15-2.0 (m, 1H), 1.91 and 1.90 (two s, 3H combined); LC/MS: 2.80 min, m/z 399 (M$^+$+1).

Example 190

2-[[(Tetrahydrofuran-2-yl)methoxy]methyl]-cis-4,5-diphenyl-4-methyl-4,5-dihydro-1H-imidazole (478)

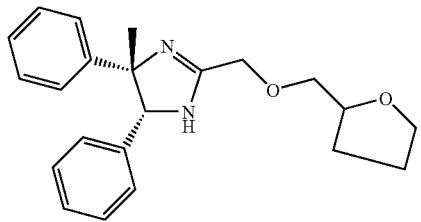

Step 1

(Tetrahydrofuran-2-ylmethoxy)acetic ethyl ester (477)

To a solution of tetrahydrofurfuryl alcohol (1.02 g, 10.0 mmol) in dichloromethane (20 mL) is added rhodium (II) acetate dimer (10 mg) followed by ethyl diazoacetate (0.95 mL, 9.0 mmol). The reaction mixture is stirred at rt for 30 min. The reaction mixture is diluted with heptane, filtered through Celite, and the filtrate is evaporated and the residue is vacuum distilled at 130° C. to give 1.02 g of the product 477. $^1$H NMR (CDCl$_3$) δ 4.11 (q, 2H), 4.10 (s, 2H), 3.93 (m, 1H), 3.72 (m, 1H), 3.61 (m, 1H), 3.44 (m, 2H), 1.95-1.75 (m, 3H), 1.61-1.53 (m, 1H), 1.20 (t, 3H).

Step 2

2-[[(Tetrahydrofuran-2-yl)methoxy]methyl]-cis-4,5-diphenyl-4-methyl-4,5-dihydro-1H-imidazole (478)

To a solution of the diamine 16 (113 mg, 0.50 mmol) in toluene (2 mL) is added 2.0M trimethylaluminum in toluene (0.65 mL, 1.30 mmol) followed by 477 (94 mg, 0.50 mmol), and the solution is heated at 80° C. for 3 h, then cooled to rt. The reaction mixture is quenched with sat. sodium bicarbonate solution (0.4 mL) and EtOAc:dichloromethane:MeOH (2:2:1) is added, and the mixture is filtered. The filtrate is evaporated, and the residue purified by chromatography on silica gel; elution with dichloromethane:MeOH (95:5) gives 126 mg of the product 478. $^1$H NMR (DMSO-d$_6$) δ 7.06-6.94 (m, 10H), 5.16 (s, 1H), 4.66 (s, 2H), 4.07 (m, 1H), 3.78 (m, 1H), 3.66 (m, 2H), 3.60 (m, 1H), 1.993 (m, 1H), 1.85 (m, 3H), 1.61 (m, 1H); LC/MS: 2.51 min, m/z 351 (M$^+$+1).

Example 191

2-[(Phenoxy)methyl]-cis-4,5-diphenyl-4,5-dimethyl-4,5-dihydro-1H-imidazole trifluoroacetate (481)

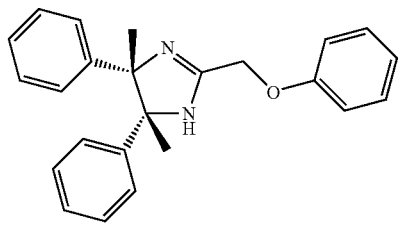

Step 1 cis-3,4-Diphenyl-3,4-dimethyl-1,2,5-thiadiazolidine-1,1-dioxide (479)

To a suspension of 3,4-diphenyl-1,1-dioxo-1,2,5-thiadiazole (14) (2.7 g, 10.0 mmol), in toluene (40 mL) is added THF (10 mL) followed by 3.0M methylmagnesium bromide in Et$_2$O (14 mL, 42 mmol). The homogenous solution is stirred at rt for 4 h, quenched with ammonium chloride solution, washed with brine, dried (MgSO$_4$), and filtered. The filtrate is evaporated and the residue purified by chromatography on silica gel; elution with dichloromethane:EtOAc:hexane (10:20:70) gives 2.61 g of the product 479. MS: m/z 303 (M$^+$+1).

Step 2 cis-2,3-Diphenylbutane-2,3-diamine (480)

A suspension of 479 (2.61 g, 8.63 mmol) in 2M HBr (75 mL) containing phenol (3.12 g) is stirred and heated at reflux for 18 h. The mixture is cooled to rt, extracted with EtOAc, and the aqueous solution is cooled (ice bath) and made basic (pH 14) with sodium hydroxide. The basic solution is extracted with Et$_2$O, and the extract is washed with water, brine, then dried (Na$_2$SO$_4$), and filtered. The filtrate is evaporated, and the residue purified by chromatography on silica gel; elution with dichloromethane:Et$_2$O:MeOH (75:20:5) gives 206 mg of the product 480. $^1$H NMR (DMSO-d$_6$) δ 7.16 (m, 10H), 1.8 (bs, 4H), 1.37 (s, 6H); MS: m/z 241 (M$^+$+1).

Step 3

2-[(Phenoxy)methyl]-cis-4,5-diphenyl-4,5-dimethyl-4,5-dihydro-1H-imidazole trifluoroacetate (481)

To a solution of the diamine 480 (84 mg, 0.35 mmol) in toluene (1.2 mL) is added 2.0M trimethylaluminum in toluene (0.49 mL, 0.98 mmol) followed by phenoxyacetic acid ethyl ester (430) (94 mg, 0.36 mmol), and the solution is heated at 85° C. for 3 h, then cooled to rt. The reaction mixture is quenched with sat. sodium bicarbonate solution (0.4 mL) and EtOAc:MeOH (2:1) is added, and the mixture is filtered.

The filtrate is evaporated, and the residue purified twice by chromatography on reversed phase silica gel; gradient elution with acetonitrile:water/0.1% TFA (40:60-100:0) gives 7 mg of the product 481. ¹H NMR (DMSO-d₆) δ 7.4-7.3 (m, 2H), 7.2-6.9 (m, 9H), 6.9-6.8 (m, 4H), 5.7 (bs, 2H), 1.97 (bs, 6H); LC/MS: 3.20 min, m/z 357 (M⁺+1).

Example 192

2-[[(Cyclopentyl)methoxy]methyl]-cis-(5-methoxyphenyl-4-phenyl)-4,5-dihydro-1H-imidazole hydrochloride (486)

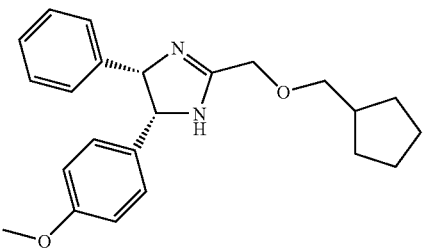

Step 1

(S)-[(N-Methoxy-N-methylcarbamoyl)phenylmethyl]carbamic acid benzyl ester (482)

To a solution of Z-L-phenylglycine (5.0 g, 17.5 mmol) in dichloromethane (35 mL) is added 1,1'-carbonyldimidazole (3.13 g, 19.3 mmol), and the solution is stirred at rt for 0.5 h. To the solution is added N,O-dimethylhydroxylamine hydrochloride (1.88 g, 19.3 mmol), and the mixture is stirred at rt overnight. To the reaction mixture is added ammonium chloride solution and EtOAc, and the organic layer is separated, washed with brine, dried (MgSO₄), and filtered. The filtrate is evaporated to give 5.65 g of the product 482. ¹H NMR (CDCl₃) δ 7.50-7.20 (m, 10 H), 6.10 (d, 1 H), 5.78 (d, 1 H), 5.20-5.00 (m, 2 H), 3.43 (s, 3 H), 3.18 (s, 3 H); MS: m/z 329 (M⁺+1).

Step 2

(S)-[(4-Methoxyphenyl)-2-oxo-1-phenylethyl]carbamic acid benzyl ester (483)

To a cold (0° C.) solution of the amide 482 (328 mg, 1.0 mmol) in THF (20 mL) is added 0.5M 4-methoxyphenylmagnesium bromide in THF (8.0 mL, 4.0 mmol), and the mixture is allowed to come to rt and stirred at this temperature for 3 h. The reaction mixture is poured into a mixture of ammonium chloride/ice followed by the addition of EtOAc. The organic layer is separated, washed with brine, dried (MgSO₄), and filtered. The filtrate is evaporated, and the residue purified by chromatography on silica gel; elution with heptane:EtOAc (85:15) gives 2.12 g of the product 483. ¹H NMR (CDCl₃) δ 7.95 (d, 2 H), 7.45-7.20 (m, 10 H), 6.88 (d, 2 H), 6.50-6.20 (m, 2 H), 5.25-5.00 (m, 2 H), 3.81 (s, 3 H)

Step 3

(S)-[2-(Hydroxylimino)-2-(4-methoxyphenyl)-1-phenylethyl]carbamic acid benzyl ester (484)

To a solution of the ketone 483 (2.47 g, 6.6 mmol) in EtOH (35 mL) is added hydroxylamine hydrochloride (1.83 g, 26.4 mmol) followed by pyridine (2.13 mL, 26.4 mmol). The mixture is stirred at 80° C. for 8 h. The reaction mixture is cooled, the solvent is evaporated, and the residue dissolved in EtOAc, washed with water, brine, then dried (MgSO₄), and filtered. The filtrate is evaporated, and the residue purified by chromatography on silica gel; elution with heptane:EtOAc (7:3) gives 1.95 g of the product 484. ¹H NMR (CDCl₃) δ 7.55 (d, 2 H), 7.50-7.10 (m, 10 H), 7.00-6.70 (m, 2 H), 6.50-6.35 (m, 1 H), 5.30-5.00 (m, 2 H), 3.80 (d, 3 H); MS: m/z 391 (M⁺+1).

Step 4 cis-[2-(4-Methoxyphenyl)-1-phenyl]ethane-1,2-diamine (485)

To a solution of the oxime 484 (2.13 g, 5.45 mmol) in EtOH (50 mL) under nitrogen is added 10% palladium-on-carbon (1 g), and the mixture treated with hydrogen (50 psi), and shaken at rt for 4 h. The reaction mixture is filtered, the filtrate evaporated, and the residue triturated with Et₂O to give 1.0 g of the product 485. ¹H NMR (CDCl₃) δ 7.50-7.25 (m, 7 H), 6.90 (d, 2 H), 4.00 (s, 2 H), 3.80 (s, 3 H), 1.61 (bs, 4 H); MS: m/z 242 (M⁺+1).

Step 5

2-[[(Cyclopentyl)methoxy]methyl]-cis-(5-methoxyphenyl-4-phenyl)-4,5-dihydro-1H-imidazole hydrochloride (486)

To a solution of the diamine 485 (242 mg, 1.0 mmol) in toluene (3 mL) is added 2.0M trimethylaluminum in toluene (1.25 mL, 2.5 mmol) followed by a solution of 2-(cyclopentylmethoxy)acetic acid ethyl ester (450) (186 mg, 1.0 mmol) in toluene (1 mL). The solution is heated at 110° C. for 2 h, and stirred at rt overnight. The reaction mixture is quenched with sat. sodium bicarbonate solution (0.4 mL), EtOAc is added, and the mixture is filtered. The filtrate is evaporated, and the residue is purified by chromatography on silica gel; elution with dichloromethane:MeOH:NH₄OH (95:5:1) followed by treatment with hydrogen chloride in Et₂O gives 115 mg of the product 486. ¹H NMR (CDCl₃) δ 7.15-7.7.00 (m, 3 H), 7.00-6.90 (m, 2 H), 6.90-6.75 (m, 1 H), 6.65-6.50 (m, 2 H), 5.30 (s, 1 H), 5.25 (s, 2 H), 4.40 (s, 2 H), 3.70 (s, 3 H), 3.50 (d, 2 H), 2.30-2.10 (m, 1 H), 1.90-1.15 (m, 8 H); MS: m/z 365 (M⁺+1).

Example 193

2-(3-Ethoxy-1-ethyl-1-propoxymethyl)-cis-4,5-diphenyl-4-methyl-4,5-dihydro-1H-imidazole ditrifluoroacetate (488)

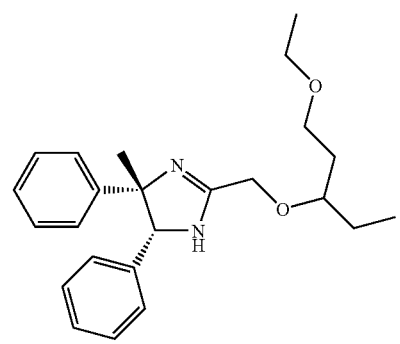

Step 1

(3-Ethoxy-1-ethylpropoxy)acetic acid ethyl ester (487)

To a solution of 1-ethoxy-3-pentanol (1.32 g, 10.0 mmol) in dichloromethane (20 mL) is added rhodium (II) acetate dimer (10 mg) followed by ethyl diazoacetate (1.0 mL, 9.5 mmol). The reaction mixture is stirred at rt for 2 h. The reaction mixture is diluted with heptane, filtered through Celite, and the filtrate is evaporated. The residue is purified by chromatography on silica gel; elution with EtOAc:heptane (1:3) gives 660 mg the product 487.

Step 2

2-(3-Ethoxy-1-ethyl-1-propoxymethyl)-cis-4,5-diphenyl-4-methyl-4,5-dihydro-1H-imidazole ditrifluoroacetate (488)

To a solution of the diamine 16 (226 mg, 1.0 mmol) in toluene (3 mL) is added 2.0M trimethylaluminum in toluene (1.25 mL, 2.50 mmol) followed by a solution of 487 (218 mg, 1.0 mmol) in toluene (1 mL), and the solution is heated at 110° C. for 4 h, then cooled to rt. The reaction mixture is quenched with sat. sodium bicarbonate solution (0.4 mL), and EtOAc is added, and the mixture is washed with brine, dried (MgSO$_4$), and filtered. The filtrate is evaporated, and the residue purified by chromatography on silica gel; elution with dichloromethane:MeOH:NH$_4$OH (95:5:1)) gives 91 mg the product 488. $^1$H NMR (CDCl$_3$) δ 7.10-6.80 (m, 10 H), 4.90-4.75 (m, 1 H), 4.60-4.30 (m, 2 H), 3.80-3.30 (m, 5 H), 1.95-1.75 (m, 5 H), 1.75-1.55 (m, 2 H), 1.20-1.10 (m, 3 H), 1.10-0.90 (m, 3 H); LC/MS: 2.94 min, m/z 381 (M$^+$+1).

Example 194

2-(Phenoxymethyl)-4,4-dimethyl-5-phenyl-4,5-dihydro-1H-imidazole trifluoroacetate (490)

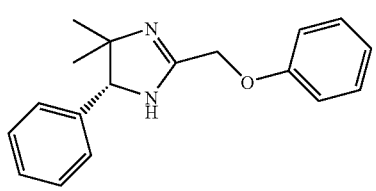

To a solution of 2-methyl-1-phenylpropane-1-2-diamine (164 mg, 1.0 mmol, J. Org. Chem., 1995, 60, 7411) in toluene (3 mL) is added 2.0M trimethylaluminum in toluene (1.3 mL, 2.6 mmol). The resulting solution is stirred for 15 min, then a solution of phenoxyacetic acid ethyl ester (430) (180 mg, 1.0 mmol) in toluene (1 mL) is added. The solution is heated at 90° C. for 2 h, then cooled to rt. The reaction mixture is quenched with sat. sodium bicarbonate solution (2 mL) and EtOAc is added, and the mixture is filtered. The filtrate is evaporated, and the residue purified by chromatography on reversed phase silica gel; gradient elution with acetonitrile:water/0.1% TFA to give 65 mg of the product 490. $^1$H NMR (CDCl$_3$) δ 11.50 (bs, 1 H), 9.73 (bs, 1 H), 7.4-7.3 (m, 5 H), 7.2-7.0 (m, 5 H), 5.3-5.2 (m, 2 H), 4.93 (s, 1 H), 1.61 (s, 3 H), 0.91 (s, 3 H); LC/MS: 3.09 min, m/z 281 (M$^+$+1).

Example 195

2-(Benzyloxymethyl)-4,4-dimethyl-5-phenyl-4,5-dihydro-1H-imidazole trifluoroacetate (491)

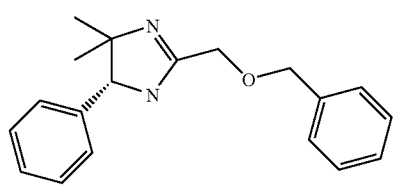

To a solution of 2-methyl-1-phenylpropane-1-2-diamine (164 mg, 1.0 mmol, J. Org. Chem., 1995, 60, 7411) in toluene (3 mL) is added 2.0M trimethylaluminum in toluene (1.3 mL, 2.6 mmol). The resulting solution is stirred for 15 min, then a solution of benzyloxyacetic acid ethyl ester (390) (194 mg, 1.0 mmol) in toluene (1 mL) is added. The solution is heated at 90° C. for 2 h, then cooled to rt. The reaction mixture is quenched with sat. sodium bicarbonate solution (2 mL) and EtOAc is added, and the mixture is filtered. The filtrate is evaporated, and the residue purified by chromatography on reversed phase silica gel; gradient elution with acetonitrile:water/0.1% TFA to give 77 mg of the product 491. $^1$H NMR (CDCl$_3$) δ 11.08 (bs, 1 H), 9.17 (bs, 1 H), 7.4-7.3 (m, 8 H), 7.2-7.1 (m, 2 H), 4.87 (s, 1 H), 4.75 (s, 2 H), 4.64 (s, 2 H), 1.58 (s, 3 H), 0.87 (s, 3 H); LC/MS: 3.10 min, m/z 295 (M$^+$+1).

Example 196

2-(3-fluorobenzyloxymethyl)-4,4-dimethyl-5-phenyl-4,5-dihydro-1H-imidazole trifluoroacetate (492)

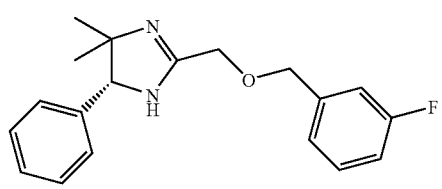

To a solution of 2-methyl-1-phenylpropane-1-2-diamine (164 mg, 1.0 mmol, J. Org. Chem., 1995, 60, 7411) in toluene (3 mL) is added 2.0M trimethylaluminum in toluene (1.3 mL, 2.6 mmol). The resulting solution is stirred for 15 min, then a solution of 3-fluorobenzyloxyacetic acid ethyl ester (392) (212 mg, 1.0 mmol) in toluene (1 mL) is added. The solution is heated at 90° C. for 2 h, then cooled to rt. The reaction mixture is quenched with sat. sodium bicarbonate solution (2 mL) and EtOAc is added, and the mixture is filtered. The filtrate is evaporated, and the residue purified by chromatography on reversed phase silica gel; gradient elution with acetonitrile:water/0.1% TFA to give 98 mg of the product 492. $^1$H NMR (CDCl$_3$) δ 10.93 (bs, 1 H), 9.21 (bs, 1 H), 7.4-7.3 (m, 4 H), 7.2-7.0 (m, 5 H), 4.92 (s, 1 H), 4.75 (s, 2 H), 4.64 (s, 2 H), 1.60 (s, 3 H), 0.89 (s, 3 H); LC/MS: 3.20 min, m/z 313 (M$^+$+1).

Example 197

2-(3-fluorophenoxymethyl)-4,4-dimethyl-5-phenyl-4,5-dihydro-1H-imidazole trifluoroacetate (493)

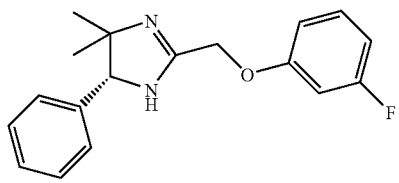

To a solution of 2-methyl-1-phenylpropane-1-2-diamine (164 mg, 1.0 mmol, J. Org. Chem., 1995, 60, 7411) in toluene (3 mL) is added 2.0M trimethylaluminum in toluene (1.3 mL, 2.6 mmol). The resulting solution is stirred for 15 min, then a solution of 3-fluorophenoxyacetic acid ethyl ester (432) (198 mg, 1.0 mmol) in toluene (1 mL) is added. The solution is heated at 90° C. for 2 h, then cooled to rt. The reaction mixture is quenched with sat. sodium bicarbonate solution (2 mL) and EtOAc is added, and the mixture is filtered. The filtrate is evaporated, and the residue purified by chromatography on reversed phase silica gel; gradient elution with acetonitrile:water/0.1% TFA to give 107 mg of the product 493. $^1$H NMR (CDCl$_3$) δ 11.41 (bs, 1 H), 10.22 (bs, 1 H), 7.4-7.2 (m, 4 H), 7.15-7.12 (m, 2 H), 6.8-6.7 (m, 3 H), 5.17 (s, 2 H), 4.92 (s, 1 H), 1.58 (s, 3 H), 0.87 (s, 3 H); LC/MS: 3.13 min, m/z 299 (M$^+$+1).

Example 198

2-Phenoxymethyl-cis-[5-phenyl-4-(pyridin-3-yl)]-4,5-dihydro-1H-imidazole ditrifluoroacetate (500)

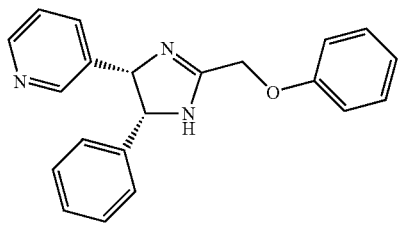

Step 1

3-(Pyridin-3-yl)-4-phenyl-1,2,5-thiadiazole-1,1-dioxide hydrochloride (497)

Hydrogen chloride gas is bubbled into a solution of 1-phenyl-2-(pyridin-3-yl)ethan-1,2-dione (1.63 g, 7.7 mmol, J. Org. Chem., 1999, 64, 6102) and sulfamide (750 mg, 7.7 mmol) in methanol (10 mL) until the solution begins to reflux. The gas flow is turned off, and the solution stirred at 65° C. for 3 h then cooled to rt. The solid that formed is filtered and dried to give 2.06 g of the product 497. MS: m/z 272 (M$^+$+1).

Step 2 cis-3-(Pyridin-3-yl)-4-phenyl-2,3-dihydro-1,2,5-thiadiazole-1,1-dioxide (498)

To a solution of 3-(pyridin-3-yl)-4-phenyl-1,2,5-thiadiazole-1,1-dioxide hydrochloride (497) (1.86 g, 6.6 mmol) in THF:methanol (20 mL, 1:1) is added sodium borohydride (1.38 g, 36.0 mmol in batches; 230 mg each). On complete addition, the solution is stirred for 1 h, then quenched with 5N HCl. The solution is then brought to pH 6 by the addition of sat. sodium bicarbonate solution, extracted with EtOAc, the organic phase is separated, washed with brine, dried (MgSO$_4$), and filtered. The filtrate is concentrated to give 1.64 g of the product 498. $^1$H NMR (DMSO-d$_6$) δ 8.28 (bs, 1H), 8.20 (bs, 1H), 8.15 (bs, 1H), 7.70 (m, 2H), 7.44 (d, 1H), 7.15-7.0 (5H), 5.19 (d, 1H), 5.17 (d, 1H); MS: m/z 276 (M$^+$+1).

Step 3 erythro-1-Phenyl-2-(pyridin-3-yl)ethylene-1,2-diamine (499)

To a solution of cis-3-(pyridin-3-yl)-4-phenyl-2,3-dihydro-1,2,5-thiadiazole-1,1-dioxide (498) (1.8 g, 6.6 mmol) in 2M HBr (75 mL) is added phenol (3.12 g, 33.2 mmol). The mixture is heated to reflux and stirred for 18 h then cooled to rt, and extracted with EtOAc. The aqueous phase is basified to pH 14 with solid sodium hydroxide, then concentrated. The solid residue is mixed thoroughly with EtOAc:methanol:dichloromethane (1:1:5). The insoluble solid is filtered, and the filtrate concentrated to give 442 mg of the product 499. $^1$H NMR (DMSO-d$_6$) δ 8.37 (d, 1H), 8.26 (bs, 1H), 7.56 (d, 1H), 7.3-7.1 (m, 6H), 3.97 (bs, 2H), 1.78 (bs, 4H); MS: m/z 214 (M$^+$+1).

Step 4

2-Phenoxymethyl-cis-[5-phenyl-4-(pyridin-3-yl)]-4,5-dihydro-1H-imidazole ditrifluoroacetate (500)

To a solution of the diamine 499 (73 mg, 0.35 mmol) in toluene (1.2 mL) is added 2.0M trimethylaluminum in toluene (0.49 mL, 0.98 mmol). The resulting solution is stirred for 10 min, then phenoxyacetic acid ethyl ester (430) (63 mg, 0.35 mmol) is added. The solution is heated at 80° C. for 2.5 h, then cooled to rt. The reaction mixture is quenched with sat. sodium bicarbonate solution (0.45 mL) and EtOAc:methanol:dichloromethane (1:1:5) is added, and the mixture is filtered. The filtrate is evaporated, and the residue purified by chromatography on reversed phase silica gel; gradient elution with acetonitrile:water/0.1% TFA to give 79 mg of the product 500. $^1$H NMR (DMSO-d$_6$) δ 11.17 (s, 1H), 11.09 (s, 1H), 8.32 (bs, 2H), 7.5-7.4 (m, 3H), 7.16-7.03 (m, 9H), 5.94 (d, 1H), 5.91 (d, 1H), 5.44 (s, 2H); LC/MS: 2.42 min, m/z 330 (M$^+$+1).

Example 199

2-[(3-Fluorophenoxy)methyl]-cis-[5-phenyl-4-(pyridin-3-yl)]-4,5-dihydro-1H-imidazole ditrifluoroacetate (501)

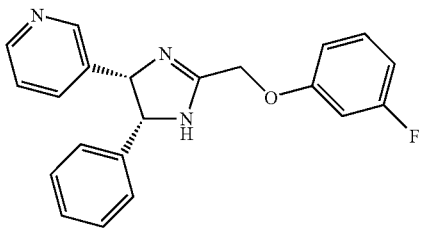

To a solution of the diamine 499 (73 mg, 0.35 mmol) in toluene (1.2 mL) is added 2.0M trimethylaluminum in toluene (0.49 mL, 0.98 mmol). The resulting solution is stirred for 10 min, then 3-fluorophenoxyacetic acid ethyl ester (432) (74 mg, 0.35 mmol) is added. The solution is heated at 80° C. for 2.5 h, then cooled to rt. The reaction mixture is quenched with sat. sodium bicarbonate solution (0.45 mL) and EtOAc:methanol:dichloromethane (1:1:5) is added, and the mixture is filtered. The filtrate is evaporated, and the residue purified by chromatography on reversed phase silica gel; gradient elution with acetonitrile:water/0.1% TFA to give 89 mg of the product 501. $^1$H NMR (DMSO-d$_6$) δ 11.17 (s, 1H), 11.09 (s, 1H), 8.32 (bs, 2H), 7.5-7.43 (m, 2H), 7.20-6.92 (m, 9H), 5.94 (d, 1H), 5.91 (d, 1H), 5.47 (s, 2H); LC/MS: 2.50 min, m/z 348 (M$^+$+1).

Example 200

2-Cyclohexyloxymethyl-cis-[5-phenyl-4-(pyridin-3-yl)]-4,5-dihydro-1H-imidazole ditrifluoroacetate (502)

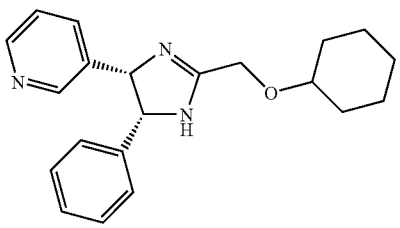

To a solution of the diamine 499 (73 mg, 0.35 mmol) in toluene (1.2 mL) is added 2.0M trimethylaluminum in toluene (0.49 mL, 0.98 mmol). The resulting solution is stirred for 10 min, then cyclohexyloxyacetic acid ethyl ester (407) (65 mg, 0.35 mmol) is added. The solution is heated at 80° C. for 2.5 h, then cooled to rt. The reaction mixture is quenched with sat. sodium bicarbonate solution (0.45 mL) and EtOAc:methanol:dichloromethane (1:1:5) is added, and the mixture is filtered. The filtrate is evaporated, and the residue purified by chromatography on reversed phase silica gel; gradient elution with acetonitrile:water/0.1% TFA to give 43 mg of the product 502. $^1$H NMR (DMSO-d$_6$) δ 10.81 (s, 1H), 10.73 (s, 1H), 8.39 (bm, 2H), 7.48 (m, 2H), 7.18-7.05 (m, 5H), 5.88 (d, 1H), 5.86 (d, 1H), 4.76 (s, 2H), 3.56 (m, 1H), 1.93 (m, 2H), 1.73 (m, 2H), 1.53 (m, 1H), 1.42-1.09 (m, 5H); LC/MS: 2.57 min, m/z 336 (M$^+$+1).

Example 201

2-Phenylthiomethyl-cis-[5-phenyl-4-(pyridin-3-yl)]-4,5-dihydro-1H-imidazole ditrifluoroacetate (503)

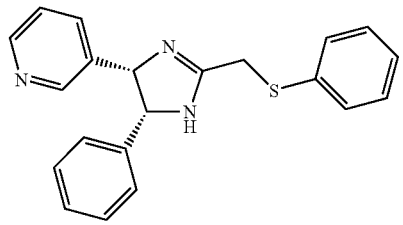

To a solution of the diamine 499 (73 mg, 0.35 mmol) in toluene (1.2 mL) is added 2.0M trimethylaluminum in toluene (0.49 mL, 0.98 mmol). The resulting solution is stirred for 10 min, then phenylthioacetic acid ethyl ester (74 mg, 0.35 mmol) is added. The solution is heated at 80° C. for 2.5 h, then cooled to rt. The reaction mixture is quenched with sat. sodium bicarbonate solution (0.45 mL) and EtOAc:methanol:dichloromethane (1:1:5) is added, and the mixture is filtered. The filtrate is evaporated, and the residue purified by chromatography on reversed phase silica gel; gradient elution with acetonitrile:water/0.1% TFA to give 69 mg of the product 503. $^1$H NMR (DMSO-d$_6$) δ 11.01 (s, 1H), 10.93 (s, 1H), 8.24 (bs, 1H), 8.10 (bs, 1H), 7.65 (d, 2H), 7.54-7.42 (m, 3H), 7.05-7.03 (m, 5H), 6.72 (m, 2H), 5.84 (d, 1H), 5.79 (d, 1H), 4.43 (s, 2H); LC/MS: 2.44 min, m/z 346 (M$^+$+1).

Example 202

2-Phenethyl-cis-[5-phenyl-4-(pyridin-3-yl)]-4,5-dihydro-1H-imidazole ditrifluoroacetate (504)

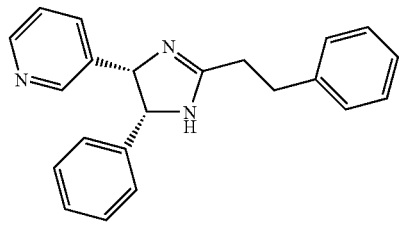

To a solution of the diamine 499 (73 mg, 0.35 mmol) in toluene (1.2 mL) is added 2.0M trimethylaluminum in toluene (0.49 mL, 0.98 mmol). The resulting solution is stirred for 10 min, then 3-phenylpropionic acid ethyl ester (63 mg, 0.35 mmol) is added. The solution is heated at 80° C. for 2.5 h, then cooled to rt. The reaction mixture is quenched with sat. sodium bicarbonate solution (0.45 mL) and EtOAc:methanol:dichloromethane (1:1:5) is added, and the mixture is filtered. The filtrate is evaporated, and the residue purified by chromatography on reversed phase silica gel; gradient elution with acetonitrile:water/0.1% TFA to give 17 mg of the product 504. $^1$H NMR (DMSO-$d_6$) δ 10.81 (s, 1H), 10.74 (s, 1H), 8.27 (bs, 1H), 8.16 (bs, 1H), 7.47-7.34 (m, 5H), 7.11-7.06 (m, 5H), 6.78 (m, 2H), 5.81 (d, 1H), 5.77 (d, 1H), 3.17 (s, 4H); LC/MS: 2.45 min, m/z 328 (M$^+$+1).

Example 203

2-Methyl-cis-[5-phenyl-4-(pyridin-3-yl)]-4,5-dihydro-1H-imidazole ditrifluoroacetate (505)

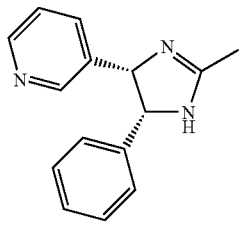

To a solution of the diamine 499 (73 mg, 0.35 mmol) in toluene (1.2 mL) is added 2.0M trimethylaluminum in toluene (0.49 mL, 0.98 mmol). The resulting solution is stirred for 10 min, then ethyl acetate (31 mg, 0.35 mmol) is added. The solution is heated at 80° C. for 2.5 h, then cooled to rt. The reaction mixture is quenched with sat. sodium bicarbonate solution (0.45 mL) and EtOAc:methanol:dichloromethane (1:1:5) is added, and the mixture is filtered. The filtrate is evaporated, and the residue purified by chromatography on reversed phase silica gel; gradient elution with acetonitrile:water/0.1% TFA to give 74 mg the product 505. $^1$H NMR (CDCl$_3$) δ 8.10 (bs, 2H), 7.4 (bs, 3H), 7.2 (m, 4H), 5.15 (bs, 2H), 2.55 (bs, 3H); LC/MS: 2.00 min, m/z 238 (M$^+$+1).

Example 204

A mixture of cis-1,2-bis-(3-fluorophenyl)ethane-1,2-diamine (5) (5 mmol) in dichloromethane and p-nitrophenyl carbonate Wang resin (1 g, 1.32 mmol/g) is shaken overnight, the resin filtered and washed with dichloromethane. A suspension of the monocarbamoylated resin (0.30 g, 0.40 mmol) is treated with a substituted phenylacetic acid (1.2 mmol), 1-(dimethylaminopropyl)-3-ethylcarbodiimide hydrochloride (1.2 mmol) in DMF (6 mL), and the mixture is shaken overnight at rt. The resin is filtered, washed with DMF, and the substituted phenylacetamide derivative is cleaved from the resin with 50% TFA/DMF at rt for 1.5 h. The solvents are evaporated, and the residue is dissolved in trimethylsilyl polyphosphate/dichloromethane solution (1:4), and the solution is microwaved at 140° C. for 2x4 min to effect imidazoline ring formation. The mixture is diluted with dichloromethane, washed with water, sat. sodium bicarbonate, brine, then dried (Na$_2$SO$_4$), and filtered. The filtrate is rotary evaporated, and the residue purified by chromatography on silica gel; elution with acetonitrile:water/0.5% TFA (80:20) gives the product.

The compounds so prepared are summarized in Table 4, which are also identified by a compound number. Also summarized in Table 4 are the amounts of the compound formed, the LC/MS retention time, m/e ion peak, and the substituted phenylacetic acid employed to make the respective compound.

TABLE 4

| # | Compound Amount (mg) | LC/MS retention time | LC/MS m/z (M$^+$ + 1). |
|---|---|---|---|
| | Substituted phenylacetic acid | | |
| 535 | 2-(3-Chlorobenzyl)-cis-4,5-bis-(3-fluorophenyl)-4,5-dihydro-1H-imidazole trifluoroacetate | | |
| | 7 mg | 2.85 min | 383 |
| | (3-chlorophenyl)acetic acid | | |
| 536 | 2-(3,4-Difluorobenzyl)-cis-4,5-bis-(3-fluorophenyl)-4,5-dihydro-1H-imidazole trifluoroacetate | | |
| | 3 mg | 2.83 min | 385 |
| | (3,4-difluorophenyl)acetic acid | | |
| 537 | 2-(2,4-Difluorobenzyl)-cis-4,5-bis-(3-fluorophenyl)-4,5-dihydro-1H-imidazole trifluoroacetate | | |
| | 5 mg | 2.80 min | 385 |
| | (2,4-difluorophenyl)acetic acid | | |
| 538 | 2-(4-Fluorobenzyl)-cis-4,5-bis-(3-fluorophenyl)-4,5-dihydro-1H-imidazole trifluoroacetate | | |
| | 11 mg | 2.76 min | 367 |
| | (4-fluorophenyl)acetic acid | | |
| 539 | 2-(2-Fluorobenzyl)-cis-4,5-bis-(3-fluorophenyl)-4,5-dihydro-1H-imidazole trifluoroacetate | | |
| | 6 mg | 2.75 min | 367 |
| | (2-fluorophenyl)acetic acid | | |

Example 205

Scheme 8, Method g

The procedure as set forth in Example 204 is essentially repeated in this Example except that cis-1,2-diphenylpropane-1,2-diamine (16) (5 mmol) is employed in the place of cis-1,2-bis-(3-fluorophenyl)ethane-1,2-diamine (5) (5 mmol). The substituted 3-phenylacetamide derivative so formed is then cleaved in accordance with the procedures of Example 204 and the compound is isolated.

The compounds so prepared are summarized in Table 5, which are also identified by a compound number. Also summarized in Table 5 are the amounts of the compound formed, the LC/MS retention time, m/e ion peak, and the substituted 3-phenylacetic acid employed to make the respective compound.

TABLE 5

| # | Product Amount (mg) | LC/MS retention time | LC/MS m/z (M$^+$ + 1). |
|---|---|---|---|
| | Substituted phenylacetic acid | | |
| 540 | 2-(4-Fluorobenzyl)-cis-4,5-diphenyl-4-methyl-4,5-dihydro-1H-imidazole trifluoroacetate | | |
| | 44 mg | 2.86 min | 345 |
| | (4-fluorophenyl)acetic acid | | |
| 541 | 2-(3,4-Difluorobenzyl)-cis-4,5-diphenyl-4-methyl-4,5-dihydro-1H-imidazole trifluoroacetate | | |
| | 29 mg | 2.87 min | 363 |
| | (3,4-difluorophenyl)acetic acid | | |
| 542 | 2-(3-Chlorobenzyl)-cis-4,5-diphenyl-4-methyl-4,5-dihydro-1H-imidazole trifluoroacetate | | |
| | 43 mg | 2.89 min | 361 |
| | (3-chlorophenyl)acetic acid | | |
| 543 | 2-(2,4-Difluorobenzyl)-cis-4,5-diphenyl-4-methyl-4,5-dihydro-1H-imidazole trifluoroacetate | | |
| | 23 mg | 2.60 min | 363 |
| | (2,4-difluorophenyl)acetic acid | | |

TABLE 5-continued

| # | Product<br>Amount (mg) | LC/MS retention time | LC/MS m/z (M+ + 1).<br>Substituted phenylacetic acid |
|---|---|---|---|
| 544 | 2-(1-Phenyl-1-ethyl)-cis-4,5-diphenyl-4-methyl-4,5-dihydro-1H-imidazole trifluoroacetate | | |
| | 12 mg | 2.84 min | 341 |
| | | | 2-phenyl-2-propionic acid |
| 545 | 2-[1-(4-Chlorophenyl)-1-ethyl]-cis-4,5-diphenyl-4-methyl-4,5-dihydro-1H-imidazole trifluoroacetate | | |
| | 14 mg | 2.95 min | 375 |
| | | | 2-(4-chlorophenyl)-2-propionic acid |

Example 206

2-(4-Fluorobenzyl)-cis-4,5-bis-(3-fluorophenyl)-4-methyl-4,5-dihydro-1H-imidazole trifluoroacetate (546)

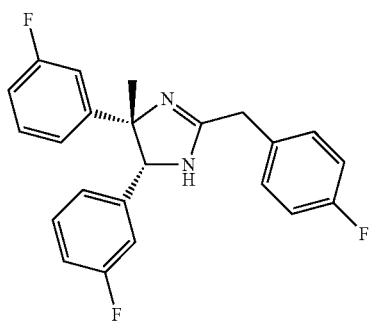

A mixture of cis-1,2-bis-(3-fluorophenyl)propane-1,2-diamine (23) (5 mmol) in dichloromethane and p-nitrophenyl carbonate Wang resin (1 g, 1.32 mmol/g) is shaken overnight, the resin filtered and washed with dichloromethane. A suspension of the monocarbamoylated resin (0.30 g, 0.40 mmol) is treated with (4-fluorophenyl)acetic acid (1.2 mmol), 1-(dimethylaminopropyl)-3-ethylcarbodiimide hydrochloride (1.2 mmol) in DMF (6 mL), and the mixture is shaken overnight at RT. The resin is filtered, washed with DMF, and the substituted (4-fluorophenyl)acetamide derivative is cleaved from the resin with 50% TFA/DMF at rt for 1.5 h. The solvents are evaporated, and the residue is dissolved in trimethylsilyl polyphosphate/dichloromethane solution (1:4), and the solution is microwaved at 140° C. for 2×4 min to effect imidazoline ring formation. The mixture is diluted with dichloromethane, washed with water, sat. sodium bicarbonate, brine, then dried ($Na_2SO_4$), and filtered. The filtrate is rotary evaporated, and the residue purified by chromatography on silica gel; elution with acetonitrile:water/0.5% TFA (80:20) gives 44 mg of the product; LC/MS: 3.02 min, m/z 381 (M++1).

Example 207

1-[(2-Methylthio)-cis-4,5-diphenyl-4,5-dihydro-imidazol-1-yl]ethanone (547)

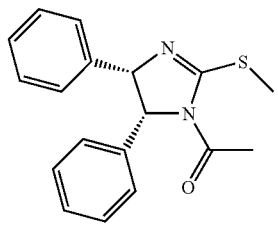

To a solution of 2-(methylthio)-cis-4,5-diphenyl-4,5-dihydro-1H-imidazole hydroiodide (42) (1.00 g, 2.52 mmol), triethylamine (0.262 mL, 2.77 mmol), 4-dimethylaminopyridine (20 mg) in dichloromethane (20 mL) is added acetic anhydride (0.033 mL, 0.262 mmol), and the mixture is stirred at rt overnight. The reaction mixture is diluted with dichloromethane and washed with water, brine, and the organic layer is dried ($MgSO_4$), filtered, and evaporated. The residue is purified by chromatography on silica gel; elution with heptane:EtOAc (1:1) followed by evaporation gives a solid that is recrystallized from heptane:dichloromethane (95:5) to give 0.47 g of the product 547. $^1$H NMR ($CDCl_3$) δ 7.10-6.90 (m, 8H), 6.90-6.70 (m, 2H), 5.65 (d, 1H), 5.45 (d, 1H), 2.55 (s, 3H), 1.95 (s, 3H); MS: m/z 311 (M++1).

Example 208

2-(Methylthio)-cis-4,5-diphenyl-4,5-dihydro-imidazole-1-carboxylic acid phenyl ester (548)

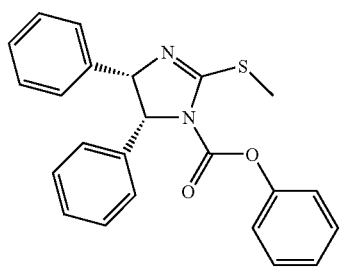

To a solution of 2-(methylthio)-cis-4,5-diphenyl-4,5-dihydro-1H-imidazole hydroiodide (42) (1.00 mg, 2.52 mmol), triethylamine (0.528 mL, 0.379 mmol), 4-dimethylaminopyridine (10 mg) in dichloromethane (20 mL) is added phenyl chloroformate (0.379 mL, 3.02 mmol), and the mixture is stirred at rt overnight. The reaction mixture is diluted with dichloromethane and washed with water, brine, and the organic layer is dried ($MgSO_4$), filtered, and evaporated. The residue is purified by chromatography on silica gel; gradient elution with heptane:EtOAc (70:30-60:40) gives 0.58 g of the product 548. $^1$H NMR ($CDCl_3$) δ 7.25-6.95 (m, 11H), 6.95-6.80 (m, 2H), 6.80-6.70 (m, 2H), 5.80-5.65 (m, 2H), 2.62 (s, 3H). MS: m/z 389 (M++1).

Example 209

1-[2-(4-Fluorobenzylthio)-cis-4,5-diphenyl-4,5-dihydro-imidazol-1-yl]ethanone (549)

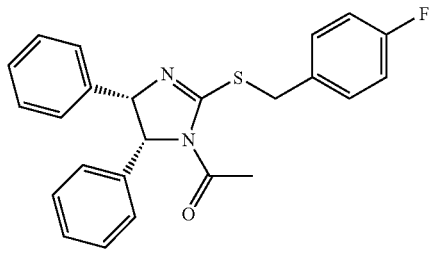

To a solution of 2-[(4-fluorobenzyl)thio]-cis-4,5-diphenyl-4,5-dihydro-1H-imidazole hydrochloride (197) (0.50 g, 1.25 mmol), triethylamine (0.384 mL, 2.75 mmol), 4-dimethylaminopyridine (20 mg) in dichloromethane (20 mL) is added acetic anhydride (0.130 mL, 1.38 mmol), and the mixture is stirred at rt for 3 h. Additional acetic anhydride (0.100 mL, 1.06 mmol) is added, and the mixture is stirred at rt overnight. The reaction mixture is diluted with dichloromethane and washed with water, brine, and the organic layer is dried (MgSO$_4$), filtered, and evaporated. The residue is recrystallized from heptane:dichloromethane (95:5) to give 0.37 g of the product 549. $^1$H NMR (CDCl$_3$) δ 7.60-7.40 (m, 2H), 7.10-6.90 (m, 8H), 6.90-6.75 (m, 2H), 6.75-6.65 (m, 2H), 5.65 (d, 1H), 5.43 (d, 1H), 4.33 (q, 2H), 1.91 (s, 3H). MS: m/z 405 (M$^+$+1).

Example 210

2-(Methoxy-phenyl-methyl)-cis-4,5-diphenyl-4,5-dihydro-1H-imidazole trifluoroacetate

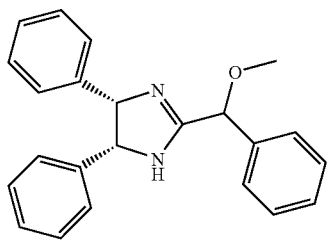

Step 1.

One of the starting materials, methoxy-(S)-phenyl-acetic acid methyl ester is made from commercially available methyl-(S)-mandelate following the procedure set forth in Tetrahedron Letters 40 (1999) 1843-1846.

Step 2:

Employing the general trimethylaluminum coupling procedure and using methoxy-(S)-phenyl-acetic acid methyl ester prepared in accordance with Step 1 as described above and meso-1,2-diphenylethylene-diamine there was made, 2-(Methoxy-phenyl-methyl)-4,5-diphenyl-4,5-dihydro-1H-imidazole trifluoroacetate. $^1$H NMR (DMSO) δ 11.11 (bs, 1 H), 7.7-7.5 (m, 5 H), 7.1-7.0 (m, 6 H), 6.90-6.85 (m, 2 H), 6.8-6.7 (m, 2 H), 5.81 (s, 2 H), 5.65 (s, 1 H), 3.49 (s, 3 H); LC/MS: 3.69 min, m/z 343 (M$^+$+1)

Example 211

(cis-4,5-Diphenyl-4,5-dihydro-1H-imidazol-2-yl)-phenyl-methanol trifluoroacetate

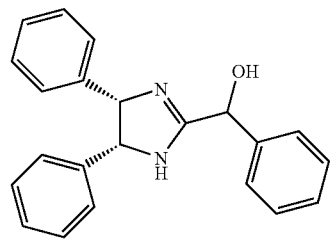

Step 1:

(tert-Butyl-dimethyl-silanyloxy)-phenyl-acetic acid methyl ester

To a solution of commercially available methyl (S)-mandelate (2.39 g, 14.4 mmol) in dichloromethane (50 mL) is added imidazole (1.18 g, 17.3 mmol), tert-butyldimethylsilyl chloride (2.38 g, 15.8 mmol) and 4-dimethylaminopyridine (176 mg, 1.44 mmol). The mixture is stirred for 16 hrs then diluted with ether, washed with water, brine, then dried (MgSO$_4$), filtered and concentrated. The residue is purified by chromatography on silica gel; elution with EtOAc:heptane (25:75) gives 3.67 g of the product. $^1$H NMR (CDCl$_3$) δ 7.45-7.40 (m, 2 H), 7.35-7.25 (m, 3 H), 5.20 (s, 1 H), 3.65 (s, 3 H), 0.90 (s, 9 H), 0.10 (s, 3 H), 0.05 (s, 3 H); MS: m/z 281 (M$^+$+1)

Step 2:

Employing the general trimethylaluminum coupling procedure and using (tert-butyl-dimethyl-silanyloxy)-phenyl-acetic acid methyl ester prepared in accordance with the procedures set out in Step 1 above and meso-1,2-diphenyl-ethylene-diamine there is made: (4,5-Diphenyl-4,5-dihydro-1H-imidazol-2-yl)-phenyl-methanol trifluoroacetate. $^1$H NMR (DMSO) δ 10.95 (bs, 2 H), 7.70-7.67 (m, 2 H), 7.57-7.46 (m, 3 H), 7.2-7.0 (m, 7 H), 6.9-6.8 (m, 4 H), 5.88 (s, 1 H), 5.77 (s, 2 H); LC/MS: 2.39 min, m/z 329 (M$^+$+1)

Example 212

Phenyl-carbamic acid (cis-4,5-diphenyl-4,5-dihydro-1H-imidazol-2-yl)-phenyl-methyl ester trifluoroacetate Step 1:

To a solution of (4,5-Diphenyl-4,5-dihydro-1H-imidazol-2-yl)-phenyl-methanol (231 mg, 0.70 mmol) in dichloromethane (2.4 mL) is added phenyl isocyanate (91 μL, 0.84 mmol) and 4-dimethylaminopyridine (8 mg, 0.07 mmol). The mixture is stirred for 2 hrs then concentrated. The residue is purified by chromatography on silica gel; eluting with MeOH:CH$_2$CL$_2$ (3:97). The residue is further purified by chromatography on reverse phase silica gel; gradient elution with acetonitrile/0.1% TFA:water/0.1% TFA (45:55 to 85:15 over 20 min) gives 19 mg of product. $^1$H NMR (DMSO) δ 10.95 (bs, 2 H), 7.78 (bs, 1 H), 7.70-7.63 (m, 2 H), 7.6-7.4 (m, 4 H), 7.2-7.0 (m, 7 H), 6.85-6.80 (m, 4 H), 6.75-6.60 (m, 3 H), 5.86 (s, 1 H), 5.77 (s, 2 H); LC/MS: 2.95 min, m/z 448 (M$^+$+1).

A few of the trans-isomeric form of the compounds of the present invention are prepared in the following Comparative Examples 1 to 20 in order to test their efficacy in inhibiting the effects of P2X7 receptor site in accordance with the procedures set forth in Example 214. The results obtained indicate that the following trans-isomers are not active in inhibiting the effects of P2X7 receptor.

Comparative Example 1

[trans-(4S,5S)-Diphenyl-4,5-dihydro-1H-imidazol-2-yl]-(2-chlorobenzyl)amine (166)

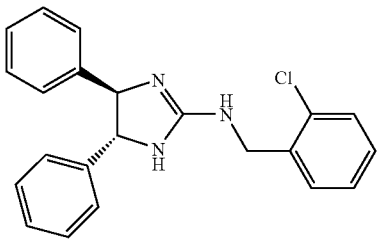

A mixture of intermediate 70 (300 mg, 0.814 mmol), 2-chlorobenzylamine (0.5 mL, 4.14 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 102 mg of the product 166. LC/MS: 1.41 min, m/z 362 (M$^+$+1).

Comparative Example 2

[trans-(4S,5S)-Diphenyl-4,5-dihydro-1H-imidazol-2-yl]-(2-trifluoromethylbenzyl)-amine (167)

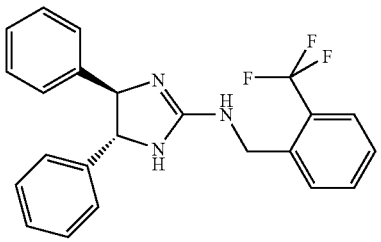

A mixture of intermediate 70 (300 mg, 0.814 mmol), 2-trifluoromethylbenzylamine (0.5 mL, 3.57 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 160 mg of the product 167. LC/MS: 1.79 min, m/z 396 (M$^+$+1).

Comparative Example 3

[trans-(4S,5S)-Diphenyl-4,5-dihydro-1H-imidazol-2-yl]-(2,4-dichlorobenzyl)amine (168)

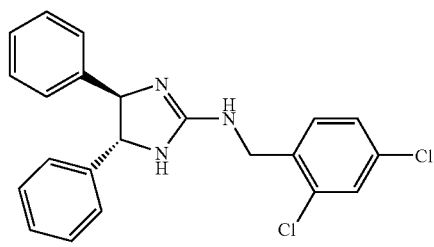

A mixture of intermediate 70 (300 mg, 0.814 mmol), 2,4-dichlorobenzylamine (0.5 mL, 3.74 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 170 mg of the product 168. LC/MS: 1.46 min, m/z 396 (M$^+$+1).

Comparative Example 4

[trans-(4S,5S)-Diphenyl-4,5-dihydro-1H-imidazol-2-yl]-(3,4-dichlorobenzyl)amine (169)

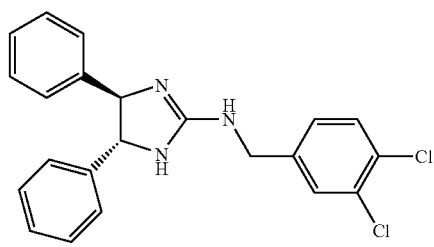

A mixture of intermediate 70 (300 mg, 0.814 mmol), 3,4-dichlorobenzylamine (0.5 mL, 3.77 mmol) is heated at 150° C. (reaction block) overnight. The reaction mixture is cooled to RT. The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 170 mg of the product 169. LC/MS: 1.82 min, m/z 396 (M$^+$+1).

Comparative Example 5

[trans-(4S,5S)-Diphenyl-4,5-dihydro-1H-imidazol-2-yl]-(3-methoxybenzyl)amine (170)

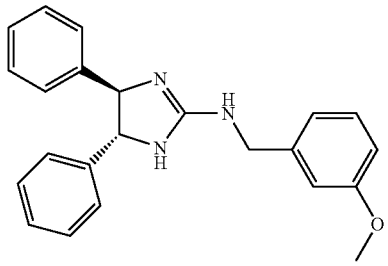

A mixture of intermediate 70 (300 mg, 0.814 mmol), 3-methoxybenzylamine (0.5 mL, 3.83 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 129 mg of the product 170. LC/MS: 1.38 min, m/z 358 (M$^+$+1).

Comparative Example 6

[trans-(4S,5S)-Diphenyl-4,5-dihydro-1H-imidazol-2-yl]-(4-trifluoromethylbenzyl)-amine (171)

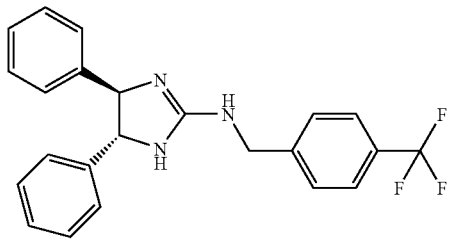

A mixture of intermediate 70 (300 mg, 0.814 mmol), 4-trifluoromethylbenzylamine (0.5 mL, 3.51 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 69 mg of the product 171. LC/MS: 1.81 min, m/z 396 (M$^+$+1).

Comparative Example 7

[trans-(4S,5S)-Diphenyl-4,5-dihydro-1H-imidazol-2-yl]-(3,4,5-trimethoxybenzyl)-amine (172)

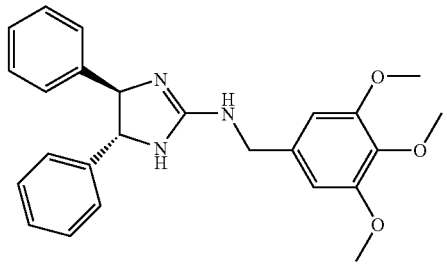

A mixture of intermediate 70 (300 mg, 0.814 mmol), 3,4,5-trimethoxybenzylamine (0.5 mL, 2.93 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 144 mg of the product 172. LC/MS: 1.36 min, m/z 418 (M$^+$+1).

Comparative Example 8

[trans-(4S,5S)-Diphenyl-4,5-dihydro-1H-imidazol-2-yl]-(4-fluorobenzyl)amine (173)

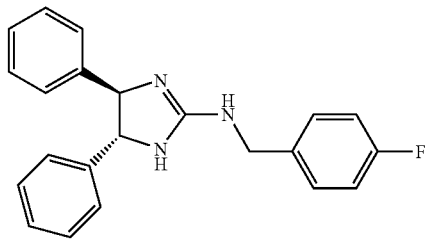

A mixture of intermediate 70 (300 mg, 0.814 mmol), 4-fluorobenzylamine (0.5 mL, 4.40 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 102 mg of the product 173. LC/MS: 1.39 min, m/z 346 (M$^+$+1).

Comparative Example 9

[trans-(4S,5S)-Diphenyl-4,5-dihydro-1H-imidazol-2-yl]amine trifluoroacetate (174)

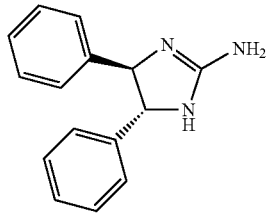

A mixture of intermediate 70 (500 mg, 1.36 mmol) in ethylene glycol (3.5 mL) is saturated with ammonia and heated at 170° C. overnight. The reaction mixture is cooled to rt, and water added. The precipitated material is filtered and purified by preparative HPLC to give 160 mg of the product 174. $^1$H NMR (CDCl$_3$) δ 8.39 (s, 2 H), 8.15 (s, 2 H), 7.50-7.25 (m, 6 H), 7.25-7.10 (m, 4 H), 4.76 (s, 2 H); LC/MS: 2.78 m/z 238 (M$^+$+1).

Comparative Example 10

[trans-(4R,5R)-Diphenyl-4,5-dihydro-1H-imidazol-2-yl]-(2-trifluoromethylbenzyl)-amine (175)

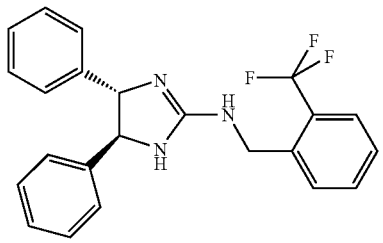

A mixture of intermediate 71 (300 mg, 0.814 mmol), 2-trifluoromethylbenzylamine (0.5 mL, 3.57 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 124 mg of the product 175. LC/MS: 1.79 min, m/z 396 (M$^+$+1).

Comparative Example 11

[trans-(4R,5R)-Diphenyl-4,5-dihydro-1H-imidazol-2-yl]-(2,4-dichlorobenzyl)amine (176)

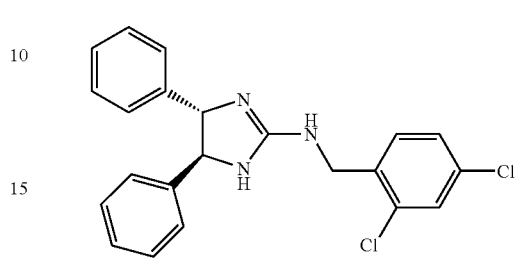

A mixture of intermediate 71 (300 mg, 0.814 mmol), 2,4-dichlorobenzylamine (0.5 mL, 3.74 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 107 mg of the product 176. LC/MS: 1.81 min, m/z 396 (M$^+$+1).

Comparative Example 12

[trans-(4R,5R)-Diphenyl-4,5-dihydro-1H-imidazol-2-yl]-(3,4-dichlorobenzyl)amine (177)

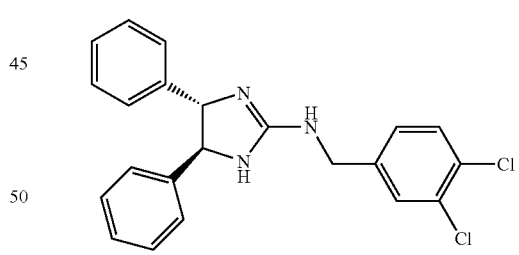

A mixture of intermediate 71 (300 mg, 0.814 mmol), 3,4-dichlorobenzylamine (0.5 mL, 3.77 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 275 mg of the product 177. LC/MS: 1.47 min, m/z 396 (M$^+$+1).

Comparative Example 13

[trans-(4R,5R)-Diphenyl-4,5-dihydro-1H-imidazol-2-yl]-(2-methoxybenzyl)amine (178)

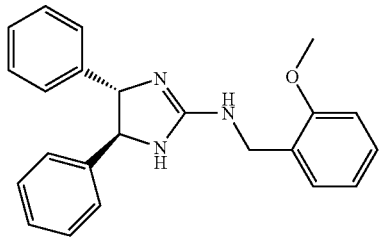

A mixture of intermediate 71 (300 mg, 0.814 mmol), 2-methoxybenzylamine (0.5 mL, 3.83 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 94 mg of the product 178. LC/MS: 1.40 min, m/z 358 ($M^+$+1).

Comparative Example 14

[trans-(4R,5R)-Diphenyl-4,5-dihydro-1H-imidazol-2-yl]-(3-methoxybenzyl)amine (179)

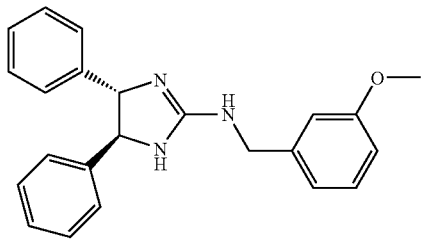

A mixture of intermediate 71 (300 mg, 0.814 mmol), 3-methoxybenzylamine (0.5 mL, 3.83 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 172 mg of the product 179. LC/MS: 1.39 min, m/z 358 ($M^+$+1).

Comparative Example 15

[trans-(4R,5R)-Diphenyl-4,5-dihydro-1H-imidazol-2-yl]-(4-trifluoromethylbenzyl)-amine (180)

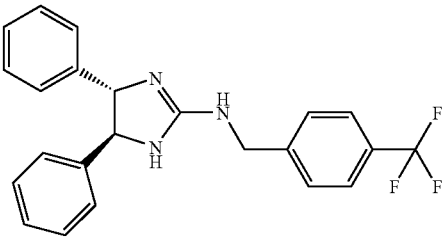

A mixture of intermediate 71 (300 mg, 0.814 mmol), 4-trifluoromethylbenzylamine (0.5 mL, 3.51 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 166 mg of the product 180. LC/MS: 1.45 min, m/z 396 ($M^+$+1).

Comparative Example 16

[trans-(4R,5R)-Diphenyl-4,5-dihydro-1H-imidazol-2-yl]-(2-fluorobenzyl)amine (181)

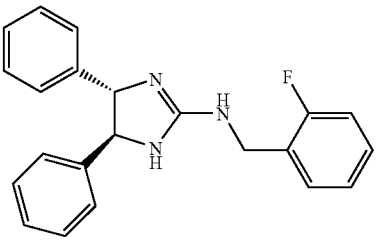

A mixture of intermediate 71 (300 mg, 0.814 mmol), 2-fluorobenzylamine (0.5 mL, 4.37 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 105 mg of the product 181. LC/MS: 1.38 min, m/z 346 ($M^+$+1).

Comparative Example 17

[trans-(4R,5R)-Diphenyl-4,5-dihydro-1H-imidazol-2-yl]-(3,4,5-trimethoxybenzyl)-amine (182)

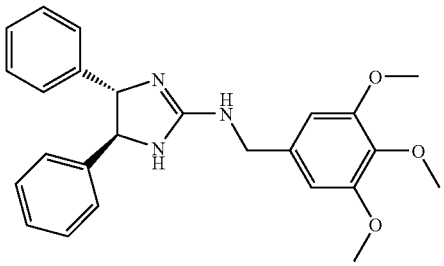

A mixture of intermediate 71 (300 mg, 0.814 mmol), 3,4,5-trimethoxybenzylamine (0.5 mL, 2.93 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 144 mg of the product 182. LC/MS: 1.36 min, m/z 418 ($M^+$+1).

Comparative Example 18

[trans-(4R,5R)-Diphenyl-4,5-dihydro-1H-imidazol-2-yl]-(4-fluorobenzyl)amine (183)

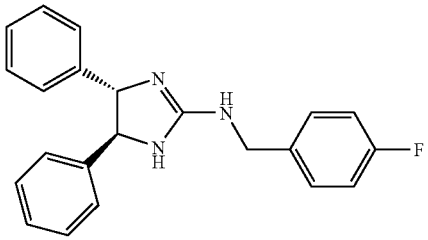

A mixture of intermediate 71 (300 mg, 0.814 mmol), 4-fluorobenzylamine (0.5 mL, 4.40 mmol) is heated at 150° C. (reaction block) overnight. The reaction mixture is cooled to rt, The corresponding N-Boc intermediate is not isolated. The reaction mixture is dissolved in EtOAc (10 mL) and hydrogen chloride is bubbled into the solution for 1 min, and the solution is stirred at rt overnight. The reaction mixture is neutralized, the solvent is evaporated, and the residue is purified by chromatography on silica gel; gradient elution with heptane:EtOAc (70:30-50:50) gives 155 mg of the product 183. LC/MS: 1.72 min, m/z 346 ($M^+$+1).

Comparative Example 19

[trans-(4R,5R)-Diphenyl-4,5-dihydro-1H-imidazol-2-yl]-amine trifluoroacetate (184)

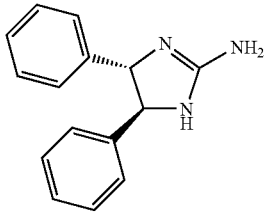

A mixture of intermediate 71 (500 mg, 1.36 mmol) in ethylene glycol (3.5 mL) is saturated with ammonia and heated at 130° C. overnight. The reaction mixture is cooled to rt, and water added. The precipitated material is filtered and purified by preparative HPLC to give 136 mg of the product 184. $^1$H NMR (CDCl$_3$) δ 8.38 (s, 2 H), 8.20 (s, 2 H), 7.50-7.30 (m, 6 H), 7.30-7.15 (m, 4 H), 4.78 (s, 2 H); LC/MS: 2.82 m/z 238 ($M^+$+1).

Comparative Example 20 trans-4,5-bis-(4-Fluorophenyl)-4-methyl-4,5-dihydro-1H-imidazol-2-yl]-(4-fluoro-benzyl)amine (187)

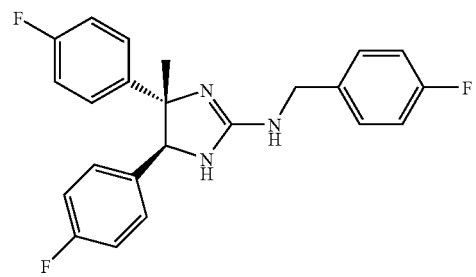

A mixture of intermediate 74 (198 mg, 0.473 mmol), 4-fluorobenzylamine (0.5 mL, 4.2 mmol) is heated at 150° C. overnight. The reaction mixture is cooled to rt, The reaction mixture is diluted with dichloromethane, washed with 3M HCl, brine, and then dried (MgSO$_4$). The mixture is filtered, the filtrate evaporated, and the residue triturated with dichloromethane:Et$_2$O:heptane, and the insoluble material filtered to give 150 mg of the product 187. $^1$H NMR (DMSO-d$_6$) δ 9.80-8.40 (m, 2 H), 7.65-7.40 (m, 4 H), 7.40-7.10 (m, 8 H), 7.15-6.80 (m, 8 H), 4.98 (s, 1 H), 4.70-4.40 (m, 2 H), 1.10 (s, 3 H); MS: m/z 396 ($M^+$+1).

BIOLOGICAL EXAMPLES

Example 213

This Example illustrates the biological efficacy of the compounds of the present invention at the P2X7 receptor site.

A human analog of the rat P2X7 clone (Suprenant et al., "The cytolytic P2Z receptor for extracellular ATP identified as a P2X receptor (P2X7)," Science vol. 272, May 3, 1996, pp. 735-738.) was identified by a BLAST search of the database maintained by Incyte Pharmaceuticals, Inc. (Palo Alto, Calif.). The complete open reading frame of human P2X7 was amplified from Incyte clone 148057 with the polymerase chain reaction using an upstream primer B299 (5'-GGTAC-CAAGCTTGAGTCACCATGCCGGCCTGCTGCAG-3') containing the initiating methionine codon and a downstream primer (M13 reverse). Restriction of the pcr product at the Hin dIII site and at the vector-derived Kpn I site produced a 2177 bp DNA suitable for cloning into the eukaryotic expression vector pcDNA3 (Stratagene). The DNA sequence of the human P2X7 cDNA was determined in its entirety; the deduced peptide sequence was identical to that submitted to GENBANK under the accession number Y09561. This inferred protein contains 595 amino acids and has a calculated MW of 68,558 Da.

U373 cells were transfected with pcDNA3-P2X7 using the calcium phosphate co-precipitation technique and grown in Dulbecco's modified Eagle's medium supplemented with 10% fetal bovine serum at 37° C. in an atmosphere of 95% air, 5% $CO_2$. Following a 24-hr exposure to DNA, cells were trypsinized and re-seeded at low density in the presence of 600 mM G418. After incubation for 2 weeks, isolated clones were selected with cloning cylinders and replated in 200 mM G418. Cell clones were then expanded. Clones were screened for P2X7 by applying ATP and recording the resultant current using patch clamp electrophysiology.

U373 cells stably expressing P2X7 were used to screen drugs via a dye uptake assay. Cells were plated overnight on collagen coated 96-well plates at a density of 35,000 cells per well. The following day, culture media was replaced with $Mg^{++}$ and $Ca^{++}$-free Hank's balanced salt solution and various concentrations of test compounds ranging from 30 nM to 3 µM. Cells were then allowed to incubate with test compounds at 37° C. for 20 minutes. Following this incubation period YO-PRO-1 dye (Molecular Probes, Eugene, Oreg., final concentration 5 µM) and 2'-&3'-O-(4-Benzolybenzoyl)-Adenosine 5'-triphosphate (Sigma Chemical, St Louis, Mo., final concentration 300 µM) were added to the cells sequentially. Cells were then incubated at 37° C. for 1.5 hours. After this period, cellular fluorescence (indicating dye uptake through P2X7) was measured using a fluorescence plate reader (excitation: 485/20, emission: 530/25). Fluorescence in the presence of test substances was compared to that in the absence of test substances (control). These data were expressed as a % of control and plotted against concentration to determine $IC_{50}$ values and are summarized in Table 6.

TABLE 6

| Compound | $IC_{50}$ (nM) |
|---|---|
| (cis-4,5-Diphenyl-4,5-dihydro-1H-imidazol-2-yl)benzylamine hydrochloride | 135 |
| (cis-4,5-Diphenyl-4,5-dihydro-1H-imidazol-2-yl)-(cyclohexylmethyl)amine hydrochloride | 124 |
| (cis-4,5-Diphenyl-4,5-dihydro-1H-imidazol-2-yl)-N-methylbenzylamine hydrochloride | 147 |
| (cis-4,5-Diphenyl-4,5-dihydro-1H-imidazol-2-yl)-(3,4,5-trifluorobenzyl)amine hydrochloride | 77 |
| (cis-4,5-Diphenyl-4,5-dihydro-1H-imidazol-2-yl)-(4-fluorobenzyl)amine hydrochloride | 96 |
| (cis-4,5-Diphenyl-4,5-dihydro-1H-imidazol-2-yl)-(3-fluorobenzyl)amine hydrochloride | 89 |
| (cis-4,5-Diphenyl-4,5-dihydro-1H-imidazol-2-yl)-(3,5-difluorobenzyl)amine hydrochloride | 102 |
| (cis-4,5-Diphenyl-4,5-dihydro-1H-imidazol-2-yl)-[2-(2-fluorophenyl)ethyl]amine hydrochloride | 87 |
| (cis-4,5-Diphenyl-4,5-dihydro-1H-imidazol-2-yl)-2-phenethylamine hydrochloride | 113 |
| (cis-4,5-Diphenyl-4,5-dihydro-1H-imidazol-2-yl)-(3-methylbenzyl)amine | 187 |
| (cis-4,5-Diphenyl-4,5-dihydro-1H-imidazol-2-yl)-(3,4-difluorobenzyl)amine | 65 |
| (cis-4,5-Diphenyl-4,5-dihydro-1H-imidazol-2-yl)-(3-chlorobenzyl)amine | 164 |
| (cis-4,5-Diphenyl-4,5-dihydro-1H-imidazol-2-yl)-(3-bromobenzyl)amine | 225 |
| (cis-4,5-Diphenyl-4,5-dihydro-1H-imidazol-2-yl)-(2-bromobenzyl)amine | 503 |
| (cis-4,5-Diphenyl-4,5-dihydro-1H-imidazol-2-yl)-(2-methylbenzyl)amine | 243 |
| (cis-4,5-Diphenyl-4,5-dihydro-1H-imidazol-2-yl)-(2-chloro-4-fluorobenzyl)amine | 247 |
| (cis-4,5-Diphenyl-4,5-dihydro-1H-imidazol-2-yl)-[2-(4-fluorophenyl)ethyl]amine | 331 |
| (cis-4,5-Diphenyl-4,5-dihydro-1H-imidazol-2-yl)-(2-chlorobenzyl)amine | 587 |
| (cis-4,5-Diphenyl-4,5-dihydro-1H-imidazol-2-yl)-(3,4-dichlorobenzyl)amine | 307 |
| (cis-4,5-Diphenyl-4,5-dihydro-1H-imidazol-2-yl)-(2,4-difluorobenzyl)amine | 289 |
| (cis-4,5-Diphenyl-4,5-dihydro-1H-imidazol-2-yl)-(2-fluorobenzyl)amine | 409 |
| (cis-4,5-Diphenyl-4,5-dihydro-1H-imidazol-2-yl)-(4-chlorobenzyl)amine | 471 |
| (cis-4,5-Diphenyl-4,5-dihydro-1H-imidazol-2-yl)-(2-methoxybenzyl)amine | 409 |
| (cis-4,5-Diphenyl-4,5-dihydro-1H-imidazol-2-yl)-(3-methoxybenzyl)amine | 386 |
| (cis-4,5-bis-(2-Fluorophenyl)-4,5-dihydro-1H-imidazol-2-yl)-benzylamine hydrochloride | 531 |
| (cis-4,5-bis-(2-Fluorophenyl)-4,5-dihydro-1H-imidazol-2-yl)-(4-fluorobenzyl)amine hydrochloride | 390 |
| [cis-4,5-bis-(2-Fluorophenyl)-4,5-dihydro-1H-imidazol-2-yl]-(3,4-difluorobenzyl)-amine hydrochloride | 312 |
| [cis-4,5-bis-(2-Fluorophenyl)-4,5-dihydro-1H-imidazol-2-yl]-(3-methylbenzyl)amine hydrochloride | 379 |
| [cis-4,5-bis-(3-Fluorophenyl)-4,5-dihydro-1H-imidazol-2-yl]-benzylamine hydrochloride | 90 |
| [cis-4,5-bis-(3-Fluorophenyl)-4,5-dihydro-1H-imidazol-2-yl]-(3-fluorobenzyl)amine hydrochloride | 42 |
| [cis-4,5-bis-(3-Fluorophenyl)-4,5-dihydro-1H-imidazol-2-yl]-(4-fluorobenzyl)amine hydrochloride | 71 |
| [cis-4,5-bis-(3-Fluorophenyl)-4,5-dihydro-1H-imidazol-2-yl]-(3,4-difluorobenzyl)-amine hydrochloride | 71 |
| [cis-4,5-bis-(2-Methylphenyl)-4,5-dihydro-1H-imidazol-2-yl]-benzylamine hydrochloride | 167 |
| [cis-4,5-bis-(2-Methylphenyl)-4,5-dihydro-1H-imidazol-2-yl]-(3-fluorobenzyl)amine hydrochloride | 121 |
| [cis-4,5-bis-(2-Methylphenyl)-4,5-dihydro-1H-imidazol-2-yl]-(4-fluorobenzyl)amine hydrochloride | 139 |

TABLE 6-continued

| Compound | IC$_{50}$ (nM) |
|---|---|
| [cis-4,5-bis-(2-Methylphenyl)-4,5-dihydro-1H-imidazol-2-yl]-(3,4-difluorobenzyl)-amine hydrochloride | 77 |
| [cis-4,5-bis-(3-Methylphenyl)-4,5-dihydro-1H-imidazol-2-yl]-benzylamine hydrochloride | 157 |
| [cis-4,5-bis-(3-Methylphenyl)-4,5-dihydro-1H-imidazol-2-yl]-(3-fluorobenzyl)amine hydrochloride | 121 |
| [cis-4,5-bis-(3-Methylphenyl)-4,5-dihydro-1H-imidazol-2-yl]-(4-fluorobenzyl)amine hydrochloride | 107 |
| [cis-4,5-bis-(3-Methylphenyl)-4,5-dihydro-1H-imidazol-2-yl]-(3,4-difluorobenzyl)-amine hydrochloride | 118 |
| [cis-4,5-bis-(4-Methylphenyl)-4,5-dihydro-1H-imidazol-2-yl]-benzylamine hydrochloride | 275 |
| [cis-4,5-bis-(4-Methylphenyl)-4,5-dihydro-1H-imidazol-2-yl]-(3-fluorobenzyl)amine hydrochloride | 134 |
| [cis-4,5-bis-(4-Methylphenyl)-4,5-dihydro-1H-imidazol-2-yl]-(4-fluorobenzyl)amine hydrochloride | 287 |
| [cis-4,5-bis-(4-Methylphenyl)-4,5-dihydro-1H-imidazol-2-yl]-(3,4-difluorobenzyl)-amine hydrochloride | 150 |
| [cis-4,5-bis-(3-Chlorophenyl)-4,5-dihydro-1H-imidazol-2-yl]-benzylamine hydrochloride | 433 |
| [cis-4,5-bis-(3-Chlorophenyl)-4,5-dihydro-1H-imidazol-2-yl]-(4-fluorobenzyl)amine hydrochloride | 318 |
| [cis-4,5-bis-(3-Chlorophenyl)-4,5-dihydro-1H-imidazol-2-yl]-(3,4-difluorobenzyl)-amine hydrochloride | 247 |
| [cis-4,5-bis-(2-Chlorophenyl)-4,5-dihydro-1H-imidazol-2-yl]-benzylamine hydrochloride | 925 |
| [cis-4,5-bis-(2-Chlorophenyl)-4,5-dihydro-1H-imidazol-2-yl]-(3-fluorobenzyl)amine hydrochloride | 592 |
| [cis-4,5-bis-(2-Chlorophenyl)-4,5-dihydro-1H-imidazol-2-yl]-(4-fluorobenzyl)amine hydrochloride | 624 |
| [cis-4,5-bis-(2-Chlorophenyl)-4,5-dihydro-1H-imidazol-2-yl]-(3,4-difluorobenzyl)-amine hydrochloride | 378 |
| [cis-4,5-bis-(4-Chlorophenyl)-4,5-dihydro-1H-imidazol-2-yl]-benzylamine hydrochloride | 404 |
| [cis-4,5-bis-(4-Chlorophenyl)-4,5-dihydro-1H-imidazol-2-yl]-(3,4-difluorobenzyl)-amine hydrochloride | 400 |
| [cis-4,5-bis-(2-Bromophenyl)-4,5-dihydro-1H-imidazol-2-yl]-(3-fluorobenzyl)amine hydrochloride | 782 |
| [cis-4,5-bis-(2-Bromophenyl)-4,5-dihydro-1H-imidazol-2-yl]-(4-fluorobenzyl)amine hydrochloride | 898 |
| [cis-4,5-bis-(4-Fluorophenyl)-4,5-dihydro-1H-imidazol-2-yl]-benzylamine hydrochloride | 371 |
| cis-4,5-bis-(4-Fluorophenyl)-4,5-dihydro-1H-imidazol-2-yl]-(4-fluorobenzyl)amine hydrochloride | 338 |
| (cis-4,5-Diphenyl-4-methyl-4,5-dihydro-1H-imidazol-2-yl)-(4-fluorobenzyl)amine hydrochloride | 63 |
| [4,5-cis-bis-(4-Fluorophenyl)-4-methyl-4,5-dihydro-1H-imidazol-2-yl]-(4-fluoro-benzyl)amine | 139 |
| cis-4,5-bis-(3-Fluorophenyl)-4-methyl-4,5-dihydro-1H-imidazol-2-yl]-(4-fluoro-benzyl)amine | 37 |
| 2-[(4-Fluorobenzyl)thio]-cis-4,5-diphenyl-4,5-dihydro-1H-imidazole hydrochloride | 300 |
| 2-(Benzylthio)-cis-4,5-diphenyl-4,5-dihydro-1H-imidazole hydrochloride | 214 |
| 2-[(3-Chlorobenzyl)thio]-cis-4,5-diphenyl-4,5-dihydro-1H-imidazole hydrochloride | 634 |
| 2-[(2-Chlorobenzyl)thio]-cis-4,5-diphenyl-4,5-dihydro-1H-imidazole hydrochloride | 630 |
| 2-[(2-Fluorobenzyl)thio]-cis-4,5-diphenyl-4,5-dihydro-1H-imidazole hydrochloride | 819 |
| 2-[(3-Methylbenzyl)thio]-cis-4,5-diphenyl-4,5-dihydro-1H-imidazole hydrochloride | 722 |
| 2-[(3,4-Difluorobenzyl)thio]-cis-4,5-diphenyl-4,5-dihydro-1H-imidazole hydrochloride | 461 |
| 2-[(3-Methoxybenzyl)thio]-cis-4,5-diphenyl-4,5-dihydro-1H-imidazole hydrochloride | 987 |
| 2-[(3-Fluorobenzyl)thio]-cis-4,5-diphenyl-4,5-dihydro-1H-imidazole hydrochloride | 240 |
| 2-[(2-Iodobenzyl)thio]-cis-4,5-diphenyl-4,5-dihydro-1H-imidazole hydrochloride | 647 |
| 2-[(3,4-Dibenzyloxybenzyl)thio]-cis-4,5-diphenyl-4,5-dihydro-1H-imidazole hydrochloride | 548 |
| 2-[(2-Methylbenzyl)thio]-cis-4,5-diphenyl-4,5-dihydro-1H-imidazole hydrochloride | 449 |
| 2-[(2-Chloro-4-fluorobenzyl)thio]-cis-4,5-diphenyl-4,5-dihydro-1H-imidazole hydrochloride | 828 |

TABLE 6-continued

| Compound | IC$_{50}$ (nM) |
|---|---|
| 2-[(2-Bromobenzyl)thio]-cis-4,5-diphenyl-4,5-dihydro-1H-imidazole hydrochloride | 521 |
| 2-Phenethyl-cis-4,5-diphenyl-4,5-dihydro-1H-imidazole hydrochloride | 77 |
| 2-Phenethyl-cis-4,5-bis-(3-fluorophenyl)-4,5-dihydro-1H-imidazole hydrochloride | 146 |
| 2-Phenethyl-cis-4,5-bis-(4-fluorophenyl)-4,5-dihydro-1H-imidazole hydrochloride | 277 |
| 2-Phenethyl-cis-4,5-diphenyl-4-methyl-4,5-dihydro-1H-imidazole hydrochloride | 22 |
| 2-Phenethyl-cis-4,5-bis-(3-fluorophenyl)-4-methyl-4,5-dihydro-1H-imidazole hydrochloride | 66 |
| 2-[2-(3,4-Difluorophenyl)ethyl]-cis-4,5-bis-(3-fluorophenyl)-4,5-dihydro-1H-imidazole | 173 |
| 2-[2-(2-Chlorophenyl)ethyl]-cis-4,5-bis-(3-fluorophenyl)-4,5-dihydro-1H-imidazole | 140 |
| 2-(cis-4,5-Diphenyl-4,5-dihydro-1H-imidazol-2-yl)-1-phenylethan-1-ol | 195 |
| 2-[2-(2-Methoxyphenyl)ethyl]-cis-4,5-diphenyl-4,5-dihydro-1H-imidazole trifluoroacetate | 832 |
| 2-[2-(2-Methylphenyl)ethyl]-cis-4,5-diphenyl-4,5-dihydro-1H-imidazole | 42 |
| 2-[2-(3,4-Difluorophenyl)ethyl]-cis-4,5-diphenyl-4,5-dihydro-1H-imidazole | 122 |
| 2-[2-[(2S)-Phenyl)propyl]-cis-4,5-diphenyl-4,5-dihydro-1H-imidazole trifluoroacetate | 13 |
| 2-[2-(2-Fluorophenyl)ethyl]-cis-4,5-diphenyl-4,5-dihydro-1H-imidazole trifluoroacetate | 164 |
| 2-[2-(3-Fluorophenyl)ethyl]-cis-4,5-diphenyl-4,5-dihydro-1H-imidazole trifluoroacetate | 31 |
| 2-[2-(4-Fluorophenyl)ethyl]-cis-4,5-diphenyl-4,5-dihydro-1H-imidazole trifluoroacetate | 218 |
| 2-[2-(2-Chlorophenyl)ethyl]-cis-4,5-diphenyl-4,5-dihydro-1H-imidazole trifluoroacetate | 48 |
| 2-[2-(3-Methylphenyl)ethyl]-cis-4,5-diphenyl-4,5-dihydro-1H-imidazole trifluoroacetate | 229 |
| 2-(3-Chlorobenzyl)-cis-4,5-diphenyl-4,5-dihydro-1H-imidazole trifluoroacetate | 34 |
| 2-(4-Trifluoromethylbenzyl)-cis-4,5-diphenyl-4,5-dihydro-1H-imidazole trifluoroacetate | 403 |
| 2-(2-Fluorobenzyl)-cis-4,5-diphenyl-4,5-dihydro-1H-imidazole trifluoroacetate | 577 |
| 2-(4-Fluorobenzyl)-cis-4,5-diphenyl-4,5-dihydro-1H-imidazole trifluoroacetate | 46 |
| 2-(2-Bromobenzyl)-cis-4,5-diphenyl-4,5-dihydro-1H-imidazole trifluoroacetate | 321 |
| 2-(2,4-Difluorobenzyl)-cis-4,5-diphenyl-4,5-dihydro-1H-imidazole trifluoroacetate | 42 |
| 2-(3,4-Difluorobenzyl)-cis-4,5-diphenyl-4,5-dihydro-1H-imidazole trifluoroacetate | 24 |
| 2-(2-Methylbenzyl)-cis-4,5-diphenyl-4,5-dihydro-1H-imidazole trifluoroacetate | 321 |
| 2-[(1-Phenyl)-(1S)-ethyl]-cis-4,5-diphenyl-4,5-dihydro-1H-imidazole trifluoroacetate | 110 |
| 2-[(1-Phenyl)-(1R)-ethyl]-cis-4,5-diphenyl-4,5-dihydro-1H-imidazole trifluoroacetate | 108 |
| 2-[1-{(4-Chlorophenyl)-1-methyl}ethyl]-cis-4,5-diphenyl-4,5-dihydro-1H-imidazole trifluoroacetate | 537 |
| 2-[1-Phenyl-1-cyclopropyl]-cis-4,5-diphenyl-4,5-dihydro-1H-imidazole trifluoroacetate | 334 |
| 2-[1-(4-Chlorophenyl)-1-ethyl]-cis-4,5-diphenyl-4,5-dihydro-1H-imidazole trifluoroacetate | 423 |
| 2-(2-Chloro-6-fluorobenzyl)-cis-4,5-diphenyl-4,5-dihydro-1H-imidazole trifluoroacetate | 826 |
| 2-(4-Methylbenzyl)-cis-4,5-diphenyl-4,5-dihydro-1H-imidazole trifluoroacetate | 83 |
| 2-(2-Chlorobenzyl)-cis-4,5-diphenyl-4,5-dihydro-1H-imidazole trifluoroacetate | 163 |
| 2-(2,5-Difluorobenzyl)-cis-4,5-diphenyl-4,5-dihydro-1H-imidazole trifluoroacetate | 142 |
| 2-(2,6-Difluorobenzyl)-cis-4,5-diphenyl-4,5-dihydro-1H-imidazole trifluoroacetate | 966 |
| 2-(3-Fluorobenzyl)-cis-4,5-diphenyl-4,5-dihydro-1H-imidazole trifluoroacetate | 84 |
| 2-(3-Methylbenzyl)-cis-4,5-diphenyl-4,5-dihydro-1H-imidazole trifluoroacetate | 376 |
| 2-(2,3-Difluorobenzyl)-cis-4,5-diphenyl-4,5-dihydro-1H-imidazole trifluoroacetate | 930 |

TABLE 6-continued

| Compound | IC$_{50}$ (nM) |
|---|---|
| 2-(4-Chlorobenzyl)-cis-4,5-diphenyl-4,5-dihydro-1H-imidazole trifluoroacetate | 269 |
| 2-(2-Chloro-4-fluorobenzyl)-cis-4,5-diphenyl-4,5-dihydro-1H-imidazole trifluoroacetate | 120 |
| 2-(3-Fluoro-4-methylbenzyl)-cis-4,5-diphenyl-4,5-dihydro-1H-imidazole trifluoroacetate | 178 |
| 2-(3-Chloro-4-fluorobenzyl)-cis-4,5-diphenyl-4,5-dihydro-1H-imidazole trifluoroacetate | 13 |
| 2-(2-Fluoro-3-chlorobenzyl)-cis-4,5-diphenyl-4,5-dihydro-1H-imidazole trifluoroacetate | 142 |
| 2-(2,6-Difluoro-3-methylbenzyl)-cis-4,5-diphenyl-4,5-dihydro-1H-imidazole trifluoroacetate | 594 |
| 2-(2-Methyl-5-fluorobenzyl)-cis-4,5-diphenyl-4,5-dihydro-1H-imidazole trifluoroacetate | 319 |
| 2-[2-(2-Fluorophenyl)ethyl]-cis-4,5-bis-(3-fluorophenyl)-4,5-dihydro-1H-imidazole trifluoroacetate | 304 |
| 2-[2-(3-Fluorophenyl)ethyl]-cis-4,5-bis-(3-fluorophenyl)-4,5-dihydro-1H-imidazole trifluoroacetate | 79 |
| 2-[2-(4-Fluorophenyl)ethyl]-cis-4,5-bis-(3-fluorophenyl)-4,5-dihydro-1H-imidazole trifluoroacetate | 572 |
| 2-[2-(3-Methylphenyl)ethyl]-cis-4,5-bis-(3-fluorophenyl)-4,5-dihydro-1H-imidazole trifluoroacetate | 385 |
| 2-[2-(2-Methylphenyl)ethyl]-cis-4,5-bis-(3-fluorophenyl)-4,5-dihydro-1H-imidazole trifluoroacetate | 94 |
| 2-[(2-Thiophen-2-yl)ethyl]-cis-4,5-bis-(3-fluorophenyl)-4,5-dihydro-1H-imidazole trifluoroacetate | 592 |
| 2-[(cis-4,5-Diphenyl-4,5-dihydro1H-imidazol-2-yl)-2-ethyl]pyridine | 720 |
| [4,5-cis-bis-(3-Fluorophenyl)-4-methyl-4,5-dihydro-1H-imidazol-2-yl]-(3-fluoro-benzyl)amine | 49 |
| [4,5-cis-bis-(4-Fluorophenyl)-4-methyl-4,5-dihydro-1H-imidazol-2-yl]-(3-fluoro-benzyl)amine | 353 |
| 2-[(Phenoxy)methyl]-cis-4,5-diphenyl-4,5-dihydro-1H-imidazole | 612 |
| 2-[(3-Fluorophenoxy)methyl]-cis-4,5-diphenyl-4,5-dihydro-1H-imidazole trifluoroacetate | 224 |
| 2-[(4-Fluorophenoxy)methyl]-cis-4,5-diphenyl-4,5-dihydro-1H-imidazole trifluoroacetate | 401 |
| 2-[(Benzyloxy)methyl]-cis-4,5-diphenyl-4,5-dihydro-1H-imidazole | 325 |
| 2-[(3-Fluorobenzyloxy)methyl]-cis-4,5-diphenyl-4,5-dihydro-1H-imidazole hydrochloride | 274 |
| 2-[(3-Methylbenzyloxy)methyl]-cis-4,5-diphenyl-4,5-dihydro-1H-imidazole hydrochloride | 415 |
| 2-[(Phenylsulfanyl)methyl]-cis-4,5-diphenyl-4,5-dihydro-1H-imidazole trifluoroacetate | 198 |
| 2-[(Benzylsulfanyl)methyl]-cis-4,5-diphenyl-4,5-dihydro-1H-imidazole trifluoroacetate | 583 |
| 2-[(Cyclohexyloxy)methyl]-cis-4,5-diphenyl-4,5-dihydro-1H-imidazole trifluoroacetate | 315 |
| 2-[(Cycloheptyloxy)methyl]-cis-4,5-diphenyl-4,5-dihydro-1H-imidazole trifluoroacetate | 603 |
| 2-[(Cyclooctyloxy)methyl]-cis-4,5-diphenyl-4,5-dihydro-1H-imidazole trifluoroacetate | 506 |
| [(cis-4,5-Diphenyl-4,5-dihydro-1H-imidazol-2-yl)methyl]benzylamine ditrifluoroacetate | 318 |
| 2-[(2-Phenethyloxy)methyl]-cis-4,5-diphenyl-4,5-dihydro-1H-imidazole | 768 |
| 2-[(2-Fluorophenoxy)methyl]-cis-4,5-bis-(3-fluorophenyl)-4,5-dihydro-1H-imidazole | 834 |
| 2-[(3-Fluorophenoxy)methyl]-cis-4,5-bis-(3-fluorophenyl)-4,5-dihydro-1H-imidazole | 316 |
| 2-[(4-Fluorophenoxy)methyl]-cis-4,5-bis-(3-fluorophenyl)-4,5-dihydro-1H-imidazole | 346 |
| 2-[(Phenoxy)methyl]-cis-4,5-diphenyl-4-methyl-4,5-dihydro-1H-imidazole trifluoroacetate | 405 |
| 2-[(3-Fluorophenoxy)methyl]-cis-4,5-diphenyl-4-methyl-4,5-dihydro-1H-imidazole trifluoroacetate | 104 |
| 2-(Cyclohexylmethoxy)-cis-4,5-diphenyl-4-methyl-4,5-dihydro-1H-imidazole trifluoroacetate | 275 |
| 2-[(Benzylsulfanyl)methyl]-cis-4,5-diphenyl-4-methyl-4,5-dihydro-1H-imidazole | 525 |
| 2-[(Cyclopentyloxy)methyl]-cis-4,5-diphenyl-4-methyl-4,5-dihydro-1H-imidazole hydrochloride | 487 |
| 2-[(1-Ethynyl-1-butoxy)methyl]-cis-4,5-diphenyl-4-methyl-4,5-dihydro-1H-imidazole hydrochloride | 739 |
| 2-[(Cyclopentylmethoxy)methyl]-cis-4,5-diphenyl-4-methyl-4,5-dihydro-1H-imidazole hydrochloride | 194 |
| 2-[(1-Cyclopentyl-1-ethoxy)methyl]-cis-4,5-diphenyl-4-methyl-4,5-dihydro-1H-imidazole hydrochloride | 160 |

TABLE 6-continued

| Compound | IC$_{50}$ (nM) |
|---|---|
| 2-[[(Cyclopropyl)methoxy]methyl]-cis-4,5-diphenyl-4-methyl-4,5-dihydro-1H-imidazole trifluoroacetate | 676 |
| 2-[(2-Chlorophenoxy)methyl]-cis-4,5-diphenyl-4-methyl-4,5-dihydro-1H-imidazole hydrochloride | 743 |
| 2-(1-Phenoxyethyl)-cis-4,5-diphenyl-4-methyl-4,5-dihydro-1H-imidazole trifluoroacetate | 356 |
| 2-[(Cyclobutoxy)methyl]-cis-4,5-diphenyl-4-methyl-4,5-dihydro-1H-imidazole trifluoroacetate | 722 |
| 2-[(1-Cyclopropyl-1-ethoxy)methyl]-cis-4,5-diphenyl-4-methyl-4,5-dihydro-1H-imidazole trifluoroacetate | 397 |
| 2-[(1-Benzopyran-4-yloxy)methyl]-cis-4,5-diphenyl-4-methyl-4,5-dihydro-1H-imidazoline hydrochloride | 490 |
| 2-Phenylthiomethyl-cis-4-phenyl-5-(pyridin-3-yl)-4,5-dihydro-1H-imidazole ditrifluoroacetate | 866 |
| 2-Phenethyl-cis-4-phenyl-5-(pyridin-3-yl)-4,5-dihydro-1H-imidazole ditrifluoroacetate | 251 |
| 2-(3-Chlorobenzyl)-cis-4,5-bis-(3-fluorophenyl)-4,5-dihydro-1H-imidazole trifluoroacetate | 330 |
| 2-(3,4-Difluorobenzyl)-cis-4,5-bis-(3-fluorophenyl)-4,5-dihydro-1H-imidazole trifluoroacetate | 79 |
| 2-(2,4-Difluorobenzyl)-cis-4,5-bis-(3-fluorophenyl)-4,5-dihydro-1H-imidazole trifluoroacetate | 409 |
| 2-(4-Fluorobenzyl)-cis-4,5-bis-(3-fluorophenyl)-4,5-dihydro-1H-imidazole trifluoroacetate | 217 |
| 2-(2-Fluorobenzyl)-cis-4,5-bis-(3-fluorophenyl)-4,5-dihydro-1H-imidazole trifluoroacetate | 449 |
| 2-(4-Fluorobenzyl)-cis-4,5-diphenyl-4-methyl-4,5-dihydro-1H-imidazole trifluoroacetate | 44 |
| 2-(3,4-Difluorobenzyl)-cis-4,5-diphenyl-4-methyl-4,5-dihydro-1H-imidazole trifluoroacetate | 19 |
| 2-(3-Chlorobenzyl)-cis-4,5-diphenyl-4-methyl-4,5-dihydro-1H-imidazole trifluoroacetate | 42 |
| 2-(2,4-Difluorobenzyl)-cis-4,5-diphenyl-4-methyl-4,5-dihydro-1H-imidazole trifluoroacetate | 16 |
| 2-(1-Phenyl-1-ethyl)-cis-4,5-diphenyl-4-methyl-4,5-dihydro-1H-imidazole trifluoroacetate | 68 |
| 2-[1-(4-Chlorophenyl)-1-ethyl]-cis-4,5-diphenyl-4-methyl-4,5-dihydro-1H-imidazole trifluoroacetate | 331 |
| 2-(4-Fluorobenzyl)-cis-4,5-bis-(3-fluorophenyl)-4-methyl-4,5-dihydro-1H-imidazole trifluoroacetate | 32 |
| 2-(Methoxy-phenyl-methyl)-4,5-diphenyl-4,5-dihydro-1H-imidazole trifluoroacetate | 101 |
| (4,5-Diphenyl-4,5-dihydro-1H-imidazol-2-yl)-phenyl-methanol trifluoroacetate | 241 |
| Phenyl-carbamic acid (4,5-diphenyl-4,5-dihydro-1H-imidazol-2-yl)-phenyl-methyl ester trifluoroacetate | 625 |
| 2-[2-Methyl-(2S)-phenyl)-propyl]-cis-4,5-diphenyl-4,5-dihydro-1H-imidazole trifluoroacetate | 10 |
| 2-[2,2-Diphenylethyl]-cis-4,5-diphenyl-4,5-dihydro-1H-imidazole trifluoroacetate | 320 |
| 2-[1-Methyl-2-phenylethyl]-cis-4,5-diphenyl-4,5-dihydro-1H-imidazole trifluoroacetate | 570 |
| 2-[3-Phenyl-propyl]-cis-4,5-diphenyl-4,5-dihydro-1H-imidazole trifluoroacetate | 540 |
| 2-[4-Phenyl-butyl]-cis-4,5-diphenyl-4,5-dihydro-1H-imidazole trifluoroacetate | 610 |
| 2-[2-(3-Chlorophenyl)ethyl]-cis-4,5-diphenyl-4,5-dihydro-1H-imidazole trifluoroacetate | 120 |
| 2-(2-Chlorobenzyl)-cis-4,5-diphenyl-4,5-dihydro-1H-imidazole trifluoroacetate | 160 |
| 2-(4-Chlorobenzyl)-cis-4,5-diphenyl-4,5-dihydro-1H-imidazole trifluoroacetate | 270 |
| 2-(3-Fluorobenzyl)-cis-4,5-diphenyl-4,5-dihydro-1H-imidazole trifluoroacetate | 80 |
| 2-(2,3-Difluorobenzyl)-cis-4,5-diphenyl-4,5-dihydro-1H-imidazole trifluoroacetate | 930 |
| 2-(4-Methylbenzyl)-cis-4,5-diphenyl-4,5-dihydro-1H-imidazole trifluoroacetate | 80 |
| 2-Indan-2-ylmethyl-cis-4,5-diphenyl-4,5-dihydro-1H-imidazole trifluoroacetate | 240 |
| 2-Indan-2-yl-4,5-diphenyl-4,5-dihydro-1H-imidazole trifluoroacetate | 50 |

Example 214

This Example demonstrates that the compounds of this invention are effective in inhibiting P2X7-mediated release of IL-1β from human macrophages activated by the Alzheimer's beta amyloid peptide 1-42.

Cell isolation: Monocytes were isolated from peripheral blood mononuclear cells (PBMCs) as follows. Whole blood was layered directly onto Histopak 1077-1 columns (Sigma Biochemicals) and centrifuged at 800×g for 15 minutes. The PBMC band of cells was removed to a fresh 50 ml culture tube and diluted 1:1 with wash buffer (Phosphate buffered saline, pH 7.4 containing 2 mM EDTA and 5 mg/ml BSA) followed by centrifugation at 800×g for 5 minutes. Cells were then washed by sequential resuspension of the cell pellet in wash buffer and centrifugation at 600×g for 5 minutes. The wash process was repeated until the supernatant was clear of contaminating platelets (5 to 6 washes). Monocytes were then purified from the PBMCs by negative selection using a monocyte isolation kit (Miltenyi Biotec, Inc) that contains antibodies to non-monocytic cells, running the cells over a magnetic column to remove antibody-bound cells, and collecting the flow through volume of monocytes. Monocytes were washed once with wash buffer and seeded at 10E5 cells per well in 100 μl serum-free RPMI 1640 in 96-well plates and incubated for 1 hour at 37° C. in a 5% $CO_2$/95% humidified tissue culture incubator. After 1 hour, the medium was replaced with 100 μl complete culture medium (RPMI 1640, 10% human serum-type AB (heat inactivated), 25 mM HEPES, 2 mM glutamine, 50 U/ml each of penicillin and streptomycin) and incubated overnight (16 hours).

Dosing regimen: The next day, the culture medium was replaced with 100 μl fresh complete culture medium in the absence or presence of human beta amyloid 1-42 peptide (5 μM) and incubated at 37° C. in a 5% $CO_2$/95% humidified tissue culture incubator for 5 hours. Medium was then removed and discarded. Each well was washed once with Hanks buffered saline (HBSS) containing 1 mM $CaCl_2$ followed by the addition of 80 μl of HBSS/$CaCl_2$. Samples were then given either 10 μl of HBSS/$CaCl_2$ or 10 μl of the P2X7 inhibiting compound of the present invention (10× stock in HBSS/$CaCl_2$ for a final concentration of 23 nM and 206 nM) and incubated 15 minutes in the tissue culture incubator followed by the addition of either 10 μl of HBSS/$CaCl_2$ or 10 μl of benzoyl ATP (BzATP; 3 mM stock in HBSS/$CaCl_2$ for a 300 μM final concentration) and incubated for a further 30 minutes in the tissue culture incubator. Medium was then removed to new 96-well plates for storage at −70° C. until the IL-1β content was quantitated by ELISA (from R&D Systems). The cells were washed once with HBSS/$CaCl_2$ followed by lysing the cells with 100 μl ice cold lysis buffer (100 mM Tris, pH 7.6, 1% triton X-100, and 1 tablet per 30 ml Complete TM protease inhibitor from Roche Biochemicals, Inc). Cell lysates were stored at −70° C. until the IL-1β was quantitated by ELISA.

The results thus obtained for percent inhibition of BzATP-induced IL-1β secretion using a few of the P2X-7 compounds of the present invention are summarized in Table 7.

TABLE 7

| Compound | $IC_{50}$ (nM) |
|---|---|
| 2-(3-Chloro-4-fluorobenzyl)-cis-4,5-diphenyl-4,5-dihydro-1H-imidazole trifluoroacetate | 157 |

TABLE 7-continued

| Compound | $IC_{50}$ (nM) |
|---|---|
| 2-(2-Methyl-2-phenyl-propyl)-4,5-diphenyl-4,5-dihydro-1H-imidazole trifluoroacetate | 178 |
| [cis-4,5-bis-(3-Fluorophenyl)-4,5-dihydro-1H-imidazol-2-yl]-(3-fluorobenzyl)amine hydrochloride | 1276 |
| (4,5-Diphenyl-4,5-dihydro-1H-imidazol-2-yl)-(4-fluorobenzyl)-amine hydrochloride | 693 |

Example 215

This example illustrates the efficacy of the compounds of this invention in the treatment of multiple sclerosis. As described herein, experimental autoimmune encephalomyelitis (EAE) model is used to show such an efficacy. The following procedures are employed in this model.

Animals:
SJL/J female mice, 8 wks. old, are obtained from Jackson Laboratories.

Antigens:
Myelin Proteolipid Protein (PLP 139-151) (HSLGK-WLGHPDKF) (Cat # H-2478) is obtained from BACHEM, Bioscience, Inc., 3700 Horizon Dr., King of Prussia, Pa. 19406, 1-610-239-0300 (phone), 1-610-239-0800 (fax).

Complete Freund's Adjuvant H37 Ra [1 mg/ml *Mycobacterium Tuberculosis* H37 Ra] is obtained from Difco 1-800-521-0851 (Cat # 3114-60-5, 6×10 ml).

*Mycobacterium Tuberculosis* is also obtained from Difco, 1-800-521-0851 (Cat # 3114-33-8, 6×100 mg).

Pertussis Toxin
*Bordetella Pertussis*, (Lyophilized powder containing PBS and lactose) is obtained from List Biological Laboratories, 1-408-866-6363 (Product #180, 50 ug @ $140.00 ea.).

Induction of EAE in Mice
PLP139-151 peptide is dissolved in $H_2O$:PBS (1:1) solution to a concentration 7.5 mg/10 ml (for 75 μg PLP per group) and emulsified with an equal volume of CFA supplemented with 40 mg/10 ml heated-killed *mycobacterium tuberculosis* H37Ra. Mice are injected s.c. with 0.2 ml of peptide emulsion in the abdominal flank (0.1 ml on each side). On the same day and 72 hours later, mice are injected i.v. with 100 μl of 35 ng and 50 ng of *Bordetella Pertussis* toxin in saline respectively.

Clinical Assessment
STAGE 0: Normal
STAGE 0.5: Partial limp tail
STAGE 1: Complete Limp Tail
STAGE 2: Impaired righting reflex
STAGE 2.5: Righting reflex is delayed (Not weak enough to be stage 3).
STAGE 3: Partial hind limb paralysis
STAGE 3.5: One leg is completely paralyzed, and one leg is partially paralyzed,
STAGE 4: Complete hind limb paralysis
STAGE 4.5: Legs are completely paralyzed and Moribund
STAGE 5: Death due to EAE Clinical Courses of EAE
Acute phase: First clinical episode (Day 10-18)
Remission: Phase of clinical improvement following a clinical episode; characterized by a reduction (>=one grade) in clinical score for at least two days after the peak score of acute phase or a disease relapse.

Relapse: Increase of at least one grade in clinical score for at least two days after remission has been attained.

The animals treated with the compounds of this invention generally would be expected to show improvements in clinical scores.

Example 216

This Example illustrates the efficacy of the compounds of the present invention for the treatment of stroke using an animal model.

Male Sprague Dawley rats (Charles River) weighing 280-320 g are given free access to food and water and acclimatized for a minimum of 4 days before use in experiments.

All rats for use in studies are to be fasted beginning at 3:00 pm the day prior to surgery but given free access to water. Prior to surgery each rat is weighed. The rat is initially induced with 5% isoflurane (Aerrane, Fort Dodge), combined with 30% $O_2$, 70% $N_2O$ for 2-5 minutes. The rat is then placed on a circulating water-heating pad and into a nose cone for spontaneous respiration of anesthetic gases. The isoflurane is reduced to 2%. A rectal probe is inserted and body temperature maintained at 36.5-37.5° C. The hair is clipped at all surgical sites and these regions will then be scrubbed with Betadine.

Surgical procedure

A temporalis muscle probe is placed into the right temporalis muscle and "brain" temperature" is monitored.

A midline neck incision is made in the upper thorax of the rat. Careful dissection, isolation and retraction of the sternomastoideus, digastricus, and sternohyoideus muscles is made to expose the right common, internal and external carotid arteries.

The right common carotid artery is isolated with a 5-0 silk suture. During surgery the suture is released allowing reperfusion every 2-4 minutes.

The right external carotid and superior thyroid arteries are also isolated and the superior thyroid is cauterized, while the external carotid is ligated distally with a 5-0 silk suture. Another 5-0 silk suture is loosely tied around the external carotid artery.

The occipital artery is isolated, ligated and incised.

The internal carotid is isolated.

With the common and external carotid arteries immobilized, an aneurysm clip is placed onto the internal carotid artery.

A small incision is made at the distal end of the external carotid.

A 3-0 nylon suture coated with poly-L-lysine is then inserted into the external carotid and up into the common carotid artery.

The loosely tied 5-0 silk suture around the external carotid is now gently tightened around the filament.

The external carotid artery is then incised and the remaining piece of the external carotid artery with the filament is rotated so that the filament may be inserted into the internal carotid artery the length of insertion depending on the weight and rat strain. In Sprague Dawley rats the monofilament is inserted 18-19 mm (18 mm for rats weighing <300 gm, 19 mm for rats weighing ≧300 gm) effectively blocking blood flow to the middle cerebral artery.

The external jugular vein will be cannulated with PE 50 tubing for I.V. administration of compounds. The cannula will be exteriorized at the previously shaven, scruff of the neck and sutured in place. The wound will be closed by means of suture.

The right femoral artery is catheterized for blood gas and glucose determination during surgery.

Two hours after the insertion of the monofilament suture the rats are re-anesthetized with the same anesthetic combination used initially and placed back into the nose cone with the reduction of isoflurane concentration to 2%.

The neck incision is reopened to expose the external carotid artery.

The restoration of blood flow is accomplished by completely withdrawing the intraluminal suture from the carotid arteries.

The incision is then closed with 3-0 silk in an interrupted stitch

Compound Administration

Five groups of 15 animals are subjected to the above methodology.

Compounds are infused (I.V.) at various doses (dose response) over different time period's post MCAo.

A pre-determined concentration is infused over a pre-selected time period beginning at various intervals post MCAo.

Vehicle-treated controls receive an infusion of normally 0.9 ml/hr.

A positive control compound is run at the same time.

Neurological Tests

Prior to surgery, 2 hours following the onset of ischaemia and 24 hours after ischaemia a battery of neurological tests are performed.

The postural reflex test, which is designed to examine upper body posture, when the rat is suspended by the tail above a flat surface. A normal rat will extend the entire body and both forelimbs towards the surface. Rats with an infarction will consistently flex the contralateral limb and show signs of body rotation.

The rats response to a gentle lateral push with a finger behind the shoulders. A normal rat would resist such a push, whereas a rat with an infarction will not.

The elicited forelimb placing in response to visual and tactile stimuli. The animal is held by the body so that the lateral or dorsal forepaw surface is placed against a bench. This test is repeated but on this occasion obstructing the view of the rat.

Upon completion of each experiment, all animals are deeply anaesthetized with isoflurane (5%), euthanized by decapitation, and the brains removed, the extent and location of the ischaemic damage is verified histologically by means of tetrazolium chloride.

Example 217

This Example illustrates the anti-inflammatory activity of the compounds of this invention using a model of 2,4-dinitrobenzenesulfonic acid (DNBS) induced distal colitis (a model of inflammatory bowel disease).

1. Test Substance and Dosing Pattern.

A compound of this invention is dissolved in vehicle of 2% Tween 80 in distilled water for oral administration at a dose of 50 mg/kg or dissolved in vehicle of 2% Tween 80 and 0.9%

NaCl for intraperitoneal injection at 30 mg/kg. The dose was given once daily for 7 consecutive days. Dosing volume was 10 ml/kg. DNBS was challenged 2 hours after dosing on the second day.

2. Animals

In these studies, male Wistar, Long Evans rats provided by animal breeding center of MDS Panlabs Taiwan, Ltd. and Balb/cByJ derived male mice (weighing 20=2 gms), provided by National Laboratory Animals Breeding Research center (NALBRC, Taiwan), were used. Space allocation of 6 animals was 45×23×15 cm. Animals were housed in APEC® cages (Allentown Caging, Allentown, N.J. 08501, USA) in a positive pressure isolator (NuAire®, Mode: Nu-605, airflow velocity 50=5 ft/min, HEPA Filter) and maintained in a controlled temperature (22° C.-24° C.) and humidity (60%-80%) environment with 12 hours light dark cycles for at least one week in MDS Panlabs Taiwan laboratory prior to being used. Free access to standard lab chow for rats (Fwusow Industry Co., Limited, Taiwan) and tap water was granted. All aspects of this work including housing, experimentation and disposal of animals were performed in general accordance with the International Guiding Principles for Biomedical Research Involving Animals (CIOMS Publication No. ISBN 92 90360194, 1985).

3. Chemicals

DNBS is obtained from TCI, Tokyo, Japan, ethanol is from Merck, Germany and Sulfasalazine is purchased from Sigma, USA.

4. Equipment

Electriconic scale (Tanita, model 1140, Japan), Electriconic scale (Sartorius, R160P, Germany), Glass syringe (2 ml, Mitsuba, Japan), Rat oral needle, Hypodermic needle (25G×1" TOP Corporation, Japan), Stainless Scissors (Klappenclear, Germany), Stainless Forceps (Klappenclear, Germany).

5. Method

Groups of 3 Wistar derived male rats weighing 180±20 gms are used. Distal colitis is induced by intra-colonic instillation of DNBS (2,4-dinitrobenzene sulfonic acid, 30 mg in 0.5 ml ethanol 30%) after which, 2 ml of air is gently injected through the cannula to ensure that the solution remains in the colon. Test substance is administered orally (PO) at a dose of 50 mg/kg or intraperitoneally (IP) at 30 mg/kg once daily for 7 consecutive days. DNBS is instillated into the distal colon of each animal 2 hours after dosing on the second day. The control group is similarly treated with vehicle alone and sulfasalazine (300 mg/kg, PO) is used as reference agent. Animals are fasted 24 hours before DNBS challenge and 24 hours after the final treatment when they are sacrificed and each colon was removed and weighed. During the experiments, presence of diarrhea is recorded daily. When the abdominal cavity is opened before removal of the colon, adhesions between the colon and other organs are noted. After weighing the colon, the extent of colonic ulceration is observed and noted as well. Colon-to-body weight ratio is then calculated for each animal according to the formula: Colon (g)/BW× 100%. The "Net" increase in ratio of Vehicle-control+DNBS group relative to Vehicle-control group is used as a base value for comparison with test substance treated groups and expressed as % decrease in inflammation. A 30 percent or more (30%) decrease in "Net" colon-to-body weight ratio for each test substance treated group relative to the "Net" vehicle+DNBS treated group is considered significant.

The results from this study indicated that the test compound at a dose of 50 mg/kg×7 oral administration showed significant anti-inflammatory activity—46% inhibition relative to the vehicle control group. However, another treatment by intraperitoneal injection at a dose of 30 mg/kg caused mortality in 3 out of 3 test animals on the $6^{th}$ day. Concurrently tested sulfasalazine (30 mg/kg×7, oral administration) showed 37% inhibition of the inflammation.

Example 218

This Example illustrates the anti-inflammatory activity of the compounds of this invention using a model of carrageenan induced paw edema (a model of inflammation, carrageenan).

1. Test Substance and Dosing Pattern.

A compound of this invention is dissolved in vehicle of 2% Tween 80/0.9% NaCl and administered intraperitoneally at a dose of 30 mg/kg 30 minutes before carrageenan (1% 0.1 ml/paw) challenge. Dosing volume is 10 ml/kg.

2. Animals

Animals are conditioned in accordance with the procedures set forth in Example 271.

3. Chemicals

Carrageenan is obtained from TCI, Japan; Pyrogen free saline is from Astar, Taiwan; and Aspirin is purchased from ICN BioMedicals, USA.

4. Equipment

Glass syringe (1 ml and 2 ml Mitsuba, Japan), Hypodermic needle 24G×1" (Top Corporation, Japan), Plethysmometer #7150 (UGO Basile, Italy), and Water cell 25 mm Diameter, #7157 (UGO Basile, Italy).

5. Method

Test substance (Example) is administered IP (30 mg/kg) to groups of 3 Long Evans derived male overnight fasted rats weighing 150±20 gms 30 minutes before right hind paw injection of carrageenan (0.1 ml of 1% suspension intraplantar). Hind paw edema, as a measure of inflammation, is recorded 3 hours after carrageenan administration using a plethysmometer (Ugo Basile Cat. # 7150) with water cell (25 mm diameter, Cat. # 7157). Reduction of hind paw edema by 30 percent or more ($\geq$30%) indicated significant acute anti-inflammatory activity.

The results from this study indicated that the compound of this invention at a dose of 30 mg/kg IP, showed significant anti-inflammatory activity—61% inhibition relative to the vehicle control group. Concurrently tested aspirin (150 mg/kg, PO) showed 38% inhibition of inflammation.

Example 219

This Example illustrates the anti-inflammatory activity of the compounds of this invention using a model of Balb/c mice subjected to monoclonal antibody (mAb) type II collagen induced arthritis.

1. Test Substance and Dosing Pattern.

A compound of this invention is dissolved in vehicle of 2% Tween 80/0.9% NaCl, at doses of 50 or 30 and administered orally (50 mg/kg) or intraperitoneally at 30 mg/kg once daily for 3 consecutive days after monoclonal antibody of collagen was injected. Dosing volume is 20 ml/kg.

2. Animals

Animals are conditioned in accordance with the procedures set forth in Example 271.

3. Chemicals

Lipopolysaccharide is obtained from Sigma, USA; Indomethacin is from Sigma, USA; Arthrogen-CIA™ Monoclonal Antibodies D8, F10, DI-2G and A2 are obtained from IBL, Japan; Phosphated-Buffer Saline is purchased from Sigma, USA; and Tween 80 is from Wako, Japan.

4. Equipment

Plethysmometer (Ugo Basile, Italy) and Water Cell (Ugo Basile, Italy).

5. Method

Groups of 5 Balb/cByJ mice strain, 6-8 weeks of age, are used for the induction of arthritis by monoclonal antibodies (mAbs) responding to type II collagen, plus lipopolysaccharide (LPS). The animals are administered intravenously with a combination of 4 different mAbs (D8, F10, DI-2G and A2) in total of 4 mg/mouse at day 0, and followed by intravenous 25 µg of LPS 72 hours later (day 3). From day 3, one hour after LPS administration, ML-659 at 50 mg/kg (PO) or 30 mg/kg (IP) and vehicle (2% Tween 80/0.9% NaCl, PO) as well as the positive control indomethacin, 3 mg/kg (PO) are administrated once daily for 3 consecutive days. A plethysmometer (Ugo Basile Cat # 7150) with water cell (12 mm diameter) is used for the measurement of increase in volume of the two hind paws at day 0, 5, 7, 10, 14, and 17. The percent inhibition of increase in volume is calculated by the following formula:

Inhibition (%): [1−(Tn−To)/(Cn−Co)]×100

Where:

Co (Cn): volume of day 0 (day n) in vehicle control

To (Tn): volume of day 0 (day n) in test compound-treated group

The reduction of both of two hind paws edema by more than 30% is considered significant.

The results from this study indicated that the compound of this invention at doses of 50 mg/kg (PO) and 30 mg/kg (IP), administered once daily for 3 consecutive days, significantly reduced inflammation. Significant reduction in inflammation is achieved relative to vehicle treated group of both hind paws edema at 30 mg/kg (IP) on days 5, 7, 10, 14 and 17 with reduction in inflammation of 100%, 72%, 71%, 86% and 85%, respectively. At a dose of 50 mg/kg (PO), on day 14, 36% reduction and on day 17, 28% reduction in inflammation are observed. Concurrently tested indomethacin (3 mg/kg×3, PO) provided an effect of 63%, 70%, 80%, 88% and 85% at days 5, 7, 10, 14 and 17 respectively, relative to the vehicle treated group.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of formula II or a pharmaceutically acceptable salt thereof:

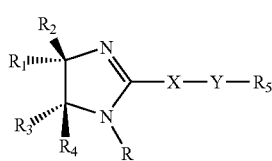

(II)

wherein:

R is hydrogen, or $C_{1-6}$ alkyl;

$R_1$ and $R_3$ taken together with the carbon atoms to which they are attached form a cyclopentane, cyclohexane, cycloheptane or cyclooctane;

$R_2$ and $R_4$ are the same or different and are each independently selected from:

hydrogen, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1;

$R_5$ is phenyl, which is optionally substituted with one or more substituents selected from the group consisting of halogen, $C_{1-4}$ alkyl, fluoroalkyl of the formula $C_nH_xF_y$, and fluoroalkoxy $OC_nH_xF_y$ wherein n is an integer from 1 to 4, x is an integer from 0 to 8, y is an integer from 1 to 9 and sum of x and y is 2n+1, $C_{1-4}$ alkoxy, $C_{1-4}$ thioalkyl, hydroxy, $C_{1-4}$ acyloxy, nitro, amino, $C_{1-4}$ alkylamino, $C_{1-4}$ dialkylamino, amino $C_{1-4}$ alkyl, $C_{1-4}$ alkylamino $C_{1-4}$ alkyl, $C_{1-4}$ dialkylamino $C_{1-4}$ alkyl, —CN, —$CO_2H$, —$CO_2C_{1-4}$ alkyl, phenyl, phenoxy and benzyloxy;

X—Y is —$(CH_2)_a$—Z—$(CH_2)_b$—, wherein $(CH_2)$ is optionally substituted with one or more groups selected independently from:

hydroxy, $C_{1-6}$ alkoxy, arylaminocarbonyloxy, $C_{3-8}$ cycloalkyl, and fluoroalkyl of the formula $C_nH_xF_y$, wherein n is an integer from 1 to 4, x is an integer from 0 to 8, y is an integer from 1 to 9 and sum of x and y is 2n+1, wherein said alkoxy or fluoroalkyl is optionally substituted with a substituent selected from the group consisting of: hydroxy, —SH, $C_{1-4}$ alkoxy, $C_{1-4}$ thioalkyl, $C_{1-4}$ acyloxy, nitro, amino, $C_{1-4}$ alkylamino, $C_{1-4}$ dialkylamino, —CN, —$CO_2H$, —$CO_2C_{1-4}$ alkyl and aryl;

Z is $NR_6$, wherein $R_6$ is selected from:

hydrogen, $C_{1-6}$ alkoxy, $C_{1-6}$ alkyl or fluoroalkyl of the formula $C_nH_xF_y$, wherein n is an integer from 1 to 4, x is an integer from 0 to 8, y is an integer from 1 to 9 and sum of x and y is 2n+1, wherein said alkoxy or alkyl or fluoroalkyl is optionally substituted with at least one substituent selected from the group consisting of: hydroxy, —SH, $C_{1-4}$ alkoxy, $C_{1-4}$ thioalkyl, $C_{1-4}$ acyloxy, nitro, amino, $C_{1-4}$ alkylamino, $C_{1-4}$ dialkylamino, —CN, —$CO_2H$, —$CO_2C_{1-4}$ alkyl and aryl; and a is 0 and b is an integer from 1 to 4.

2. The compound as set forth in claim 1 wherein X—Y is —$(CH_2)_a$—Z—$(CH_2)_b$— and wherein Z is $NR_6$ and wherein $R_6$ is hydrogen or methyl, and a is 0 and b is 1.

3. The compound as set forth in claim 2 wherein $R_1$ and $R_3$ taken together with the carbon atoms to which they are attached form a cyclohexane, and R, $R_2$ and $R_4$ are hydrogen.

4. The compound as set forth in claim 3 which is selected from the group consisting of:

(cis-3a,4,5,6,7,7a-hexahydro-1H-benzimidazol-2-yl)-benzylamine, (cis-3a,4,5,6,7,7a-hexahydro-1H-benzimidazol-2-yl)-(3-fluorobenzyl)amine, (cis-3a,4,5,6,7,7a-hexahydro-1H-benzimidazol-2-yl)-(4-fluorobenzyl)amine, and (cis-3a,4,5,6,7,7a-hexahydro-1H-benzimidazol-2-yl)-(3,4-difluorobenzyl)amine.

5. The compound as set forth in claim 1 wherein X—Y is —(CH$_2$)$_a$—Z—(CH$_2$)$_b$—and wherein Z is NR$_6$ and wherein R$_6$, is hydrogen, a is 0 and b is 2.

6. A pharmaceutical composition comprising a compound or a pharmaceutically acceptable salt thereof in combination with at least one pharmaceutically acceptable carrier, wherein said compound is of the formula (II):

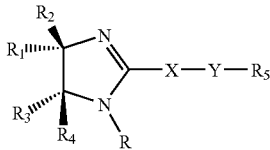

wherein:
R is hydrogen, or C$_{1-6}$ alkyl;
R$_1$ and R$_3$ taken together with the carbon atoms to which they are attached form a cyclopentane, cyclohexane, cycloheptane or cyclooctane;
R$_2$ and R$_4$ are the same or different and are each independently selected from: hydrogen, C$_{1-6}$ alkyl or fluoroalkyl of the formula C$_n$H$_x$F$_y$, wherein n is an integer from 1 to 4, x is an integer from 0 to 8, y is an integer from 1 to 9 and sum of x and y is 2n+1;
R$_5$ is phenyl, which is optionally substituted with one or more substituents selected from the group consisting of halogen, C$_{1-4}$ alkyl, fluoroalkyl of the formula C$_n$H$_x$F$_y$, and fluoroalkoxy OC$_n$H$_x$F$_y$, wherein n is an integer from 1 to 4, x is an integer from 0 to 8, y is an integer from 1 to 9 and sum of x and y is 2n+1, C$_{1-4}$ alkoxy, C$_{1-4}$ thioalkyl, hydroxy, C$_{1-4}$ acyloxy, nitro, amino, C$_{1-4}$ alkylamino, C$_{1-4}$ dialkylamino, amino C$_{1-4}$ alkyl, C$_{1-4}$ alkylamino C$_{1-4}$ alkyl, C$_{1-4}$ dialkylamino C$_{1-4}$ alkyl, —CN, —CO$_2$H, —CO$_2$C$_{1-4}$ alkyl, phenyl, phenoxy and benzyloxy;
X—Y is —(CH$_2$)$_a$—Z—(CH$_2$)$_b$—,
wherein (CH$_2$) is optionally substituted with one or more groups selected independently from:
hydroxy, C$_{1-6}$ alkoxy, arylaminocarbonyloxy, C$_{3-8}$ cycloalkyl, and fluoroalkyl of the formula C$_n$H$_x$F$_y$, wherein n is an integer from 1 to 4, x is an integer from 0 to 8, y is an integer from 1 to 9 and sum of x and y is 2n+1, wherein said alkoxy or fluoroalkyl is optionally substituted with a substituent selected from the group consisting of: hydroxy, —SH, C$_{1-4}$ alkoxy, C$_{1-4}$ thioalkyl, C$_{1-4}$ acyloxy, nitro, amino, C$_{1-4}$ alkylamino, C$_{1-4}$ dialkylamino, —CN, —CO$_2$H, —CO$_2$C$_{1-4}$ alkyl and aryl;
Z is NR$_6$,
wherein R$_6$ is selected from:
hydrogen, C$_{1-6}$ alkoxy, C$_{1-6}$ alkyl or fluoroalkyl of the formula C$_n$H$_x$F$_y$, wherein n is an integer from 1 to 4, x is an integer from 0 to 8, y is an integer from 1 to 9 and sum of x and y is 2n+1, wherein said alkoxy or alkyl or fluoroalkyl is optionally substituted with at least one substituent selected from the group consisting of: hydroxy, —SH, C$_{1-4}$ alkoxy, C$_{1-4}$ thioalkyl, C$_{1-4}$ acyloxy, nitro, amino, C$_{1-4}$ alkylamino, C$_{1-4}$ dialkylamino, —CN, —CO$_2$H, —CO$_2$C$_{1-4}$ alkyl and aryl; and
a is 0 and b is an integer from 1 to 4.

7. The composition as set forth in claim 6 wherein X—Y is —(CH$_2$)$_a$—Z—(CH$_2$)$_b$— and wherein Z is NR$_6$ and wherein R$_6$ is hydrogen or methyl, and a is 0 and b is 1.

8. The composition as set forth in claim 7 wherein R$_1$ and R$_3$ taken together with the carbon atoms to which they are attached form a cyclohexane, and R, R$_2$ and R$_4$ are hydrogen.

9. The composition as set forth in claim 8 wherein the compound is selected from the group consisting of:
(cis-3a,4,5,6,7,7a-hexahydro-1H-benzimidazol-2-yl)-benzylamine,
(cis-3a,4,5,6,7,7a-hexahydro-1H-benzimidazol-2-yl)-(3-fluorobenzyl)amine,
(cis-3a,4,5,6,7,7a-hexahydro-1H-benzimidazol-2-yl)-(4-fluorobenzyl)amine, and
(cis-3a,4,5,6,7,7a-hexahydro-1H-benzimidazol-2-yl)-(3,4-difluorobenzyl)amine.

10. The composition as set forth in claim 6 wherein X—Y is —(CH$_2$)$_a$—Z—(CH$_2$)$_b$— and wherein Z is NR$_6$ and wherein R$_6$ is hydrogen, a is 0 and b is 2.

* * * * *